United States Patent
Baldwin et al.

(10) Patent No.: US 7,872,028 B2
(45) Date of Patent: Jan. 18, 2011

(54) DIAMINOPROPANOL RENIN INHIBITORS

(75) Inventors: John J. Baldwin, Gwynedd Valley, PA (US); David A. Claremon, Maple Glen, PA (US); Colin M. Tice, Ambler, PA (US); Salvacion Cacatian, Blue Bell, PA (US); Lawrence W. Dillard, Yardley, PA (US); Alexey V. Ishchenko, Somerville, MA (US); Jing Yuan, Lansdale, PA (US); Zhenrong Xu, Horsham, PA (US); Gerard McGeehan, Garnet Valley, PA (US); Wei Zhao, Eagleville, PA (US); Robert D. Simpson, Wilmington, DE (US); Suresh B. Singh, Kendall Park, NJ (US); Patrick T. Flaherty, Pittsburgh, PA (US)

(73) Assignee: Vitae Pharmaceuticals, Inc., Fort Washington, PA (US)

( * ) Notice: Subject to any disclaimer, the term of this patent is extended or adjusted under 35 U.S.C. 154(b) by 0 days.

(21) Appl. No.: 12/225,985

(22) PCT Filed: Apr. 5, 2007

(86) PCT No.: PCT/US2007/008518

§ 371 (c)(1),
(2), (4) Date: Feb. 4, 2009

(87) PCT Pub. No.: WO2007/117557

PCT Pub. Date: Oct. 18, 2007

(65) Prior Publication Data

US 2009/0186884 A1 Jul. 23, 2009

Related U.S. Application Data

(60) Provisional application No. 60/789,713, filed on Apr. 5, 2006, provisional application No. 60/789,789, filed on Apr. 5, 2006.

(51) Int. Cl.
*C07D 211/22* (2006.01)
*A61K 31/445* (2006.01)

(52) U.S. Cl. .................. 514/330; 514/331; 546/226; 546/233; 546/234; 546/235

(58) Field of Classification Search ............ 546/245, 546/247, 246

See application file for complete search history.

(56) References Cited

U.S. PATENT DOCUMENTS

7,176,242 B2 * 2/2007 John et al. ............... 514/615
2007/0265331 A1 * 11/2007 Decicco et al. ............ 514/424
2009/0018103 A1 1/2009 Baldwin et al.

FOREIGN PATENT DOCUMENTS

| WO | WO 03/006423 A1 | 1/2003 |
| WO | WO 2006/042150 A1 | 4/2006 |
| WO | WO 2007/070201 A1 | 6/2007 |

OTHER PUBLICATIONS

Jordan, V. C. Nature Reviews: Drug Discovery, 2, 2003, pp. 205-213.*
Dörwald, F. Zaragoza. Side Reactions in Organic Synthesis: A Guide to Successful Synthesis Design, Weinheim: WILEY-VCH Verlag GmbH & Co. KGaA, 2005, Preface.*
International Search Report, International Application No. PCT/US2007/008518 (Oct. 10, 2007).
Rahuel, J. et al., "Structure-Based Drug Design: The Discovery of Novel Nonpeptide Orally Active Inhibitors of Human Renin," *Chemistry & Biology*, 7:493-504 (2000).
Written Opinion of the International Searching Authority, International Application No. PCT/US2007/008518 (Oct. 10, 2007).
Notification Concerning Transmittal of International Preliminary Report on Patentability, and International Preliminary Report on Patentability, International Application No. PCT/US2007/008518, mail date Oct. 8, 2008.

* cited by examiner

*Primary Examiner*—Joseph R Kosack
*Assistant Examiner*—Matthew P Coughlin
(74) *Attorney, Agent, or Firm*—Hamilton, Brook, Smith & Reynolds, P.C.

(57) ABSTRACT

Described are diaminopropanols of which are orally active and bind to renin to inhibit its activity. They are useful in the treatment or amelioration of diseases associated with elevated. levels of renin activity or in the treatment of aspartic protease mediated disorders. Also described is a method for the use of the diaminopropanols in ameliorating or treating renin related disorders in a subject in need thereof.

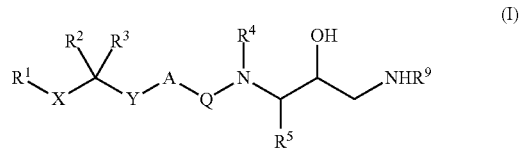

(I)

10 Claims, No Drawings

DIAMINOPROPANOL RENIN INHIBITORS

RELATED APPLICATIONS

This application is the U.S. National Stage of International Application No. PCT/US2007/008518, filed Apr. 5, 2007, published in English, and claims priority under 35 U.S.C. §119 or 365 to U.S. Provisional Application No. 60/789,713, filed Apr. 5, 2006, and U.S. Provisional Application No. 60/789,789, filed Apr. 5, 2006, the entire teachings of which are incorporated herein by reference.

BACKGROUND OF THE INVENTION

In the renin-angiotensin-aldosterone system (RAAS) the biologically active peptide angiotensin II (Ang II) is generated by a two-step mechanism. The highly specific aspartic protease renin cleaves angiotensinogen to angiotensin I (Ang I), which is then further processed to Ang II by the less specific angiotensin-converting enzyme (ACE). Ang II is known to work on at least two receptor subtypes called $AT_1$ and $AT_2$. Whereas $AT_1$ seems to transmit most of the known functions of Ang II, the role of $AT_2$ is still unknown.

Modulation of the RAAS represents a major advance in the treatment of cardiovascular diseases (Zaman, M. A. et al *Nature Reviews Drug Discovery* 2002, 1, 621-636). ACE inhibitors and $AT_1$ blockers have been accepted as treatments of hypertension (Waeber B. et al., "The renin-angiotensin system: role in experimental and human hypertension", in Berkenhager W. H., Reid J. L. (eds): *Hypertension*, Amsterdam, Elsevier Science Publishing Co, 1996, 489-519; Weber M. A., *Am. J. Hypertens.*, 1992, 5, 247S). In addition, ACE inhibitors are used for renal protection (Rosenberg M. E. et al., *Kidney International*, 1994, 45, 403; Breyer J. A. et al., *Kidney International*, 1994, 45, S156), in the prevention of congestive heart failure (Vaughan D. E. et al., *Cardiovasc. Res.*, 1994, 28, 159; Fouad-Tarazi F. et al., *Am. J. Med.*, 1988, 84 (Suppl. 3A), 83) and myocardial infarction (Pfeffer M. A. et al., *N Engl. J: Med*, 1992, 327, 669).

Interest in the development of renin inhibitors stems from the specificity of renin (Kleinert H. D., *Cardiovasc. Drugs*, 1995, 9, 645). The only substrate known for renin is angiotensinogen, which can only be processed (under physiological conditions) by renin. In contrast, ACE can also cleave bradykinin besides Ang I and can be bypassed by chymase, a serine protease (Husain A., *J. Hypertens.*, 1993, 11, 1155). In patients, inhibition of ACE thus leads to bradykinin accumulation causing cough (5-20%) and potentially life-threatening angioneurotic edema (0.1-0.2%) (Israili Z. H. et al., *Annals of Internal Medicine*, 1992, 117, 234). Chymase is not inhibited by ACE inhibitors. Therefore, the formation of Ang II is still possible in patients treated with ACE inhibitors. Blockade of the ATI receptor (e.g., by losartan) on the other hand overexposes other AT-receptor subtypes to Ang II, whose concentration is dramatically increased by the blockade of AT1 receptors. In summary, renin inhibitors are not only expected to be superior to ACE inhibitors and $AT_1$ blockers with regard to safety, but more importantly also with regard to their efficacy in blocking the RAAS.

Only limited clinical experience (Azizi M. et al., *J. Hypertens.*, 1994, 12, 419; Neutel J. M. et al., *Am. Heart*, 1991, 122, 1094) has been generated with renin inhibitors because their peptidomimetic character imparts insufficient oral activity (Kleinert H. D., *Cardiovasc. Drugs*, 1995, 9, 645). The clinical development of several compounds has been stopped because of this problem together with the high cost of goods. It appears as though only one compound has entered clinical trials (Rahuel J. et al., *Chem. Biol.*, 2000, 7, 493; Mealy N. E., *Drugs of the Future*, 2001, 26, 1139). Thus, metabolically stable, orally bioavailable and sufficiently soluble renin inhibitors that can be prepared on a large scale are not available. Recently, the first non-peptide renin inhibitors were described which show high in vitro activity (Oefner C. et al., *Chem. Biol.*, 1999, 6, 127; Patent Application WO 97/09311; Maerki H. P. et al., *Il Farmaco*, 2001, 56, 21). The present invention relates to the unexpected identification of renin inhibitors of a non-peptidic nature and of low molecular weight. Orally active renin inhibitors which are active in indications beyond blood pressure regulation where the tissular renin-chymase system may be activated leading to pathophysiologically altered local functions such as renal, cardiac and vascular remodeling, atherosclerosis, and restenosis, are described.

All documents cited herein are incorporated by reference.

SUMMARY OF THE INVENTION

Diaminopropanols described herein have been found which are orally active and bind to renin to inhibit its activity. They are useful in the treatment or amelioration of diseases associated with renin activity or in the treatment of an aspartic protease mediated disorders generally.

In one embodiment the present invention is directed to a compound represented by Formula I:

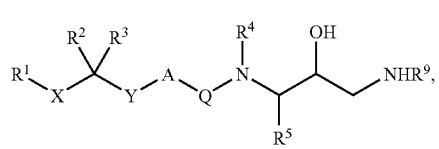

or an enantiomer, diastereomer or salt thereof.

$R^1$ is:

a) $(C_1-C_{12})$alkyl, $(C_3-C_7)$cycloalkyl, $(C_4-C_{12})$cycloalkylalkyl, halo$(C_1-C_{12})$alkyl, halo$(C_3-C_7)$-cycloalkyl, halo$(C_4-C_{12})$cycloalkylalkyl or saturated heterocyclyl each optionally substituted with 1 to 5 groups independently selected from the group consisting of halogen, $(C_1-C_6)$alkyl, halo$(C_1-C_6)$alkyl and oxo; or b) phenyl, napthyl, heteroaryl or bicyclic heteroaryl each optionally substituted with 1 to 5 groups independently selected from the groups consisting of:

1) fluorine, chlorine, bromine, iodine, cyano, nitro, amino, hydroxy, carboxy, $(C_1-C_8)$alkyl, $(C_3-C_8)$cycloalkyl, $(C_1-C_3)$alkyl$(C_3-C_8)$cycloalkyl, di$(C_1-C_3)$alkyl$(C_3-C_8)$cycloalkyl, $(C_4-C_8)$cycloalkylalkyl, $(C_2-C_6)$alkenyl, $(C_5-C_8)$cycloalkenyl, $(C_5-C_8)$cycloalkylalkenyl, $(C_2-C_8)$alkynyl, $(C_3-C_8)$cycloalkyl$(C_2-C_4)$alkynyl, halo$(C_1-C_3)$alkyl, halo$(C_3-C_6)$cycloalkyl, halo$(C_4-C_8)$cycloalkylalkyl, $(C_1-C_3)$alkyl$(C_4-C_8)$cycloalkylalkyl, di$(C_1-C_3)$alkyl$(C_4-C_8)$cycloalkylalkyl, halo$(C_2-C_8)$alkenyl, halo$(C_5-C_8)$cycloalkenyl, halo$(C_6-C_8)$cycloalkenylalkyl, halo$(C_3-C_8)$alkynyl, halo$(C_5-C_8)$cycloalkylalkynyl, $(C_1-C_8)$alkoxy, $(C_3-C_8)$cycloalkoxy, $(C_4-C_8)$cycloalkylalkoxy, $(C_1-C_3)$alkyl$(C_3-C_8)$cycloalkoxy, $(C_1-C_3)$alkyl$(C_4-C_8)$cycloalkylalkoxy, di$(C_1-C_3)$alkyl$(C_3-C_8)$cycloalkoxy, di$(C_1-C_3)$alkyl$(C_4-C_8)$cycloalkylalkoxy, halo$(C_1-C_6)$alkoxy, halo$(C_3-C_6)$cycloalkoxy, halo$(C_4-C_8)$cycloalkylalkoxy, $(C_1-C_8)$alkylthio, $(C_3-C_8)$cycloalkylthio, $(C_4-C_8)$cycloalkylalkylthio, $(C_1-C_3)$alkyl$(C_3-C_8)$cycloalkylthio, $(C_1-C_3)$alkyl$(C_4-C_8)$cycloalkylalkylthio, di$(C_1-C_3)$alkyl$(C_3-C_8)$-cycloalkylthio, di$(C_1-C_3)$alkyl$(C_4-C_8)$cycloalkylalkylthio, halo(C$_1$-C$_8$)alkylthio, halo(C$_3$-C$_8$)-cycloalkylthio, halo(C$_4$-C$_8$)cycloalkylalkylthio, (C$_1$-C$_8$) alkanesulfinyl, (C$_3$-C$_8$)-cycloalkane-sulfinyl; (C$_4$-C$_8$) cycloalkyl-alkanesulfinyl, (C$_1$-C$_3$)alkyl(C$_3$-C$_8$)cycloalkane-sulfinyl, (C$_1$-C$_3$)alkyl(C$_4$-C$_8$)cycloalkyl-alkanesulfinyl, di(C$_1$-C$_3$)alkyl(C$_3$-C$_8$)cycloalkane-sulfinyl, di(C$_1$-C$_3$)alkyl (C$_4$-C$_8$)cycloalkyl-alkanesulfinyl, halo(C$_1$-C$_8$)alkanesulfinyl, halo(C$_3$-C$_8$)cycloalkanesulfinyl, halo(C$_4$-C$_8$)cycloalkylalkanesulfinyl, (C$_1$-C$_8$)alkane-sulfonyl, (C$_3$-C$_8$)cycloalkanesulfonyl, (C$_4$-C$_8$)cycloalkylalkanesulfonyl, (C$_1$-C$_3$) alkyl(C$_3$-C$_8$)cycloalkanesulfonyl, (C$_1$-C$_3$)alkyl(C$_4$-C$_8$)-cycloalkyl-alkanesulfonyl, di(C$_1$-C$_3$)alkyl(C$_3$-C$_8$) cycloalkanesulfonyl, di(C$_1$-C$_3$)alkyl(C$_4$-C$_8$)-cycloalkyl-alkanesulfonyl, halo(C$_1$-C$_3$)alkanesulfonyl, halo(C$_3$-C$_8$) cycloalkanesulfonyl, halo(C$_4$-C$_8$)cycloalkylalkanesulfonyl, (C$_1$-C$_8$)alkylamino, di(C$_1$-C$_8$)alkylamino, (C$_1$-C$_6$)alkoxy-(C$_1$-C$_6$)-alkoxy, halo(C$_1$-C$_6$)alkoxy(C$_1$-C$_6$)alkoxy, (C$_1$-C$_8$) alkoxycarbonyl, aminocarbonyl, (C$_1$-C$_8$)alkyl-amino-carbonyl, di(C$_1$-C$_8$)alkylaminocarbonyl, piperidino, pyrrolidino, cyano(C$_1$-C$_6$)alkyl, hydroxy(C$_1$-C$_6$)alkyl, carboxy(C$_1$-C$_6$) alkyl, (C$_1$-C$_8$)alkoxy(C$_1$-C$_6$)alkyl, (C$_3$-C$_8$)cycloalkoxy(C$_1$-C$_6$)alkyl, (C$_4$-C$_8$)cycloalkylalkoxy(C$_1$-C$_6$)alkyl, halo(C$_1$-C$_6$)alkoxy(C$_1$-C$_6$)alkyl, halo(C$_3$-C$_6$)cyclo-alkoxy(C$_1$-C$_6$) alkyl, halo(C$_4$-C$_8$)-cycloalkylalkoxy(C$_1$-C$_6$)alkyl, (C$_1$-C$_6$) alkylthio-(C$_1$-C$_6$)alkyl, (C$_3$-C$_8$)cycloalkylthio(C$_1$-C$_6$)alkyl, (C$_4$-C$_8$)cycloalkylalkylthio(C$_1$-C$_6$)alkyl, halo(C$_1$-C$_8$)alkylthio(C$_1$-C$_6$)alkyl, halo(C$_3$-C$_8$)cycloalkylthio(C$_1$-C$_6$)alkyl, halo(C$_4$-C$_8$)-cycloalkylalkylthio-(C$_1$-C$_6$)alkyl, (C$_1$-C$_8$)alkanesulfinyl(C$_1$-C$_6$)alkyl, (C$_3$-C$_8$)-cycloalkanesulfinyl(C$_1$-C$_6$)alkyl, (C$_4$-C$_8$)cycloalkyl-alkanesulfinyl(C$_1$-C$_6$)alkyl, halo(C$_1$-C$_8$)alkanesulfinyl(C$_1$-C$_6$)alkyl, halo(C$_3$-C$_8$)cycloalkane-sulfinyl(C$_1$-C$_6$)alkyl, halo(C$_4$-C$_8$)cycloalkylalkanesulfinyl(C$_1$-C$_6$)alkyl, (C$_1$-C$_8$)alkane-sulfonyl(C$_1$-C$_6$)alkyl, (C$_3$-C$_8$)cycloalkanesulfonyl(C$_1$-C$_6$)alkyl, (C$_4$-C$_8$)cycloalkylalkanesulfonyl(C$_1$-C$_6$)alkyl, halo(C$_1$-C$_8$)alkanesulfonyl (C$_1$-C$_6$)alkyl, halo(C$_3$-C$_8$)cycloalkanesulfonyl(C$_1$-C$_6$)alkyl, halo(C$_4$-C$_8$)cycloalkylalkane-sulfonyl(C$_1$-C$_6$)alkyl, (C$_1$-C$_8$) alkylamino(C$_1$-C$_6$)alkyl, di(C$_1$-C$_8$)alkylamino-(C$_1$-C$_6$) alkyl, (C$_1$-C$_8$)alkoxycarbonyl(C$_1$-C$_6$)alkyl, (C$_1$-C$_8$)acyloxy (C$_1$-C$_6$)alkyl, aminocarbonyl-(C$_1$-C$_6$)alkyl, (C$_1$-C$_8$) alkylamino-carbonyl(C$_1$-C$_6$)alkyl, di(C$_1$-C$_8$)alkylamino-carbonyl(C$_1$-C$_6$)alkyl, (C$_1$-C$_8$)acylamino(C$_1$-C$_6$)alkyl, piperidino(C$_1$-C$_6$)alkyl, pyrrolidino(C$_1$-C$_6$)alkyl, (C$_1$-C$_8$) alkoxy-carbonylamino, (C$_1$-C$_8$)alkoxycarbonylamino(C$_1$-C$_6$)alkyl, aminocarboxy(C$_1$-C$_6$)alkyl, (C$_1$-C$_8$)alkylamino-carboxy(C$_1$-C$_6$)alkyl, and di(C$_1$-C$_8$)alkylaminocarboxy(C$_1$-C$_6$)alkyl; or 2) phenyl, napthyl, heteroaryl, bicyclic heteroaryl, phenoxy, naphthyloxy, heteroaryloxy, bicyclic heteroaryloxy, phenylthio, naphthylthio, heteroarylthio, bicyclic heteroarylthio, phenylsulfinyl, naphthylsulfinyl, heteroarylsulfinyl, bicyclic heteroarylsulfinyl, phenylsulfonyl, naphthylsulfonyl, heteroarylsulfonyl, bicyclic heteroarylsulfonyl, phenyl (C$_1$-C$_3$)alkyl, naphthyl(C$_1$-C$_3$)alkyl, heteroaryl(C$_1$-C$_3$)alkyl, bicyclic heteroaryl(C$_1$-C$_3$)alkyl, phenyl(C$_1$-C$_3$)alkoxy, naphthyl(C$_1$-C$_3$)alkoxy, heteroaryl(C$_1$-C$_3$)alkoxy, and bicyclic heteroaryl(C$_1$-C$_3$)alkoxy, each optionally substituted with 1 to 5 groups independently selected from the group consisting of fluorine, chlorine, cyano, (C$_1$-C$_6$)alkyl, halo(C$_1$-C$_6$)alkyl, (C$_1$-C$_6$)alkoxy, halo(C$_1$-C$_6$)alkoxy, (C$_1$-C$_6$)alkanesulfonyl, (C$_1$-C$_6$)alkoxy-carbonyl and aminocarbonyl.

X and Y are each independently CH$_2$ or a single bond.

R$^2$ is a substituted or unsubstituted (C$_1$-C$_{12}$)alkyl, (C$_2$-C$_{12}$) alkenyl, (C$_2$-C$_{12}$)alkynyl, (C$_1$-C$_{12}$)alkoxy, (C$_2$-C$_{12}$)alkenyloxy,(C$_1$-C$_{12}$)alkylthio, (C$_1$-C$_6$)alkoxy(C$_1$-C$_6$)alkyl, (C$_1$-C$_6$) alkylthio-(C$_1$-C$_6$)alkyl, (C$_1$-C$_6$)alkoxy(C$_1$-C$_6$)alkoxy, (C$_1$-C$_6$)alkoxy(C$_1$-C$_6$)alkylthio, (C$_1$-C$_6$)alkylthio(C$_1$-C$_6$)alkoxy, (C$_1$-C$_6$)alkylthio(C$_1$-C$_6$)alkylthio, (C$_1$-C$_4$)alkoxy(C$_1$-C$_4$) alkoxy(C$_1$-C$_4$)alkyl, aminocarbonylamino(C$_1$-C$_{12}$)alkyl, aminocarbonylamino(C$_1$-C$_{12}$)alkoxy, aminocarbonyl-amino (C$_1$-C$_{12}$)alkylthio, (C$_1$-C$_6$)-alkanoylamino(C$_1$-C$_6$)alkyl, (C$_1$-C$_6$)alkanoylamino(C$_1$-C$_6$)alkoxy, (C$_1$-C$_6$)alkanoylamino(C$_1$-C$_6$)alkylthio, (C$_3$-C$_4$)cycloalkanecarbonyl-amino(C$_1$-C$_6$)alkyl, (C$_3$-C$_4$)-cycloalkanecarbonylamino(C$_1$-C$_6$)alkoxy, (C$_3$-C$_4$)cycloalkanecarbonyl-amino(C$_1$-C$_6$) alkylthio, aminosulfonylamino(C$_1$-C$_{12}$)alkyl, aminosulfonylamino(C$_1$-C$_{12}$)alkoxy, aminosulfonylamino (C$_1$-C$_{12}$)alkylthio, (C$_1$-C$_6$)alkanesulfonylamino(C$_1$-C$_6$) alkyl, (C$_1$-C$_6$)alkane-sulfonylamino(C$_1$-C$_6$)-alkoxy, (C$_1$-C$_6$) alkanesulfonylamino(C$_1$-C$_6$)alkylthio, formylamino(C$_1$-C$_6$) alkyl, formylamino(C$_1$-C$_6$)alkoxy, formylamino(C$_1$-C$_6$) alkylthio, (C$_1$-C$_6$)alkoxycarbonylamino(C$_1$-C$_6$)alkyl, (C$_1$-C$_6$)alkoxycarbonyl-amino(C$_1$-C$_6$)alkoxy, (C$_1$-C$_6$) alkoxycarbonyl-amino(C$_1$-C$_6$)alkylthio, (C$_1$-C$_6$) alkylaminocarbonylamino(C$_1$-C$_6$)alkyl, di(C$_1$-C$_6$) alkylaminocarbonyl-amino(C$_1$-C$_6$)alkyl, (C$_1$-C$_6$) alkylaminocarbonylamino(C$_1$-C$_6$)alkoxy, di(C$_1$-C$_6$)alkyl aminocarbonylamino(C$_1$-C$_6$)alkoxy, (C$_1$-C$_6$)alkylaminocarbonylamino(C$_1$-C$_6$)alkylthio, di(C$_1$-C$_6$)alkylaminocarbonylamino(C$_1$-C$_6$)-alkylthio, aminocarbonyl(C$_1$-C$_6$)alkyl, aminocarbonyl(C$_1$-C$_6$)alkoxy, aminocarbonyl(C$_1$-C$_6$)-alkylthio, (C$_1$-C$_6$)alkylaminocarbonyl-(C$_1$-C$_6$)alkyl, (C$_1$-C$_6$)alkylaminocarbonyl-(C$_1$-C$_6$)alkoxy, (C$_1$-C$_6$)alkylaminocarbonyl-(C$_1$-C$_6$)alkylthio, aminocarboxy(C$_1$-C$_6$)alkyl, aminocarboxy (C$_1$-C$_6$)alkoxy, aminocarboxy(C$_1$-C$_6$)alkylthio, (C$_1$-C$_6$) alkylamino-carboxy(C$_1$-C$_6$)alkyl, (C$_1$-C$_6$) alkylaminocarboxy(C$_1$-C$_6$)alkoxy, (C$_1$-C$_6$) alkylaminocarboxy(C$_1$-C$_6$)alkylthio, (C$_1$-C$_{12}$) alkoxycarbonylamino, (C$_1$-C$_{12}$)alkylaminocarbonylamino or (C$_1$-C$_2$)alkanoylamino, wherein the substituted (C$_1$-C$_{12}$) alkyl, (C$_2$-C$_{12}$)alkenyl, (C$_2$-C$_{12}$)alkynyl, (C$_1$-C$_{12}$)alkoxy, (C$_1$-C$_{12}$)alkylthio, (C$_1$-C$_6$)alkoxy(C$_1$-C$_6$)alkyl, (C$_1$-C$_6$)alkylthio(C$_1$-C$_6$)alkyl, (C$_1$-C$_6$)alkoxy(C$_1$-C$_6$)alkoxy, (C$_1$-C$_6$) alkoxy(C$_1$-C$_6$)alkylthio, (C$_1$-C$_6$)alkylthio(C$_1$-C$_6$)alkoxy, (C$_1$-C$_6$)alkylthio(C$_1$-C$_6$)alkylthio, (C$_1$-C$_4$)alkoxy(C$_1$-C$_4$) alkoxy(C$_1$-C$_4$)alkyl, aminocarbonylamino-(C$_1$-C$_{12}$)alkyl, aminocarbonylamino(C$_1$-C$_{12}$)alkoxy, aminocarbonylamino (C$_1$-C$_{12}$)alkylthio, (C$_1$-C$_6$)-alkanoylamino(C$_1$-C$_6$)alkyl, (C$_1$-C$_6$)alkanoylamino(C$_1$-C$_6$)alkoxy, (C$_1$-C$_6$)alkanoyl-amino(C$_1$-C$_6$)alkylthio, (C$_3$-C$_4$)cycloalkanecarbonylamino (C$_1$-C$_6$)alkyl, (C$_3$-C$_4$)cycloalkane-carbonyl-amino(C$_1$-C$_6$) alkoxy, (C$_3$-C$_4$)cycloalkanecarbonylamino(C$_1$-C$_6$)alkylthio, aminosulfonylamino(C$_1$-C$_{12}$)alkyl, aminosulfonylamino (C$_1$-C$_{12}$)alkoxy, aminosulfonyl-amino(C$_1$-C$_2$)alkylthio, C$_1$-C$_6$)alkanesulfonylamino(C$_1$-C$_6$)alkyl, (C$_1$-C$_6$)alkanesulfonyl-amino(C$_1$-C$_6$)alkoxy, (C$_1$-C$_6$)alkanesulfonylamino (C$_1$-C$_6$)alkylthio, formylamino(C$_1$-C$_6$)alkyl, formylamino (C$_1$-C$_6$)alkoxy, formylamino(C$_1$-C$_6$)alkylthio, (C$_1$-C$_6$) alkoxy-carbonylamino(C$_1$-C$_6$)alkyl, (C$_1$-C$_6$) alkoxycarbonyl-amino(C$_1$-C$_6$)alkoxy, (C$_1$-C$_6$)-alkoxycarbonyl-amino(C$_1$-C$_6$)alkylthio, (C$_1$-C$_6$) alkylaminocarbonylamino(C$_1$-C$_6$)alkyl, di(C$_1$-C$_6$) alkylaminocarbonyl-amino(C$_1$-C$_6$)alkyl, (C$_1$-C$_6$) alkylaminocarbonylamino(C$_1$-C$_6$)alkoxy, di(C$_1$-C$_6$) alkylaminocarbonylamino(C$_1$-C$_6$)alkoxy, (C$_1$-C$_6$) alkylamino-carbonylamino(C$_1$-C$_6$)alkylthio, di(C$_1$-C$_6$) alkylaminocarbonylamino(C$_1$-C$_6$)alkylthio, aminocarbonyl (C$_1$-C$_6$)alkyl, aminocarbonyl(C$_1$-C$_6$)alkoxy, aminocarbonyl (C$_1$-C$_6$)alkylthio, (C$_1$-C$_6$)alkylaminocarbonyl(C$_1$-C$_6$)alkyl, (C$_1$-C$_6$)alkylaminocarbonyl-(C$_1$-C$_6$)alkoxy, (C$_1$-C$_6$)alkylaminocarbonyl-(C$_1$-C$_6$)alkylthio, aminocarboxy(C$_1$-C$_6$) alkyl, aminocarboxy(C$_1$-C$_6$)alkoxy, aminocarboxy(C$_1$-C$_6$) alkylthio, (C$_1$-C$_6$)alkylamino-carboxy(C$_1$-C$_6$)alkyl, (C$_1$-C$_6$) alkylaminocarboxy(C$_1$-C$_6$)alkoxy, (C$_1$-C$_6$)

alkylaminocarboxy($C_1$-$C_6$)alkylthio, ($C_1$-$C_{12}$) alkoxycarbonylamino, ($C_1$-$C_{12}$)alkylaminocarbonylamino or ($C_1$-$C_{12}$)alkanoylamino represented by $R^2$ is substituted by at least one of:

a) 1 to 6 halogen atoms; or b) one substituent selected from the group consisting of cyano, hydroxyl, ($C_1$-$C_3$)alkoxy, ($C_3$-$C_6$)cycloalkyl, ($C_3$-$C_6$)cycloalkoxy, halo($C_1$-$C_3$)alkoxy, halo($C_3$-$C_6$)cycloalkyl and halo($C_3$-$C_6$)cycloalkoxy; and wherein the thio-moiety of said unsubstituted or substituted ($C_1$-$C_{12}$)alkylthio, ($C_1$-$C_6$)alkoxy($C_1$-$C_6$)alkylthio, ($C_1$-$C_6$)alkylthio($C_1$-$C_6$)alkylthio, aminocarbonylamino($C_1$-$C_{12}$)alkylthio, ($C_1$-$C_6$)alkanoylamino($C_1$-$C_6$)alkylthio($C_3$-$C_4$)cycloalkanecarbonyl-amino($C_1$-$C_6$)alkylthio, aminosulfonylamino($C_1$-$C_{12}$)alkylthio, ($C_1$-$C_6$)alkane-sulfonylamino ($C_1$-$C_6$)alkylthio, formylamino($C_1$-$C_6$)alkylthio, ($C_1$-$C_6$) alkoxycarbonyl-amino($C_1$-$C_6$)alkylthio, ($C_1$-$C_6$) alkylaminocarbonylamino($C_1$-$C_6$)alkylthio, di($C_1$-$C_6$) alkylaminocarbonylamino($C_1$-$C_6$)alkylthio, aminocarbonyl ($C_1$-$C_6$)alkylthio, ($C_1$-$C_6$)alkylaminocarbonyl-($C_1$-$C_6$) alkylthio, aminocarboxy($C_1$-$C_6$)alkylthio, or ($C_1$-$C_6$) alkylaminocarboxy($C_1$-$C_6$)alkylthio is optionally replaced by —S(O)— or —S(O)$_2$—; and wherein the carbonyl moiety of said unsubstituted or substituted aminocarbonylamino($C_1$-$C_{12}$)alkyl, aminocarbonylamino($C_1$-$C_{12}$)alkoxy, aminocarbonylamino($C_1$-$C_{12}$)alkylthio, ($C_1$-$C_6$)-alkanoylamino($C_1$-$C_6$)alkyl, ($C_1$-$C_6$)alkanoylamino($C_1$-$C_6$)alkoxy, ($C_1$-$C_6$)alkanoylamino($C_1$-$C_6$) alkylthio, ($C_3$-$C_4$)cycloalkanecarbonyl-amino($C_1$-$C_6$)alkyl, ($C_3$-$C_4$)cycloalkanecarbonylamino($C_1$-$C_6$)alkoxy, ($C_3$-$C_4$) cycloalkane-carbonylamino($C_1$-$C_6$)alkylthio, formylamino ($C_1$-$C_6$)alkyl, formylamino($C_1$-$C_6$)alkoxy, formylamino($C_1$-$C_6$)alkylthio, ($C_1$-$C_6$)alkoxycarbonyl-amino(q, —$C_6$)alkyl, ($C_1$-$C_6$)alkoxycarbonyl-amino($C_1$-$C_6$)alkoxy, ($C_1$-$C_6$) alkoxycarbonyl-amino($C_1$-$C_6$)alkylthio, ($C_1$-$C_6$)alkylaminocarbonylamino($C_1$-$C_6$)alkyl, di($C_1$-$C_6$)alkylaminocarbonyl-amino($C_1$-$C_6$)alkyl, ($C_1$-$C_6$)alkylaminocarbonylamino ($C_1$-$C_6$)alkoxy, di($C_1$-$C_6$)alkylaminocarbonylamino($C_1$-$C_6$) alkoxy, ($C_1$-$C_6$)alkylaminocarbonyl-amino($C_1$-$C_6$)alkylthio, di($C_1$-$C_6$)alkylaminocarbonylamino($C_1$-$C_6$)alkylthio, aminocarbonyl($C_1$-$C_6$)alkyl, aminocarbonyl($C_1$-$C_6$)alkoxy, aminocarbonyl($C_1$-$C_6$)alkylthio, ($C_1$-$C_6$)alkylaminocarbonyl ($C_1$-$C_6$)alkyl, ($C_1$-$C_6$)alkylaminocarbonyl-($C_1$-$C_6$)alkoxy, ($C_1$-$C_6$)alkylaminocarbonyl-($C_1$-$C_6$)alkylthio, aminocarboxy($C_1$-$C_6$)alkyl, aminocarboxy($C_1$-$C_6$)alkoxy, aminocarboxy($C_1$-$C_6$)alkylthio, ($C_1$-$C_6$)alkylamino-carboxy($C_1$-$C_6$) alkyl, ($C_1$-$C_6$)alkylaminocarboxy($C_1$-$C_6$)alkoxy, ($C_1$-$C_6$) alkylaminocarboxy($C_1$-$C_6$)alkylthio, ($C_1$-$C_{12}$) alkoxycarbonylamino, ($C_1$-$C_{12}$)alkylaminocarbonylamino or ($C_1$-$C_{12}$)alkanoylamino is optionally replaced by a thiocarbonyl moiety.

$R^3$ is:

a) —H, halogen, ($C_1$-$C_6$)alkyl, ($C_1$-$C_6$)alkoxy, hydroxyl, hydroxy($C_1$-$C_6$)alkyl, hydroxy($C_1$-$C_6$)alkoxy, ($C_1$-$C_6$)alkanoylamino, ($C_1$-$C_6$)-alkoxycarbonylamino, ($C_1$-$C_6$)alkylamino-carbonylamino, di($C_1$-$C_6$)alkylaminocarbonylamino, ($C_1$-$C_6$)alkanesulfonylamino, ($C_1$-$C_6$) alkylaminosulfonylamino, or di($C_1$-$C_6$)alkylaminosulfonylamino; or b) phenylamino or heteroarylamino in which each phenylamino or heteroarylamino group is optionally substituted with 1 to 5 groups independently selected from the group consisting of fluorine, chlorine, bromine, iodine, cyano, nitro, amino, hydroxy, carboxy, ($C_1$-$C_6$)alkyl, ($C_3$-$C_6$)cycloalkyl, ($C_4$-$C_7$)cycloalkylalkyl, ($C_2$-$C_6$)alkenyl, ($C_3$-$C_6$)-cycloalkyl ($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy($C_1$-$C_6$)alkylthio, ($C_3$-$C_6$)cycloalkylthio, ($C_4$-$C_7$)cycloalkylalkylthio, halo($C_1$-$C_6$)alkylthio, halo($C_3$-$C_6$)cycloalkylthio, halo ($C_4$-$C_7$)cycloalkylalkylthio, ($C_1$-$C_6$)alkanesulfinyl, ($C_3$-$C_6$) cycloalkanesulfinyl, ($C_4$-$C_7$)cycloalkylalkanesulfinyl, halo ($C_1$-$C_6$)alkane-sulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkylalkanesulfonyl, halo($C_1$-$C_6$)alkanesulfonyl, halo($C_3$-$C_6$)cycloalkane-sulfonyl, halo($C_4$-$C_7$)cyclo-alkylalkanesulfonyl, ($C_1$-$C_6$)alkylamino, di($C_1$-$C_6$)alkylamino, ($C_1$-$C_6$)alkoxy($C_1$-$C_6$) alkoxy, halo($C_1$-$C_6$)alkoxy($C_1$-$C_6$)alkoxy, ($C_1$-$C_6$) alkoxycarbonyl, amino-carbonyl, ($C_1$-$C_6$) alkylaminocarbonyl, and di($C_1$-$C_6$)alkylaminocarbonyl, cyano($C_1$-$C_6$)alkyl, hydroxy($C_1$-$C_6$)alkyl, carboxy($C_1$-$C_6$) alkyl, ($C_1$-$C_6$)alkoxy($C_1$-$C_6$)alkyl, ($C_3$-$C_8$)cycloalkoxy($C_1$-$C_6$)alkyl, ($C_4$-$C_8$)cycloalkylalkoxy($C_1$-$C_6$)alkyl, halo($C_1$-$C_6$)alkoxy($C_1$-$C_6$)alkyl, halo($C_3$-$C_6$)cycloalkoxy($C_1$-$C_6$) alkyl, halo($C_4$-$C_8$)-cycloalkylalkoxy($C_1$-$C_6$)alkyl, ($C_1$-$C_8$) alkylthio($C_1$-$C_6$)alkyl, ($C_3$-$C_8$)cycloalkylthio($C_1$-$C_6$)alkyl, ($C_4$-$C_8$)cycloalkylalkylthio-($C_1$-$C_6$)alkyl, halo($C_1$-$C_8$)alkylthio($C_1$-$C_6$)alkyl, halo($C_3$-$C_8$)cycloalkylthio($C_1$-$C_6$)alkyl, halo($C_4$-$C_8$)-cycloalkylalkylthio($C_1$-$C_6$)alkyl, ($C_1$-$C_8$)alkanesulfinyl($C_1$-$C_6$)alkyl, ($C_3$-$C_8$)-cycloalkanesulfinyl($C_1$-$C_6$)alkyl, ($C_4$-$C_8$)cycloalkyl-alkanesulfinyl($C_1$-$C_6$)alkyl, halo($C_1$-$C_6$)alkanesulfinyl($C_1$-$C_6$)alkyl, halo($C_3$-$C_8$)cycloalkanesulfinyl($C_1$-$C_6$)alkyl, halo($C_4$-$C_8$)cycloalkylalkanesulfinyl($C_1$-$C_6$)alkyl, ($C_1$-$C_8$)alkane-sulfonyl($C_1$-$C_6$)alkyl, ($C_3$-$C_8$)cycloalkanesulfonyl($C_1$-$C_6$)alkyl, ($C_4$-$C_8$) cycloalkylalkanesulfonyl($C_1$-$C_6$)alkyl, halo($C_1$-$C_8$)alkanesulfonyl($C_1$-$C_6$)alkyl, halo($C_3$-$C_8$)cycloalkanesulfonyl($C_1$-$C_6$)alkyl, halo($C_4$-$C_8$)cycloalkylalkane-sulfonyl($C_1$-$C_6$) alkyl, ($C_1$-$C_8$)alkylamino($C_1$-$C_6$)alkyl, di($C_1$-$C_8$)alkylamino ($C_1$-$C_6$)alkyl, ($C_1$-$C_8$)alkoxycarbonyl($C_1$-$C_6$)alkyl, ($C_1$-$C_8$) acyloxy($C_1$-$C_6$)alkyl, aminocarbonyl($C_1$-$C_6$)alkyl, ($C_1$-$C_8$) alkylamino-carbonyl($C_1$-$C_6$)alkyl, di($C_1$-$C_8$) alkylaminocarbonyl($C_1$-$C_6$)alkyl($C_1$-$C_8$)acylamino($C_1$-$C_6$) alkyl, ($C_1$-$C_8$)alkoxycarbonylamino, ($C_1$-$C_8$) alkoxycarbonylamino($C_1$-$C_6$)alkyl, aminocarboxy($C_1$-$C_6$) alkyl, ($C_1$-$C_8$)alkylamino-carboxy($C_1$-$C_6$)alkyl, and di($C_1$-$C_8$)alkylaminocarboxy($C_1$-$C_6$)alkyl;

provided that:

1) when $R^3$ is hydroxyl, halogen or optionally substituted phenylamino or heteroarylamino, then $R^2$ is not a substituted or unsubstituted ($C_1$-$C_{12}$)alkoxy, ($C_1$-$C_6$)alkoxy($C_1$-$C_6$) alkoxy, ($C_1$-$C_6$)alkylthio($C_1$-$C_6$)alkoxy, aminocarbonylamino($C_1$-$C_{12}$)alkyl, aminocarbonyl-amino($C_1$-$C_{12}$)alkoxy, ($C_1$-$C_6$)alkanoyl-amino($C_1$-$C_6$)alkoxy, ($C_3$-$C_4$)cycloalkanecarbonylamino-($C_1$-$C_6$)alkoxy, aminosulfonylamino($C_1$-$C_{12}$)alkoxy, ($C_1$-$C_6$)alkane-sulfonylamino($C_1$-$C_6$)alkoxy, formylamino($C_1$-$C_6$)alkoxy, ($C_1$-$C_6$)alkoxycarbonyl-amino ($C_1$-$C_6$)alkoxy, ($C_1$-$C_6$)alkylamino-carbonylamino($C_1$-$C_6$) alkoxy, di($C_1$-$C_6$)alkylaminocarbonylamino($C_1$-$C_6$)alkoxy, aminocarbonyl($C_1$-$C_6$)alkoxy, ($C_1$-$C_6$)alkylaminocarbonyl-($C_1$-$C_6$)alkoxy, aminocarboxy($C_1$-$C_6$)alkoxy, ($C_1$-$C_6$)alkylaminocarboxy($C_1$-$C_6$)alkoxy, ($C_1$-$C_{12}$)alkoxycarbonylamino, ($C_1$-$C_{12}$)alkylaminocarbonylamino, or ($C_1$-$C_{12}$) alkanoylamino;

2) when $R^3$ is hydroxyl, halogen, or optionally substituted phenylamino or heteroarylamino, then $R^2$ is not a unsubstituted or substituted ($C_1$-$C_{12}$)alkylthio, ($C_1$-$C_6$)alkoxy($C_1$-$C_6$) alkylthio, ($C_1$-$C_6$)alkylthio($C_1$-$C_6$)alkylthio, aminocarbonylamino($C_1$-$C_{12}$)alkylthio, ($C_1$-$C_6$)alkanoylamino($C_1$-$C_6$) alkylthio, ($C_3$-$C_4$)cycloalkanecarbonylamino($C_1$-$C_6$) alkylthio, aminosulfonylamino($C_1$-$C_{12}$)alkylthio, ($C_1$-$C_6$) alkanesulfonylamino($C_1$-$C_6$)alkylthio, formylamino($C_1$-$C_6$)

alkylthio, (C₁-C₆)alkoxycarbonyl-amino(C₁-C₆)alkylthio, (C₁-C₆)alkylaminocarbonylamino(C₁-C₆)alkylthio, di(C₁-C₆)alkylaminocarbonylamino(C₁-C₆)alkylthio, aminocarbonyl(C₁-C₆)alkylthio, (C₁-C₆)alkylaminocarbonyl-(C₁-C₆)alkylthio, aminocarboxy(C₁-C₆)alkylthio or (C₁-C₆)alkylaminocarboxy(C₁-C₆)alkylthio, wherein the thiomoiety is replaced by —S(O)— or —S(O)₂—; and 3) when $R^3$ is hydroxyl, halogen, or optionally substituted phenylamino or heteroarylamino, then $R^2$ is not a unsubstituted or substituted aminocarbonylamino(C₁-C₁₂)alkoxy, aminocarbonylamino(C₁-C₁₂)alkylthio, (C₁-C₆)alkanoylamino(C₁-C₆)alkoxy, (C₁-C₆)alkanoylamino(C₁-C₆)alkylthio, (C₃-C₄)cycloalkanecarbonylamino(C₁-C₆)alkoxy, (C₃-C₄)cycloalkane-carbonylamino(C₁-C₆)alkylthio, formylamino(C₁-C₆)alkoxy, formylamino(C₁-C₆)alkylthio, (C₁-C₆)alkoxycarbonyl-amino(C₁-C₆)alkoxy, (C₁-C₆)alkoxycarbonyl-amino(C₁-C₆)alkylthio, (C₁-C₆)alkylaminocarbonylamino(C₁-C₆)alkoxy, di(C₁-C₆)alkylamino-carbonylamino(C₁-C₆)alkoxy, (C₁-C₆)alkylaminocarbonylamino(C₁-C₆)alkylthio, di(C₁-C₆)alkylaminocarbonylamino(C₁-C₆)alkylthio, aminocarbonyl(C₁-C₆)alkoxy, aminocarbonyl(C₁-C₆)alkylthio, (C₁-C₆)alkylaminocarbonyl-(C₁-C₆)alkoxy, (C₁-C₆)alkylaminocarbonyl-(C₁-C₆)alkylthio, aminocarboxy(C₁-C₆)alkoxy, aminocarboxy(C₁-C₆)alkylthio, (C₁-C₆)alkylamino-carboxy(C₁-C₆)alkoxy, (C₁-C₆)alkylaminocarboxy(C₁-C₆)alkylthio, (C₁-C₂)alkoxycarbonylamino, (C₁-C₁₂)alkylaminocarbonylamino, or (C₁-C₁₂)alkanoylamino, wherein the carbonyl moiety is replaced by a thiocarbonyl moiety.

A is a saturated or unsaturated 4-, 5-, 6-, or 7-membered ring which is optionally bridged by $(CH_2)_m$ via bonds to two members of said ring, wherein said ring is composed of carbon atoms, and 0-2 hetero atoms selected from 0, 1, or 2 nitrogen atoms, 0 or 1 oxygen atoms, and 0 or 1 sulfur atoms, said ring being optionally substituted with up to four moieties independently selected from the group consisting of halogen, (C₁-C₆)alkyl, halo(C₁-C₆)alkyl, and oxo.

m is 1 to 3.

Q and Y are attached to carbon or nitrogen atoms in ring A in a 1,2 or 1,3 or 1,4 relationship.

Q is:

Q1
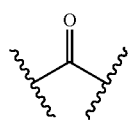

Q2
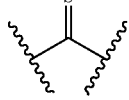

Q3
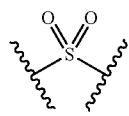

Q4
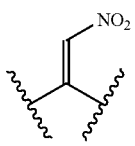

-continued

Q5
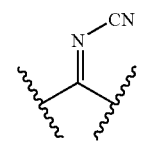

Q6
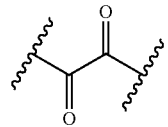

Q7
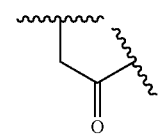

Q8
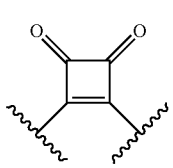

Q9
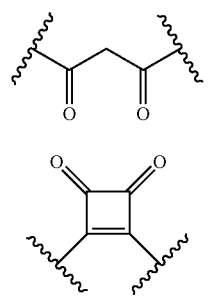

Q10
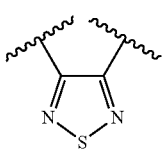

Q11
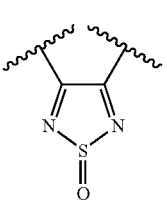

Q12
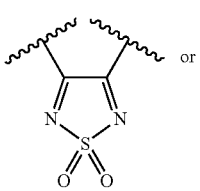

or

Q13
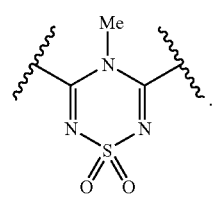

wherein A and N are attached to the truncated bonds $R^4$ is —H, (C₁-C₆)alkyl, halo(C₁-C₆)alkyl, (C₁-C₃)alkoxy(C₁-C₃)alkyl, or cyano(C₁-C₆)alkyl.

$R^5$ is:

a) —H;

b) $(C_1-C_{12})$alkyl, $(C_3-C_8)$cycloalkyl, $(C_3-C_8)$cycloalkyl$(C_1-C_3)$alkyl, $(C_2-C_{12})$alkenyl, $(C_3-C_8)$cycloalkyl$(C_1-C_3)$alkenyl, $(C_2-C_{12})$alkynyl, $(C_3-C_8)$cycloalkyl$(C_1-C_3)$alkynyl, $(C_4-C_{12})$bicycloalkyl$(C_1-C_3)$alkyl, $(C_8-C_{14})$tricycloalkyl$(C_1-C_3)$alkyl, $(C_1-C_6)$alkoxy$(C_1-C_6)$alkyl, $(C_3-C_8)$cycloalkoxy$(C_1-C_3)$alkyl, $(C_1-C_6)$alkylthio$(C_1-C_6)$alkyl, $(C_3-C_8)$cycloalkylthio$(C_1-C_3)$alkyl, saturated heterocyclyl, or saturated heterocyclyl$(C_1-C_3)$alkyl, each optionally substituted with 1 to 6 groups independently selected from the group consisting of halogen, cyano, hydroxyl, $(C_1-C_3)$alkyl, $(C_1-C_3)$alkoxy, $(C_3-C_6)$cycloalkyl, $(C_3-C_6)$cycloalkoxy, halo$(C_1-C_3)$alkyl, halo$(C_1-C_3)$alkoxy, halo$(C_3-C_6)$cycloalkyl, and halo$(C_3-C_6)$cycloalkoxy; wherein divalent sulfur atoms are optionally oxidized to sulfoxide or sulfone; or c) phenyl, naphthyl, heteroaryl, phenyl$(C_1-C_3)$alkyl, naphthyl$(C_1-C_3)$alkyl, or heteroaryl$(C_1-C_3)$alkyl, each optionally substituted with 1 to 3 groups independently selected from the group consisting of fluorine, chlorine, bromine, iodine, cyano, nitro, amino, hydroxy, carboxy, $(C_1-C_6)$alkyl, $(C_3-C_6)$cycloalkyl, $(C_4-C_7)$cycloalkylalkyl, $(C_2-C_6)$alkynyl, $(C_3-C_6)$cycloalkyl-$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylthio, $(C_4-C_7)$cycloalkylalkylthio, halo$(C_1-C_6)$alkylthio, halo$(C_3-C_6)$cycloalkylthio, halo$(C_4-C_7)$cycloalkylalkylthio, $(C_1-C_6)$-alkanesulfinyl, $(C_3-C_6)$cycloalkanesulfinyl, $(C_4-C_7)$cycloalkylalkanesulfinyl, halo$(C_1-C_6)$-alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$-cycloalkylalkanesulfonyl, $(C_1-C_6)$alkylamino, di$(C_1-C_6)$alkylamino, $(C_1-C_6)$-alkoxy$(C_1-C_6)$alkoxy, halo$(C_1-C_6)$alkoxy$(C_1-C_6)$alkoxy, $(C_1-C_6)$alkoxycarbonyl, aminocarbonyl, $(C_1-C_6)$alkylaminocarbonyl, di$(C_1-C_6)$alkylaminocarbonyl, cyano$(C_1-C_6)$alkyl, hydroxy$(C_1-C_6)$alkyl, carboxy$(C_1-C_6)$alkyl, $(C_1-C_6)$alkoxy$(C_1-C_6)$alkyl, $(C_3-C_8)$cycloalkoxy$(C_1-C_6)$alkyl, $(C_4-C_8)$cycloalkylalkoxy$(C_1-C_6)$alkyl, halo$(C_1-C_6)$alkoxy$(C_1-C_6)$alkyl, halo$(C_3-C_6)$cycloalkoxy$(C_1-C_6)$alkyl, halo$(C_4-C_8)$-cycloalkylalkoxy$(C_1-C_6)$alkyl, $(C_1-C_8)$alkylthio$(C_1-C_6)$alkyl, $(C_3-C_8)$cycloalkylthio$(C_1-C_6)$alkyl, $(C_4-C_8)$cycloalkylalkylthio$(C_1-C_6)$alkyl, halo$(C_1-C_8)$alkylthio$(C_1-C_6)$alkyl, halo$(C_3-C_8)$cycloalkylthio$(C_1-C_6)$alkyl, halo$(C_4-C_8)$-cycloalkylalkylthio$(C_1-C_6)$alkyl, $(C_1-C_8)$alkanesulfinyl$(C_1-C_6)$alkyl, $(C_3-C_8)$cycloalkanesulfinyl$(C_1-C_6)$alkyl, $(C_4-C_8)$cycloalkyl-alkanesulfinyl$(C_1-C_6)$alkyl, halo$(C_1-C_8)$alkanesulfinyl$(C_1-C_6)$alkyl, halo$(C_3-C_8)$cycloalkanesulfinyl$(C_1-C_6)$alkyl, halo$(C_4-C_8)$cycloalkylalkane-sulfinyl$(C_1-C_6)$alkyl, $(C_1-C_6)$alkane-sulfonyl$(C_1-C_6)$alkyl, $(C_3-C_8)$cycloalkanesulfonyl$(C_1-C_6)$alkyl, $(C_4-C_8)$cycloalkylalkanesulfonyl$(C_1-C_6)$alkyl, halo$(C_1-C_8)$alkanesulfonyl$(C_1-C_6)$alkyl, halo$(C_3-C_8)$cycloalkanesulfonyl$(C_1-C_6)$alkyl, halo$(C_4-C_8)$cycloalkylalkane-sulfonyl$(C_1-C_6)$alkyl, $(C_1-C_8)$alkylamino$(C_1-C_6)$alkyl, di$(C_1-C_8)$-alkylamino$(C_1-C_6)$alkyl, $(C_1-C_8)$alkoxycarbonyl$(C_1-C_6)$alkyl, $(C_1-C_8)$acyloxy$(C_1-C_6)$alkyl, aminocarbonyl$(C_1-C_6)$alkyl, $(C_1-C_8)$alkylamino-carbonyl$(C_1-C_6)$alkyl, di$(C_1-C_8)$alkylaminocarbonyl$(C_1-C_6)$alkyl$(C_1-C_8)$acylamino$(C_1-C_6)$alkyl, $(C_1-C_8)$alkoxy-carbonylamino, $(C_1-C_8)$alkoxycarbonylamino$(C_1-C_6)$alkyl, aminoxy$(C_1-C_8)$alkyl, $(C_1-C_8)$alkylamino-carboxy$(C_1-C_6)$alkyl, di$(C_1-C_8)$alkylaminocarboxy$(C_1-C_6)$alkyl, phenyl, napthyl, heteroaryl, bicyclic heteroaryl, phenoxy, naphthyloxy, heteroaryloxy, bicyclic heteroaryloxy, phenylthio, naphthylthio, heteroarylthio, bicyclic heteroarylthio, phenylsulfinyl, naphthylsulfinyl, heteroarylsulfinyl, bicyclic heteroarylsulfinyl, phenylsulfonyl, naphthylsulfonyl, heteroarylsulfonyl, bicyclic heteroarylsulfonyl, phenyl$(C_1-C_3)$alkyl, napthyl$(C_1-C_3)$alkyl, heteroaryl$(C_1-C_3)$alkyl, and bicyclic heteroaryl$(C_1-C_3)$alkyl, wherein the aromatic and heteroaromatic groups are optionally substituted with 1 to 3 groups independently selected from fluorine, chlorine, cyano, $(C_1-C_3)$alkyl, halo$(C_1-C_3)$alkyl, $(C_1-C_3)$alkoxy, halo$(C_1-C_3)$-alkoxy, $(C_1-C_3)$alkanesulfonyl, and $(C_1-C_3)$alkoxycarbonyl.

$R^9$ is:

a) —H, $(C_1-C_{12})$alkyl, $(C_4-C_{12})$cycloalkylalkyl, halo$(C_1-C_{12})$alkyl, halo$(C_4-C_{12})$cycloalkylalkyl, $(C_2-C_{12})$alkenyl, $(C_5-C_{12})$cycloalkylalkenyl, halo$(C_2-C_{12})$alkenyl, halo$(C_5-C_{12})$cycloalkylalkenyl, $(C_2-C_{12})$alkynyl, $(C_5-C_{12})$cycloalkylalkynyl, halo$(C_2-C_{12})$alkynyl, halo$(C_5-C_{12})$cycloalkylalkynyl, $(C_1-C_6)$alkoxy$(C_1-C_6)$alkyl, halo$(C_1-C_6)$alkoxy$(C_1-C_6)$alkyl, $(C_1-C_6)$alkylthio$(C_1-C_6)$alkyl, halo$(C_1-C_6)$alkylthio$(C_1-C_6)$alkyl, $(C_1-C_6)$alkanesulfinyl$(C_1-C_6)$alkyl, halo$(C_1-C_6)$alkane-sulfinyl$(C_1-C_6)$alkyl, $(C_1-C_6)$alkanesulfonyl$(C_1-C_6)$alkyl, halo$(C_1-C_6)$alkanesulfonyl$(C_1-C_6)$alkyl, aminocarbonyl$(C_1-C_6)$alkyl, $(C_1-C_6)$alkylaminocarbonyl$(C_1-C_6)$alkyl, di$(C_1-C_6)$alkylamino-carbonyl$(C_1-C_6)$alkyl, cyano$(C_1-C_6)$alkyl, carboxy$(C_1-C_6)$alkyl, $(C_1-C_6)$alkoxycarbonyl$(C_1-C_6)$alkyl, saturated heterocyclyl, or saturated heterocyclyl$(C_1-C_6)$alkyl; or b) phenyl, naphthyl, heteroaryl, phenyl$(C_1-C_3)$alkyl, naphthyl$(C_1-C_3)$alkyl, or heteroaryl$(C_1-C_3)$alkyl, each optionally substituted by 1 to 3 groups independently selected from the groups consisting of:

1) fluorine, chlorine, bromine, iodine, cyano, nitro, amino, hydroxy, carboxy, $(C_1-C_6)$alkyl, $(C_3-C_6)$cycloalkyl, $(C_4-C_7)$cycloalkylalkyl, $(C_2-C_6)$alkynyl, $(C_3-C_6)$cycloalkyl-$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylthio, $(C_4-C_7)$cycloalkylalkylthio, halo$(C_1-C_6)$alkylthio, halo$(C_3-C_6)$cycloalkylthio, halo$(C_4-C_7)$cycloalkylalkylthio, $(C_1-C_6)$alkanesulfinyl, $(C_3-C_6)$cycloalkanesulfinyl, $(C_4-C_7)$-cycloalkylalkanesulfinyl, halo$(C_1-C_6)$alkanesulfinyl, halo$(C_3-C_6)$cycloalkane-sulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkane-sulfonyl, halo$(C_4-C_7)$-cycloalkylalkanesulfonyl, $(C_1-C_6)$alkylamino, di$(C_1-C_6)$alkylamino, $(C_1-C_6)$alkoxy-$(C_1-C_6)$alkoxy, halo$(C_1-C_6)$alkoxy$(C_1-C_6)$alkoxy, $(C_1-C_6)$alkoxycarbonyl, aminocarbonyl, $(C_1-C_6)$alkylaminocarbonyl and di$(C_1-C_6)$alkylaminocarbonyl, cyano$(C_1-C_6)$alkyl, hydroxy$(C_1-C_6)$alkyl, carboxy$(C_1-C_6)$alkyl, $(C_1-C_6)$alkoxy$(C_1-C_6)$alkyl, $(C_3-C_8)$cycloalkoxy$(C_1-C_6)$alkyl, $(C_4-C_8)$cycloalkylalkoxy$(C_1-C_6)$alkyl, halo$(C_1-C_6)$alkoxy$(C_1-C_6)$alkyl, halo$(C_3-C_6)$cycloalkoxy$(C_1-C_6)$alkyl, halo$(C_4-C_8)$-cycloalkylalkoxy$(C_1-C_6)$alkyl, $(C_1-C_8)$alkylthio$(C_1-C_6)$alkyl, $(C_3-C_8)$cycloalkylthio$(C_1-C_6)$alkyl, $(C_4-C_8)$cycloalkylalkylthio-$(C_1-C_6)$alkyl, halo$(C_1-C_8)$alkylthio$(C_1-C_6)$alkyl, halo$(C_3-C_8)$cycloalkylthio$(C_1-C_6)$alkyl; halo$(C_4-C_8)$-cycloalkylalkylthio$(C_1-C_6)$alkyl, $(C_1-C_8)$alkanesulfinyl$(C_1-C_6)$alkyl, $(C_3-C_8)$-cycloalkanesulfinyl$(C_1-C_6)$alkyl, $(C_4-C_8)$cycloalkyl-alkanesulfinyl$(C_1-C_6)$alkyl, halo$(C_1-C_8)$alkanesulfinyl$(C_1-C_6)$alkyl, halo$(C_3-C_8)$cycloalkanesulfinyl$(C_1-C_6)$alkyl, halo$(C_4-C_8)$cycloalkylalkanesulfinyl$(C_1-C_6)$alkyl, $(C_1-C_8)$alkane-sulfonyl$(C_1-C_6)$alkyl, $(C_3-C_8)$cycloalkanesulfonyl$(C_1-C_6)$alkyl, $(C_4-C_8)$ cycloalkylalkanesulfonyl($C_1$-$C_6$)alkyl, halo($C_1$-$C_8$)alkanesulfonyl($C_1$-$C_6$)alkyl, halo($C_3$-$C_8$)cycloalkanesulfonyl($C_1$-$C_6$)alkyl, halo($C_4$-$C_8$)cycloalkylalkane-sulfonyl($C_1$-$C_6$) alkyl, ($C_1$-$C_8$)alkylamino($C_1$-$C_6$)alkyl, di($C_1$-$C_8$)alkylamino ($C_1$-$C_6$)alkyl, ($C_1$-$C_8$)alkoxycarbonyl($C_1$-$C_6$)alkyl, ($C_1$-$C_8$) acyloxy($C_1$-$C_6$)alkyl, aminocarbonyl($C_1$-$C_6$)alkyl, ($C_3$-$C_8$) alkylamino-carbonyl($C_1$-$C_6$)alkyl, di($C_1$-$C_8$)alkylaminocarbonyl($C_1$-$C_6$)alkyl($C_1$-$C_8$)acylamino($C_1$-$C_6$) alkyl, ($C_1$-$C_8$)alkoxy-carbonylamino, ($C_1$-$C_8$) alkoxycarbonylamino($C_1$-$C_6$)alkyl, aminocarboxy($C_1$-$C_6$) alkyl, ($C_1$-$C_8$)alkylamino-carboxy($C_1$-$C_6$)alkyl and di($C_1$-$C_8$)alkylaminocarboxy($C_1$-$C_6$)alkyl; and 2) phenyl, napthyl, heteroaryl, bicyclic heteroaryl, phenoxy, naphthyloxy, heteroaryloxy, bicyclic heteroaryloxy, phenylthio, naphthylthio, heteroarylthio, bicyclic heteroarylthio, phenylsulfinyl, naphthylsulfinyl, heteroarylsulfinyl, bicyclic heteroarylsulfinyl, phenylsulfonyl, naphthylsulfonyl, heteroarylsulfonyl, bicyclic heteroarylsulfonyl, phenyl ($C_1$-$C_3$)alkyl, napthyl($C_1$-$C_3$)alkyl, heteroaryl($C_1$-$C_3$)alkyl, and bicyclic heteroaryl($C_1$-$C_3$)alkyl, each optionally substituted with 1 to 3 groups independently selected from fluorine, chlorine, cyano, ($C_1$-$C_3$)alkyl, halo($C_1$-$C_3$)alkyl, ($C_1$-$C_3$) alkoxy, halo($C_1$-$C_3$)alkoxy, ($C_1$-$C_3$)alkanesulfonyl, and ($C_1$-$C_3$)-alkoxycarbonyl.

In one embodiment the present invention is directed to a pharmaceutical composition comprising a therapeutically effective amount of a compound described herein or an enantiomer, diastereomer, or salt thereof and a pharmaceutically acceptable carrier or excipient.

In one embodiment the present invention is directed to a method for treating or ameliorating an aspartic protease mediated disorder in a subject in need thereof comprising administering to said subject a therapeutically effective amount of a compound described herein or an enantiomer, diastereomer, or salt thereof.

In another embodiment the present invention is a method for treating or ameliorating a renin mediated disorder in a subject in need thereof comprising administering to said subject a therapeutically effective amount of a compound described herein or enantiomer, diastereomer, or salt thereof.

DETAILED DESCRIPTION OF THE INVENTION

A description of preferred embodiments of the invention follows.

The invention provides compounds of Formula I

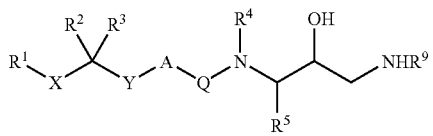

I wherein $R^1$ is a) ($C_1$-$C_{12}$)alkyl, ($C_3$-$C_7$)cycloalkyl, ($C_4$-$C_{12}$)cycloalkylalkyl, halo($C_1$-$C_{12}$)alkyl, halo($C_3$-$C_7$)-cycloalkyl, halo($C_4$-$C_{12}$)cycloalkylalkyl, saturated heterocyclyl optionally substituted with 1 to 5 groups independently selected from: halogen, ($C_1$-$C_6$)alkyl, halo($C_1$-$C_6$)alkyl, and oxo; or b) phenyl, napthyl, heteroaryl, or bicyclic heteroaryl each optionally substituted with 1 to 5 groups independently selected from:

1) fluorine, chlorine, bromine, iodine, cyano, nitro, amino, hydroxy, carboxy, ($C_1$-$C_8$)alkyl, ($C_3$-$C_8$)cycloalkyl, ($C_1$-$C_3$) alkyl($C_3$-$C_8$)cycloalkyl, di($C_1$-$C_3$)alkyl($C_3$-$C_8$)cycloalkyl, ($C_4$-$C_8$)cycloalkylalkyl, ($C_2$-$C_6$)alkenyl, ($C_5$-$C_8$)cycloalkenyl, ($C_5$-$C_8$)cyclo-alkylalkenyl, ($C_2$-$C_8$)alkynyl, ($C_3$-$C_8$)cycloalkyl($C_2$-$C_4$)alkynyl, halo($C_1$-$C_8$)alkyl, halo($C_3$-$C_6$)cycloalkyl, halo($C_4$-$C_8$)cycloalkylalkyl, ($C_1$-$C_3$)alkyl($C_4$-$C_8$) cycloalkylalkyl, di($C_1$-$C_3$)alkyl($C_4$-$C_8$)cycloalkylalkyl, halo ($C_2$-$C_8$)alkenyl, halo($C_5$-$C_8$)cycloalkenyl, halo($C_6$-$C_8$) cycloalkenylalkyl, halo($C_3$-$C_8$)alkynyl, halo($C_5$-$C_8$) cycloalkylalkynyl, ($C_1$-$C_8$)alkoxy, ($C_3$-$C_8$)cycloalkoxy, ($C_4$-$C_8$)cycloalkylalkoxy, ($C_1$-$C_3$)alkyl($C_3$-$C_8$)cycloalkoxy, ($C_1$-$C_3$)alkyl($C_4$-$C_8$)cycloalkylalkoxy, di($C_1$-$C_3$)alkyl($C_3$-$C_8$)-cycloalkoxy, di($C_1$-$C_3$)alkyl($C_4$-$C_8$)cycloalkylalkoxy, halo ($C_1$-$C_6$)alkoxy, halo($C_3$-$C_6$)Cycloalkoxy, halo($C_4$-$C_8$) cycloalkylalkoxy, ($C_1$-$C_8$)alkylthio, ($C_3$-$C_8$)cycloalkylthio, ($C_4$-$C_8$)cycloalkylalkylthio, ($C_1$-$C_3$)alkyl($C_3$-$C_8$)cycloalkylthio, ($C_1$-$C_3$)alkyl($C_4$-$C_8$)cycloalkylalkylthio, di($C_1$-$C_3$) alkyl($C_3$-$C_8$)-cycloalkylthio, di($C_1$-$C_3$)alkyl($C_4$-$C_8$)cycloalkylalkylthio, halo($C_1$-$C_8$)alkylthio, halo($C_3$-$C_8$)-cycloalkylthio, halo($C_4$-$C_8$)-cycloalkylalkylthio, ($C_1$-$C_8$) alkanesulfinyl, ($C_3$-$C_8$)-cycloalkane-sulfinyl, ($C_4$-$C_8$) cycloalkyl-alkanesulfinyl, ($C_1$-$C_3$)alkyl($C_3$-$C_8$)cycloalkanesulfinyl, ($C_1$-$C_3$)alkyl($C_4$-$C_8$)cycloalkyl-alkanesulfinyl, di($C_1$-$C_3$)alkyl($C_3$-$C_8$)cycloalkane-sulfinyl, di($C_1$-$C_3$)alkyl, ($C_4$-$C_8$)cycloalkyl-alkanesulfinyl, halo($C_1$-$C_8$)alkanesulfinyl, halo($C_3$-$C_8$)cycloalkanesulfinyl, halo($C_4$-$C_8$)cycloalkylalkanesulfinyl, ($C_1$-$C_8$)alkane-sulfonyl, ($C_3$-$C_8$)cycloalkanesulfonyl, ($C_4$-$C_8$) cycloalkylalkanesulfonyl, ($C_1$-$C_3$) alkyl($C_3$-$C_8$)cycloalkanesulfonyl, ($C_1$-$C_3$)alkyl($C_4$-$C_8$)-cycloalkyl-alkanesulfonyl, di($C_1$-$C_3$)alkyl($C_3$-$C_8$) cycloalkanesulfonyl, di($C_1$-$C_3$)alkyl($C_4$-$C_8$)-cycloalkylalkanesulfonyl, halo($C_1$-$C_8$)alkanesulfonyl, halo($C_3$-$C_8$) cycloalkanesulfonyl, halo($C_4$-$C_8$)cycloalkylalkane-sulfonyl, ($C_1$-$C_8$)alkylamino, di($C_1$-$C_8$)alkylamino, ($C_1$-$C_6$)alkoxy-($C_1$-$C_6$)-alkoxy, halo($C_1$-$C_6$)alkoxy($C_1$-$C_6$)alkoxy, ($C_1$-$C_8$) alkoxycarbonyl, aminocarbonyl, ($C_1$-$C_8$)alkyl-amino-carbonyl, di($C_1$-$C_8$)alkylaminocarbonyl, piperidino, pyrrolidino, cyano($C_1$-$C_6$)alkyl, hydroxy($C_1$-$C_6$)alkyl, carboxy($C_1$-$C_6$) alkyl, ($C_1$-$C_8$)alkoxy($C_1$-$C_6$)alkyl, ($C_3$-$C_8$)-cycloalkoxy($C_1$-$C_6$)alkyl, ($C_4$-$C_8$)cycloalkylalkoxy($C_1$-$C_6$)alkyl, halo($C_1$-$C_6$)alkoxy($C_1$-$C_6$)alkyl, halo($C_3$-$C_6$)cyclo-alkoxy($C_1$-$C_6$) alkyl, halo($C_4$-$C_8$)cycloalkylalkoxy($C_1$-$C_6$)alkyl, ($C_1$-$C_8$) alkylthio-($C_1$-$C_6$)alkyl, ($C_3$-$C_8$)cycloalkylthio($C_1$-$C_6$)alkyl, ($C_4$-$C_8$)cycloalkylalkylthio($C_1$-$C_6$)alkyl, halo($C_1$-$C_8$)alkylthio($C_1$-$C_6$)alkyl, halo($C_3$-$C_8$)cycloalkylthio($C_1$-$C_6$)alkyl, halo($C_4$-$C_8$)-cycloalkylalkylthio-($C_1$-$C_6$)alkyl, ($C_1$-$C_8$)alkanesulfinyl($C_1$-$C_6$)alkyl, ($C_3$-$C_8$)-cycloalkanesulfinyl($C_1$-$C_6$)alkyl, ($C_4$-$C_8$)cycloalkyl-alkanesulfinyl($C_1$-$C_6$)alkyl, halo($C_1$-$C_8$)alkanesulfinyl($C_1$-$C_6$)alkyl, halo($C_3$-$C_8$)cycloalkane-sulfinyl($C_1$-$C_6$)alkyl, halo($C_4$-$C_8$)cycloalkylalkane-sulfinyl($C_1$-$C_6$)alkyl, ($C_1$-$C_8$)alkane-sulfonyl($C_1$-$C_6$)alkyl, ($C_3$-$C_8$)cycloalkanesulfonyl($C_1$-$C_6$)alkyl, ($C_4$-$C_8$)cycloalkylalkane-sulfonyl($C_1$-$C_6$)alkyl, halo($C_1$-$C_8$)alkanesulfonyl ($C_1$-$C_6$)alkyl, halo($C_3$-$C_8$)cycloalkanesulfonyl($C_1$-$C_6$)alkyl, halo($C_4$-$C_8$)Cycloalkylalkane-sulfonyl($C_1$-$C_6$)alkyl, ($C_1$-$C_8$)alkylamino($C_1$-$C_6$)alkyl, di($C_1$-$C_8$)alkylamino-($C_1$-$C_6$) alkyl, ($C_1$-$C_8$)alkoxycarbonyl($C_1$-$C_6$)alkyl, ($C_1$-$C_8$)acyloxy ($C_1$-$C_6$)alkyl, aminocarbonyl-($C_1$-$C_6$)alkyl, ($C_1$-$C_8$) alkylamino-carbonyl($C_1$-$C_6$)alkyl, di($C_1$-$C_8$)alkylaminocarbonyl($C_1$-$C_6$)alkyl, ($C_1$-$C_8$)acylamino($C_1$-$C_6$)alkyl, piperidino($C_1$-$C_6$)alkyl, pyrrolidino($C_1$-$C_6$)alkyl, ($C_1$-$C_8$) alkoxy-carbonylamino, ($C_1$-$C_8$)alkoxycarbonylamino($C_1$-$C_6$)alkyl, aminocarboxy($C_1$-$C_6$)alkyl, ($C_1$-$C_8$)alkylaminocarboxy($C_1$-$C_6$)alkyl, and di($C_1$-$C_8$)alkylaminocarboxy($C_1$-$C_6$)alkyl; or 2) phenyl, napthyl, heteroaryl, bicyclic heteroaryl, phenoxy, naphthyloxy, heteroaryloxy, bicyclic heteroaryloxy, phenylthio, naphthylthio, heteroarylthio, bicyclic heteroarylthio, phenylsulfinyl, naphthylsulfinyl, heteroarylsulfinyl, bicyclic heteroarylsulfinyl, phenylsulfonyl, naphthylsulfonyl, heteroarylsulfonyl, bicyclic heteroarylsulfonyl, phenyl($C_1$-$C_3$)alkyl, naphthyl($C_1$-$C_3$)alkyl, heteroaryl($C_1$-$C_3$)alkyl, bicyclic heteroaryl($C_1$-$C_3$)alkyl, phenyl($C_1$-$C_3$)alkoxy, naphthyl($C_1$-$C_3$)alkoxy, heteroaryl($C_1$-$C_3$)alkoxy, or bicyclic heteroaryl($C_1$-$C_3$)alkoxy, each optionally substituted with 1 to 5 groups independently selected from: fluorine, chlorine, cyano, ($C_1$-$C_6$)alkyl, halo($C_1$-$C_6$)alkyl, ($C_1$-$C_6$)alkoxy, halo($C_1$-$C_6$)alkoxy, ($C_1$-$C_6$)alkanesulfonyl, ($C_1$-$C_6$)alkoxy-carbonyl, and aminocarbonyl;

X and Y is each independently $CH_2$ or a single bond;

$R^2$ is substituted or unsubstituted ($C_1$-$C_{12}$)alkyl, ($C_2$-$C_{12}$)alkenyl, ($C_2$-$C_{12}$)alkynyl, ($C_1$-$C_{12}$)alkoxy, ($C_2$-$C_{12}$)alkenyloxy, ($C_1$-$C_{12}$)alkylthio, ($C_1$-$C_6$)alkoxy($C_1$-$C_6$)alkyl, ($C_1$-$C_6$)alkylthio-($C_1$-$C_6$)alkyl, ($C_1$-$C_6$)alkoxy($C_1$-$C_6$)alkoxy, ($C_1$-$C_6$)alkoxy($C_1$-$C_6$)alkylthio, ($C_1$-$C_6$)alkylthio($C_1$-$C_6$)alkoxy, ($C_1$-$C_6$)alkylthio($C_1$-$C_6$)alkylthio, ($C_1$-$C_4$)alkoxy($C_1$-$C_4$)alkoxy($C_1$-$C_4$)alkyl, aminocarbonylamino($C_1$-$C_{12}$)alkyl, aminocarbonylamino($C_1$-$C_{12}$)alkoxy, aminocarbonyl-amino($C_1$-$C_{12}$)alkylthio, ($C_1$-$C_6$)-alkanoylamino($C_1$-$C_6$)alkyl, ($C_1$-$C_6$)alkanoylamino($C_1$-$C_6$)alkoxy, ($C_1$-$C_6$)alkanoylamino($C_1$-$C_6$)alkylthio, ($C_3$-$C_4$)cycloalkanecarbonylamino($C_1$-$C_6$)alkyl, ($C_3$-$C_4$)-cycloalkanecarbonylamino($C_1$-$C_6$)alkoxy, ($C_3$-$C_4$)cycloalkanecarbonyl-amino($C_1$-$C_6$)alkylthio, aminosulfonylamino($C_1$-$C_{12}$)alkyl, aminosulfonylamino($C_1$-$C_{12}$)alkoxy, aminosulfonylamino($C_1$-$C_{12}$)alkylthio, ($C_1$-$C_6$)alkanesulfonylamino($C_1$-$C_6$)alkyl, ($C_1$-$C_6$)alkane-sulfonylamino($C_1$-$C_6$)-alkoxy, ($C_1$-$C_6$)alkanesulfonylamino($C_1$-$C_6$)alkylthio, formylamino($C_1$-$C_6$)alkyl, formylamino($C_1$-$C_6$)alkoxy, formylamino($C_1$-$C_6$)alkylthio, ($C_1$-$C_6$)alkoxycarbonylamino($C_1$-$C_6$)alkyl, ($C_1$-$C_6$)alkoxycarbonyl-amino($C_1$-$C_6$)alkoxy, ($C_1$-$C_6$)alkoxycarbonyl-amino($C_1$-$C_6$)alkylthio, ($C_1$-$C_6$)alkylaminocarbonylamino($C_1$-$C_6$)alkyl, di($C_1$-$C_6$)arylaminocarbonyl-amino($C_1$-$C_6$)alkyl, ($C_1$-$C_6$)alkylaminocarbonylamino($C_1$-$C_6$)alkoxy, di($C_1$-$C_6$)alkylaminocarbonylamino($C_1$-$C_6$)alkoxy, ($C_1$-$C_6$)alkylaminocarbonylamino($C_1$-$C_6$)alkylthio, di($C_1$-$C_6$)alkylaminocarbonylamino($C_1$-$C_6$)-alkylthio, aminocarbonyl($C_1$-$C_6$)alkyl, aminocarbonyl($C_1$-$C_6$)alkoxy, aminocarbonyl($C_1$-$C_6$)-alkylthio, ($C_1$-$C_6$)alkylaminocarbonyl($C_1$-$C_6$)alkyl, ($C_1$-$C_6$)alkylaminocarbonyl-($C_1$-$C_6$)alkoxy, ($C_1$-$C_6$)alkylaminocarbonyl-($C_1$-$C_6$)alkylthio, aminocarboxy($C_1$-$C_6$)alkyl, aminocarboxy($C_1$-$C_6$)alkoxy, aminocarboxy($C_1$-$C_6$)alkylthio, ($C_1$-$C_6$)alkylamino-carboxy($C_1$-$C_6$)alkyl, ($C_1$-$C_6$)alkylaminocarboxy($C_1$-$C_6$)alkoxy, ($C_1$-$C_6$)alkylaminocarboxy($C_1$-$C_6$)alkylthio, ($C_1$-$C_{12}$)alkoxycarbonylamino, ($C_1$-$C_2$)alkylaminocarbonylamino, ($C_1$-$C_{12}$)alkanoylamino, wherein the substituted ($C_1$-$C_{12}$)alkyl, ($C_2$-$C_{12}$)alkenyl, ($C_2$-$C_{12}$)alkynyl, ($C_1$-$C_{12}$)alkoxy, ($C_1$-$C_{12}$)alkylthio, ($C_1$-$C_6$)alkoxy($C_1$-$C_6$)alkyl, ($C_1$-$C_6$)alkylthio($C_1$-$C_6$)alkyl, ($C_1$-$C_6$)alkoxy($C_1$-$C_6$)alkoxy, ($C_1$-$C_6$)alkoxy($C_1$-$C_6$)alkylthio, ($C_1$-$C_6$)alkylthio($C_1$-$C_6$)alkoxy, ($C_1$-$C_6$)alkylthio($C_1$-$C_6$)alkylthio, ($C_1$-$C_4$)alkoxy($C_1$-$C_4$)alkoxy($C_1$-$C_4$)alkyl, aminocarbonylamino-($C_1$-$C_{12}$)alkyl, aminocarbonylamino($C_1$-$C_2$)alkoxy, aminocarbonylamino($C_1$-$C_{12}$)alkylthio, ($C_1$-$C_6$)-alkanoylamino($C_1$-$C_6$)alkyl, ($C_1$-$C_6$)alkanoylamino($C_1$-$C_6$)alkoxy, ($C_1$-$C_6$)alkanoyl-amino($C_1$-$C_6$)alkylthio, ($C_3$-$C_4$)cycloalkanecarbonylamino($C_1$-$C_6$)alkyl, ($C_3$-$C_4$)cycloalkane-carbonyl-amino($C_1$-$C_6$)alkoxy, ($C_3$-$C_4$)cycloalkanecarbonylamino($C_1$-$C_6$)alkylthio, aminosulfonylamino($C_1$-$C_{12}$)alkyl, aminosulfonylamino($C_1$-$C_{12}$)alkoxy, aminosulfonyl-amino($C_1$-$C_{12}$)alkylthio, $C_1$-$C_6$)alkanesulfonylamino($C_1$-$C_6$)alkyl, ($C_1$-$C_6$)alkanesulfonyl-amino($C_1$-$C_6$)alkoxy, ($C_1$-$C_6$)alkanesulfonylamino ($C_1$-$C_6$)alkylthio, formylamino($C_1$-$C_6$)alkyl, formylamino($C_1$-$C_6$)alkoxy, formylamino($C_1$-$C_6$)alkylthio, ($C_1$-$C_6$)alkoxy-carbonylamino($C_1$-$C_6$)alkyl, ($C_1$-$C_6$)alkoxycarbonyl-amino($C_1$-$C_6$)alkoxy, ($C_1$-$C_6$)-alkoxycarbonyl-amino($C_1$-$C_6$)alkylthio, ($C_1$-$C_6$)alkylaminocarbonylamino($C_1$-$C_6$)alkyl, di($C_1$-$C_6$)alkylaminocarbonyl-amino($C_1$-$C_6$)alkyl, ($C_1$-$C_6$)alkylaminocarbonylamino($C_1$-$C_6$)alkoxy, di($C_1$-$C_6$)alkylaminocarbonylamino($C_1$-$C_6$)alkoxy, ($C_1$-$C_6$)alkylamino-carbonylamino($C_1$-$C_6$)alkylthio, di($C_1$-$C_6$)alkylaminocarbonylamino($C_1$-$C_6$)alkylthio, aminocarbonyl($C_1$-$C_6$)alkyl, aminocarbonyl($C_1$-$C_6$)alkoxy, aminocarbonyl($C_1$-$C_6$)alkylthio, ($C_1$-$C_6$)alkylaminocarbonyl($C_1$-$C_6$)alkyl, ($C_1$-$C_6$)alkylaminocarbonyl-($C_1$-$C_8$)alkoxy, ($C_1$-$C_6$)alkylaminocarbonyl-($C_1$-$C_6$)alkylthio, aminocarboxy($C_1$-$C_6$)alkyl, aminocarboxy($C_1$-$C_6$)alkoxy, aminocarboxy($C_1$-$C_6$)alkylthio, ($C_1$-$C_6$)alkylamino-carboxy($C_1$-$C_6$)alkyl, ($C_1$-$C_6$)alkylaminocarboxy($C_1$-$C_6$)alkoxy, ($C_1$-$C_6$)alkylaminocarboxy($C_1$-$C_6$)alkylthio, ($C_1$-$C_{12}$)alkoxycarbonylamino, ($C_1$-$C_{12}$)alkylaminocarbonylamino, or ($C_1$-$C_{12}$)alkanoylamino represented by $R^2$ is substituted by at least one of:

a) 1 to 6 halogen atoms, and b) one substituent selected from cyano, hydroxyl, ($C_1$-$C_3$)alkoxy, ($C_3$-$C_6$)cycloalkyl, ($C_3$-$C_6$)cycloalkoxy, halo($C_1$-$C_3$)alkoxy, halo($C_3$-$C_6$)cycloalkyl, and halo($C_3$-$C_6$)cycloalkoxy, and wherein the thio-moiety of said unsubstituted or substituted ($C_1$-$C_{12}$)alkylthio, ($C_1$-$C_6$)alkoxy($C_1$-$C_6$)alkylthio, ($C_1$-$C_6$)alkylthio($C_1$-$C_6$)alkylthio, aminocarbonylamino($C_1$-$C_{12}$)alkylthio, ($C_1$-$C_6$)alkanoylamino($C_1$-$C_6$)alkylthio, ($C_3$-$C_4$)cycloalkanecarbonyl-amino($C_1$-$C_6$)alkylthio, aminosulfonylamino($C_1$-$C_{12}$)alkylthio, ($C_1$-$C_6$)alkane-sulfonylamino($C_1$-$C_6$)alkylthio, formylamino($C_1$-$C_6$)alkylthio, ($C_1$-$C_6$)alkoxycarbonyl-amino($C_1$-$C_6$)alkylthio, ($C_1$-$C_6$)alkylaminocarbonylamino($C_1$-$C_6$)alkylthio, di($C_1$-$C_6$)alkylaminocarbonylamino($C_1$-$C_6$)alkylthio, aminocarbonyl($C_1$-$C_6$)alkylthio, ($C_1$-$C_6$)alkylaminocarbonyl-($C_1$-$C_6$)alkylthio, aminocarboxy($C_1$-$C_6$)alkylthio, and ($C_1$-$C_6$)alkylaminocarboxy($C_1$-$C_6$)alkylthio is optionally replaced by a sulfinyl (sulfoxide, i.e., —S(O)—) or a sulfonyl (sulfone, i.e., —S(O)$_2$—) moiety, and wherein the carbonyl moiety of said unsubstituted or substituted aminocarbonylamino($C_1$-$C_{12}$)alkyl, aminocarbonylamino($C_1$-$C_{12}$)alkoxy, aminocarbonylamino($C_1$-$C_{12}$)alkylthio, ($C_1$-$C_6$)-alkanoylamino($C_1$-$C_6$)alkyl, ($C_1$-$C_6$)alkanoyl-amino($C_1$-$C_6$)alkoxy, ($C_1$-$C_6$)alkanoylamino($C_1$-$C_6$)alkylthio, ($C_3$-$C_4$)cycloalkanecarbonyl-amino($C_1$-$C_6$)alkyl, ($C_3$-$C_4$)cycloalkanecarbonylamino($C_1$-$C_6$)alkoxy, ($C_3$-$C_4$)cycloalkane-carbonylamino($C_1$-$C_6$)alkylthio, formylamino($C_1$-$C_6$)alkyl, formylamino($C_1$-$C_6$)alkoxy, formylamino($C_1$-$C_6$)alkylthio, ($C_1$-$C_6$)alkoxycarbonyl-amino($C_1$-$C_6$)alkyl, ($C_1$-$C_6$)alkyloxycarbonyl-amino($C_1$-$C_6$)alkoxy, ($C_1$-$C_6$)alkoxycarbonyl-amino($C_1$-$C_6$)alkylthio, ($C_1$-$C_6$)alkylaminocarbonylamino($C_1$-$C_6$)alkyl, di($C_1$-$C_6$)arylaminocarbonyl-amino($C_1$-$C_6$)alkyl, ($C_1$-$C_6$)alkylaminocarbonylamino($C_1$-$C_6$)alkoxy, di($C_1$-$C_6$)alkylaminocarbonylamino($C_1$-$C_6$)alkoxy, ($C_1$-$C_6$)alkylaminocarbonyl-amino($C_1$-$C_6$)alkylthio, di($C_1$-$C_6$)alkylaminocarbonylamino($C_1$-$C_6$)alkylthio, aminocarbonyl($C_1$-$C_6$)alkyl, aminocarbonyl($C_1$-$C_6$)alkoxy, aminocarbonyl($C_1$-$C_6$)alkylthio, ($C_1$-$C_6$)alkylaminocarbonyl($C_1$-$C_6$)alkyl, ($C_1$-$C_6$)alkylaminocarbonyl-($C_1$-$C_6$)alkoxy, ($C_1$-$C_6$)alkylaminocarbonyl-($C_1$-$C_6$)alkylthio, aminocarboxy($C_1$-$C_6$)alkyl, aminocarboxy($C_1$-$C_6$)alkoxy, aminocarboxy($C_1$-$C_6$)alkylthio, ($C_1$-$C_6$)alkylamino-carboxy($C_1$-$C_6$)alkyl, ($C_1$-$C_6$)alkylaminocarboxy($C_1$-$C_6$)alkoxy, ($C_1$-$C_6$)alkylaminocarboxy($C_1$-$C_6$)alkylthio, ($C_1$-$C_{12}$)

alkoxycarbonylamino, $(C_1-C_{12})$alkylaminocarbonylamino, or $(C_1-C_{12})$alkanoylamino is optionally replaced by a thiocarbonyl moiety, $R^3$ is 1) H, halogen, $(C_1-C_6)$alkyl, $(C_1-C_6)$alkoxy, hydroxyl, hydroxy$(C_1-C_6)$alkyl, hydroxy$(C_1-C_6)$alkoxy, $(C_1-C_6)$alkanoylamino, $(C_1-C_6)$-alkoxycarbonylamino, $(C_1-C_6)$alkylamino-carbonylamino, di$(C_1-C_6)$alkylaminocarbonylamino, $(C_1-C_6)$alkanesulfonylamino, $(C_1-C_6)$alkylaminosulfonylamino, or di$(C_1-C_6)$alkylaminosulfonylamino, or 2) phenylamino or heteroarylamino in which each phenylamino and heteroarylamino group is optionally substituted with 1 to 5 groups independently selected from:

fluorine, chlorine, bromine, iodine, cyano, nitro, amino, hydroxy, carboxy, $(C_1-C_6)$alkyl, $(C_3-C_6)$cycloalkyl, $(C_4-C_7)$cycloalkylalkyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylthio, $(C_4-C_7)$cycloalkylalkylthio, halo$(C_1-C_6)$alkylthio, halo$(C_3-C_6)$cycloalkylthio, halo$(C_4-C_7)$-cycloalkylalkylthio, $(C_1-C_6)$alkanesulfinyl, $(C_3-C_6)$ cycloalkanesulfinyl, $(C_4-C_7)$cyclo-alkylalkanesulfinyl, halo$(C_1-C_6)$alkane-sulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$ cycloalkylalkanesulfonyl, halo$(C_1-C_6)$alkanesulfonyl, halo$(C_3-C_6)$cycloalkane-sulfonyl, halo$(C_4-C_7)$cycloalkylalkanesulfonyl, $(C_1-C_6)$alkylamino, di$(C_1-C_6)$ alkylamino, $(C_1-C_6)$alkoxy$(C_1-C_6)$alkoxy, halo$(C_1-C_6)$ alkoxy$(C_1-C_6)$alkoxy, $(C_1-C_6)$alkoxycarbonyl, aminocarbonyl, $(C_1-C_6)$alkylaminocarbonyl, and di$(C_1-C_6)$ alkylaminocarbonyl, cyano$(C_1-C_6)$alkyl, hydroxy$(C_1-C_6)$alkyl, carboxy$(C_1-C_6)$alkyl, $(C_1-C_6)$alkoxy$(C_1-C_6)$ alkyl, $(C_3-C_8)$cycloalkoxy$(C_1-C_6)$alkyl, $(C_4-C_8)$ cycloalkylalkoxy$(C_1-C_6)$alkyl, halo$(C_1-C_6)$alkoxy$(C_1-C_6)$alkyl, halo$(C_3-C_6)$cycloalkoxy$(C_1-C_6)$alkyl, halo$(C_4-C_8)$-cycloalkylalkoxy$(C_1-C_6)$alkyl, $(C_1-C_8)$ alkylthio$(C_1-C_6)$alkyl, $(C_3-C_8)$cycloalkylthio$(C_1-C_6)$ alkyl, $(C_4-C_8)$cycloalkylalkylthio-$(C_1-C_6)$alkyl, halo$(C_1-C_8)$alkylthio$(C_1-C_6)$alkyl, halo$(C_3-C_8)$ cycloalkylthio$(C_1-C_6)$alkyl, halo$(C_4-C_8)$-cycloalkylalkylthio$(C_1-C_6)$alkyl, $(C_1-C_8)$alkanesulfinyl$(C_1-C_6)$alkyl, $(C_3-C_8)$-cycloalkanesulfinyl$(C_1-C_6)$ alkyl, $(C_4-C_8)$cycloalkyl-alkanesulfinyl$(C_1-C_6)$alkyl, halo$(C_1-C_8)$alkanesulfinyl$(C_1-C_6)$alkyl, halo$(C_3-C_8)$ cycloalkanesulfinyl$(C_1-C_6)$alkyl, halo$(C_4-C_8)$cycloalkylalkanesulfinyl$(C_1-C_6)$alkyl, $(C_1-C_8)$alkane-sulfonyl$(C_1-C_6)$alkyl, $(C_3-C_8)$cycloalkanesulfonyl$(C_1-C_6)$ alkyl, $(C_4-C_8)$ cycloalkylalkanesulfonyl$(C_1-C_6)$alkyl, halo$(C_1-C_8)$alkanesulfonyl$(C_1-C_6)$alkyl, halo$(C_3-C_8)$ cycloalkanesulfonyl$(C_1-C_6)$alkyl, halo$(C_4-C_8)$cycloalkylalkane-sulfonyl$(C_1-C_6)$alkyl, $(C_1-C_8)$alkylamino$(C_1-C_6)$alkyl, di$(C_1-C_8)$alkylamino$(C_1-C_6)$alkyl, $(C_1-C_8)$alkoxycarbonyl$(C_1-C_6)$alkyl, $(C_1-C_8)$acyloxy $(C_1-C_6)$alkyl, aminocarbonyl$(C_1-C_6)$alkyl, $(C_1-C_8)$ alkylamino-carbonyl$(C_1-C_6)$alkyl, di$(C_1-C_8)$alkylaminocarbonyl$(C_1-C_6)$alkyl$(C_1-C_8)$acylamino$(C_1-C_6)$ alkyl, $(C_1-C_8)$alkoxy-carbonylamino, $(C_1-C_8)$ alkoxycarbonylamino$(C_1-C_6)$alkyl, aminocarboxy$(C_1-C_6)$alkyl, $(C_1-C_8)$alkylamino-carboxy$(C_1-C_6)$alkyl, and di$(C_1-C_8)$alkylaminocarboxy$(C_1-C_6)$alkyl;

provided that when $R^3$ is hydroxyl, halogen or optionally substituted phenylamino or heteroarylamino, then $R^2$ is not a substituted or unsubstituted $(C_1-C_{12})$alkoxy, $(C_1-C_6)$alkoxy $(C_1-C_6)$alkoxy, $(C_1-C_6)$alkylthio$(C_1-C_6)$alkoxy, aminocarbonylamino$(C_1-C_{12})$alkyl, aminocarbonyl-amino$(C_1-C_{12})$ alkoxy, $(C_1-C_6)$alkanoyl-amino$(C_1-C_6)$alkoxy, $(C_3-C_4)$ cycloalkanecarbonylamino-$(C_1-C_6)$alkoxy, aminosulfonylamino$(C_1-C_{12})$alkoxy, $(C_1-C_6)$alkane-sulfonylamino$(C_1-C_6)$alkoxy, formylamino$(C_1-C_6)$alkoxy, $(C_1-C_6)$alkoxycarbonyl-amino$(C_1-C_6)$alkoxy, $(C_1-C_6)$alkylamino-carbonylamino$(C_1-C_6)$alkoxy, di$(C_1-C_6)$ alkylaminocarbonylamino$(C_1-C_6)$alkoxy, aminocarbonyl $(C_1-C_6)$alkoxy, $(C_1-C_6)$alkylaminocarbonyl-$(C_1-C_6)$alkoxy, aminocarboxy$(C_1-C_6)$alkoxy, $(C_1-C_6)$alkylaminocarboxy $(C_1-C_6)$alkoxy, $(C_1-C_{12})$alkoxycarbonylamino, $(C_1-C_{12})$ alkylaminocarbonylamino, or $(C_1-C_{12})$alkanoylamino;

provided further that when $R^3$ is hydroxyl, halogen, or optionally substituted phenylamino or heteroarylamino, then $R^2$ is not a unsubstituted or substituted $(C_1-C_{12})$alkylthio, $(C_1-C_6)$alkoxy$(C_1-C_6)$alkylthio, $(C_1-C_6)$alkylthio$(C_1-C_6)$ alkylthio, aminocarbonylamino$(C_1-C_{12})$alkylthio, $(C_1-C_6)$ alkanoylamino$(C_1-C_6)$alkylthio, $(C_3-C_4)$cycloalkanecarbonylamino$(C_1-C_6)$alkylthio, aminosulfonylamino$(C_1-C_{12})$ alkylthio, $(C_1-C_6)$alkanesulfonylamino$(C_1-C_6)$alkylthio, formylamino$(C_1-C_6)$alkylthio, $(C_1-C_6)$alkoxycarbonyl-amino$(C_1-C_6)$alkylthio, $(C_1-C_6)$alkylamino-carbonylamino $(C_1-C_6)$alkylthio, di$(C_1-C_6)$alkylaminocarbonylamino$(C_1-C_6)$alkylthio, amino-carbonyl$(C_1-C_6)$alkylthio, $(C_1-C_6)$ alkylaminocarbonyl-$(C_1-C_6)$alkylthio, aminocarboxy$(C_1-C_6)$alkylthio or $(C_1-C_6)$alkylaminocarboxy$(C_1-C_6)$alkylthio, wherein the thiomoiety moiety is replaced by a sulfinyl (sulfoxide, i.e., —S(O)—) or a sulfonyl (sulfone, i.e., —S(O)$_2$—) moiety, and provided further that when $R^3$ is hydroxyl, halogen, or optionally substituted phenylamino or heteroarylamino, then $R^2$ is not a unsubstituted or substituted aminocarbonyl amino $(C_1-C_{12})$alkoxy, aminocarbonylamino$(C_1-C_{12})$alkylthio, $(C_1-C_6)$alkanoyl-amino$(C_1-C_6)$alkoxy, $(C_1-C_6)$alkanoylamino$(C_1-C_6)$alkylthio, $(C_3-C_4)$cycloalkanecarbonylamino $(C_1-C_6)$alkoxy, $(C_3-C_4)$cycloalkane-carbonylamino$(C_1-C_6)$ alkylthio, formylamino$(C_1-C_6)$alkoxy, formylamino$(C_1-C_6)$ alkylthio, $(C_1-C_6)$alkoxycarbonyl-amino$(C_1-C_6)$alkoxy, $(C_1-C_6)$alkoxycarbonyl-amino$(C_1-C_6)$alkylthio, $(C_1-C_6)$ alkylaminocarbonylamino$(C_1-C_6)$alkoxy, di$(C_1-C_6)$ alkylaminocarbonyl-amino$(C_1-C_6)$alkoxy, $(C_1-C_6)$ alkylaminocarbonylamino$(C_1-C_6)$alkylthio, di$(C_1-C_6)$ alkylamino-carbonylamino$(C_1-C_6)$alkylthio, aminocarbonyl $(C_1-C_6)$alkoxy, aminocarbonyl$(C_1-C_6)$alkylthio, $(C_1-C_6)$ alkylaminocarbonyl-$(C_1-C_6)$alkoxy, $(C_1-C_6)$ alkylaminocarbonyl-$(C_1-C_6)$alkylthio, aminocarboxy$(C_1-C_6)$alkoxy, aminocarboxy$(C_1-C_6)$alkylthio, $(C_1-C_6)$ alkylamino-carboxy$(C_1-C_6)$alkoxy, $(C_1-C_6)$ alkylaminocarboxy$(C_1-C_6)$alkylthio, $(C_1-C_{12})$ alkoxycarbonylamino, $(C_1-C_{12})$alkylaminocarbonylamino, $(C_1-C_{12})$alkanoylamino, wherein the carbonyl moiety is replaced by a thiocarbonyl moiety;

A is a saturated or unsaturated 4-, 5-, 6-, or 7-membered ring which is optionally bridged by $(CH_2)_m$ via bonds to two members of said ring, wherein said ring is composed of carbon atoms, and 0-2 hetero atoms selected from 0, 1, or 2 nitrogen atoms, 0 or 1 oxygen atoms, and 0 or 1 sulfur atoms, said ring atoms being substituted with the appropriate number of hydrogen atoms, said ring being optionally substituted with up to four moieties independently selected halogen, $(C_1-C_6)$alkyl, halo$(C_1-C_6)$alkyl, and oxo, and wherein m is 1 to 3;

Q and Y are attached to carbon or nitrogen atoms in ring A in a 1,2 or 1,3 or 1,4 relationship;

Q is a divalent radical selected from

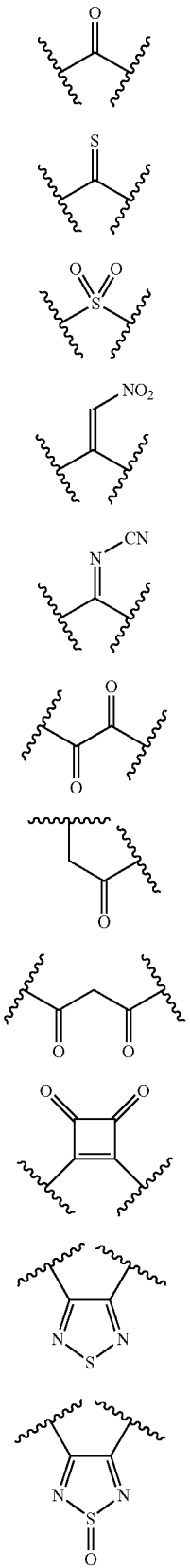

Q1
Q2
Q3
Q4
Q5
Q6
Q7
Q8
Q9
Q10
Q11

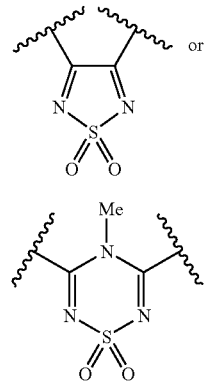

Q12
Q13 wherein A and N are attached to the truncated bonds $R^4$ is H, $(C_1-C_6)$alkyl, halo$(C_1-C_6)$alkyl, $(C_1-C_3)$alkoxy $(C_1-C_3)$alkyl, or cyano$(C_1-C_6)$alkyl;

$R^5$ is 1) hydrogen, 2) $(C_1-C_{12})$alkyl, $(C_3-C_8)$cycloalkyl, $(C_3-C_8)$cycloalkyl$(C_1-C_3)$alkyl, $(C_2-C_{12})$alkenyl, $(C_5-C_8)$cycloalkyl$(C_1-C_3)$alkenyl, $(C_2-C_{12})$alkynyl, $(C_3-C_8)$cycloalkyl $(C_1-C_3)$alkynyl, $(C_4-C_{12})$bicycloalkyl$(C_1-C_3)$alkyl, $(C_8-C_{14})$ tricycloalkyl$(C_1-C_3)$alkyl, $(C_1-C_6)$alkoxy$(C_1-C_6)$allyl, $(C_3-C_8)$cycloalkoxy$(C_1-C_3)$alkyl, $(C_1-C_6)$alkylthio$(C_1-C_6)$alkyl, $(C_3-C_8)$cycloalkylthio$(C_1-C_3)$alkyl, saturated heterocyclyl, or saturated heterocyclyl$(C_1-C_3)$alkyl wherein (a) each of these groups are optionally substituted by 1 to 6 groups independently selected from halogen, cyano, hydroxyl, $(C_1-C_3)$alkyl, $(C_1-C_3)$alkoxy, $(C_3-C_6)$cycloalkyl, $(C_3-C_6)$cycloalkoxy, halo$(C_1-C_3)$alkyl, halo$(C_1-C_3)$alkoxy, halo$(C_3-C_6)$cycloalkyl, and halo$(C_3-C_6)$cycloalkoxy and wherein (b) divalent sulfur atoms are optionally oxidized to sulfoxide or sulfone; or 3) phenyl, naphthyl, heteroaryl, phenyl$(C_1-C_3)$alkyl, naphthyl$(C_1-C_3)$alkyl, or heteroaryl$(C_1-C_3)$alkyl, each optionally substituted with 1 to 3 groups independently selected from:

fluorine, chlorine, bromine, iodine, cyano, nitro, amino, hydroxy, carboxy, $(C_1-C_6)$alkyl, $(C_3-C_6)$cycloalkyl, $(C_4-C_7)$cycloalkylalkyl, $(C_2-C_6)$alkynyl, $(C_3-C_6)$cycloalkyl-$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cyclo-alkylthio, $(C_4-C_7)$cycloalkylalkylthio, halo$(C_1-C_6)$alkylthio, halo$(C_3-C_6)$cycloalkylthio, halo$(C_4-C_7)$cycloalkylalkylthio, $(C_1-C_6)$-alkanesulfinyl, $(C_3-C_6)$cycloalkanesulfinyl, $(C_4-C_7)$cycloalkylalkanesulfinyl, halo$(C_1-C_6)$-alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$-cycloalkylalkanesulfonyl, $(C_1-C_6)$alkylamino, di$(C_1-C_6)$alkylamino, $(C_1-C_6)$-alkoxy$(C_1-C_6)$alkoxy, halo$(C_1-C_6)$alkoxy$(C_1-C_6)$alkoxy, $(C_1-C_6)$alkoxycarbonyl, aminocarbonyl, $(C_1-C_6)$arylaminocarbonyl, di$(C_1-C_6)$alkylaminocarbonyl, cyano$(C_1-C_6)$alkyl, hydroxy$(C_1-C_6)$alkyl, carboxy$(C_1-C_6)$alkyl, $(C_1-C_6)$alkoxy$(C_1-C_6)$alkyl, $(C_3-C_8)$cycloalkoxy$(C_1-C_6)$alkyl, $(C_4-C_8)$cycloalkylalkoxy$(C_1-C_6)$alkyl, halo$(C_1-C_6)$alkoxy$(C_1-C_6)$alkyl, halo$(C_3-C_6)$cycloalkoxy$(C_1-C_6)$alkyl, halo$(C_4-C_8)$-cycloalkylalkoxy$(C_1-C_6)$alkyl, $(C_1-C_8)$alkylthio$(C_1-C_6)$alkyl, $(C_3-C_8)$cycloalkylthio$(C_1-C_6)$alkyl, $(C_4-C_8)$ cycloalkylalkylthio($C_1$-$C_6$)alkyl, halo($C_1$-$C_8$)alkylthio($C_1$-$C_6$)alkyl, halo($C_3$-$C_8$)cycloalkylthio($C_1$-$C_6$)alkyl, halo($C_4$-$C_8$)-cycloalkylalkylthio($C_1$-$C_6$)alkyl, ($C_1$-$C_6$)alkanesulfinyl($C_1$-$C_6$)alkyl, ($C_3$-$C_8$)-cycloalkanesulfinyl($C_1$-$C_6$)alkyl, ($C_4$-$C_8$)cycloalkyl-alkanesulfinyl($C_1$-$C_6$)alkyl, halo($C_1$-$C_8$)alkane-sulfinyl($C_1$-$C_6$)alkyl, halo($C_3$-$C_8$)cycloalkanesulfinyl($C_1$-$C_6$)alkyl, halo($C_4$-$C_8$)cycloalkylalkane-sulfinyl($C_1$-$C_6$)alkyl, ($C_1$-$C_8$)alkane-sulfonyl($C_1$-$C_6$)alkyl, ($C_3$-$C_8$)cycloalkanesulfonyl($C_1$-$C_6$)alkyl, ($C_4$-$C_8$) cycloalkylalkanesulfonyl($C_1$-$C_6$)alkyl, halo($C_1$-$C_8$)alkanesulfonyl($C_1$-$C_6$)alkyl, halo($C_3$-$C_8$)cycloalkanesulfonyl($C_1$-$C_6$)alkyl, halo($C_4$-$C_8$)cycloalkylalkane-sulfonyl($C_1$-$C_6$)alkyl, ($C_1$-$C_8$)alkylamino($C_1$-$C_6$)alkyl, di($C_1$-$C_8$)-alkylamino($C_1$-$C_6$)alkyl, ($C_1$-$C_8$)alkoxycarbonyl($C_1$-$C_6$)alkyl, ($C_1$-$C_8$)acyloxy($C_1$-$C_6$)alkyl, aminocarbonyl($C_1$-$C_6$)alkyl, ($C_1$-$C_8$)alkylamino-carbonyl($C_1$-$C_6$)alkyl, di($C_1$-$C_8$)-alkylaminocarbonyl($C_1$-$C_6$)alkyl ($C_1$-$C_8$)acylamino($C_1$-$C_6$)alkyl, ($C_1$-$C_8$)alkoxy-carbonylamino, ($C_1$-$C_8$)alkoxycarbonylamino($C_1$-$C_6$)alkyl, aminocarboxy($C_1$-$C_6$)alkyl, ($C_1$-$C_8$)alkylamino-carboxy($C_1$-$C_6$)alkyl, di($C_1$-$C_8$)alkylaminocarboxy($C_1$-$C_6$)alkyl, phenyl, napthyl, heteroaryl, bicyclic heteroaryl, phenoxy, naphthyloxy, heteroaryloxy, bicyclic heteroaryloxy, phenylthio, naphthylthio, heteroarylthio, bicyclic heteroarylthio, phenylsulfinyl, naphthylsulfinyl, heteroarylsulfinyl, bicyclic heteroarylsulfinyl, phenylsulfonyl, naphthylsulfonyl, heteroarylsulfonyl, bicyclic heteroarylsulfonyl, phenyl($C_1$-$C_3$)alkyl, napthyl($C_1$-$C_3$)alkyl, heteroaryl($C_1$-$C_3$)alkyl, and bicyclic heteroaryl($C_1$-$C_3$)alkyl, wherein the aromatic and heteroaromatic groups are optionally substituted with 1 to 3 groups independently selected from fluorine, chlorine, cyano, ($C_1$-$C_3$)alkyl, halo($C_1$-$C_3$)alkyl, ($C_1$-$C_3$)alkoxy, halo($C_1$-$C_3$)alkoxy, ($C_1$-$C_3$)alkanesulfonyl, and ($C_1$-$C_3$)alkoxycarbonyl;

$R^9$ is a) ($C_1$-$C_{12}$)alkyl, ($C_4$-$C_{12}$)cycloalkylalkyl, halo($C_1$-$C_{12}$)alkyl, halo($C_4$-$C_{12}$)cycloalkylalkyl, ($C_2$-$C_{12}$)alkenyl, ($C_5$-$C_{12}$)cycloalkylalkenyl, halo($C_2$-$C_{12}$)alkenyl, halo($C_5$-$C_{12}$)cycloalkylalkenyl, ($C_2$-$C_{12}$)alkynyl, ($C_5$-$C_{12}$)cycloalkylalkynyl, halo($C_2$-$C_{12}$)alkynyl, halo($C_5$-$C_{12}$)cycloalkylalkynyl, ($C_1$-$C_6$)alkoxy($C_1$-$C_6$)alkyl, halo($C_1$-$C_6$)alkoxy($C_1$-$C_6$)alkyl, ($C_1$-$C_6$)alkylthio($C_1$-$C_6$)alkyl, halo($C_1$-$C_6$)alkylthio($C_1$-$C_6$)alkyl, ($C_1$-$C_6$)alkanesulfinyl($C_1$-$C_6$)alkyl, halo($C_1$-$C_6$)alkane-sulfinyl($C_1$-$C_6$)alkyl, ($C_1$-$C_6$)alkanesulfonyl($C_1$-$C_6$)alkyl, halo($C_1$-$C_6$)alkanesulfonyl($C_1$-$C_6$)alkyl, aminocarbonyl($C_1$-$C_6$)alkyl, ($C_1$-$C_6$)alkylaminocarbonyl($C_1$-$C_6$)alkyl, di($C_1$-$C_6$)alkylamino-carbonyl($C_1$-$C_6$)alkyl, cyano($C_1$-$C_6$)alkyl, carboxy($C_1$-$C_6$)alkyl, ($C_1$-$C_6$)alkoxycarbonyl($C_1$-$C_6$)alkyl, saturated heterocyclyl, or saturated heterocyclyl($C_1$-$C_6$)alkyl; an additional value for $R^9$ is —H; or b) phenyl, naphthyl, heteroaryl, phenyl($C_1$-$C_3$)alkyl, naphthyl($C_1$-$C_3$)alkyl, or heteroaryl($C_1$-$C_3$)alkyl, each optionally substituted by 1 to 3 groups independently selected from:

1) fluorine, chlorine, bromine, iodine, cyano, nitro, amino, hydroxy, carboxy, ($C_1$-$C_6$)alkyl, ($C_3$-$C_6$)cycloalkyl, ($C_4$-$C_7$)cycloalkylalkyl, ($C_2$-$C_6$)alkynyl, ($C_3$-$C_6$)cycloalkyl-($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkylthio, ($C_4$-$C_7$)cycloalkylalkylthio, halo($C_1$-$C_6$)alkylthio, halo($C_3$-$C_6$)cycloalkylthio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)-cycloalkylalkanesulfinyl, halo($C_1$-$C_6$)alkanesulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkylalkanesulfonyl, halo($C_1$-$C_6$)alkanesulfonyl, halo($C_3$-$C_6$)cycloalkane-sulfonyl, halo($C_4$-$C_7$)-cycloalkylalkanesulfonyl, ($C_1$-$C_6$)alkylamino, di($C_1$-$C_6$) alkylamino, ($C_1$-$C_6$)alkoxy-($C_1$-$C_6$)alkoxy, halo($C_1$-$C_6$)alkoxy($C_1$-$C_6$)alkoxy, ($C_1$-$C_6$)alkoxycarbonyl, aminocarbonyl, ($C_1$-$C_6$)alkylaminocarbonyl and di($C_1$-$C_6$)alkylaminocarbonyl, cyano($C_1$-$C_6$)alkyl, hydroxy ($C_1$-$C_6$)alkyl, carboxy($C_1$-$C_6$)alkyl, ($C_1$-$C_6$)alkoxy($C_1$-$C_6$)alkyl, ($C_3$-$C_8$)cycloalkoxy($C_1$-$C_6$)alkyl, ($C_4$-$C_8$)cycloalkylalkoxy($C_1$-$C_6$)alkyl, halo($C_1$-$C_6$)alkoxy($C_1$-$C_6$)alkyl, halo($C_3$-$C_6$)cycloalkoxy($C_1$-$C_6$)alkyl, halo($C_4$-$C_8$)-cycloalkylalkoxy($C_1$-$C_6$)alkyl, ($C_1$-$C_8$)alkylthio($C_1$-$C_6$)alkyl, ($C_3$-$C_8$)cycloalkylthio($C_1$-$C_6$)alkyl, ($C_4$-$C_8$)cycloalkylalkylthio-($C_1$-$C_6$)alkyl, halo($C_1$-$C_8$)alkylthio($C_1$-$C_6$)alkyl, halo($C_3$-$C_8$)cycloalkylthio($C_1$-$C_6$)alkyl, halo($C_4$-$C_8$)-cycloalkylalkylthio($C_1$-$C_6$)alkyl, ($C_1$-$C_8$)alkanesulfinyl($C_1$-$C_6$)alkyl, ($C_3$-$C_8$)-cycloalkanesulfinyl($C_1$-$C_6$)alkyl, ($C_4$—$C_8$)cycloalkyl-alkanesulfinyl($C_1$-$C_6$)alkyl, halo($C_1$-$C_8$)alkanesulfinyl($C_1$-$C_6$)alkyl, halo($C_3$-$C_8$)cycloalkanesulfinyl($C_1$-$C_6$)alkyl, halo($C_4$-$C_8$)cycloalkylalkanesulfinyl($C_1$-$C_6$)alkyl, ($C_1$-$C_8$)alkane-sulfonyl($C_1$-$C_6$)alkyl, ($C_3$-$C_8$)cycloalkanesulfonyl($C_1$-$C_6$) alkyl, ($C_4$-$C_8$) cycloalkylalkanesulfonyl($C_1$-$C_6$)alkyl, halo($C_1$-$C_8$)alkanesulfonyl($C_1$-$C_6$)alkyl, halo($C_3$-$C_8$)cycloalkanesulfonyl($C_1$-$C_6$)alkyl, halo($C_4$-$C_8$)cycloalkylalkane-sulfonyl($C_1$-$C_6$)alkyl, ($C_1$-$C_8$ alkylamino($C_1$-$C_6$)alkyl, di($C_1$-$C_8$)-alkylamino($C_1$-$C_6$) alkyl, ($C_1$-$C_8$)alkoxycarbonyl($C_1$-$C_6$)alkyl, ($C_1$-$C_8$) acyloxy($C_1$-$C_6$)alkyl, aminocarbonyl($C_1$-$C_6$)alkyl, ($C_1$-$C_8$)alkylamino-carbonyl($C_1$-$C_6$)alkyl, di($C_1$-$C_8$)-alkylaminocarbonyl($C_1$-$C_6$)alkyl($C_1$-$C_8$)acylamino ($C_1$-$C_6$)alkyl, ($C_1$-$C_8$)alkoxy-carbonylamino, ($C_1$-$C_8$) alkoxycarbonylamino($C_1$-$C_6$)alkyl, aminocarboxy($C_1$-$C_6$)alkyl, ($C_1$-$C_8$)alkylamino-carboxy($C_1$-$C_6$)alkyl and di($C_1$-$C_8$)alkylaminocarboxy($C_1$-$C_6$)alkyl; or 2) phenyl, napthyl, heteroaryl, bicyclic heteroaryl, phenoxy, naphthyloxy, heteroaryloxy, bicyclic heteroaryloxy, phenylthio, naphthylthio, heteroarylthio, bicyclic heteroarylthio, phenylsulfinyl, naphthylsulfinyl, heteroarylsulfinyl, bicyclic heteroarylsulfinyl, phenylsulfonyl, naphthylsulfonyl, heteroarylsulfonyl, bicyclic heteroarylsulfonyl, phenyl($C_1$-$C_3$)alkyl, napthyl($C_1$-$C_3$)alkyl, heteroaryl($C_1$-$C_3$)alkyl, and bicyclic heteroaryl($C_1$-$C_3$)alkyl, each optionally substituted with 1 to 3 groups independently selected from fluorine, chlorine, cyano, ($C_1$-$C_3$)alkyl, halo($C_1$-$C_3$)alkyl, ($C_1$-$C_3$)alkoxy, halo($C_1$-$C_3$)alkoxy, ($C_1$-$C_3$)alkanesulfonyl, and ($C_1$-$C_3$)-alkoxycarbonyl;

or an enantiomer, diastereomer or salt thereof.

In one embodiment the present invention is directed to compounds of Formula Ia

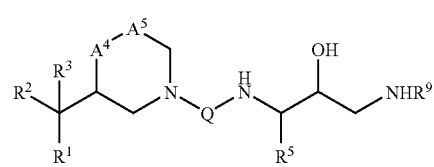

Ia wherein $R^1$ is a) ($C_1$-$C_9$)alkyl, ($C_3$-$C_7$)cycloalkyl, ($C_4$-$C_9$)cycloalkylalkyl, halo($C_1$-$C_9$)alkyl, halo($C_3$-$C_7$)cycloalkyl, halo($C_4$-$C_9$)cycloalkylalkyl, or saturated heterocyclyl each optionally substituted with 1 to 3 groups independently selected from fluorine, $(C_1-C_3)$alkyl, halo$(C_1-C_3)$alkyl, and oxo;

or b) phenyl, napthyl, heteroaryl, or bicyclic heteroaryl each optionally substituted with 1 to 3 groups independently selected from:

1) fluorine, chlorine, bromine, cyano, nitro, $(C_1-C_6)$alkyl, $(C_3-C_6)$cycloalkyl, $(C_4-C_7)$cycloalkylalkyl, $(C_2-C_6)$alkenyl, $(C_5-C_6)$cycloalkenyl, $(C_5-C_8)$cycloalkylalkenyl, $(C_2-C_6)$alkynyl, $(C_3-C_6)$cycloalkylethynyl, halo$(C_1-C_6)$alkyl, halo$(C_3-C_6)$cycloalkyl, halo$(C_4-C_7)$-cycloalkylalkyl, halo$(C_2-C_6)$alkenyl, halo$(C_3-C_6)$alkynyl, halo$(C_3-C_6)$cycloalkylethynyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_3-C_6)$alkenyloxy, and $(C_1-C_6)$alkanesulfonyl; or 2) phenyl, heteroaryl, phenoxy, heteroaryloxy, phenylthio, heteroarylthio, benzyl, heteroarylmethyl, benzyloxy, and heteroaryloxy, each optionally substituted with 1 to 3 groups independently selected from:

fluorine, chlorine, cyano, $(C_1-C_3)$alkyl, halo$(C_1-C_3)$alkyl, $(C_1-C_3)$-alkoxy, halo$(C_1-C_3)$alkoxy, and aminocarbonyl;

$R^2$ is hydrogen, $(C_1-C_8)$alkyl, $(C_4-C_8)$cycloalkylalkyl, fluoro$(C_1-C_8)$alkyl, fluoro$(C_4-C_8)$-cycloalkylalkyl, $(C_1-C_8)$alkoxy, $(C_4-C_8)$cycloalkylalkoxy, fluoro$(C_1-C_8)$alkoxy, hydroxy$(C_1-C_8)$alkyl, $(C_1-C_5)$alkoxy$(C_1-C_5)$alkyl, halo$(C_1-C_5)$alkylamino$(C_1-C_5)$alkyl, $(C_1-C_5)$alkoxy$(C_1-C_5)$hydroxyalkyl, $(C_3-C_4)$cycloalkoxy$(C_1-C_5)$alkyl, fluoro$(C_1-C_5)$alkoxy$(C_1-C_5)$alkyl, fluoro$(C_3-C_4)$cycloalkoxy$(C_1-C_5)$alkyl, $(C_1-C_5)$alkylthio$(C_1-C_5)$alkyl, $(C_1-C_5)$alkoxy$(C_1-C_5)$alkoxy, hydroxy$(C_1-C_8)$alkoxy, $(C_3-C_4)$cycloalkoxy$(C_1-C_5)$alkoxy, fluoro$(C_1-C_5)$alkoxy$(C_1-C_5)$alkoxy, fluoro$(C_3-C_4)$cycloalkoxy$(C_1-C_5)$alkoxy, $(C_1-C_3)$alkoxy$(C_1-C_3)$alkoxy$(C_1-C_3)$alkyl, fluoro$(C_1-C_3)$-alkoxy$(C_1-C_3)$alkoxy$(C_1-C_3)$alkyl, aminocarbonylamino$(C_1-C_8)$alkyl, aminocarbonylamino$(C_1-C_8)$alkoxy, $(C_1-C_5)$alkanoylamino$(C_1-C_5)$alkyl, $(C_1-C_8)$alkanoylamino$(C_1-C_8)$alkoxy, fluoro$(C_1-C_5)$alkanoylamino$(C_1-C_5)$alkyl, fluoro$(C_1-C_5)$alkanoylamino$(C_1-C_5)$alkoxy, $(C_1-C_3)$alkoxy$(C_1-C_5)$alkanoylamino$(C_1-C_5)$alkyl, $(C_1-C_3)$alkoxy$(C_1-C_5)$alkanoylamino$(C_1-C_5)$alkoxy, $(C_3-C_4)$-cycloalkanecarbonyllamino$(C_1-C_5)$alkyl, $(C_3-C_4)$cycloalkanecarbonylamino$(C_1-C_5)$alkoxy, aminosulfonylamino$(C_1-C_8)$alkyl, aminosulfonylamino$(C_1-C_8)$alkoxy, $(C_1-C_5)$alkanesulfonyl-amino$(C_1-C_5)$alkyl, $(C_1-C_5)$alkanesulfonylamino$(C_1-C_5)$alkoxy, formylamino$(C_1-C_5)$alkyl, formylamino$(C_1-C_5)$alkoxy, $(C_1-C_5)$alkoxycarbonylamino$(C_1-C_5)$alkyl, $(C_1-C_5)$alkoxycarbonyl-amino$(C_1-C_5)$alkoxy, $(C_1-C_5)$alkylaminocarbonylamino$(C_1-C_5)$alkyl, $(C_1-C_5)$alkylaminocarbonyl-amino$(C_1-C_5)$alkyl, di$(C_1-C_5)$alkylaminocarbonylamino$(C_1-C_5)$alkoxy, aminocarbonyl$(C_1-C_5)$alkyl, aminocarbonyl$(C_1-C_5)$alkoxy, $(C_1-C_5)$alkylaminocarbonyl$(C_1-C_5)$alkyl, $(C_1-C_5)$-alkylaminocarbonyl-$(C_1-C_5)$alkoxy, aminocarboxy$(C_1-C_5)$alkyl, aminocarboxy$(C_1-C_5)$alkoxy, $(C_1-C_5)$alkylamino-carboxy$(C_1-C_5)$alkyl, $(C_1-C_5)$alkylaminocarboxy$(C_1-C_5)$alkoxy, $(C_1-C_8)$-alkoxycarbonylamino, $(C_1-C_8)$alkylaminocarbonylamino, $(C_1-C_8)$alkanoylamino, fluoro$(C_1-C_8)$alkoxycarbonylamino, fluoro$(C_1-C_8)$alkylaminocarbonylamino, or fluoro$(C_1-C_8)$-alkanoylamino, an additional value for $R^2$ is $(C_1-C_8)$oxoalkyl;

$R^3$ is H, halogen, OH, $(C_1-C_4)$alkanoylamino, or $(C_1-C_3)$alkoxy;

provided that (i) $R^2$ and $R^3$ are not both hydrogen and (ii) when $R^3$ is OH or halogen, $R^2$ is not $(C_1-C_8)$alkoxy, $(C_4-C_8)$cycloalkylalkoxy, fluoro$(C_1-C_8)$alkoxy, $(C_1-C_5)$alkoxy$(C_1-C_5)$alkoxy, hydroxy$(C_1-C_8)$alkoxy, $(C_3-C_4)$cycloalkoxy$(C_1-C_5)$alkoxy, fluoro$(C_1-C_5)$alkoxy$(C_1-C_5)$alkoxy, fluoro$(C_3-C_4)$cycloalkoxy$(C_1-C_5)$alkoxy, aminocarbonyl-amino$(C_1-C_8)$alkoxy, $(C_1-C_5)$alkanoylamino$(C_1-C_5)$alkoxy, fluoro$(C_1-C_5)$alkanoyl-amino$(C_1-C_5)$alkoxy, $(C_1-C_3)$alkoxy$(C_1-C_5)$alkanoylamino$(C_1-C_5)$alkoxy, $(C_3-C_4)$-cycloalkanecarbonylamino$(C_1-C_5)$alkoxy, aminosulfonylamino$(C_1-C_8)$alkoxy, $(C_1-C_5)$alkanesulfonylamino$(C_1-C_5)$alkoxy, formylamino$(C_1-C_5)$alkoxy, $(C_1-C_5)$alkoxy-arbonylamino$(C_1-C_5)$alkoxy, di$(C_1-C_5)$alkylaminocarbonylamino$(C_1-C_5)$alkoxy, aminocarbonyl$(C_1-C_5)$alkoxy, $(C_1-C_5)$alkylaminocarbonyl$(C_1-C_5)$alkoxy, aminocarboxy$(C_1-C_5)$alkoxy, $(C_1-C_5)$alkylaminocarboxy$(C_1-C_5)$alkoxy, $(C_1-C_8)$alkoxycarbonylamino, $(C_1-C_8)$alkylaminocarbonylamino, $(C_1-C_8)$alkanoylamino, fluoro$(C_1-C_8)$alkoxycarbonylamino, fluoro$(C_1-C_8)$alkylaminocarbonylamino, or fluoro$(C_1-C_8)$alkanoylamino;

$A^4$ is $CH_2$ and $A^5$ is $CH_2$; or $A^4$ is O and $A^5$ is $CH_2$; or $A^4$ is $CH_2$ and $A_5$ is a single bond;

Q is Q1, Q2, Q4, Q5, Q6, Q7, Q9, or Q10

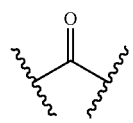

Q1

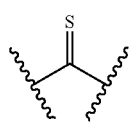

Q2

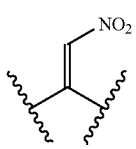

Q4

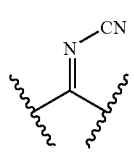

Q5

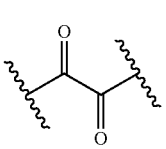

Q6

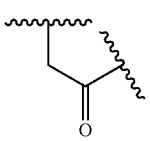

Q7

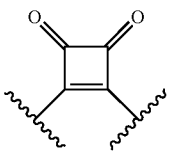

Q9

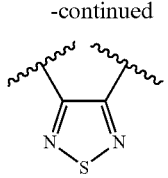

wherein A and N are attached to the truncated bonds

R⁵ is a) hydrogen; or b) (C₁-C₁₀)alkyl, (C₃-C₇)cycloalkyl(C₁-C₂)alkyl, (C₄-C₁₀)bicycloalkyl(C₁-C₂)alkyl, (C₈-C₁₂)tricycloalkyl(C₁-C₂)alkyl, (C₁-C₆)alkoxy(C₁-C₆)alkyl, (C₃-C₇)cycloalkoxy(C₁-C₃)alkyl, (C₁-C₅)alkylthio(C₁-C₅)alkyl, or saturated heterocyclyl(C₁-C₃)alkyl.

wherein each of these groups are optionally substituted by 1 to 3 groups independently selected from halogen, cyano, hydroxyl, (C₁-C₂)alkyl, (C₁-C₂)alkoxy, (C₃-C₆)cycloalkyl, (C₃-C₆)cycloalkoxy, halo(C₁-C₂)alkyl, halo(C₁-C₂)alkoxy, halo(C₃-C₆)cycloalkyl, and halo(C₃-C₆)cycloalkoxy; or c) phenyl(C₁-C₂)alkyl or heteroaryl(C₁-C₂)alkyl each optionally substituted with 1 to 3 groups independently selected from fluorine, chlorine, cyano, (C₁-C₃)alkyl, halo(C₁-C₃)alkyl, (C₁-C₃)alkoxy, and halo(C₁-C₃)alkoxy;

R⁹ is a) (C₁-C₆)alkyl, halo(C₁-C₆)alkyl, (C₄-C₁₀)cycloalkylalkyl, (C₁-C₅)alkoxy(C₁-C₅)alkyl, aminocarbonyl(C₁-C₅)alkyl, (C₁-C₆)alkylaminocarbonyl(C₁-C₆)alkyl, or di(C₁-C₆)alkyl-aminocarbonyl(C₁-C₆)alkyl; or b) phenyl(C₁-C₂)alkyl optionally substituted with 1 to 3 groups independently selected from fluorine, chlorine, cyano, (C₁-C₃)alkyl, halo(C₁-C₃)alkyl, (C₁-C₃)alkoxy, and halo(C₁-C₃)alkoxy;

or an enantiomer, diastereomer or salt thereof.

Another embodiment of the invention is a compound of Formula Ia, wherein R¹ is a) isopropyl, cyclohexyl, or trifluoromethyl; or b) phenyl, 2-thienyl, 3-thienyl, 2-pyridyl, 2-imidazolyl, 2-thiazolyl, 2-benzothienyl, 4-benzofuryl, 4-benzothienyl, 7-benzofuryl, 2,3-dihydro-7-benzofuryl, 7-benzothienyl, 1,3-benzodioxol-4-yl, 7-indazolyl, or 8-quinolinyl each optionally substituted with 1 to 3 substituents independently selected from:

fluorine, chlorine, bromine, cyano, methyl, ethyl, isopropyl, t-butyl, isobutyl, trifluoromethyl, allyl, cyclohexyl, cyclohexen-1-yl, cyclopropylethynyl, methoxy, trifluoromethoxy, neopentyloxy, methylthio, allyloxy, cyclopropylmethoxy, 2-(cyclopropyl)ethoxy, cyclopentyloxy, cyclopentylmethoxy, benzyloxy, hydroxyl, aminocarbonyl, methoxycarbonyl, phenyl, phenoxy, benzyloxy, and heteroaryloxy, wherein the phenyl phenoxy, benzyloxy and heteroaryloxy groups are optionally substituted with 1 to 3 substituents independently selected from fluorine, chlorine, cyano, methyl, trifluoromethyl, and aminocarbonyl;

R² is hydrogen, methyl, ethyl, propyl, butyl, hexyl, 5-pentenyl, 3,3,3-trifluoropropyl, 4,4-difluoropentyl, 3-(cyclopropyl)propyl, 4-(cyclopropyl)butyl, 3-hydroxypropyl, 4-hydroxybutyl, 4-hydroxypentyl, 4-hydroxyhexyl, 5-hydroxyhexyl, 2-hydroxyethoxy, 5-oxohexyl, 3-ethoxypropyl, 4-methoxybutyl, 4-ethoxybutyl, butoxy, hexyloxy, 2-(ethoxy)-ethoxy, 3-methoxypropoxy, 3-ethoxypropoxy, 3-propoxypropoxy, 2-cyclopropylethoxy, (2-(methoxy)ethoxy)methyl, 3-(2,2,2-trifluoroethylamino)propyl, 3-(formylamino)propyl, 3-(acetylamino)propyl, 3-(propionyl-amino)propyl, 3-(butanoylamino)propyl, 3-((2-methoxypropionyl)amino)propyl, 3-(cyclopropane-carbonylamino)propyl, 3-(trifluoroacetylamino)propyl, 3-(methoxycarbonylamino)propyl, 3-(ethoxycarbonylamino)propyl, 2-(methoxycarbonylamino)ethoxy, 2-(ethoxycarbonylamino)-ethoxy, 3-(methylaminocarbonylamino)propyl, 3-(dimethylaminocarbonyl-amino)propyl, 3-(aminocarbonyl)propyl, 3-(methylaminocarbonyl)propyl, 3-(ethylamino-carbonyl)propyl, 2-(acetylamino)ethoxy, 2-(propionylamino)ethoxy, aminocarbonylmethoxy, methylamino-carbonylmethoxy, ethylaminocarbonylmethoxy, propylaminocarbonylmethoxy, 2-(methylaminocarbonyl)ethoxy, 2-(ethylaminocarbonyl)ethoxy, 2-(propylaminocarbonyl)ethoxy, (2-(methoxy)ethoxy)carbonylamino, methoxymethylcarbonylaminomethyl, or 3-(aminosulfonylamino)propyl, additional values for R² are 2-(methoxy)-ethoxy, 4-(methoxy)-butoxy;

R³ is H, F, OH, methoxy, acetylamino, propionylamino, (2-methylpropionyl)amino, or butanoylamino, provided that when R³ is F or OH, R² is not butoxy, hexyloxy, 2-(ethoxy)ethoxy, 3-methoxypropoxy, 3-ethoxypropoxy, 3-propoxypropoxy, 2-cyclopropylethoxy, 2-2-(methoxycarbonylamino)ethoxy, 2-(ethoxycarbonylamino)ethoxy, (acetylamino)ethoxy, 2-(propionylamino)ethoxy, aminocarbonylmethoxy, methylaminocarbonylmethoxy, ethylaminocarbonylmethoxy, propylaminocarbonylmethoxy, 2-(methylaminocarbonyl)ethoxy, 2-(ethylaminocarbonyl)ethoxy, 2-(propylaminocarbonyl)ethoxy, or (2-(methoxy)ethoxy)-carbonylamino;

A⁴ is CH₂ and A⁵ is CH₂; or A⁴ is O and A⁵ is CH₂; or A⁴ is CH₂ and A⁵ is a single bond;

Q is Q1, Q2, Q4, Q5, Q6, Q7, Q9, or Q10

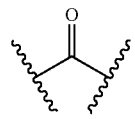
Q1

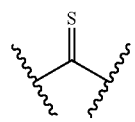
Q2

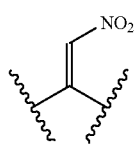
Q4

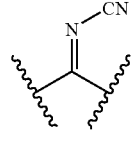
Q5

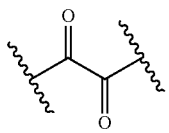
Q6

-continued

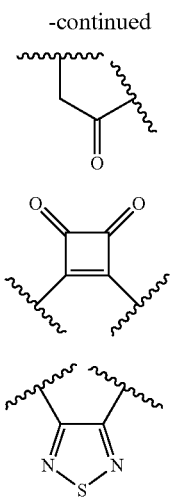

Q7

Q9

Q10 wherein A and N are attached to the truncated bonds

R⁵ is hydrogen, methyl, isobutyl, t-butylmethyl, 2,2,2-trifluoroethyl, 2-(trifluoromethyl)propyl, cyclopentylmethyl, cyclohexylmethyl, (3,3-difluorocyclobutyl)methyl, 3,4-difluorocyclopentyl)methyl, 4,4-difluoro-cyclohexylmethyl, (4-methylcyclohexyl)methyl, tert-butoxymethyl, (4-tetrahydropyranyl)methyl, benzyl, (1-fluorocyclohexyl)methyl, (4-fluorocyclohexyl)methyl, 1-hydroxy-2-methylpropyl, (cyclopentyl)(hydroxy)methyl, (cyclohexyl)(hydroxy)methyl, (cycloheptyl)(hydroxy)methyl, (1-hydroxycyclohexyl)methyl, (4-hydroxycyclohexyl)methyl, (4-hydroxy-4-methylcyclohexyl)methyl, (3-noradamantyl)(hydroxy)methyl, 2-methoxy-2-methylpropyl, 2,2-dimethyl-3-methoxypropyl, (3-tetrahydrofuryl)methyl, (3-tetrahydropyranyl)methyl or (4-tetrahydropyranyl)methyl;

R⁹ is methyl, ethyl, propyl, butyl, isobutyl, t-butyl, pentyl, isopentyl, aminocarbonylmethyl, an additional value for R⁹ is —H;

or an enantiomer, diastereomer or salt thereof.

Another embodiment of the invention is a compound of Formula Ia wherein R⁵ is R⁵ is methyl, isobutyl, t-butylmethyl, 2,2,2-trifluoroethyl, 2-(trifluoromethyl)propyl, cyclopentylmethyl, cyclohexylmethyl, (3,3-difluorocyclobutyl)methyl, 4,4-difluoro-cyclohexylmethyl, (4-methylcyclohexyl)methyl, tert-butoxymethyl, (4-tetrahydropyranyl)methyl, benzyl, (1-fluorocyclohexyl)methyl, (4-fluorocyclohexyl)methyl, 1-hydroxy-2-methylpropyl, (cyclopentyl)(hydroxy)methyl, (cyclohexyl)(hydroxy)methyl, (cycloheptyl)(hydroxy)methyl, (1-hydroxycyclohexyl)methyl, (4-hydroxycyclohexyl)methyl, (4-hydroxy-4-methylcyclohexyl)methyl, (3-noradamantyl)(hydroxy)methyl, 2-methoxy-2-methylpropyl or 2,2-dimethyl-3-methoxypropyl; R⁹ is methyl, ethyl, propyl, butyl, isobutyl, pentyl, isopentyl, aminocarbonylmethyl, an additional value for R⁹ is —H; and the remainder of the variables are as just described in the immediately preceding variables. Enantiomers, diastereomers and salts thereof are also included.

Another embodiment of the invention is a compound of Formula Ia, wherein R¹ is a) isopropyl; or b) phenyl, optionally substituted with 1 to 3 substituents independently selected from:

fluorine, chlorine, cyano, methyl and phenoxy, wherein the phenoxy group is optionally substituted with 1 to 3 substituents independently selected from fluorine, chlorine, methyl, and ethyl;

R² is hydrogen, butoxy, hexyloxy, 2-(methoxy)ethoxy, 3-(methoxy)propoxy, 4-(methoxy)butoxy, 4-(methoxy)butyl, 3-(methoxycarbonylamino)propyl, or 2-(methoxycarbonylamino)ethoxy;

R³ is H or OH; provided that when R³ is OH, R² is not 2-(methoxy)ethoxy, 3-(methoxy)propoxy, 4-(methoxy)butoxy, or 2-(methoxycarbonylamino)ethoxy;

A⁴ is CH₂ and A⁵ is CH₂; or A⁴ is O and A⁵ is CH₂; or A⁴ is CH₂ and A⁵ is a single bond;

Q is Q1, Q6, Q7, or Q9;

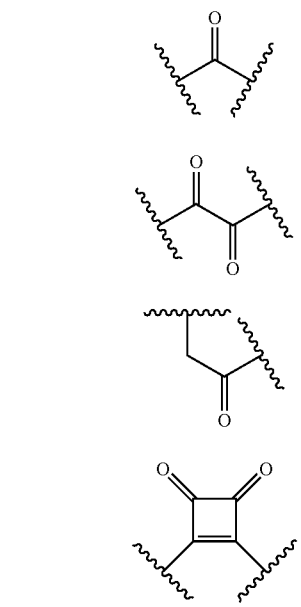

Q1

Q6

Q7

Q9

R⁵ is hydrogen, isobutyl, cyclohexylmethyl, (3-tetrahydropyranyl)methyl or (4-tetrahydropyranyl)methyl;

R⁹ is hydrogen, methyl, t-butyl, 4-cyanobenzyl, or 3,5-dimethoxybenzyl;

or an enantiomer, diastereomer or salt thereof.

Another embodiment of the invention is a compound of Formula Ia defined by Formula Ib:

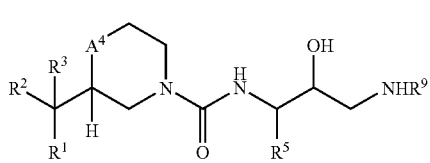

Ib wherein R¹, R², R³, A⁴, R⁵, and R⁹ are as defined for Formula Ia, or an enantiomer, diastereomer or salt thereof.

Another embodiment of the invention is a compound of Formula Ic with the stereochemical configuration shown:

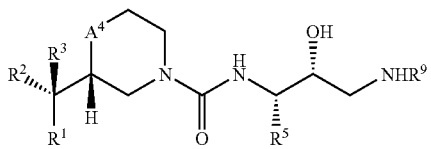

wherein $R^1$, $R^2$, $R^3$, $A^4$, $R^5$ and $R^9$ are as defined for formula Ia, and the salts thereof.

Another embodiment of the invention is each of the following compounds and their enantiomers, diastereomers, and salts:

I-1   N-(3-amino-2-hydroxypropyl)-3-(1-(2-(2-ethylphenoxy)phenyl)-1-hydroxy-5-methoxypentyl)piperidine-1-carboxamide
I-2   3-(4-amino-1-cyclohexyl-3-hydroxybutan-2-ylamino)-4-(3-((3-methoxypropoxy)(phenyl)methyl)piperidin-1-yl)cyclobut-3-ene-1,2-dione
I-3   3-(1-(3-chlorophenyl)-1-hydroxy-5-methoxypentyl)-N-(1-cyclohexyl-3-hydroxy-4-(methylamino)butan-2-yl)piperidine-1-carboxamide
I-4   N-(1-cyclohexyl-3-hydroxy-4-(methylamino)butan-2-yl)-3-(1-(2,3-difluorophenyl)-1-hydroxy-5-methoxypentyl)piperidine-1-carboxamide
I-5   N-(4-amino-1-cyclohexyl-3-hydroxybutan-2-yl)-3-(1-(3-chloro-2-fluorophenyl)-1-hydroxy-5-methoxypentyl)piperidine-1-carboxamide
I-5   N-(4-amino-1-cyclohexyl-3-hydroxybutan-2-yl)-3-(1-(3-chloro-2-fluorophenyl)-1-hydroxy-5-methoxypentyl)piperidine-1-carboxamide
I-6   N-(4-amino-1-cyclohexyl-3-hydroxybutan-2-yl)-2-(1-(3-chloro-2-fluorophenyl)-1-hydroxy-5-methoxypentyl)morpholine-4-carboxamide
I-7   methyl 4-(1-(4-amino-1-cyclohexyl-3-hydroxybutan-2-ylcarbamoyl)piperidin-3-yl)-4-(3-chlorophenyl)-4-hydroxybutylcarbamate
I-8   3-(1-(3-chloro-2-fluorophenyl)-1-hydroxy-5-methoxypentyl)-N-(1-cyclohexyl-3-hydroxy-4-(methylamino)butan-2-yl)piperidine-1-carboxamide
I-9   2-(1-(3-chloro-2-fluorophenyl)-1-hydroxy-5-methoxypentyl)-N-(1-cyclohexyl-3-hydroxy-4-(methylamino)butan-2-yl)morpholine-4-carboxamide
I-10  N-(4-(4-cyanobenzylamino)-1-cyclohexyl-3-hydroxybutan-2-yl)-3-((3-methoxypropoxy)(phenyl)methyl)piperidine-1-carboxamide
I-11  3-(1-cyclohexyl-4-(3,5-dimethoxybenzylamino)-3-hydroxybutan-2-ylamino)-4-(3-(hydroxy(phenyl)methyl)piperidin-1-yl)cyclobut-3-ene-1,2-dione
I-12  N-(1-cyclohexyl-4-(3,5-dimethoxybenzylamino)-3-hydroxybutan-2-yl)-2-(3-((2-methoxyethoxy)(phenyl)methyl)pyrrolidin-1-yl)-2-oxoacetamide
I-13  N-(1-cyclohexyl-4-(3,5-dimethoxybenzylamino)-3-hydroxybutan-2-yl)-2-(3-((3-methoxypropoxy)(phenyl)methyl)pyrrolidin-1-yl)-2-oxoacetamide
I-14  N-(1-cyclohexyl-4-(3,5-dimethoxybenzylamino)-3-hydroxybutan-2-yl)-2-(3-((3-methoxypropoxy)(phenyl)methyl)piperidin-1-yl)acetamide
I-15  4-((4-cyclohexyl-2-hydroxy-3-(2-(3-((3-methoxypropoxy)(phenyl)methyl)piperidin-1-yl)-3,4-dioxocyclobut-1-enylamino)butylamino)methyl)benzonitrile
I-15  4-((4-cyclohexyl-2-hydroxy-3-(2-(3-((3-methoxypropoxy)(phenyl)methyl)piperidin-1-yl)-3,4-dioxocyclobut-1-enylamino)butylamino)methyl)benzonitrile
I-16  3-(1-cyclohexyl-4-(3,5-dimethoxybenzylamino)-3-hydroxybutan-2-ylamino)-4-(3-(1-(3-methoxypropoxy)-2-methylpropyl)piperidin-1-yl)cyclobut-3-ene-1,2-dione
I-17  N-(1-cyclohexyl-4-(3,5-dimethoxybenzylamino)-3-hydroxybutan-2-yl)-2-(3-((4-methoxybutoxy)(phenyl)methyl)pyrrolidin-1-yl)-2-oxoacetamide
I-18  N-(1-cyclohexyl-4-(3,5-dimethoxybenzylamino)-3-hydroxybutan-2-yl)-2-(3-(1-hydroxy-5-methoxy-1-phenylpentyl)pyrrolidin-1-yl)-2-oxoacetamide
I-19  4-((4-cyclohexyl-3-(2-(3-(hexyloxy(phenyl)methyl)piperidin-1-yl)-3,4-dioxocyclobut-1-enylamino)-2-hydroxybutylamino)methyl)benzonitrile
I-20  4-((4-cyclohexyl-2-hydroxy-3-(2-(3-((4-methoxybutoxy)(phenyl)methyl)piperidin-1-yl)-3,4-dioxocyclobut-1-enylamino)butylamino)methyl)benzonitrile
I-21  3-(3-(butoxy(phenyl)methyl)piperidin-1-yl)-4-(1-cyclohexyl-4-(3,5-dimethoxybenzylamino)-3-hydroxybutan-2-ylamino)cyclobut-3-ene-1,2-dione
I-22  3-(1-cyclohexyl-4-(3,5-dimethoxybenzylamino)-3-hydroxybutan-2-ylamino)-4-(3-((2-methoxyethoxy)(phenyl)methyl)piperidin-1-yl)cyclobut-3-ene-1,2-dione
I-23  3-(1-cyclohexyl-4-(3,5-dimethoxybenzylamino)-3-hydroxybutan-2-ylamino)-4-(3-((3-methoxypropoxy)(phenyl)methyl)piperidin-1-yl)cyclobut-3-ene-1,2-dione
I-24  methyl 2-((1-(4-amino-1-cyclohexyl-3-hydroxybutan-2-ylcarbamoyl)piperidin-3-yl)(3-chlorophenyl)methoxy)ethylcarbamate
I-25  methyl 2-((3-chlorophenyl)(1-(1-cyclohexyl-3-hydroxy-4-(methylamino)butan-2-ylcarbamoyl)piperidin-3-yl)methoxy)ethylcarbamate
I-26  methyl 2-((1-(1-cyclohexyl-3-hydroxy-4-(methylamino)butan-2-ylcarbamoyl)piperidin-3-yl)(3-fluorophenyl)methoxy)ethylcarbamate
I-27  methyl 2-((3-chlorophenyl)(4-(1-cyclohexyl-3-hydroxy-4-(methylamino)butan-2-ylcarbamoyl)morpholin-2-yl)methoxy)ethylcarbamate

| | -continued |
|---|---|
| I-28 | methyl 2-((3-chlorophenyl)(4-(3-hydroxy-4-(methylamino)-1-(tetrahydro-2H-pyran-4-yl)butan-2-ylcarbamoyl)morpholin-2-yl)methoxy)ethylcarbamate |
| I-29 | methyl 2-((1-(1-(tert-butylamino)-2-hydroxy-5-methylhexan-3-ylcarbamoyl)piperidin-3-yl)(3-chlorophenyl)methoxy)ethylcarbamate |

Another embodiment of the invention is each of the compounds listed below and their salts, especially their pharmaceutically acceptable salts:

I-1a 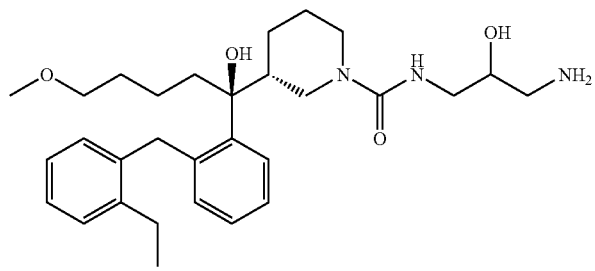 (R)-N-((R)-3-amino-2-hydroxypropyl)-3-((S)-1-(2-(2-ethylphenoxy)phenyl)-1-hydroxy-5-methoxypentyl)piperidine-1-carboxamide I-2a 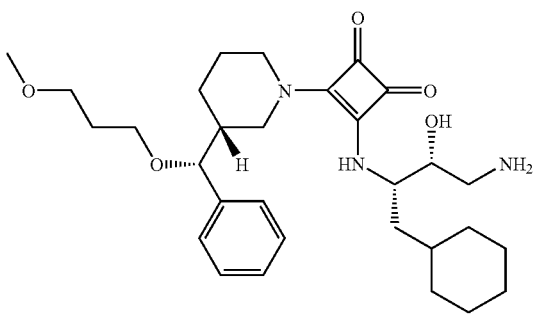 3-((2S,3R)-4-amino-1-cyclohexyl-3-hydroxybutan-2-ylamino)-4-((R)-3-((R)-(3-methoxypropoxy)(phenyl)methyl)piperidin-1-yl)cyclobut-3-ene-1,2-dione I-3a 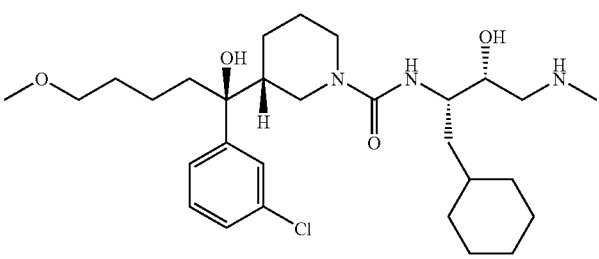 (R)-3-((S)-1-(3-chlorophenyl)-1-hydroxy-5-methoxypentyl)-N-((2S,3R)-1-cyclohexyl-3-hydroxy-4-(methylamino)butan-2-yl)piperidine-1-carboxamide I-4a 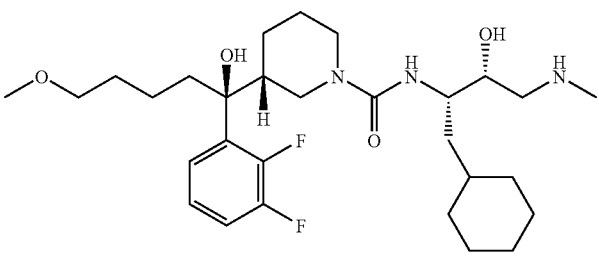 (R)-N-((2S,3R)-1-cyclohexyl-3-hydroxy-4-(methylamino)butan-2-yl)-3-((S)-1-(2,3-difluorophenyl)-1-hydroxy-5-methoxypentyl)piperidine-1-carboxamide -continued I-5a 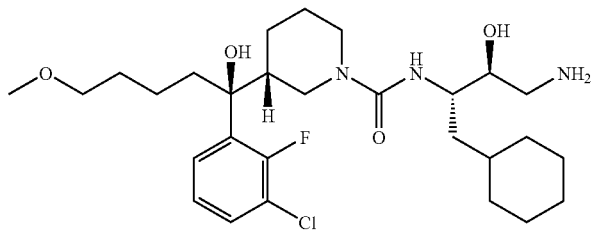 (R)-N-((2S,3S)-4-amino-1-cyclohexyl-3-hydroxybutan-2-yl)-3-((S)-1-(3-chloro-2-fluorophenyl)-1-hydroxy-5-methoxypentyl)piperidine-1-carboxamide I-5b 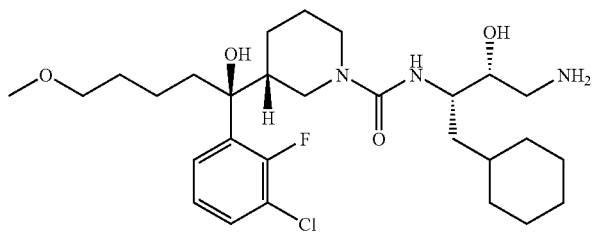 (R)-N-((2S,3R)-4-amino-1-cyclohexyl-3-hydroxybutan-2-yl)-3-((S)-1-(3-chloro-2-fluorophenyl)-1-hydroxy-5-methoxypentyl)piperidine-1-carboxamide I-6a 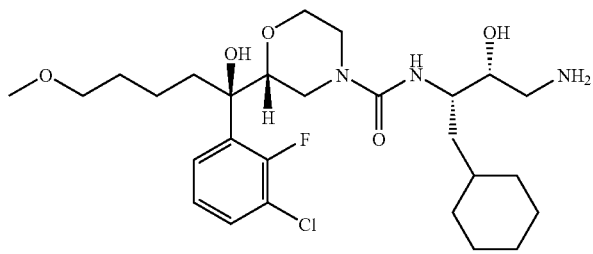 (R)-N-((2S,3R)-4-amino-1-cyclohexyl-3-hydroxybutan-2-yl)-2-((R)-1-(3-chloro-2-fluorophenyl)-1-hydroxy-5-methoxypentyl)morpholine-4-carboxamide I-6b 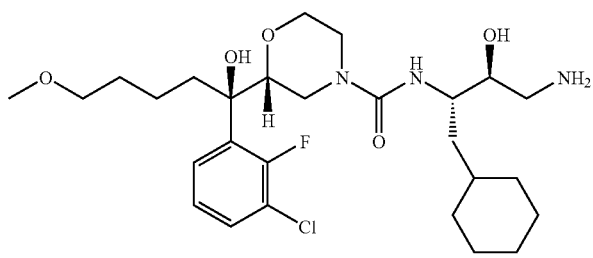 (R)-N-((2S,3S)-4-amino-1-cyclohexyl-3-hydroxybutan-2-yl)-2-((R)-1-(3-chloro-2-fluorophenyl)-1-hydroxy-5-methoxypentyl)morpholine-4-carboxamide I-7a 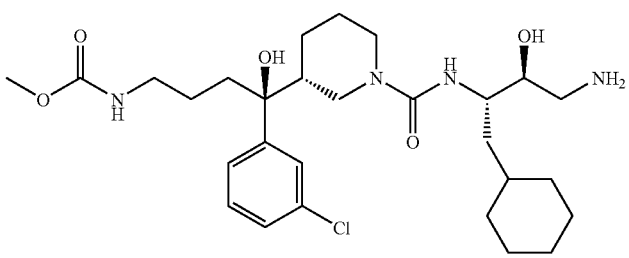 methyl (S)-4-((R)-1-((2S,3S)-4-amino-1-cyclohexyl-3-hydroxybutan-2-ylcarbamoyl)piperidin-3-yl)-4-(3-chlorophenyl)-4-hydroxybutylcarbamate I-7b 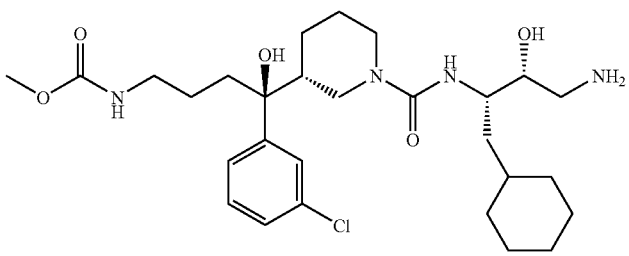 methyl (S)-4-((R)-1-((2S,3R)-4-amino-1-cyclohexyl-3-hydroxybutan-2-ylcarbamoyl)piperidin-3-yl)-4-(3-chlorophenyl)-4-hydroxybutylcarbamate

| | | |
|---|---|---|
| I-8a | 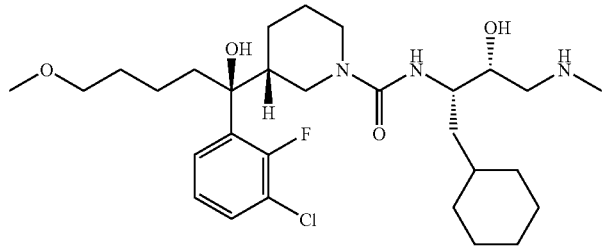 | (R)-3-((S)-1-(3-chloro-2-fluorophenyl)-1-hydroxy-5-methoxypentyl)-N-((2S,3R)-1-cyclohexyl-3-hydroxy-4-(methylamino)butan-2-yl)piperidine-1-carboxamide |
| I-9a | 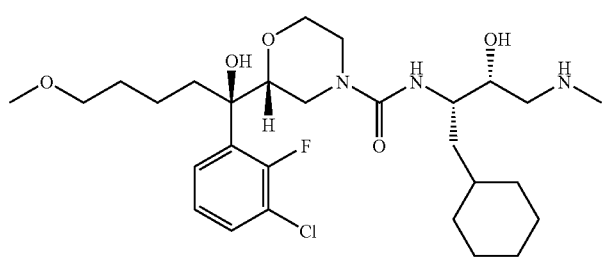 | (R)-2-((R)-1-(3-chloro-2-fluorophenyl)-1-hydroxy-5-methoxypentyl)-N-((2S,3R)-1-cyclohexyl-3-hydroxy-4-(methylamino)butan-2-yl)morpholine-4-carboxamide |
| I-10a | 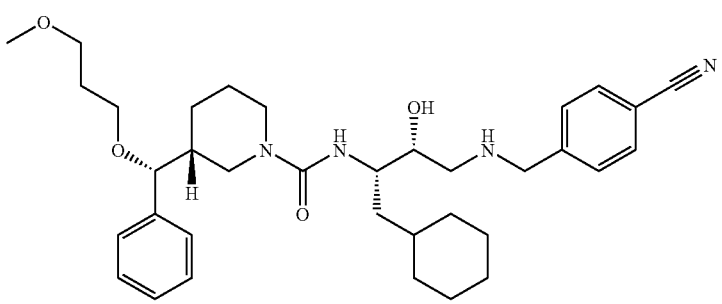 | (R)-N-((2S,3R)-4-(4-cyanobenzylamino)-1-cyclohexyl-3-hydroxybutan-2-yl)-3-((R)-(3-methoxypropoxy)(phenyl)methyl)piperidine-1-carboxamide |
| I-11a | 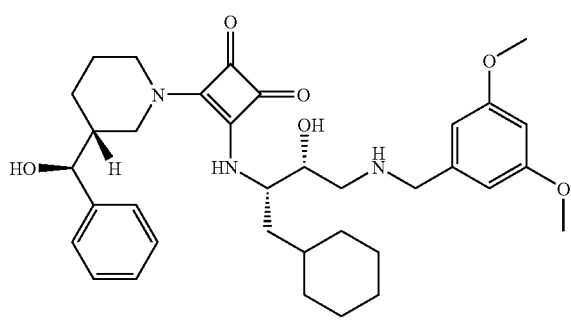 | 3-((2S,3R)-1-cyclohexyl-4-(3,5-dimethoxybenzylamino)-3-hydroxybutan-2-ylamino)-4-((R)-3-((S)-hydroxy(phenyl)methyl)piperidin-1-yl)cyclobut-3-ene-1,2-dione |
| I-12a | 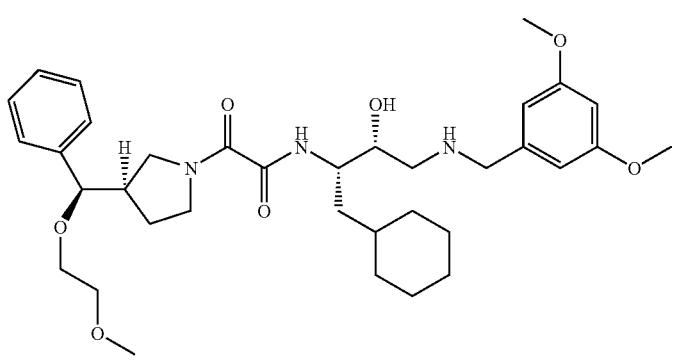 | N-((2S,3R)-1-cyclohexyl-4-(3,5-dimethoxybenzylamino)-3-hydroxybutan-2-yl)-2-((R)-3-((R)-(2-methoxyethoxy)(phenyl)methyl)pyrrolidin-1-yl)-2-oxoacetamide |

-continued

I-13a 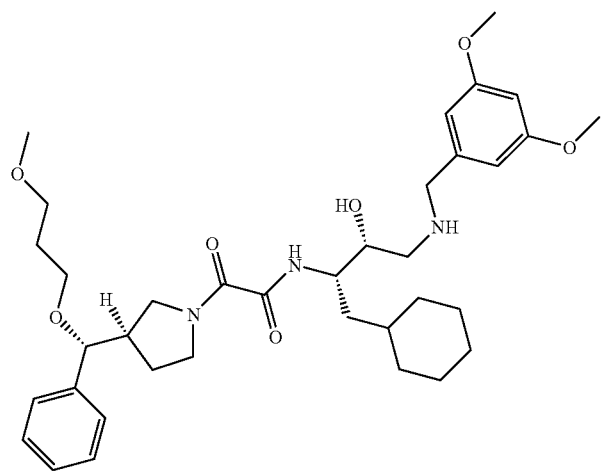
N-((2S,3R)-1-cyclohexyl-4-(3,5-dimethoxybenzylamino)-3-hydroxybutan-2-yl)-2-((R)-3-((R)-(3-methoxypropoxy)(phenyl)methyl)pyrrolidin-yl)-2-oxoacetamide I-14a 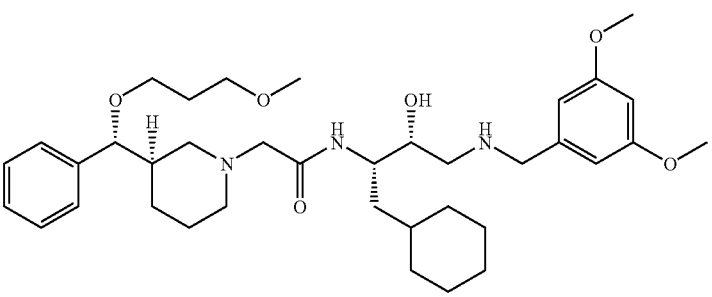
N-((2S,3R)-1-cyclohexyl-4-(3,5-dimethoxybenzylamino)-3-hydroxybutan-2-yl)-2-((R)-3-((R)-(3-methoxypropoxy)(phenyl)methyl)piperidin-1-yl)acetamide I-15a 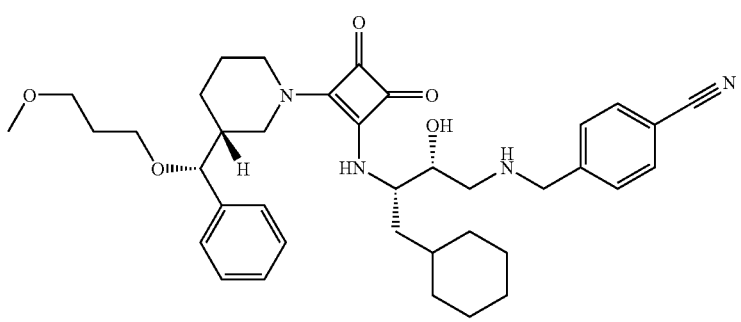
4-(((2R,3S)-4-cyclohexyl-2-hydroxy-3-(2-((R)-3-((R)-(3-methoxypropoxy)(phenyl)methyl)piperidin-1-yl)-3,4-dioxocyclobut-1-enylamino)butylamino)methyl)benzonitrile I-15b 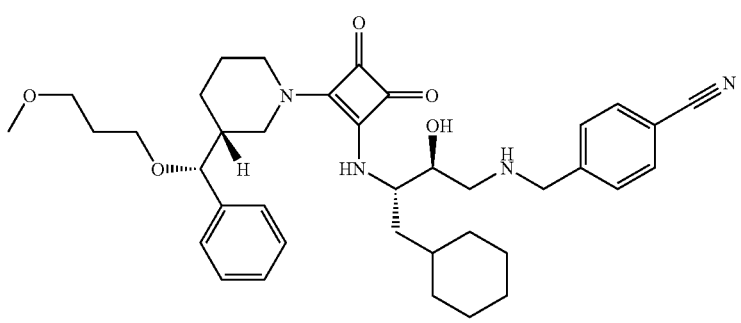
4-(((2S,3S)-4-cyclohexyl-2-hydroxy-3-(2-((R)-3-((R)-(3-methoxypropoxy)(phenyl)methyl)piperidin-1-yl)-3,4-dioxocyclobut-1-enylamino)butylamino)methyl)benzonitrile

| | | |
|---|---|---|
| I-16a | 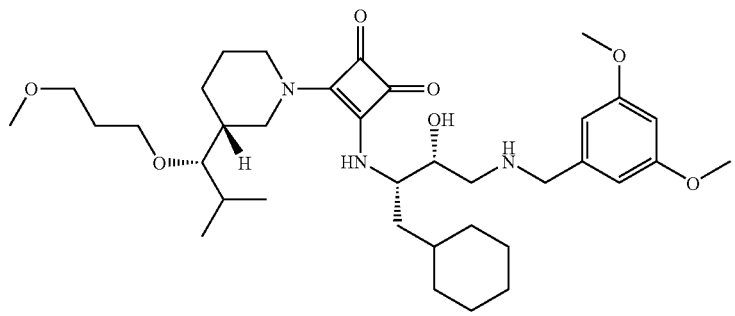 | 3-((2S,3R)-1-cyclohexyl-4-(3,5-dimethoxybenzylamino)-3-hydroxybutan-2-ylamino)-4-((R)-3-((S)-1-(3-methoxypropoxy)-2-methylpropyl)piperidin-1-yl)cyclobut-3-ene-1,2-dione |
| I-17a | 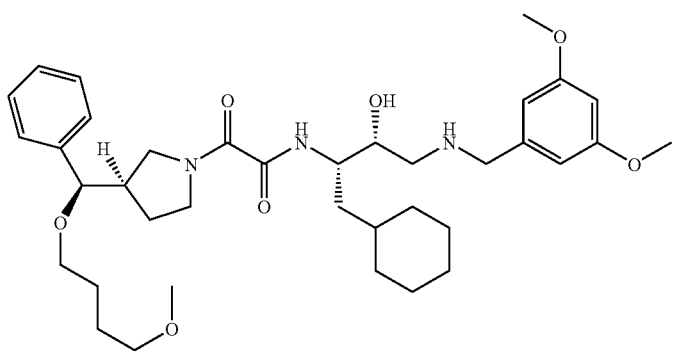 | N-((2S,3R)-1-cyclohexyl-4-(3,5-dimethoxybenzylamino)-3-hydroxybutan-2-yl)-2-((R)-3-((R)-(4-methoxybutoxy)(phenyl)methyl)pyrrolidin-1-yl)-2-oxoacetamide |
| I-18a | 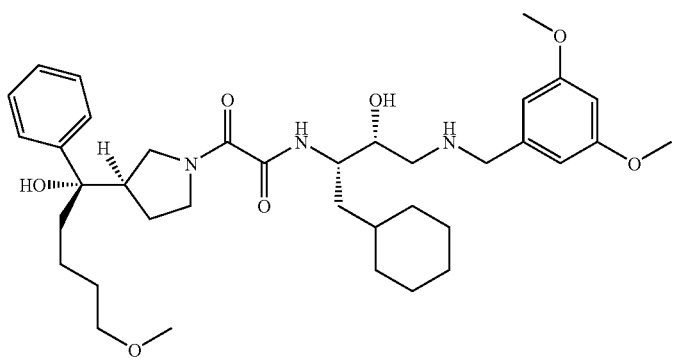 | N-((2S,3R)-1-cyclohexyl-4-(3,5-dimethoxybenzylamino)-3-hydroxybutan-2-yl)-2-((R)-3-((S)-1-hydroxy-5-methoxy-1-phenylpentyl)pyrrolidin-1-yl)-2-oxoacetamide |
| I-19a | 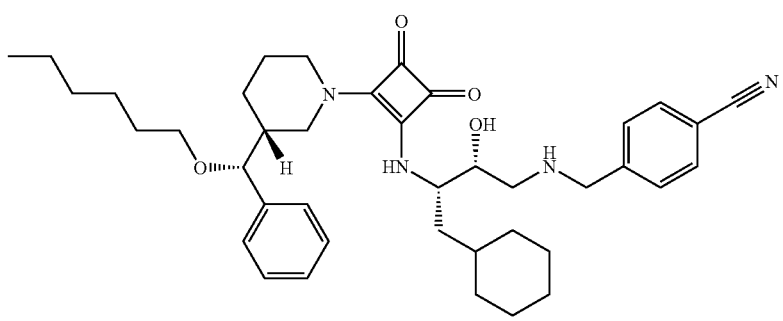 | 4-(((2R,3S)-4-cyclohexyl-3-(2-((R)-3-((R)-hexyloxy(phenyl)methyl)piperidin-1-yl)-3,4-dioxocyclobut-1-enylamino)-2-hydroxybutylamino)methyl)benzonitrile |

| | | |
|---|---|---|
| I-20a | 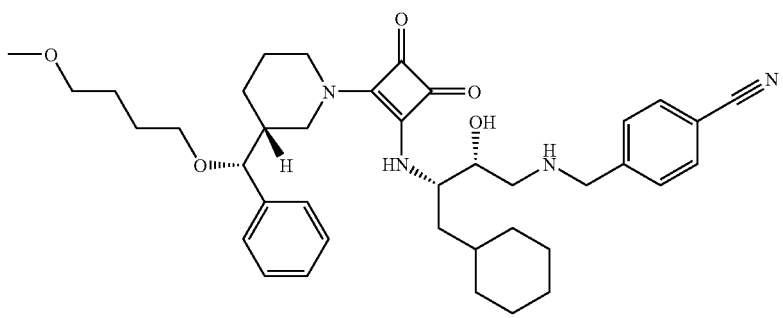 | 4-(((2R,3S)-4-cyclohexyl-2-hydroxy-3-(2-((R)-3-((R)-(4-methoxybutoxy)(phenyl)methyl)piperidin-1-yl)-3,4-dioxocyclobut-1-enylamino)butylamino)methyl)benzonitrile |
| I-21a | 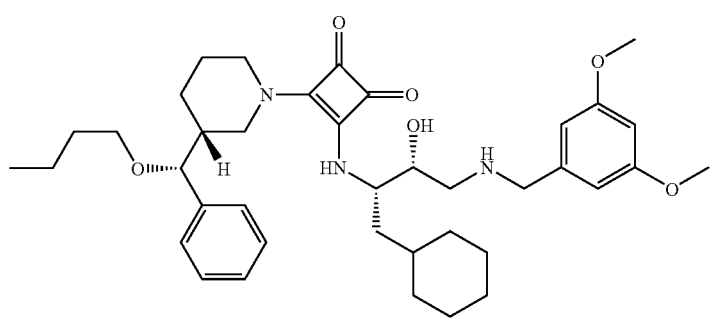 | 3-((R)-3-((R)-butoxy(phenyl)methyl)piperidin-1-yl)-4-((2S,3R)-1-cyclohexyl-4-(3,5-dimethoxybenzylamino)-3-hydroxybutan-2-ylamino)cyclobut-3-ene-1,2-dione |
| I-22a | 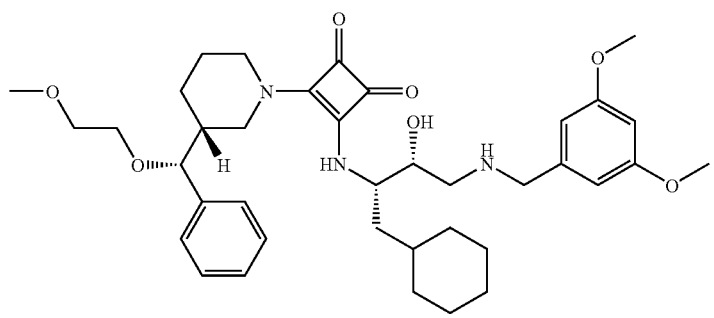 | 3-((2S,3R)-1-cyclohexyl-4-(3,5-dimethoxybenzylamino)-3-hydroxybutan-2-ylamino)-4-((R)-3-((R)-(2-methoxyethoxy)(phenyl)methyl)piperidin-1-yl)cyclobut-3-ene-1,2-dione |
| I-23a | 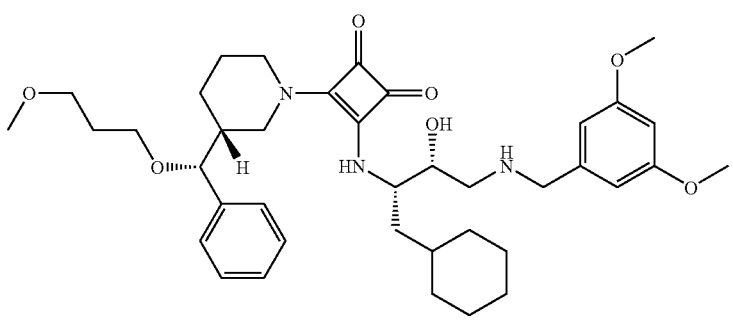 | 3-((2S,3R)-1-cyclohexyl-4-(3,5-dimethoxybenzylamino)-3-hydroxybutan-2-ylamino)-4-((R)-3-((R)-(3-methoxypropoxy)(phenyl)methyl)piperidin-1-yl)cyclobut-3-ene-1,2-dione |
| I-24a | 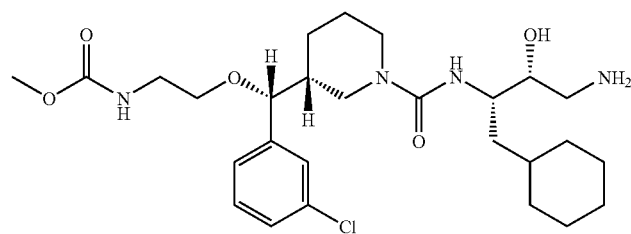 | methyl 2-((R)-((R)-1-((2S,3R)-4-amino-1-cyclohexyl-3-hydroxybutan-2-ylcarbamoyl)piperidin-3-yl)(3-chlorophenyl)methoxy)ethylcarbamate |

-continued

| | | |
|---|---|---|
| I-25a | 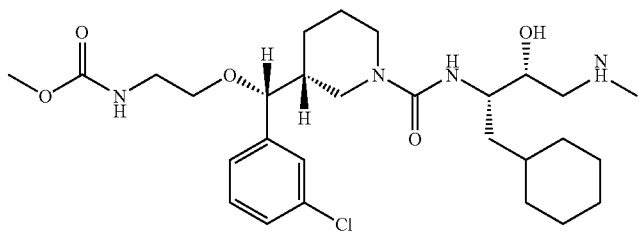 | methyl 2-((R)-(3-chlorophenyl)((R)-1-((2S,3R)-1-cyclohexyl-3-hydroxy-4-(methylamino)butan-2-ylcarbamoyl)piperidin-3-yl)methoxy)ethylcarbamate |
| I-26a | 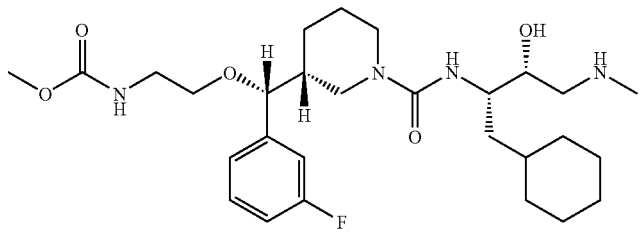 | methyl 2-((R)-((R)-1-((2S,3R)-1-cyclohexyl-3-hydroxy-4-(methylamino)butan-2-ylcarbamoyl)piperidin-3-yl)(3-fluorophenyl)methoxy)ethylcarbamate |
| I-27a | 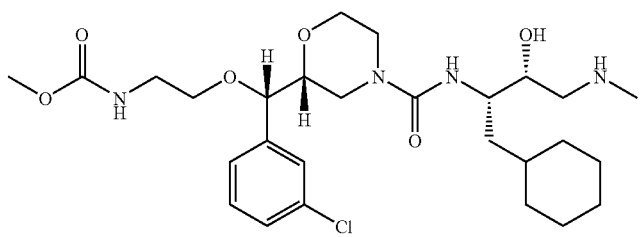 | methyl 2-((S)-(3-chlorophenyl)((R)-4-((2S,3R)-1-cyclohexyl-3-hydroxy-4-(methylamino)butan-2-ylcarbamoyl)morpholin-2-yl)methoxy)ethylcarbamate |
| I-28a | 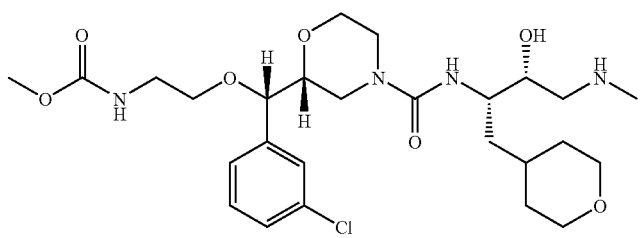 | methyl 2-((S)-(3-chlorophenyl)((R)-4-((2S,3R)-3-hydroxy-4-(methylamino)-1-(tetrahydro-2H-pyran-4-yl)butan-2-ylcarbamoyl)morpholin-2-yl)methoxy)ethylcarbamate |
| I-29a | 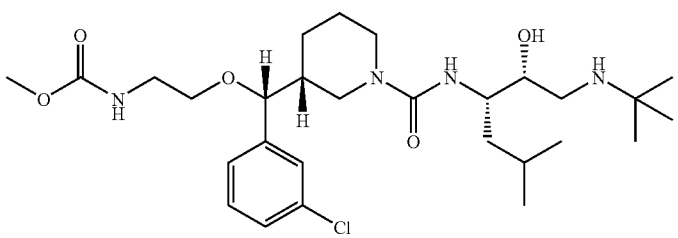 | methyl 2-((R)-((R)-1-((2R,3S)-1-(tert-butylamino)-2-hydroxy-5-methylhexan-3-ylcarbamoyl)piperidin-3-yl)(3-chlorophenyl)methoxy)ethylcarbamate |

The following, including pharmaceutically acceptable salts thereof, are preferred compounds of Formula I.

I-3a  (R)-3-((S)-1-(3-chlorophenyl)-1-hydroxy-5-methoxypentyl)-N-((2S,3R)-1-cyclohexyl-3-hydroxy-4-(methylamino)butan-2-yl)piperidine-1-carboxamide I-4a  (R)—N-((2S,3R)-1-cyclohexyl-3-hydroxy-4-(methylamino)butan-2-yl)-3-((S)-1-(2,3-difluorophenyl)-1-hydroxy-5-methoxypentyl)piperidine-1-carboxamide I-5b  (R)—N-((2S,3R)-4-amino-1-cyclohexyl-3-hydroxybutan-2-yl)-3-((S)-1-(3-chloro-2-fluorophenyl)-1-hydroxy-5-methoxypentyl)piperidine-1-carboxamide I-5a  (R)—N-((2S,3S)-4-amino-1-cyclohexyl-3-hydroxybutan-2-yl)-3-((S)-1-(3-chloro-2-fluorophenyl)-1-hydroxy-5-methoxypentyl)piperidine-1-carboxamide I-6a  (R)—N-((2S,3R)-4-amino-1-cyclohexyl-3-hydroxybutan-2-yl)-2-((R)-1-(3-chloro-2-fluorophenyl)-1-hydroxy-5-methoxypentyl)morpholine-4-carboxamide I-7b  methyl (S)-4-((R)-1-((2S,3S)-4-amino-1-cyclohexyl-3-hydroxybutan-2-ylcarbamoyl)piperidin-3-yl)-4-(3-chlorophenyl)-4-hydroxybutylcarbamate I-7a  methyl (S)-4-((R)-1-((2S,3S)-4-amino-1-cyclohexyl-3-hydroxybutan-2-ylcarbamoyl)piperidin-3-yl)-4-(3-chlorophenyl)-4-hydroxybutylcarbamate I-8a  (R)-3-((S)-1-(3-chloro-2-fluorophenyl)-1-hydroxy-5-methoxypentyl)-N-((2S,3R)-1-cyclohexyl-3-hydroxy-4-(methylamino)butan-2-yl)piperidine-1-carboxamide -continued

| | |
|---|---|
| I-9a | (R)-2-((R)-1-(3-chloro-2-fluorophenyl)-1-hydroxy-5-methoxypentyl)-N-((2S,3R)-1-cyclohexyl-3-hydroxy-4-(methylamino)butan-2-yl)morpholine-4-carboxamide |
| I-15a | 4-(((2R,3S)-4-cyclohexyl-2-hydroxy-3-(2-((R)-3-((R)-(3-methoxypropoxy)(phenyl)methyl)piperidin-1-yl)-3,4-dioxocyclobut-1-enylamino)butylamino)methyl)benzonitrile |
| I-20a | 4-(((2R,3S)-4-cyclohexyl-2-hydroxy-3-(2-((R)-3-((R)-(4-methoxybutoxy)(phenyl)methyl)piperidin-1-yl)-3,4-dioxocyclobut-1-enylamino)butylamino)methyl)benzonitrile |
| I-23a | 3-((2S,3R)-1-cyclohexyl-4-(3,5-dimethoxybenzylamino)-3-hydroxybutan-2-ylamino)-4-((R)-3-((R)-(3-methoxypropoxy)(phenyl)methyl)piperidin-1-yl)cyclobut-3-ene-1,2-dione |
| I-24a | methyl 2-((R)-((R)-1-((2S,3R)-4-amino-1-cyclohexyl-3-hydroxybutan-2-ylcarbamoyl)piperidin-3-yl)(3-chlorophenyl)methoxy)ethylcarbamate |
| I-25a | methyl 2-((R)-(3-chlorophenyl)((R)-1-((2S,3R)-1-cyclohexyl-3-hydroxy-4-(methylamino)butan-2-ylcarbamoyl)piperidin-3-yl)methoxy)ethylcarbamate |
| I-26a | methyl 2-((R)-((R)-1-((2S,3R)-1-cyclohexyl-3-hydroxy-4-(methylamino)butan-2-ylcarbamoyl)piperidin-3-yl)(3-fluorophenyl)methoxy)ethylcarbamate |
| I-27a | methyl 2-((S)-(3-chlorophenyl)((R)-4-((2S,3R)-1-cyclohexyl-3-hydroxy-4-(methylamino)butan-2-ylcarbamoyl)morpholin-2-yl)methoxy)ethylcarbamate |
| I-29a | methyl 2-((R)-((R)-1-((2R,3S)-1-(tert-butylamino)-2-hydroxy-5-methylhexan-3-ylcarbamoyl)piperidin-3-yl)(3-chlorophenyl)methoxy)ethylcarbamate |

The following, including pharmaceutically acceptable salts thereof, are more preferred compounds of Formula I.

| | |
|---|---|
| I-3a | (R)-3-((S)-1-(3-chlorophenyl)-1-hydroxy-5-methoxypentyl)-N-((2S,3R)-1-cyclohexyl-3-hydroxy-4-(methylamino)butan-2-yl)piperidine-1-carboxamide |
| I-5b | (R)—N-((2S,3R)-4-amino-1-cyclohexyl-3-hydroxybutan-2-yl)-3-((S)-1-(3-chloro-2-fluorophenyl)-1-hydroxy-5-methoxypentyl)piperidine-1-carboxamide |
| I-7b | methyl (S)-4-((R)-1-((2S,3R)-4-amino-1-cyclohexyl-3-hydroxybutan-2-ylcarbamoyl)piperidin-3-yl)-4-(3-chlorophenyl)-4-hydroxybutylcarbamate |
| I-8a | (R)-3-((S)-1-(3-chloro-2-fluorophenyl)-1-hydroxy-5-methoxypentyl)-N-((2S,3R)-1-cyclohexyl-3-hydroxy-4-(methylamino)butan-2-yl)piperidine-1-carboxamide |
| I-9a | (R)-2-((R)-1-(3-chloro-2-fluorophenyl)-1-hydroxy-5-methoxypentyl)-N-((2S,2R)-1-cyclohexyl-3-hydroxy-4-(methylamino)butan-2-yl)morpholine-4-carboxamide |
| I-24a | methyl 2-((R)-((R)-1-((2S,3R)-4-amino-1-cyclohexyl-3-hydroxybutan-2-ylcarbamoyl)piperidin-3-yl)(3-chlorophenyl)methoxy)ethylcarbamate |
| I-25a | methyl 2-((R)-(3-chlorophenyl)((R)-1-((2S,3R)-1-cyclohexyl-3-hydroxy-4-(methylamino)butan-2-ylcarbamoyl)piperidin-3-yl)methoxy)ethylcarbamate |
| I-26a | methyl 2-((R)-((R)-1-((2S,3R)-1-cyclohexyl-3-hydroxy-4-(methylamino)butan-2-ylcarbamoyl)piperidin-3-yl)(3-fluorophenyl)methoxy)ethylcarbamate |
| I-27a | methyl 2-((S)-(3-chlorophenyl)((R)-4-((2S,3R)-1-cyclohexyl-3-hydroxy-4-(methylamino)butan-2-ylcarbamoyl)morpholin-2-yl)methoxy)ethylcarbamate |

The following, including pharmaceutically acceptable salts thereof, are highly preferred compounds of Formula I: I-24a, I-25a, I-26a and I-27a.

When any variable (e.g., aryl, heterocyclyl, $R_1$, $R_2$, etc.) occurs more than once in a compound, its definition on each occurrence is independent of any other occurrence.

"Alkyl" means a saturated aliphatic branched or straight-chain mono- or di-valent hydrocarbon radical having the specified number of carbon atoms. Thus, "$(C_1-C_8)$alkyl" means a radical having from 1-8 carbon atoms in a linear or branched arrangement. "$(C_1-C_6)$alkyl" includes methyl, ethyl, propyl, butyl, pentyl, and hexyl.

"Cycloalkyl" means a saturated aliphatic cyclic hydrocarbon radical having the specified number of carbon atoms. Thus, $(C_3-C_7)$cycloalkyl means a radical having from 3-8 carbon atoms arranged in a ring. $(C_3-C_7)$cycloalkyl includes cyclopropyl, cyclobutyl, cyclopentyl, cyclohexyl, and cycloheptyl.

Haloalkyl and halocycloalkyl include mono, poly, and perhaloalkyl groups where the halogens are independently selected from fluorine, chlorine, and bromine Saturated heterocyclic rings are 4-, 5-, 6-, and 7-membered heterocyclic rings containing 1 to 4 heteroatoms independently selected from N, O, and S, and include pyrrolidine, piperidine, tetrahydrofuran, tetrahydropyran, tetrahydrothiophene, tetrahydrothiopyran, isoxazolidine, 1,3-dioxolane, 1,3-dithiolane, 1,3-dioxane, 1,4-dioxane, 1,3-dithiane, 1,4-dithiane, morpholine, thiomorpholine, thiomorpholine 1,1-dioxide, tetrahydro-2H-1,2-thiazine 1,1-dioxide, and isothiazolidine 1,1-dioxide. Oxo substituted saturated heterocyclic rings include tetrahydrothiophene 1-oxide, tetrahydrothiophene 1,1-dioxide, thiomorpholine 1-oxide, thiomorpholine 1,1-dioxide, tetrahydro-2H-1,2-thiazine 1,1-dioxide, and isothiazolidine 1,1-dioxide, pyrrolidin-2-one, piperidin-2-one, piperazin-2-one, and morpholin-2-one.

"Heteroaryl" means a monovalent heteroaromatic monocyclic and polycyclic ring radical containing 1 to 4 heteroatoms independently selected from N, O, and S. Heteroaryl rings include furyl, thienyl, thiophenyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridinyl-N-oxide, pyridazinyl, pyrimidinyl, pyrazinyl, indolizinyl, indolyl, isoindolyl, benzo[b]furyl, benzo[b]thienyl, indazolyl, benzimidazolyl, benzthiazolyl, purinyl, 4H-quinolizinyl, quinolinyl, isoquinolinyl, cinnolinyl, phthalzinyl, quinazolinyl, quinoxalinyl, 1,8-naphthyridinyl, 1,2,3-triazolyl, 1,2,4-triazolyl, 1,3,4-oxadiazolyl, 1,2,5-thiadiazolyl, 1,2,5-thiadiazolyl-1-oxide, 1,2,5-thiadiazolyl-1,1-dioxide, 1,3,4-thiadiazolyl, 1,2,4-triazinyl, 1,3,5-triazinyl, tetrazolyl, and pteridinyl.

Bicyclic heteroaryl rings are bicyclo[4.4.0] and bicyclo[4,3.0] fused ring systems of which at least one ring is aromatic containing 1 to 4 heteroatoms independently selected from N, O, and S, and include indole, quinoline, isoquinoline, quinazoline, benzothiophene, benzofuran, 2,3-dihydrobenzofuran, benzodioxole, benzimidazole, indazole, benzisoxazole, benzoxazole, and benzothiazole.

Bicycloalkyl rings are fused, bridged and spiro ring systems and include bicyclo[1.1.0]butane, bicyclo[1.2.0]pentane, bicyclo[2.2.0]hexane, bicyclo[3.2.0]heptane, bicyclo[3.3.0]octane, bicyclo[4.2.0]octane, bicyclo[2.2.1]heptane, bicyclo[2.2.2]octane, bicyclo[3.2.1]octane, bicyclo[3.2.2]nonane, bicyclo[3.3.1]nonane, bicyclo[3.3.2]decane and bicyclo[3.3.3]undecane, spiro[2.2]pentane, spiro[2.3]hexane, spiro[3.3]heptane, spiro[2.4]heptane, spiro[3.4]octane, and spiro[2.5]octane.

Tricycloalkyl rings are fused, bridged and spiro ring systems and include tricyclo[3.3.1.0$^{3,7}$]nonane (noradamantane) and tricyclo[3.3.1.1$^{3,7}$]decane (adamantane).

"Alkoxy" means an alkyl radical attached through an oxygen linking atom. "$(C_1-C_4)$-alkoxy" includes the methoxy, ethoxy, propoxy, and butoxy.

"Aromatic" means an unsaturated cycloalkyl ring system.

"Aryl" means an aromatic monocyclic or polycyclic ring system. Aryl systems include phenyl, naphthalenyl, fluorenyl, indenyl, azulenyl, and anthracenyl.

"Hetero" refers to the replacement of at least one carbon atom member in a ring system with at least one heteroatom selected from N, S, and O. A hetero ring may have 1, 2, 3, or 4 carbon atom members replaced by a heteroatom.

Enantiomers Diastereomers, and Salts

Certain compounds of Formula I may exist in various stereoisomeric or tautomeric forms. The invention encompasses all such forms, including those not depicted structurally such as active compounds in the form of essentially pure enantiomers, racemic mixtures, and tautomers.

The compounds of the invention may be present in the form of pharmaceutically acceptable salts. For use in medicines, the salts of the compounds of the invention refer to non-toxic "pharmaceutically acceptable salts." Pharmaceutically acceptable salt forms include pharmaceutically acceptable acidic/anionic or basic/cationic salts.

Pharmaceutically acceptable acidic/anionic salts include, the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate, and triethiodide salts.

Salts of the disclosed compounds containing a carboxylic acid or other acidic functional group can be prepared by reacting with a suitable base. Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N'-bisdehydroabietylamine, glucamine, N-methylglucamine, collidine, quinine, quinoline, and basic amino acid such as lysine and arginine.

When a disclosed compound or its pharmaceutically acceptable salt is named or depicted by structure, it is to be understood that solvates or hydrates of the disclosed compound or its pharmaceutically acceptable salts are also included. "Solvates" refer to crystalline forms wherein solvent molecules are incorporated into the crystal lattice during crystallization. Solvate may include water or nonaqueous solvents such as ethanol, isopropanol, DMSO, acetic acid, ethanolamine, and EtOAc. Solvates, wherein water is the solvent molecule incorporated into the crystal lattice, are typically referred to as "hydrates." Hydrates include stoichiometric hydrates as well as compositions containing variable amounts of water.

When a disclosed compound or its pharmaceutically acceptable salt is named or depicted by structure, it is to be understood that the compound, including solvates thereof, may exist in crystalline forms, non-crystalline forms or a mixture thereof. The disclosed compound or its pharmaceutically acceptable salts or solvates may also exhibit polymorphism (i.e. the capacity to occur in different crystalline forms). These different crystalline forms are typically known as "polymorphs." It is to be understood that when named or depicted by structure, the disclosed compounds and their pharmaceutically acceptable salts, solvates or hydrates also include all polymorphs thereof. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. One of ordinary skill in the art will appreciate that different polymorphs may be produced, for example, by changing or adjusting the conditions used in solidifying the compound. For example, changes in temperature, pressure, or solvent may result in different polymorphs. In addition, one polymorph may spontaneously convert to another polymorph under certain conditions.

It may be necessary and/or desirable during synthesis to protect sensitive or reactive groups on any of the molecules concerned. Representative conventional protecting groups are described in T. W. Greene and P. G. M. Wuts "Protective Groups in Organic Synthesis" John Wiley & Sons, Inc., New York 1999. Protecting groups may be added and removed using methods well known in the art.

The invention also includes various isomers and mixtures thereof. "Isomer" refers to compounds that have the same composition and molecular weight but differ in physical and/or chemical properties. The structural difference may be in constitution (geometric isomers) or in the ability to rotate the plane of polarized light (stereoisomers).

Stereoisomers are compounds which differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms. The symbol "*" in a structural formula represents the presence of a chiral carbon center. "R" and "S" represent the configuration of substituents around one or more chiral carbon atoms. Thus, "R*" and "S*" denote the relative configurations of substituents around one or more chiral carbon atoms. When a chiral center is not defined as R or S, a mixture of both configurations is present.

"Racemate" or "racemic mixture" means a compound of equimolar quantities of two enantiomers, wherein such mixtures exhibit no optical activity; i.e., they do not rotate the plane of polarized light.

"Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on opposite sides of the carbon-carbon double bond) or Z (substituents are oriented on the same side) configuration.

Atoms (other than H) attached to a carbocyclic ring may be in a cis or trans configuration. In the "cis" configuration, the substituents are on the same side in relationship to the plane of the ring; in the "trans" configuration, the substituents are on opposite sides in relationship to the plane of the ring. A mixture of "cis" and "trans" species is designated "cis/trans".

"R," "S," "S*," "R*," "E," "Z," "cis," and "trans," indicate configurations relative to the core molecule.

The point at which a group or moiety is attached to the remainder of the compound or another group or moiety can be indicated by "⁓" which represents "▬◁", "◀▬" or "⎯".

The compounds of the invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods.

When the stereochemistry of a compound is named or depicted by structure, the named or depicted stereoisomer is at least 60%, 70%, 80%, 90%, 99% or 99.9% by weight pure relative to the other stereoisomers. When a single enantiomer is named or depicted by structure, the depicted or named enantiomer is at least 60%, 70%, 80%, 90%, 99% or 99.9% by weight optically pure. Percent optical purity by weight is the ratio of the weight of the enantiomer over the weight of the enantiomer plus the weight of its optical isomer.

When a disclosed compound is named or depicted by structure without indicating the stereochemistry, and the inhibitor has at least one chiral center, it is to be understood that the name or structure encompasses one enantiomer of inhibitor free from the corresponding optical isomer, a racemic mixture of the inhibitor and mixtures enriched in one enantiomer relative to its corresponding optical isomer.

When a disclosed compound is named or depicted by structure without indicating the stereochemistry and has at least two chiral centers, it is to be understood that the name or structure encompasses a diastereomer free of other diastereomers, a pair of diastereomers free from other diastereomeric pairs, mixtures of diastereomers, mixtures of diastereomeric pairs, mixtures of diastereomers in which one diastereomer is enriched relative to the other diastereomer(s) and mixtures of diastereomeric pairs in which one diastereomeric pair is enriched relative to the other diastereomeric pair(s).

For oral dosing, the renin inhibitors were formulated in 0.5% methylcellulose at dose levels of 10 and 30 mg/kg (5 mL/kg) by infant feeding tubes. For intravenous delivery, a silastic catheter was implanted into posterior vena cava via a femoral vein. The catheter was attached to the delivery pump via a tether system and a swivel joint. Test compound (dose levels of 0.1 to 10 mg/kg, formulated at 5% dextrose) was administered by continuous infusion (1.67 mL:/kg/h) or by bolus injection (3.33 mL/kg in 2 min).

Arterial blood pressures (systolic, diastolic and mean) and body temperature were recorded continuously at 500 Hz and 50 Hz, respectively, using the Dataquest™ A.R.T. (Advanced Research Technology) software. Heart rate was derived from the phasic blood pressure tracing. During the recording period, the monkeys were kept in a separate room without human presence to avoid pressure changes secondary to stress. All data were expressed as mean±SEM. Effects of the renin inhibitors on blood pressure were assessed by ANOVA, taking into account the factors dose and time compared with the vehicle group.

Beagle Dogs: Non-naive Beagle dogs (2 per sex) weighing between 9 and 11 kg were used in the studies. Each animal was implanted subcutaneously with a telemetry transmitter (Data Sciences) and the blood pressure catheter was inserted into the left femoral artery. The electrocardiogram leads were also tunneled subcutaneously to the appropriate anatomical regions. The animals were housed under constant temperature and lighting conditions, were fed once daily, and were allowed free access to water. A sodium depleted state was produced by placing them on a low-sodium diet (<4 meq/day, a combination of canned Prescription Diet canine h/d, from Hill's Pet Products and dry pellets from Bio-Serv Inc., Frenchtown, N.J.) beginning 10 days before the experiment, and furosemide (3 mg/kg i.m.; Aventis Pharmaceuticals) was administered at −40 and −16 h prior to administration of test compound.

A renin inhibitor was orally administered by orogastric gavage to all overnight fasted animals at a dose level of 30 mg/kg (4 mL/kg formulated in 0.5% methylcellulose). Food was given 4 h postdose. In some experiments, the renin inhibitor was administered by bolus i.v. at increasing dose levels of 1, 3 and 6 mg/kg (2, 6 and 20 mg/mL formulated in sterile saline). Cardiovascular parameters were collected continuously at least 80 min predose and 3 h postdose, followed by every 10 min for 5 h and every 30 min for 16 h postdose. The Dataquest™ ART (version 2.2) software package from DSI (Data Sciences International) was used to collect telemetered cardiovascular data.

The efficacy of the renin inhibitors was also evaluated in vivo in double transgenic rats engineered to express human renin and human angiotensinogen (Bohlender J, Fukamizu A, Lippoldt A, Nomura T, Dietz R, Menard J, Murakami K, Luft F C, Ganten D. High human renin hypertension in transgenic rats. *Hypertension* 1997, 29, 428-434).

Experiments were conducted in 6-week-old double transgenic rats (dTGRs). The model has been described in detail earlier. Briefly, the human renin construct used to generate transgenic animals made up the entire genomic human renin gene (10 exons and 9 introns), with 3.0 kB of the 5'-promoter region and 1.2 kB of 3' additional sequences. The human angiotensinogen construct made up the entire human angiotensinogen gene (5 exons and 4 introns), with 1.3 kB of 5'-flanking and 2.4 kB of 3'-flanking sequences. The rats were purchased from RCC Ltd (Fullinsdorf, Switzerland). Radio telemetry transmitters were surgically implanted at 4 weeks of age. The telemetry system provided 24-h recordings of systolic, mean, diastolic arterial pressure (SAP, MAP, DAP, respectively) and heart rate (HR). Beginning on day 42, animals were transferred to telemetry cages. A 24 h telemetry reading was obtained. Rats were then dosed orally on the following 4 consecutive days (days 43-46). The rats were monitored continuously and allowed free access to standard 0.3%-sodium rat chow and drinking water.

The compounds of the invention are useful for ameliorating or treating disorders or diseases in which decreasing the levels of renin products is effective in treating a disease state. In hypertension elevated levels of angiotensin I, the product of renin catalyzed cleavage of angioteninogen are present. Thus, the compounds of the invention can be used in the treatment of hypertension, heart failure such as (acute and chronic) congestive heart failure; left ventricular dysfunction; cardiac hypertrophy; cardiac fibrosis; cardiomyopathy (e.g., diabetic cardiac myopathy and post-infarction cardiac myopathy); supraventricular and ventricular arrhythmias; arial fibrillation; atrial flutter; detrimental vascular remodeling; myocardial infarction and its sequelae; atherosclerosis; angina (whether unstable or stable); renal failure conditions, such as diabetic nephropathy; glomerulonephritis; renal fibrosis; scleroderma; glomerular sclerosis; microvascular complications, for example, diabetic retinopathy; renal vascular hypertension; vasculopathy; neuropathy; complications resulting from diabetes, such as nephropathy, vasculopathy and neuropathy; diseases of the coronary vessels; proteinuria;

albumenuria; post-surgical hypertension; metabolic syndrome; obesity, restenosis following angioplasty, ocular vascular complications, for example, raised intra-ocular pressure, glaucoma, and retinopathy; abnormal vascular growth, angiogenesis-related disorders, such as neovascular age related macular degeneration; hyperaldosteronism; anxiety states; and cognitive disorders (Fisher N. D.; Hollenberg N. K. *Expert Opin. Investig. Drugs.* 2001, 10, 417-26).

A pharmaceutical composition of the invention may, alternatively or in addition to a compound of Formula I, comprise a pharmaceutically acceptable salt of a compound of Formula I or a prodrug or pharmaceutically active metabolite of such a compound or salt and one or more pharmaceutically acceptable carriers therefor.

The compositions of the invention are aspartic protease inhibitors. Said compositions contain compounds having a mean inhibition constant ($IC_{50}$) against aspartic proteases of between about 5,000 nM to about 0.001 nM; preferably between about 100 nM to about 0.001 nM; and more preferably between about 10 nM to about 0.01 nM.

The compositions of the invention reduce blood pressure. Said compositions include compounds having an $IC_{50}$ for renin of between about 5,000 nM to about 0.001 nM; preferably between about 100 nM to about 0.001 nM; and more preferably between about 10 nM to about 0.01 nM.

The invention includes a therapeutic method for treating or ameliorating an aspartic protease mediated disorder in a subject in need thereof comprising administering to a subject in need thereof an effective amount of a compound of Formula I, or the enantiomers, diastereomers, or salts thereof or composition thereof.

Administration methods include administering an effective amount (i.e., a therapeutically effective amount) of a compound or composition of the invention at different times during the course of therapy or concurrently in a combination form. The methods of the invention include all known therapeutic treatment regimens.

"Prodrug" means a pharmaceutically acceptable form of an effective derivative of a compound (or a salt thereof) of the invention, wherein the prodrug may be: 1) a relatively active precursor which converts in vivo to a compound of the invention; 2) a relatively inactive precursor which converts in vivo to a compound of the invention; or 3) a relatively less active component of the compound that contributes to therapeutic activity after becoming available in vivo (i.e., as a metabolite). See "Design of Prodrugs", ed. H. Bundgaard, Elsevier, 1985.

"Metabolite" means a pharmaceutically acceptable form of a metabolic derivative of a compound (or a salt thereof) of the invention, wherein the derivative is an active compound that contributes to therapeutic activity after becoming available in vivo.

"Effective amount" means that amount of active compound agent that elicits the desired biological response in a subject. Such response includes alleviation of the symptoms of the disease or disorder being treated. The effective amount of a compound of the invention in such a therapeutic method is from about 10 mg/kg/day to about 0.01 mg/kg/day, preferably from about 0.5 mg/kg/day to 5 mg/kg/day.

The invention includes the use of a compound of the invention for the preparation of a composition for treating or ameliorating an aspartic protease mediated chronic disorder or disease or infection in a subject in need thereof, wherein the composition comprises a mixture one or more compounds of the invention and an optional pharmaceutically acceptable carrier.

"Pharmaceutically acceptable carrier" means compounds and compositions that are of sufficient purity and quality for use in the formulation of a composition of the invention and that, when appropriately administered to an animal or human, do not produce an adverse reaction.

An embodiment of the invention includes administering a renin inhibiting compound of Formula I or composition thereof in a combination therapy (see U.S. Pat. No. 5,821,232, U.S. Pat. No. 6,716,875, U.S. Pat. No. 5,663,188, or Fossa, A. A.; DePasquale, M. J.; Ringer, L. J.; Winslow, R. L. "Synergistic effect on reduction in blood pressure with coadministration of a renin inhibitor or an angiotensin-converting enzyme inhibitor with an angiotensin II receptor antagonist" *Drug Development Research* 1994, 33(4), 422-8) with one or more additional agents for the treatment of hypertension including α-blockers, β-blockers, calcium channel blockers, diuretics, natriuretics, saluretics, centrally acting antihypertensives, angiotensin converting enzyme (ACE) inhibitors, dual ACE and neutral endopeptidase (NEP) inhibitors, angiotensin-receptor blockers (ARBs), aldosterone synthase inhibitors, aldosterone-receptor antagonists, or endothelin receptor antagonists.

α-Blockers include doxazosin, prazosin, tamsulosin, and terazosin.

β-Blockers for combination therapy are selected from atenolol, bisoprol, metoprolol, acetutolol, esmolol, celiprolol, taliprolol, acebutolol, oxprenolol, pindolol, propanolol, bupranolol, penbutolol, mepindolol, carteolol, nadolol, carvedilol, and their pharmaceutically acceptable salts.

Calcium channel blockers include dihydropyridines (DHPs) and non-DHPs. The preferred DHPs are amlodipine, felodipine, ryosidine, isradipine, lacidipine, nicardipine, nifedipine, nigulpidine, niludipine, nimodiphine, nisoldipine, nitrendipine, and nivaldipine, and their pharmaceutically acceptable salts. Non-DHPs are flunarizine, prenylamine, diltiazem, fendiline, gallopamil, mibefradil, anipamil, tiapamil, and verampimil, and their pharmaceutically acceptable salts.

A diuretic is, for example, a thiazide derivative selected from amiloride, chlorothiazide, hydrochlorothiazide, methylchlorothiazide, and chlorothalidon.

Centrally acting antihypertensives include clonidine, guanabenz, guanfacine and methyldopa.

ACE inhibitors include alacepril, benazepril, benazaprilat, captopril, ceronapril, cilazapril, delapril, enalapril, enalaprilat, fosinopril, lisinopril, moexipiril, moveltopril, perindopril, quinapril, quinaprilat, ramipril, ramiprilat, spirapril, temocapril, trandolapril, and zofenopril. Preferred ACE inhibitors are benazepril, enalpril, lisinopril, and ramipril.

Dual ACE/NEP inhibitors are, for example, omapatrilat, fasidotril, and fasidotrilat.

Preferred ARBs include candesartan, eprosartan, irbesartan, losartan, olmesartan, tasosartan, telmisartan, and valsartan.

Preferred aldosterone synthase inhibitors are anastrozole, fadrozole, and exemestane.

Preferred aldosterone-receptor antagonists are spironolactone and eplerenone.

A preferred endothelin antagonist is, for example, bosentan, enrasentan, atrasentan, darusentan, sitaxsentan, and tezosentan, and their pharmaceutically acceptable salts.

An embodiment of the invention includes administering a disclosed compound or composition thereof in a combination therapy with one or more additional agents for the treatment of AIDS including reverse transcriptase inhibitors, non-nucleoside reverse transcriptase inhibitors, other HIV protease inhibitors, HIV integrase inhibitors, entry inhibitors (including attachment, co-receptor and fusion inhibitors), antisense drugs, and immune stimulators.

Specific reverse transcriptase inhibitors are zidovudine, didanosine, zalcitabine, stavudine, lamivudine, abacavir, tenofovir, and emtricitabine.

Specific non-nucleoside reverse transcriptase inhibitors are nevirapine, delaviridine, and efavirenz.

Specific HIV protease inhibitors are saquinavir, ritonavir, indinavir, nelfinavir, amprenavir, lopinavir, atazanavir, and fosamprenavir.

Specific HIV integrase inhibitors are L-870,810 and S-1360.

Entry inhibitors include compounds that bind to the CD4 receptor, the CCR5 receptor or the CXCR4 receptor. Specific examples of entry inhibitors include enfuvirtide (a peptido-mimetic of the HR2 domain in gp41) and sifurvitide.

A specific attachment and fusion inhibitor is enfuvirtide.

An embodiment of the invention includes administering a disclosed compound or composition thereof in a combination therapy with one or more additional agents for the treatment of Alzheimer's disease including tacrine, donepezil, rivastigmine, galantamine, and memantine.

Combination therapy includes co-administration of the compound of the invention and said other agent, sequential administration of the compound and the other agent, administration of a composition containing the compound and the other agent, or simultaneous administration of separate compositions containing the compound and the other agent.

The invention further includes the process for making the composition comprising mixing one or more of the present compounds and an optional pharmaceutically acceptable carrier; and includes those compositions resulting from such a process, which process includes conventional pharmaceutical techniques.

The compositions of the invention include ocular, oral, nasal, transdermal, topical with or without occlusion, intravenous (both bolus and infusion), and injection (intraperitoneally, subcutaneously, intramuscularly, intratumorally, or parenterally). The composition may be in a dosage unit such as a tablet, pill, capsule, powder, granule, liposome, ion exchange resin, sterile ocular solution, or ocular delivery device (such as a contact lens and the like facilitating immediate release, timed release, or sustained release), parenteral solution or suspension, metered aerosol or liquid spray, drop, ampoule, auto-injector device, or suppository; for administration ocularly, orally, intranasally, sublingually, parenterally, or rectally, or by inhalation or insufflation.

Compositions of the invention suitable for oral administration include solid forms such as pills, tablets, caplets, capsules (each including immediate release, timed release, and sustained release formulations), granules and powders; and, liquid forms such as solutions, syrups, elixirs, emulsions, and suspensions. Forms useful for ocular administration include sterile solutions or ocular delivery devices. Forms useful for parenteral administration include sterile solutions, emulsions, and suspensions.

The compositions of the invention may be administered in a form suitable for once-weekly or once-monthly administration. For example, an insoluble salt of the active compound may be adapted to provide a depot preparation for intramuscular injection (e.g., a decanoate salt) or to provide a solution for ophthalmic administration.

The dosage form containing the composition of the invention contains a therapeutically effective amount of the active ingredient necessary to provide a therapeutic effect. The composition may contain from about 5,000 mg to about 0.5 mg (preferably, from about 1,000 mg to about 0.5 mg) of a compound of the invention or salt form thereof and may be constituted into any form suitable for the selected mode of administration. The composition may be administered about 1 to about 5 times per day. Daily administration or post-periodic dosing may be employed.

For oral administration, the composition is preferably in the form of a tablet or capsule containing, e.g., 500 to 0.5 milligrams of the active compound. Dosages will vary depending on factors associated with the particular patient being treated (e.g., age, weight, diet, and time of administration), the severity of the condition being treated, the compound being employed, the mode of administration, and the strength of the preparation.

The oral composition is preferably formulated as a homogeneous composition, wherein the active ingredient is dispersed evenly throughout the mixture, which may be readily subdivided into dosage units containing equal amounts of a compound of the invention. Preferably, the compositions are prepared by mixing a compound of the invention (or pharmaceutically acceptable salt thereof) with one or more optionally present pharmaceutical carriers (such as a starch, sugar, diluent, granulating agent, lubricant, glidant, binding agent, and disintegrating agent), one or more optionally present inert pharmaceutical excipients (such as water, glycols, oils, alcohols, flavoring agents, preservatives, coloring agents, and syrup), one or more optionally present conventional tableting ingredients (such as corn starch, lactose, sucrose, sorbitol, talc, stearic acid, magnesium stearate, dicalcium phosphate, and any of a variety of gums), and an optional diluent (such as water).

Binder agents include starch, gelatin, natural sugars (e.g., glucose and beta-lactose), corn sweeteners and natural and synthetic gums (e.g., acacia, and tragacanth). Disintegrating agents include starch, methyl cellulose, agar, and bentonite.

Tablets and capsules represent an advantageous oral dosage unit form. Tablets may be sugarcoated or filmcoated using standard techniques. Tablets may also be coated or otherwise compounded to provide a prolonged, control-release therapeutic effect. The dosage form may comprise an inner dosage and an outer dosage component, wherein the outer component is in the form of an envelope over the inner component. The two components may further be separated by a layer which resists disintegration in the stomach (such as an enteric layer) and permits the inner component to pass intact into the duodenum or a layer which delays or sustains release. A variety of enteric and non-enteric layer or coating materials (such as polymeric acids, shellacs, acetyl alcohol, and cellulose acetate or combinations thereof) may be used.

Compounds of the invention may also be administered via a slow release composition; wherein the composition includes a compound of the invention and a biodegradable slow release carrier (e.g., a polymeric carrier) or a pharmaceutically acceptable non-biodegradable slow release carrier (e.g., an ion exchange carrier).

Biodegradable and non-biodegradable slow release carriers are well known in the art. Biodegradable carriers are used to form particles or matrices which retain an active agent(s) and which slowly degrade/dissolve in a suitable environment (e.g., aqueous, acidic, basic and the like) to release the agent. Such particles degrade/dissolve in body fluids to release the active compound(s) therein. The particles are preferably nanoparticles (e.g., in the range of about 1 to 500 nm in diameter, preferably about 50-200 nm in diameter, and most preferably about 100 nm in diameter). In a process for preparing a slow release composition, a slow release carrier and a compound of the invention are first dissolved or dispersed in an organic solvent. The resulting mixture is added into an aqueous solution containing an optional surface-active agent(s) to produce an emulsion. The organic solvent is then evaporated from the emulsion to provide a colloidal suspension of particles containing the slow release carrier and the compound of the invention.

The compound of Formula I may be incorporated for administration orally or by injection in a liquid form such as aqueous solutions, suitably flavored syrups, aqueous or oil suspensions, flavored emulsions with edible oils such as cottonseed oil, sesame oil, coconut oil or peanut oil and the like, or in elixirs or similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone, and gelatin. The liquid forms in suitably flavored suspending or dispersing agents may also include synthetic and natural gums. For parenteral administration, sterile suspensions and solutions are desired. Isotonic preparations, which generally contain suitable preservatives, are employed when intravenous administration is desired.

The compounds may be administered parenterally via injection. A parenteral formulation may consist of the active ingredient dissolved in or mixed with an appropriate inert liquid carrier. Acceptable liquid carriers usually comprise aqueous solvents and other optional ingredients for aiding solubility or preservation. Such aqueous solvents include sterile water, Ringer's solution, or an isotonic aqueous saline solution. Other optional ingredients include vegetable oils (such as peanut oil, cottonseed oil, and sesame oil), and organic solvents (such as solketal, glycerol, and formyl). A sterile, non-volatile oil may be employed as a solvent or suspending agent. The parenteral formulation is prepared by dissolving or suspending the active ingredient in the liquid carrier whereby the final dosage unit contains from 0.005 to 10% by weight of the active ingredient. Other additives include preservatives, isotonizers, solubilizers, stabilizers, and pain-soothing agents, Injectable suspensions may also be prepared, in which case appropriate liquid carriers, suspending agents and the like may be employed.

Compounds of the invention may be administered intranasally using a suitable intranasal vehicle.

Compounds of the invention may also be administered topically using a suitable topical transdermal vehicle or a transdermal patch.

For ocular administration, the composition is preferably in the form of an ophthalmic composition. The ophthalmic compositions are preferably formulated as eye-drop formulations and filled in appropriate containers to facilitate administration to the eye, for example a dropper fitted with a suitable pipette. Preferably, the compositions are sterile and aqueous based, using purified water. In addition to the compound of the invention, an ophthalmic composition may contain one or more of: a) a surfactant such as a polyoxyethylene fatty acid ester; b) a thickening agents such as cellulose, cellulose derivatives, carboxyvinyl polymers, polyvinyl polymers, and polyvinylpyrrolidones, typically at a concentration n in the range of about 0.05 to about 5.0% (wt/vol); c) (as an alternative to or in addition to storing the composition in a container containing nitrogen and optionally including a free oxygen absorber such as Fe), an anti-oxidant such as butylated hydroxyanisol, ascorbic acid, sodium thiosulfate, or butylated hydroxytoluene at a concentration of about 0.00005 to about 0.1% (wt/vol); d) ethanol at a concentration of about 0.01 to 0.5% (wt/vol); and e) other excipients such as an isotonic agent, buffer, preservative, and/or pH-controlling agent. The pH of the ophthalmic composition is desirably within the range of 4 to 8.

Methods of Preparation

In the discussion below $R^1$, $R^2$, $R^3$, X, Y, A, Q, $R^4$, L, $R^5$, and $R^9$ are defined as described above for compounds of Formula I. In cases where the synthetic intermediates and final products of Formula I described below contain potentially reactive functional groups, for example amino, hydroxyl, thiol and carboxylic acid groups, that may interfere with the desired reaction, it may be advantageous to employ protected forms of the intermediate. Methods for the selection, introduction and subsequent removal of protecting groups are well known to those skilled in the art. (T. W. Greene and P. G. M. Wuts "Protective Groups in Organic Synthesis" John Wiley & Sons, Inc., New York 1999). Such protecting group manipulations are assumed in the discussion below and not described explicitly.

In the first process of the invention a compound of Formula I is prepared by reaction of an intermediate of Formula II with an amine intermediate of formula III:

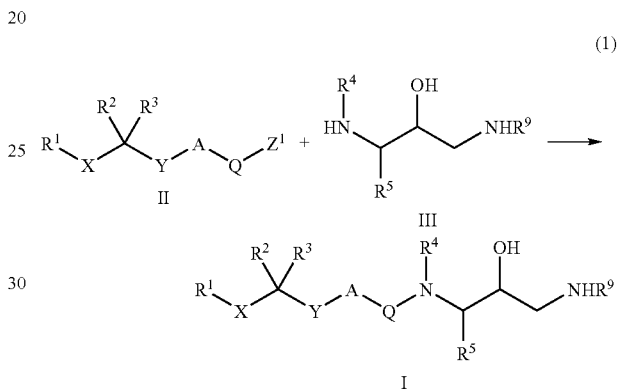

(1)

wherein $Z^1$ in II is a leaving group such as halide, alkanesulfonate, haloalkanesulfonate, arylsulfonate, aryloxide, heteroaryloxide, azole, azolium salt, or alkoxide.

In a second process of the invention, a compound of Formula I is prepared by reaction of a compound of formula IV with a compound of formula V wherein $Z^1$ is a leaving group such as halide, alkanesulfonate, arylsulfonate, aryloxide, azole, azolium salt, or alkoxide:

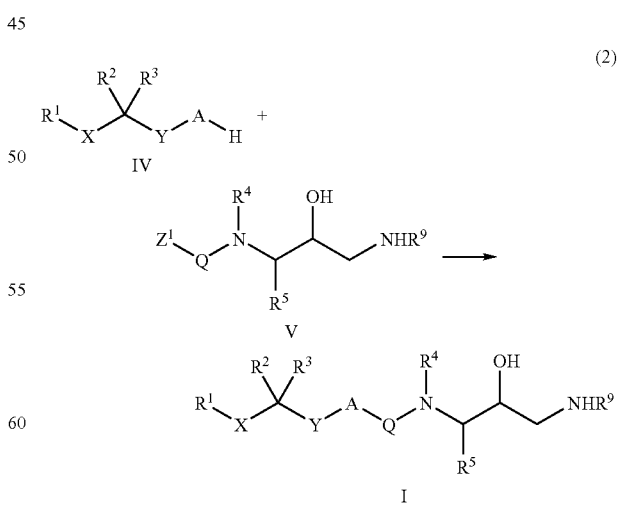

(2)

wherein the H atom in IV is attached to a nitrogen atom that is part of A.

In a third process of the invention, compounds of Formula I can be prepared from other compounds of Formula I and protected compounds of Formula I:

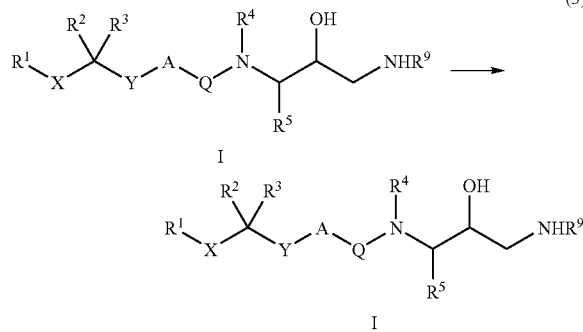

For example, when a bromophenyl, iodophenyl or trifluoromethanesulfonyloxyphenyl group is present in a compound of Formula I, it may be transformed into a biphenyl using a Suzuki coupling, to an alkynylbenzene using a Sonogashira coupling, to an allylbenzene using a Stille coupling, to a cyanobenzene using CuCN or to a methoxycarbonylbenzene using a palladium catalyzed carbonylation in the presence of methanol. Another example is the transformation of a compound of Formula I wherein $R^3$=OH to the analogous compound wherein $R^3$=H by dehydration followed by hydrogenation or, in a single step, by deoxygenation using Raney nickel. A third example is the deoxygenation of a compound of Formula I wherein Q=Q11 to a compound of Formula I where Q=Q10. A fourth example is the reaction of a compound of Formula I wherein $R^2$=OH and $R^3$=H with an alcohol in the presence of acid to afford a compound of Formula I wherein $R^2$ is a group attached through an ether linkage. A fifth example is the alkylkation of a compound of Formula I wherein $R^1$ is a hydroxyoxyphenyl group to provide a compound of formula I wherein $R^1$ is an alkoxyphenyl, cycloalkoxyphenyl, cycloalkylalkoxyphenyl, or arylalkoxyphenyl group.

In a fourth process of the invention, a compound of formula I can be prepared by reaction of an epoxide compound of formula VI with an amine of formula VII:

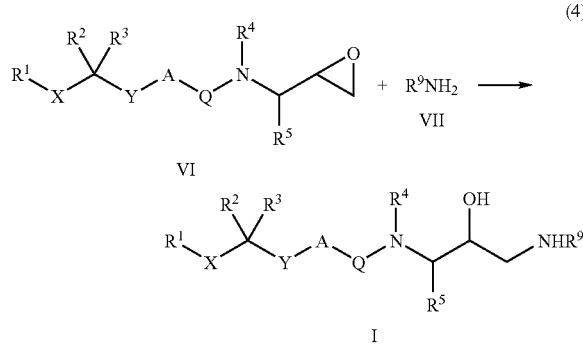

Intermediates of Formula II wherein $Z^1$=chlorine and Q is Q1, Q3, or Q6 that is attached to a carbon atom that is part of A, or Q7 that is attached to a carbon or nitrogen atom that is part of A, are prepared from intermediates of formula VIII:

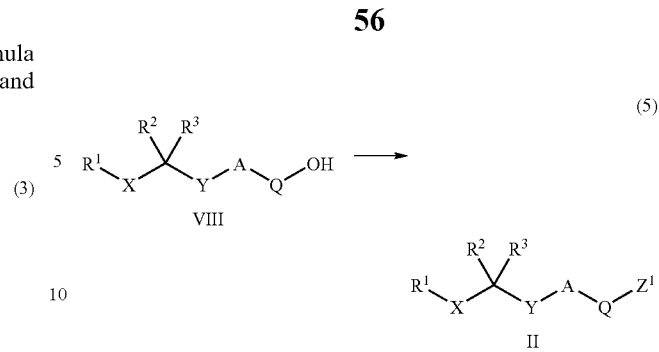

by reaction with, for example, thionyl chloride, oxalyl chloride, or phosphorus oxychloride.

Intermediates of Formula II wherein Q is Q9 or Q11 or Q12, Q is attached to a nitrogen atom that is part of A and $Z^1$ is methoxy are prepared from intermediates IV by reaction with 3,4-dimethoxy-3-cyclobutene-1,2-dione, 3,4-dimethoxy-1,2,5-thiadiazole-1-oxide, and 3,4-dimethoxy-1,2,5-thiadiazole-1,1-dioxide, respectively:

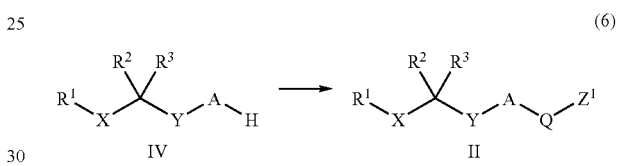

Intermediates of Formula II wherein Q is Q1, Q1 is attached to a nitrogen atom that is part of A, and $Z^1$ is chlorine, 1-imidazolyl, or p-nitrophenoxy are prepared from intermediates of formula IV wherein H is attached to a nitrogen atom that is part of A by reaction with phosgene, 1,1'-carbonyldiimidazole, or p-nitrophenyl chloroformate, respectively.

Intermediates of formula IV wherein H is attached to a nitrogen atom that is part of A are prepared from intermediates of Formula IX:

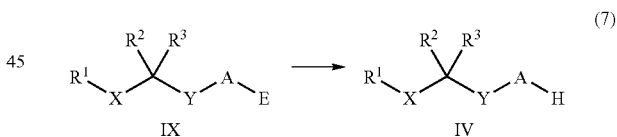

wherein E is an amine protecting group, including carbamate, amide, and sulfonamide protecting groups known in the art (T. W. Greene and P. G. M. Wuts "Protective Groups in Organic Synthesis" John Wiley & Sons, Inc., New York 1999).

Intermediates of Formula IX wherein $R^3$=OH are prepared from ketone intermediates of formula X by addition of an organometallic reagent of formula XI, wherein M is for example Li, MgCl, MgBr, or MgI:

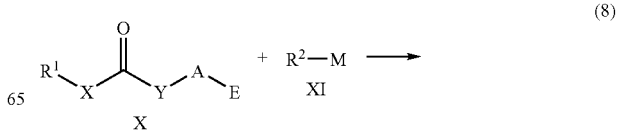

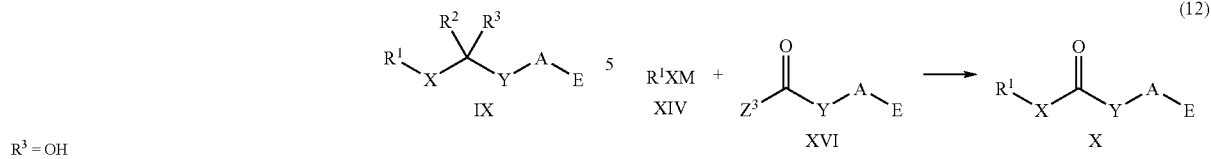

Intermediates of Formula IX wherein $R^2$ is a group $R^cO$ attached by an ether linkage, are prepared from alcohol intermediates of formula XII by reaction under basic conditions with alkylating agents of formula XIII wherein $Z^2$ is a leaving group such as halide, alkanesulfonate, haloalkanesulfonate or arylsulfonate:

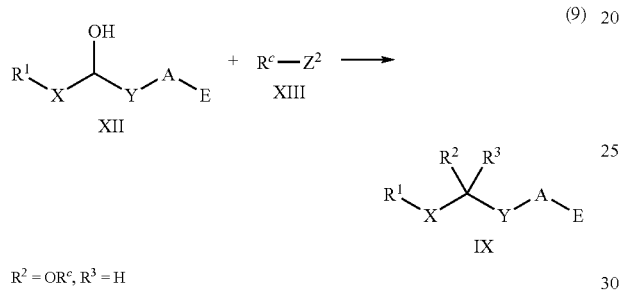

or by reaction with an alcohol of formula $R^cOH$ under acidic conditions.

Alcohol Intermediates of formula XII are prepared by reduction of ketone intermediates of formula X with, for example, a hydride reducing agent such $NaBH_4$, $LiAlH_4$ or diisobutylaluminum hydride:

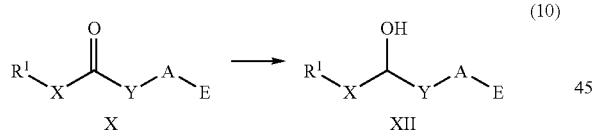

or by addition of an organometallic reagent of formula XIV wherein M is, for example, Li, MgCl, MgBr, or MgI to an aldehyde of Formula XV:

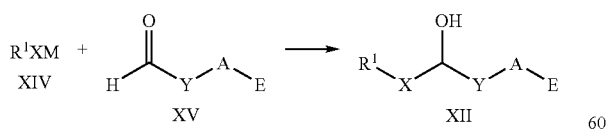

Ketone intermediates of formula X are prepared by the addition of an organometallic reagent of formula XIV to a carboxylic acid derivative of formula XVI wherein $Z^3$ is an alkoxide, dialkylamino group, or an N-alkoxy-N-alkylamino group:

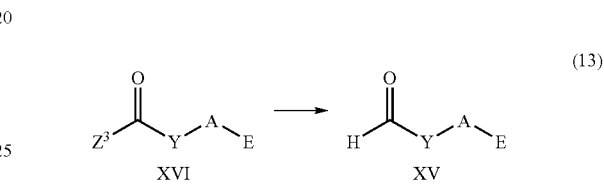

Organometallic reagents of formula XIV are prepared by known process including halogen-lithium exchange, ortho-lithiation and treatment of halides $R^1X$-Hal with magnesium or lithium metal.

Aldehyde intermediates of formula XV are prepared by reduction of carboxylic acid derivatives of formula XVI wherein $Z^3$ is an alkoxy or an N-alkoxy-N-alkylamino group using, for example, a hydride reducing agent such as $LiAlH_4$ or diisobutylaluminum hydride:

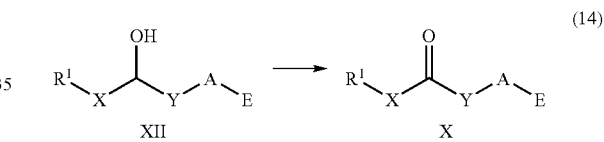

Ketone intermediates of formula X are also prepared by oxidation of alcohol intermediates of formula XII:

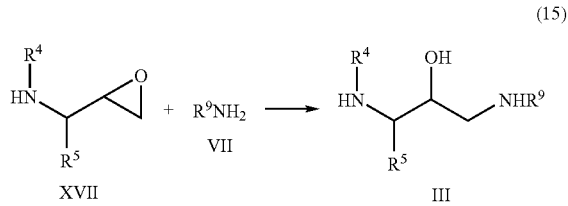

Optionally protected amine intermediates of formula III are prepared by reaction of epoxide intermediates of formula XVII with amines of formula VII:

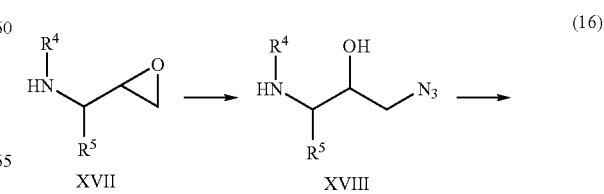

Amine intermediates of formula III wherein $R^9$=H are prepared by reduction of azides of formula XVIII which are prepared by treatment of epoxides of formula XVII with sodium azide:

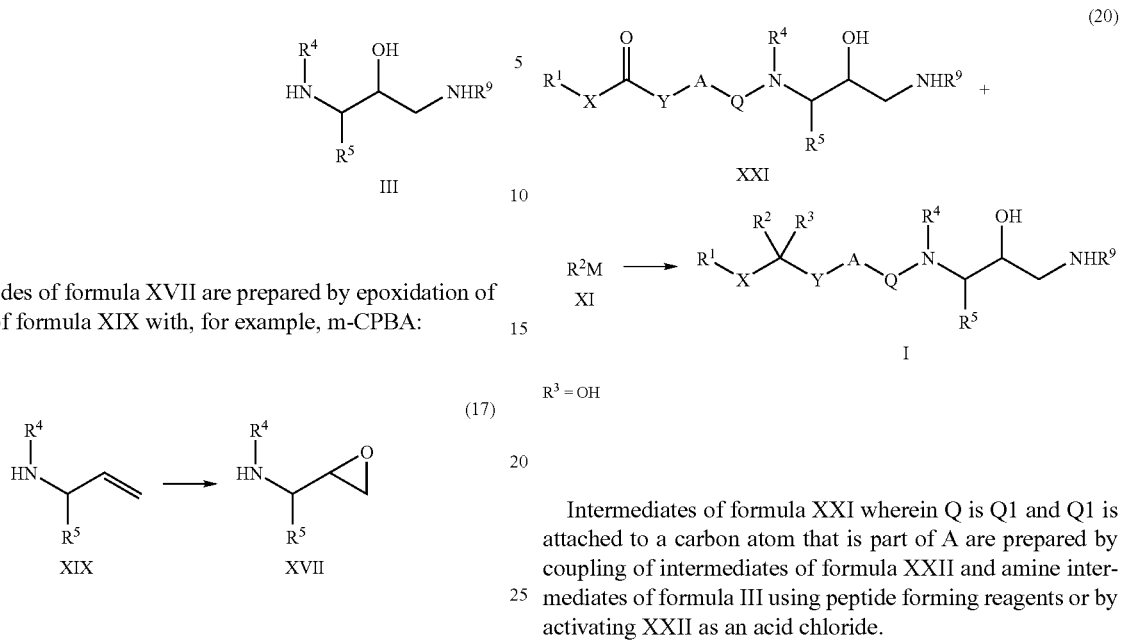

(20)

(17)

Epoxides of formula XVII are prepared by epoxidation of olefins of formula XIX with, for example, m-CPBA:

Olefins of formula XIX are prepared from appropriately protected α-aminoaldehydes of formula XX by treatment with Tebbe reagent or triphenylphosphonium methylide:

(18)

Appropriately protected α-aminoaldehydes of formula XX are prepared from α-amino acids and 1,2-aminoalcohols using methods well known to those skilled in the art.

Epoxides of formula XVII are also prepared by the reaction of aldehydes of formula XX with trimethylsulfoxonium Iodide or trimethylsulfonium iodide (J. Aube "Epoxidation and Related Processes" Chapter 3.2 in Volume 1 of "Comprehensive Organic Synthesis" edited by B. M. Trost, I. Fleming and Stuart L. Schreiber, Pergamon Press New York, 1992):

(19)

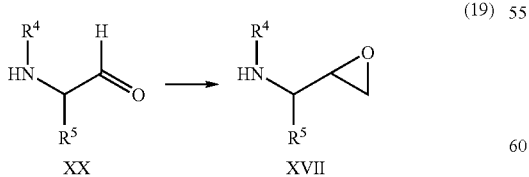

In a fifth process of the invention optionally protected compounds of Formula I are prepared from ketone compounds of formula XXI by addition of an organometallic $R^2M$:

Intermediates of formula XXI wherein Q is Q1 and Q1 is attached to a carbon atom that is part of A are prepared by coupling of intermediates of formula XXII and amine intermediates of formula III using peptide forming reagents or by activating XXII as an acid chloride.

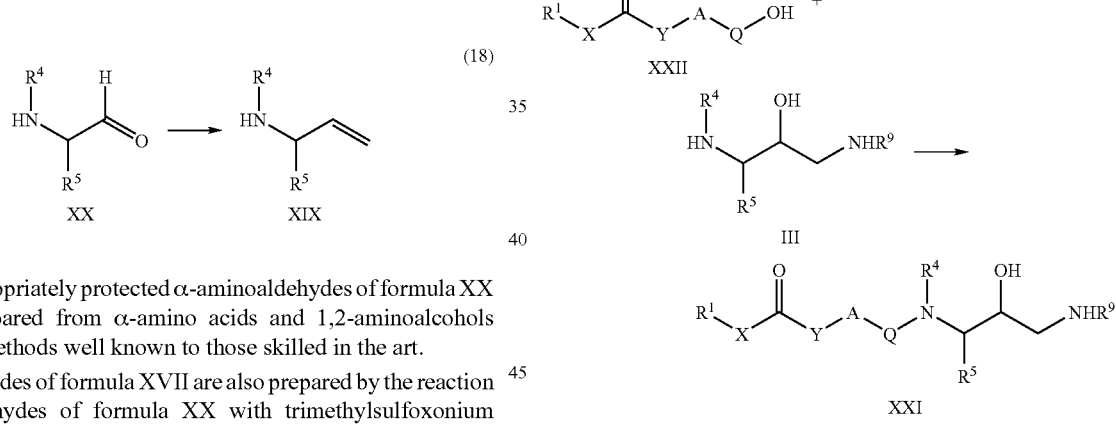

(21)

In the discussion below $R^1$, $R^2$, $R^3$, $A^4$, $A^5$, Q, $R^4$, L, $R^5$, and $R^9$ are defined as described above for compounds of Formula Ia. In cases where the synthetic intermediates and final products of Formula Ia described below contain potentially reactive functional groups, for example amino, hydroxyl, thiol and carboxylic acid groups, that may interfere with the desired reaction, it may be advantageous to employ protected forms of the intermediate. Methods for the selection, introduction and subsequent removal of protecting groups are well known to those skilled in the art. (T. W. Greene and P. G. M. Wuts "Protective Groups in Organic Synthesis" John Wiley & Sons, Inc., New York 1999). Such protecting group manipulations are assumed in the discussion below and not described explicitly.

In the first process of the invention, a compound of Formula Ia is prepared by reaction of an intermediate of Formula IIa with an amine intermediate of formula IIIa:

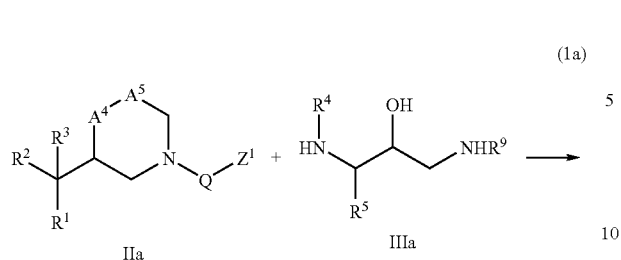

(1a)

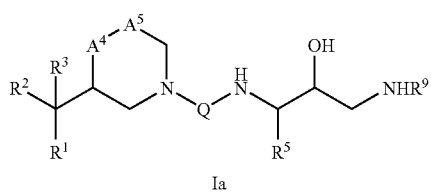

Ia wherein $Z^1$ in IIa is a leaving group such as halide, alkanesulfonate, haloalkanesulfonate, arylsulfonate, aryloxide, heteroaryloxide, azole, azolium salt, or alkoxide.

In a second process of the invention, a compound of Formula Ia is prepared by reaction of a compound of formula IVa with a compound of formula Va wherein $Z^1$ is a leaving group such as halide, alkanesulfonate, arylsulfonate, aryloxide, azole, azolium salt, or alkoxide:

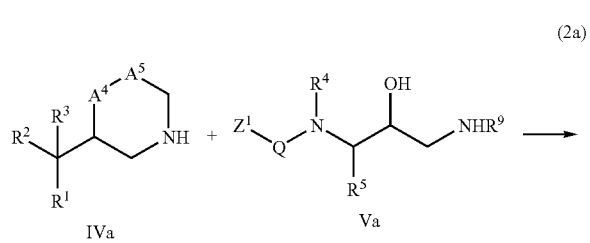

(2a)

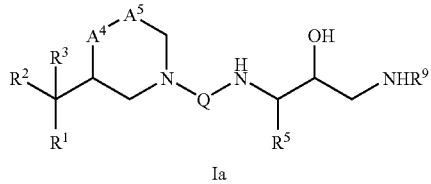

Ia

In a third process of the invention, compounds of Formula Ia can be prepared from other compounds of Formula Ia and protected compounds of Formula Ia:

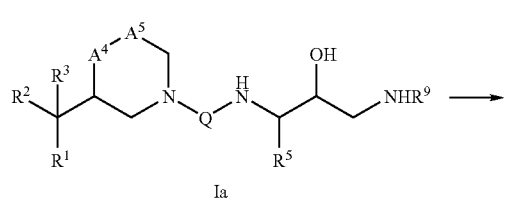

(3a)

For example, when a bromophenyl, iodophenyl or trifluoromethanesulfonyloxyphenyl group is present in a compound of Formula Ia, it may be transformed into a biphenyl using a Suzuki coupling, into an alkynylbenzene using a Sonogashira coupling, into an allylbenzene using a Stille coupling, into a cyanobenzene using CuCN, or into a methoxycarbonylbenzene using a palladium catalyzed carbonylation in the presence of methanol. Another example is the transformation of a compound of Formula Ia wherein $R^3$=OH to the analogous compound wherein $R^3$=H by dehydration followed by hydrogenation or in a single step by deoxygenation using Raney nickel. A third example is the deoxygenation of a compound of Formula Ia wherein Q=Q11 to a compound of Formula Ia where Q=Q10. A fourth example is the reaction of a compound of Formula Ia wherein $R^2$=OH and $R^3$=H with an alcohol in the presence of acid to afford a compound of Formula Ia wherein $R^2$ is a group attached through an ether linkage. A fifth example is the alkylation of a compound of Formula Ia wherein $R^1$ is a hydroxyoxyphenyl group to provide a compound of formula Ia wherein $R^1$ is an alkoxyphenyl, cycloalkoxyphenyl, cycloalkylalkoxyphenyl, or arylalkoxyphenyl group.

In a fourth process of the invention, a compound of formula Ia is prepared by reaction of an epoxide compound of formula VIa with an amine of formula VIIa:

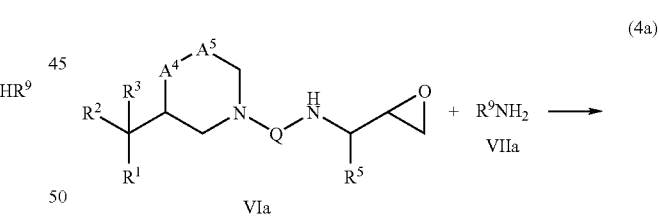

(4a)

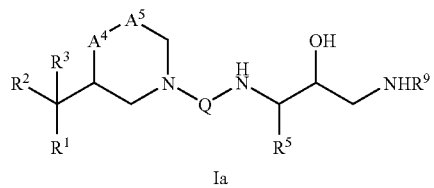

Ia

Intermediates of Formula IIa wherein Q is Q9 or Q11 or Q12, and $Z^1$ is methoxy are prepared from intermediates IVa by reaction with 3,4-dimethoxy-3-cyclobutene-1,2-dione, 3,4-dimethoxy-1,2,5-thiadiazole-1-oxide, or 3,4-dimethoxy-1,2,5-thiadiazole-1,1-dioxide, respectively:

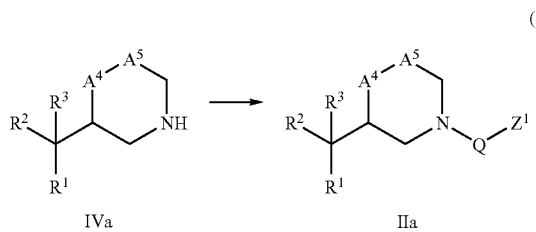
(6a)

Intermediates of Formula IIa wherein Q is Q1 and $Z^1$ is chlorine, 1-imidazolyl, or p-nitrophenoxy are prepared from intermediates of formula IVa by reaction with phosgene, 1,1'-carbonyldiimidazole, or p-nitrophenyl chloroformate respectively.

Intermediates of formula IVa are prepared from intermediates of Formula IX:

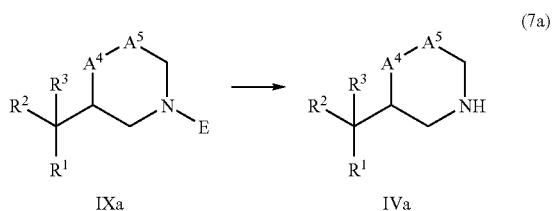
(7a)

wherein E is an amine protecting group, including carbamate, amide, and sulfonamide protecting groups known in the art (T. W. Greene and P. G. M. Wuts "Protective Groups in Organic Synthesis" John Wiley & Sons, Inc., New York 1999).

Intermediates of Formula IX wherein $R^3$=OH are prepared from ketone intermediates of formula X by addition of an organometallic reagent of formula XI, wherein M is, for example, Li, MgCl, MgBr, or MgI:

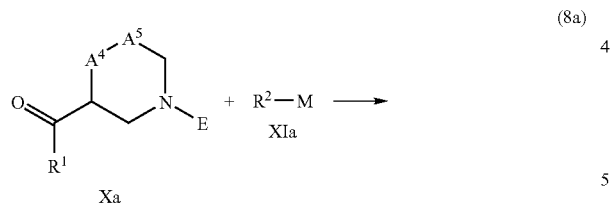
(8a)

$R^3$ = OH

Intermediates of Formula IXa wherein $R^2$ is a group $R^cO$ attached by an ether linkage are prepared from alcohol intermediates of formula XIIa under basic conditions with alkylating agents of formula XIII wherein $Z^2$ is a leaving group such as halide, alkanesulfonate, haloalkanesulfonate or arylsulfonate:

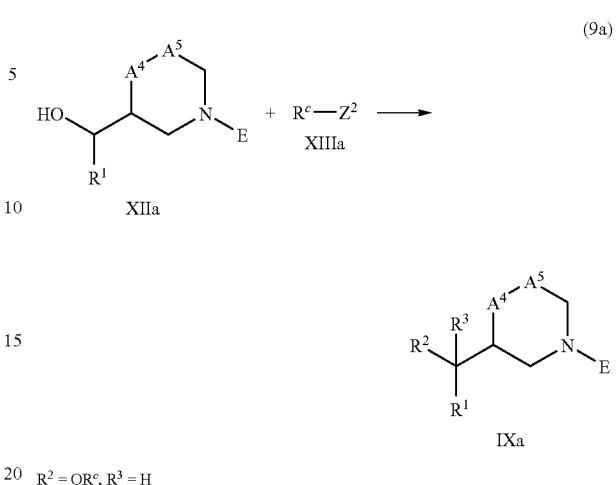
(9a)

$R^2 = OR^c$, $R^3$ = H

Alcohol Intermediates of formula XIIa are prepared by reduction of ketone intermediates of formula Xa with, for example, a hydride reducing agent such $NaBH_4$, $LiAlH_4$, or diisobutylaluminum hydride:

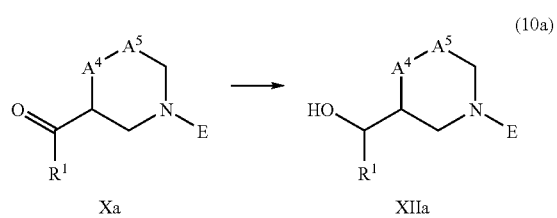
(10a)

or by addition of an organometallic reagent of formula XIVa wherein M is, for example, Li, MgCl, MgBr, or MgI to an aldehyde of Formula XVa:

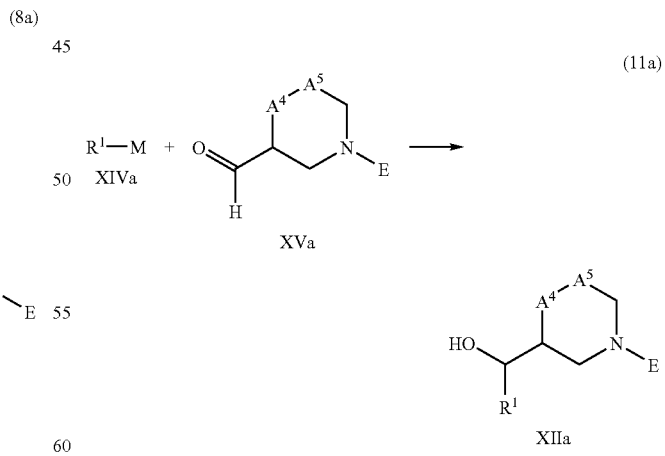
(11a)

Ketone intermediates of formula Xa are prepared by the addition of an organometallic reagent of formula XIVa to a carboxylic acid derivative of formula XVIa wherein $Z^3$ is an alkoxide, dialkylamino group, or an N-alkoxy-N-alkylamino group:

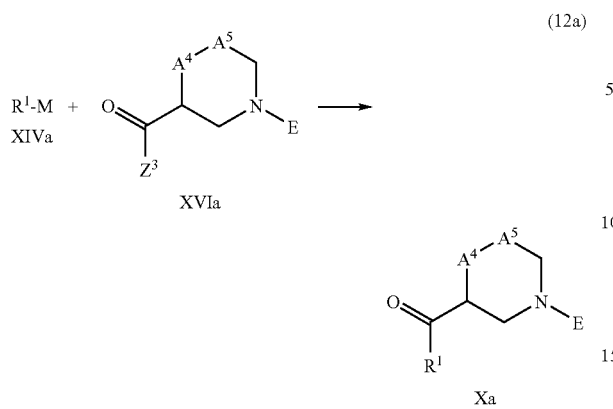

Organometallic reagents of formula XIVa are prepared by known processes including halogen-lithium exchange, ortho-lithiation, and treatment of halides $R^1$-Hal with magnesium or lithium metal.

Aldehyde intermediates of formula XVa are prepared by reduction of carboxylic acid derivatives of formula XVIa wherein $Z^3$ is an alkoxy or an N-alkoxy-N-alkylamino group using, for example, a hydride reducing agent such as $LiAlH_4$ or diisobutylaluminum hydride:

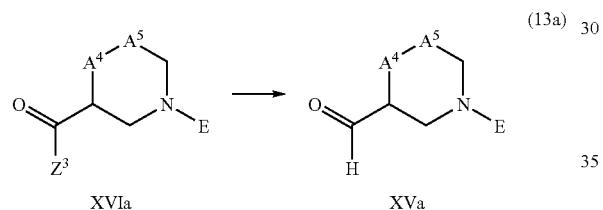

Ketone intermediates of formula Xa are also prepared by oxidation of alcohol intermediates of formula XIIa:

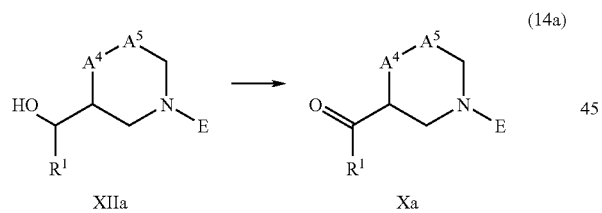

Optionally protected amine intermediates of formula IIIa are prepared by reaction of epoxide intermediates of formula XVIIa with amines of formula VIIa:

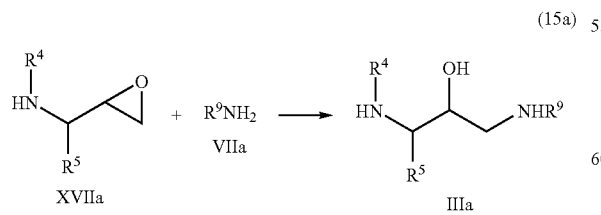

Amine intermediates of formula IIIa wherein $R^9$=H are prepared by reduction of azides of formula XVIIIa which are prepared treatment of epoxides of formula XVIIa with sodium azide:

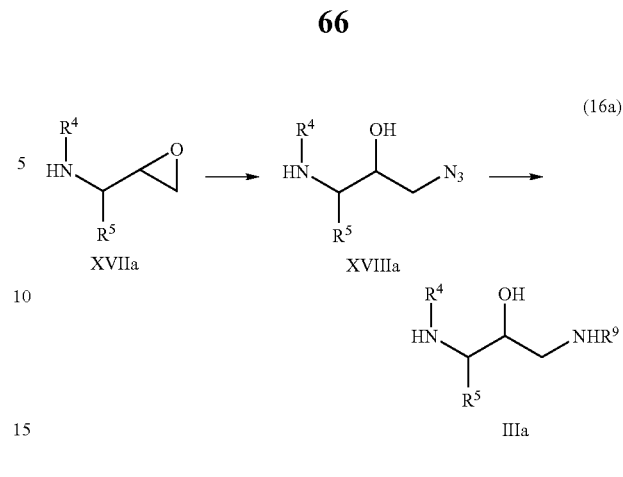

Epoxides of formula XVIIa are prepared by oxidation of olefins of formula XIXa with, for example, m-CPBA:

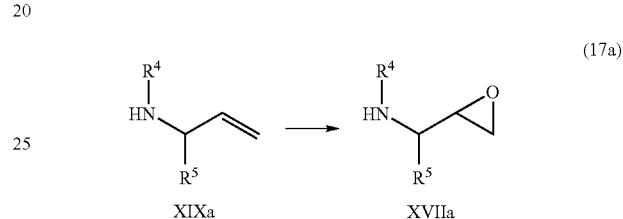

Olefins of formula XIXa are prepared from appropriately protected α-aminoaldehydes of formula XXa by treatment with Tebbe reagent or triphenylphosphonium methylide:

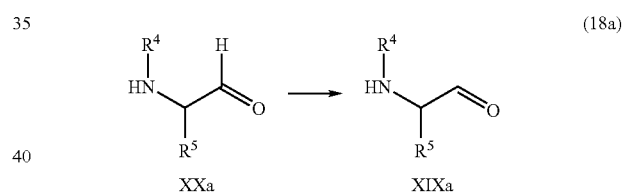

Appropriately protected α-aminoaldehydes of formula XXa are prepared from α-amino acids and from 1,2-aminoalcohols using methods well known to those skilled in the art.

Epoxides of formula XVIIa are also prepared by reaction of aldehydes of formula XXa with trimethylsulfoxonium Iodide or trimethylsulfonium iodide (J. Aube "Epoxidation and Related Processes" Chapter 3.2 in Volume 1 of "Comprehensive Organic Synthesis" edited by B. M. Trost, I. Fleming and Stuart L. Schreiber, Pergamon Press New York, 1992):

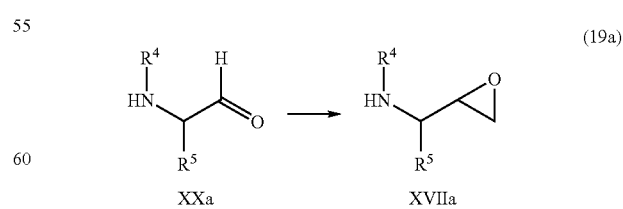

In a fifth process of the invention optionally protected compounds of Formula Ia wherein $R^3$=OH are prepared from optionally protected ketone compounds of formula XXIa by addition of an organometallic $R^2M$:

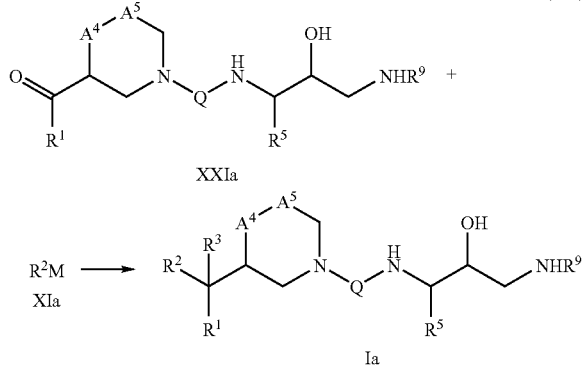

Ketones of formula XXIa wherein Q is Q1 and Q1 is attached to a carbon atom that is part of A are prepared by coupling of intermediates of formula XXIIa and amine intermediates of formula IIIa using peptide forming reagents or by activating XXIIa as its acid chloride.

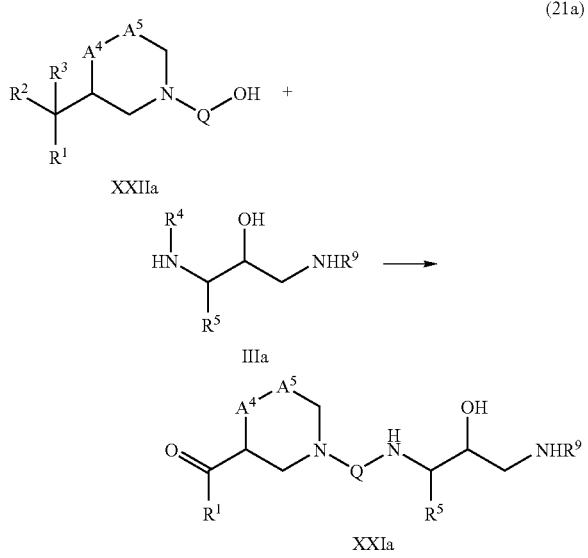

The invention is further defined by reference to the examples, which are intended to be illustrative and not limiting.

Representative compounds of the invention can be synthesized in accordance with the general synthetic schemes described above and are illustrated in the examples that follow. The methods for preparing the various starting materials used in the schemes and examples are well within the knowledge of persons skilled in the art.

The following abbreviations have the indicated meanings:

| Abbreviation | Meaning |
| --- | --- |
| Aq | aqueous |
| Boc | tert-butoxy carbonyl or t-butoxy carbonyl |
| (Boc)$_2$O | di-tert-butyl dicarbonate |
| Brine | saturated aqueous NaCl |
| Cbz | benzyloxycarbonyl |
| CbzCl | benzyl chloroformate |
| CDI | carbonyl diimidazole |
| CH$_2$Cl$_2$ | methylene chloride |
| CH$_3$CN or MeCN | acetonitrile |
| Cpd | compound |
| D | day |
| DAST | diethylaminosulfur trifluoride |
| DBU | 1,8-diazabicyclo[5.4.0]undec-7-ene |
| DCC | N,N'-dicyclohexylcarbodiimide |
| DCU | N,N'-dicyclohexylurea |
| DIAD | diisopropyl azodicarboxylate |
| DIEA | N,N-diisopropylethylamine |
| DMAP | 4-(dimethylamino)pyridine |
| DMF | N,N-dimethylformamide |
| DMPU | 1,3-dimethyl-3,4,5,6-tetrahydro-2(1H)-pyrimidinone |
| 2,4-DNP | 2,4-dinitrophenylhydrazine |
| EDC•HCl | 1-[3-(dimethylamino)propyl]-3-ethylcarbodiimide hydrochloride |
| Equiv | equivalents |
| Et | ethyl |
| Et$_2$O | ethyl ether |
| EtOAc | EtOAc |
| Fmoc | 1-[[(9H-fluoren-9-ylmethoxy)carbonyl]oxy]- |
| Fmoc-OSu | 1-[[(9H-fluoren-9-ylmethoxy)carbonyl]oxy]-2,5-pyrrolidinedione |
| h, hr | hour |
| HOBt | 1-hydroxybenzotriazole |
| HATU | 2-(7-aza-1H-benzotriazole-1-yl)-1,1,3,3-tetramethyluronium hexafluorophosphate |
| HBTU | 2-(1H-benzotriazole-1-yl)-1,1,3,3-tetramethyluronium hexafluorophosphate |
| KHMDS | potassium hexamethyldisilazane |
| LAH or LiAlH$_4$ | lithium aluminum hydride |
| LC-MS | liquid chromatography-mass spectroscopy |
| LHMDS | lithium hexamethyldisilazane |
| Me | methyl |
| MeCN | acetonitrile |
| MeOH | methanol |
| MsCl | methanesulfonyl chloride |
| Min | minute |
| MS | mass spectrum |
| NaH | sodium hydride |
| NaHCO$_3$ | sodium bicarbonate |
| NaN$_3$ | sodium azide |
| NaOH | sodium hydroxide |
| Na$_2$SO$_4$ | sodium sulfate |
| NMM | N-methylmorpholine |
| NMP | N-methylpyrrolidinone |
| Pd$_2$(dba)$_3$ | tris(dibenzylideneacetone)dipalladium(0) |
| PE | petroleum ether |
| Ph | phenyl |
| Quant | quantitative yield |
| Rt | room temperature |
| Satd | saturated |
| SOCl$_2$ | thionyl chloride |
| SPE | solid phase extraction |
| TBS | t-butyldimethylsilyl |
| TBSCl | t-butyldimethylsilyl chloride |
| TEA | triethylamine or Et$_3$N |
| TEMPO | 2,2,6,6-tetramethyl-1-piperidinyloxy free radical |
| Teoc | 1-[2-(trimethylsilyl)ethoxycarbonyloxy]- |
| Teoc-OSu | 1-[2-(trimethylsilyl)ethoxycarbonyloxy]pyrrolidin-2,5-dione |
| TFA | trifluoroacetic acid |
| THF | tetrahydrofuran |
| Tlc | thin layer chromatography |
| TMS | trimethylsilyl |
| TMSCl | chlorotrimethylsilane or trimethylsilyl chloride |
| $t_R$ | retention time |
| TsOH | p-toluenesulfonic acid |

Purification Methods

Prep HPLC refers to preparative reverse phase HPLC on a C-18 column eluted with a water/acetonitrile gradient containing 0.01% TFA run on a Gilson 215 system.

Analytical Methods

LC-MS (3 min)

Column: Chromolith SpeedRod, RP-18e, 50×4.6 mm; Mobil phase: A: 0.01% TFA/water, B: 0.01% TFA/CH$_3$CN; Flow rate: 1 mL/min; Gradient:

| Time (min) | A % | B % |
|---|---|---|
| 0.0 | 90 | 10 |
| 2.0 | 10 | 90 |
| 2.4 | 10 | 90 |
| 2.5 | 90 | 10 |
| 3.0 | 90 | 10 |

LC-MS (16 min)

Column: Chromolith SpeedRod, RP-18e, 50×4.6 mm; Mobil phase: A: 0.01% TFA/water, B: 0.01% TFA/CH$_3$CN; Flow rate: 1 mL/min; Gradient:

| Time (min) | A % | B % |
|---|---|---|
| 0.0 | 90 | 10 |
| 14.0 | 10 | 90 |
| 15.0 | 10 | 90 |
| 15.1 | 90 | 10 |
| 16.0 | 90 | 10 |

Chiral HPLC

Column: Chiralpak AD-H, 0.46 cm×25 cm
Solvent A: 0.025% Diethylamine in Hexane
Solvent B: Isopropanol
Flow rate: 1 mL/min.
40 min. run Gradient:

| Time (min) | A (%) | B (%) |
|---|---|---|
| 0 | 95 | 5 |
| 40 | 90 | 10 |

Methods for the preparation of intermediates used in the synthesis of compounds of Formula I are described below.

Preparation 1

(S)-1-(3-chlorophenyl)-5-methoxy-1-((R)-piperidin-3-yl)pentan-1-ol

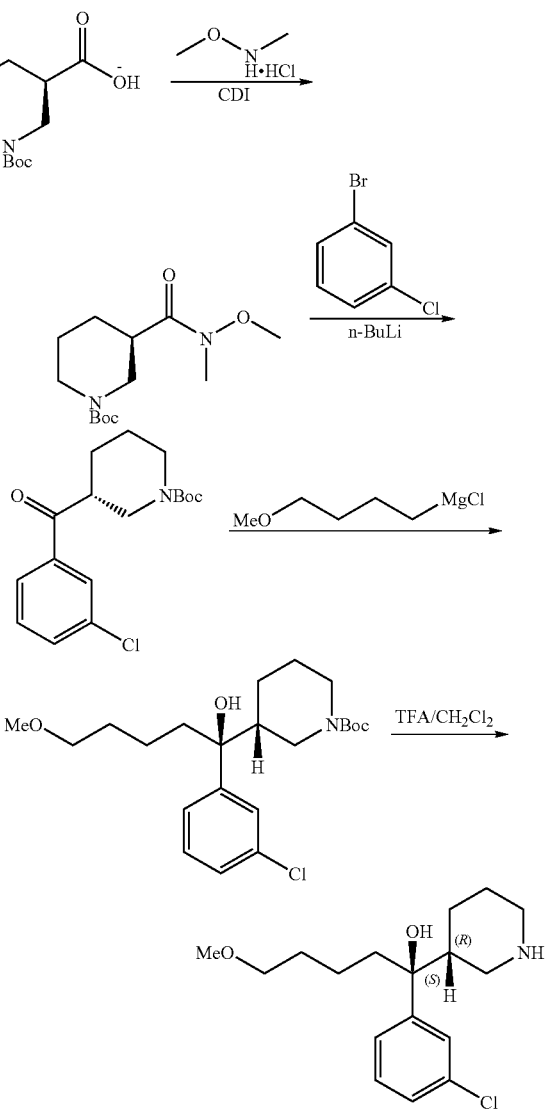

Step 1. (R)-tert-butyl 3-(methoxy(methyl)carbamoyl)piperidine-1-carboxylate

To a stirred solution of R-piperidine-1,3-dicarboxylic acid 1-tert-butyl ester (233 g, 1.2 mol) in THF (1.2 L) was added carbonyldiimidazole (230 g, 1.42 mol). The mixture was stirred for 1 h in an ice-water bath. A suspension of triethylamine (207 mL, 1.41 mol) and N,O-dimethylhydroxylamine hydrochloride (138 g, 1.42 mol) in THF (900 mL) was added. The reaction mixture was allowed to warm to rt and stirred overnight. After TLC showed the reaction was complete, solvent was evaporated to give a residue, which was dissolved in CH$_2$Cl$_2$ (1.2 L) and washed successively with 0.5 N aq HCl, satd aq Na$_2$CO$_3$ and brine, dried over anhydrous sodium sulfate and evaporated to give the crude compound (R)-tert-butyl 3-(methoxy(methyl)-carbamoyl)piperidine-1-carboxylate (250 g, 91%), which was used in the next step directly without purification. ¹H NMR (400 MHz, CDCl₃): 1.44 (s, 9H), 1.60-1.78 (m, 2H), 1.90 (m, 1H), 2.65 (m, 1H), 2.75-2.85 (m, 2H), 3.16 (s, 3H), 3.71 (s, 3H), 4.05-4.19 (m, 2H). MS (E/Z): 273 (M+H⁺).

Step 2. (R)-tert-butyl 3-(3-chlorobenzoyl)piperidine-1-carboxylate

To a solution of 1-bromo-3-chlorobenzene (15 g, 78.3 mmol) in anhydrous THF (150 mL) cooled to −78° C. was added dropwise a solution of 2.5 M n-BuLi in hexane (31.3 mL, 78.34 mmol). The reaction mixture was stirred at −78° C. for 1 h and a solution of (R)-tert-butyl 3-(methoxy(methyl) carbamoyl)piperidine-1-carboxylate (17.8 g, 65.3 mmol) in anhydrous THF (50 mL) was added dropwise. After addition, the mixture was allowed to warm to rt and stirred for 2 h. The mixture was quenched with satd aq NH₄Cl (250 mL) and extracted with EtOAc (3×150 mL). The combined organic layers were washed with brine, dried over Na₂SO₄ and concentrated in vacuo. The residue was purified by flash column chromatography (PE/EtOAc 5:95) to give (R)-tert-butyl 3-(3-chlorobenzoyl)piperidine-1-carboxylate (12.9 g, 51%). ¹H NMR (400 MHz, CDCl₃): 1.45 (s, 9H), 1.54-1.73 (m, 2H), 1.75 (m, 1H), 2.00 (m, 1H), 2.71-2.78 (m, 1H), 2.93 (m, 2H), 3.30-3.35 (m, 1H), 4.22 (m, 1H), 7.39-7.42 (t, 1H), 7.52 (d, 1H), 7.89 (d, 1H), 7.90 (m, 1H). MS (E/Z): 324 (M+H⁺).

Step 3. (R)-tert-butyl 3-((S)-1-(3-chlorophenyl)-1-hydroxy-5-methoxypentyl)piperidine-1-carboxylate A 250 mL three-necked flask was charged with magnesium turnings (2.88 g, 0.12 mol) and a small crystal of iodine in THF (20 mL). The flask was evacuated and refilled with N₂. A solution of 1-chloro-4-methoxybutane (15 g, 0.12 mol) in THF (40 mL) was added dropwise to the above mixture. After heating under reflux for 1 h, most of the magnesium had been consumed and the reaction mixture cooled to rt. Another 250-mL, three-necked flask was charged with (R)-3-(3-chloro-benzoyl)-piperidine-1-carboxylic acid tert-butyl ester (3.24 g, 10 mmol) and THF (50 mL), which was evacuated and refilled with N₂. The mixture was cooled in a dry ice-acetone bath and the Grignard reagent derived from 1-chloro-4-methoxybutane (20 mL) was added dropwise. After addition, the mixture was allowed to warm slowly to rt and stirred for 2 h. The mixture was quenched with satd aq NH₄Cl (100 mL) and extracted with EtOAc (3×80 mL). The combined organic layers were washed with brine, dried over Na₂SO₄ and concentrated in vacuo. The residue was purified by flash column chromatography (10:90 EA/PE) to give (R)-tert-butyl 3-((S)-1-(3-chlorophenyl)-1-hydroxy-5-methoxypentyl)piperidine-1-carboxylate (3.0 g, 73%). ¹H NMR (400 MHz, CDCl₃): 1.45 (s, 9H), 1.52-1.58 (m, 3H), 1.75 (m, 1H); 1.92 (m, 2H), 2.52 (m, 2H), 3.25 (s, 3H), 3.27 (m, 2H), 3.95 (m, 1H), 4.35 (m, 1H), 7.20-7.26 (m, 3H), 7.36 (m, 1H). MS (E/Z): 412 (M+H⁺).

Step 4. (S)-1-(3-chlorophenyl)-5-methoxy-1-((R)-piperidin-3-yl)pentan-1-ol (R)-tert-butyl 3-((S)-1-(3-chlorophenyl)-1-hydroxy-5-methoxypentyl)piperidine-1-carboxylate (4.1 g, 0.01 mol) was dissolved in 20% TFA/CH₂Cl₂ (40 mL). The reaction mixture was stirred at rt for 2 h, tlc showed the reaction was complete. A solution of satd aq Na₂CO₃ was added dropwise to adjust the pH to 8~9 and the mixture was extracted with EtOAc (3×50 mL). The combined organic layers were washed with brine, dried over Na₂SO₄ and concentrated in vacuo to give crude (S)-1-(3-chlorophenyl)-5-methoxy-1-((R)-piperidin-3-yl)pentan-1-ol (3.0 g, 97%), which was used without purification.

The following intermediates were prepared using procedures analogous to those described above:
(S)-1-(2,3-difluorophenyl)-5-methoxy-1-((R)-piperidin-3-yl)pentan-1-ol using 2,3-difluorobromobenzene in Step 2.

Preparation 2

(S)-1-(3-chloro-2-fluorophenyl-5-methoxy-1-((R)-piperidin-3-yl)pentan-1-ol

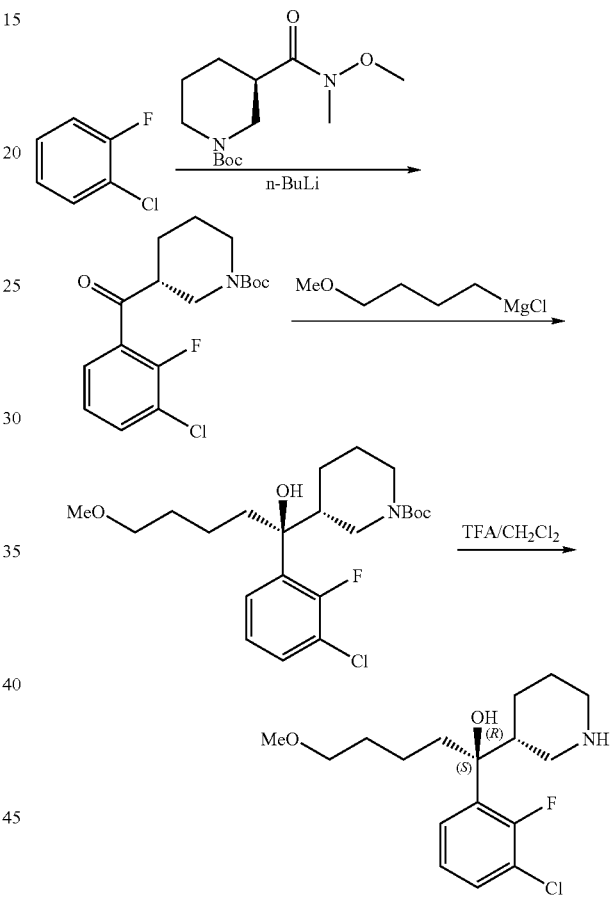

Step 1. (R)-tert-butyl 3-(3-chloro-2-fluorobenzoyl) piperidine-1-carboxylate To a stirred solution of 1-chloro-2-fluoro-benzene (13.0 g, 0.1 mol) in THF (250 mL) at −75° C. was added dropwise 2.5 M BuLi in hexane (40 mL, 0.1 mol) over 45 min. After additional stirring for 30 min at −75° C., a solution of (R)-tert-butyl 3-(methoxy(methyl)carbamoyl)-piperidine-1-carboxylate (21.76 g, 0.08 mol) in THF (100 mL) was added dropwise over 30 min. The mixture was allowed to warm from −70° C. to 0° C. The mixture was quenched with satd aq NH₄Cl, extracted with EtOAc (3×) and the combined organic layers were dried over Na₂SO₄. Solvent removal and flash column chromatography, eluting with 5% EtOAc/PE afforded (R)-tert-butyl 3-(3-chloro-2-fluorobenzoyl)piperidine-1-carboxylate (19.2 g, 70%). ¹H NMR (400 MHz, CDCl₃): 1.45 (s, 9H), 1.63 (m, 2H), 1.76 (m, 1H), 2.06 (m, 1H), 2.87 (m, 1H), 3.15 (m, 1H), 3.25 (m, 1H), 3.9 (m, 1H), 4.2 (m, 1H), 7.18 (m, 1H), 7.60 (m, 2H). MS (E/Z): 342 (M+H$^+$).

Step 2. (R)-tert-butyl 3-((S)-1-(3-chloro-2-fluorophenyl)-1-hydroxy-5-methoxypentyl)piperidine-1-carboxylate A flame dried 250 mL three-necked flask was charged with magnesium turnings (7.02 g, 0.293 mol), a small crystal of iodine and THF (30 mL). The flask was evacuated and refilled with N$_2$. A solution of 1-chloro-4-methoxybutane (28.69 g, 0.234 mol) in THF (120 mL) was added dropwise slowly to the mixture. The reaction mixture was stirred under reflux for 2.5 h and most of magnesium was consumed. The resulting Grignard reagent was used as follows To another 100 mL three-necked flask was added (R)-tert-butyl 3-(3-chloro-2-fluorobenzoyl)-piperidine-1-carboxylate (10 g, 0.0293 mol) and THF (100 mL). The flask was evacuated and refilled with N$_2$. The mixture was cooled in a dry ice-acetone bath and the Grignard reagent (250 mL) was added. The reaction mixture was allowed to warm slowly to rt while stirring overnight. The mixture was quenched with satd aq NH$_4$Cl (50 mL), extracted with EtOAc (3×), and the combined organic layers were dried over Na$_2$SO$_4$. Evaporation of the solvent gave the crude product. LC-MS analysis of the crude product indicated the presence of two isomers (95:5). Flash column chromatography, eluting with 10% EtOAc/PE afforded (R)-tert-butyl 3-((S)-1-(3-chloro-2-fluorophenyl)-1-hydroxy-5-methoxypentyl)piperidine-1-carboxylate (9.4 g, 75% yield). $^1$H NMR (400 MHz, DMSO): 0.68 (m, 1H), 1.50-1.01 (m, 7H), 1.37 (s, 9H), 1.75 (m, 2H), 2.01 (m, 1H), 3.11 (s, 3H), 3.17 (m, 2H), 3.85 (m, 1H), 7.2 (t, 1H), 7.45 (m, 2H). MS (E/Z): 430 (M+H$^+$).

Step 3. (S)-1-(3-chloro-2-fluorophenyl)-5-methoxy-1-((R)-piperidin-3-yl)pentan-1-ol A solution of (R)-tert-butyl 3-((S)-1-(3-chloro-2-fluorophenyl)-1-hydroxy-5-methoxypentyl)piperidine-1-carboxylate (100 mg) in 20% TFA/CH$_2$Cl$_2$ was stirred at 0° C. for 30 min. The mixture was neutralized by addition of satd aq NaHCO$_3$, extracted with CH$_2$Cl$_2$ (3×) and dried over Na$_2$SO$_4$. Evaporation of the solvent gave (S)-1-(3-chloro-2-fluorophenyl)-5-methoxy-1-((R)-piperidin-3-yl)pentan-1-ol (70 mg, 91%), which was used without further purification. $^1$H NMR (400 MHz, CDCl$_3$): 0.90(m, 1H), 1.52-1.24 (m, 6H), 1.78 (m, 1H), 1.83 (m, 1H), 1.93 (m, 1H), 2.21 (m, 1H), 2.40 (m, 1H), 2.83 (m, 1H), 3.00 (m, 1H), 3.12 (s, 3H), 3.31 (m, 2H), 3.63 (m, 1H), 7.06 (m, 1H), 7.30 (m, 1H), 7.55 (t, 1H). MS (E/Z): 330 (M+H$^+$).

Preparation 3

Methyl (S)-4-(3-chlorophenyl)-4-hydroxy-4-((R)-piperidin-3-yl)butylcarbamate

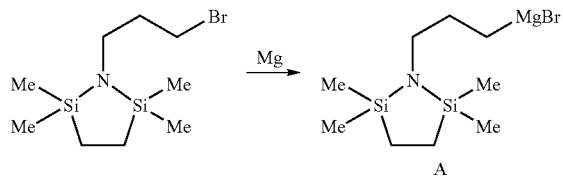

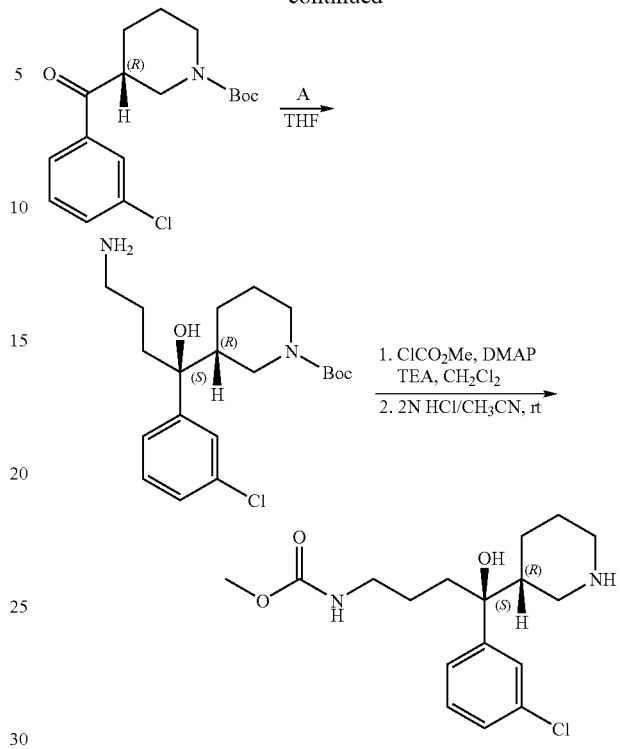

Step 1. [3-(2,2,5,5-tetramethyl-1-aza-2,5-disilacyclopent-1-yl)propyl]magnesium bromide A 250 mL, round bottom flask was charged with magnesium turnings (0.528 g, 21.7 mmol, 1.16 equiv) and THF (10 mL). The flask was degassed and heated to 100° C. A small crystal of iodine was then added. A solution of 1-(3-bromopropyl)-2,2,5,5-tetramethyl-1-aza-2,5-disilacyclopentane (5.239 g, 18.7 mmol, 1.0 equiv) in THF (15 mL) was added dropwise to the boiling THF mixture over 10 min. The reaction mixture was stirred and heated under reflux for 2.5 h and most of magnesium was consumed. The resulting Grignard reagent (A) was used in the next step.

Step 2. (R)-tert-butyl 3-((S)-4-amino-1-(3-chlorophenyl)-1-hydroxybutyl)piperidine-1-carboxylate To a 250 mL, round bottom flask were added (3-chlorophenyl)((R)-N-Boc-piperidin-3-yl)methanone (0.800 g, 2.47 mmol) and THF (10 mL). The flask was evacuated and refilled with N$_2$. The mixture was cooled with a dry ice-acetone bath and the [3-(2,2,5,5-tetramethyl-1-aza-2,5-disilacyclopent-1-yl)propyl]magnesium bromide solution (A), obtained in Step 1, was added via a cannula. The reaction mixture was allowed to slowly warm to −8° C. while stirring overnight. The mixture was quenched with 10% aq Na$_2$CO$_3$ (10 mL), stirred at rt for 3 h, extracted with CH$_2$Cl$_2$ (3×), and dried over Na$_2$SO$_4$. The crude product was purified by reversed-phase HPLC (Phenomenex® Luna 5 µ C18(2) 100 A, 250×21.20 mm, 5 micron, 10% →90% CH$_3$CN/H$_2$O, 0.1% CF$_3$COOH over 13 min and then 90% CH$_3$CN/H$_2$O, 0.1% CF$_3$COOH over 3.5 min, flow rate 25 mL/min) to give 0.883 g (72%) of TFA salt of (R)-tert-butyl 3-((S)-4-amino-1-(3-chlorophenyl)-1-hydroxybutyl)piperidine-1-carboxylate. LC-MS (3 min) t$_R$=1.30 min, m/z 383, 385 (MH$^+$), 327, 329; $^1$H NMR (400

MHz, CD$_3$OD) δ 7.36 (m, 1H), 7.27-7.13 (m, 3H), 4.26 (br s, 1H), 3.89 (d, J=12.9 Hz, 1H), 2.82-2.68 (m, 2H), 2.44 (br s, 1H), 2.36 (t, J=12.2 Hz, 1H), 1.97-1.79 (m, 2H), 1.64-1.08 (m, 16H), 1.34 (s); $^{13}$C NMR (100 MHz, CD$_3$OD) δ 156.69, 148.15, 135.39, 130.69, 127.74, 127.36, 125.41, 81.04, 78.10, 40.95, 28.69, 26.64, 26.51, 23.30.

Step 3. (R)-tert-butyl 3-((S)-4-(methoxycarbonylamino)-1-(3-chlorophenyl)-1-hydroxybutyl)-piperidine-1-carboxylate To a 100 mL round bottom flask were added the TFA salt of (R)-tert-butyl 3-((S)-4-amino-1-(3-chlorophenyl)-1-hydroxybutyl)piperidine-1-carboxylate (0.8164 g, 1.64 mmol, 1.0 equiv), DMAP (0.542 g), CH$_2$Cl$_2$ (40 mL) and triethylamine (6 mL). The mixture was cooled in an ice bath and a solution of methyl chloroformate (0.550 g, 5.82 mmol, 3.5 equiv) in CH$_2$Cl$_2$ (10 mL) was added. The reaction mixture was allowed to slowly warm to rt and stirred overnight. After the solvents were removed in vacuo, the residue was purified by reversed-phase HPLC (Phenomenex® Luna 5μ C18(2) 100 A, 250×21.20 mm, 5 micron, 70%→90% CH$_3$CN/H$_2$O, 0.1% CF$_3$COOH over 8 min and then 90% CH$_3$CN/H$_2$O, 0.1% CF$_3$COOH over 1.5 min, flow rate 25 mL/min) to give 0.5020 g (69%) of (R)-tert-butyl 3-((S)-4-(methoxycarbonylamino)-1'-(3-chlorophenyl)1-hydroxybutyl)piperidine-1-carboxylate. LC-MS (3 min) t$_R$=1.91 min, m/z 463 (MNa$^+$), 441 (MH$^+$), 343 341; $^1$H NMR (400 MHz, CDCl$_3$) δ 7.37-7.36 (m, 1H), 7.28-7.17 (m, 3H), 4.90 (br s, 2H), 4.37 (d, J=12.0 Hz, 1H), 3.97 (d, J=12.3 Hz, 1H), 3.64 (s, 3H), 3.16-3.04 (m, 2H), 2.58-2.49 (m, 2H), 1.98-1.86 (m, 2H), 1.76-1.70 (m, 1H), 1.61-1.56 (m, 1H), 1.45 (s, 9H), 1.48-1.13 (m, 5H); $^{13}$C NMR (100 MHz, CDCl$_3$) δ 157.60, 155.31, 146.51, 134.31, 129.36, 126.72, 125.96, 123.76, 80.08, 77.65, 52.21, 46.45, 44.91, 44.56, 40.91, 35.97, 28.42, 25.33, 25.25, 24.34.

Step 4. Methyl (S)-4-(3-chlorophenyl)-4-hydroxy-4-((R)-piperidin-3-yl)butylcarbamate A mixture of (R)-tert-butyl 3-((S)-4-(methoxycarbonylamino)-1-(3-chlorophenyl)-1-hydroxybutyl)piperidine-1-carboxylate (0.0322 g, 0.073 mmol), obtained as described above, in CH$_3$CN (30 mL) and 2 N aq HCl (25 mL) was vigorously stirred at rt for 24 h. The solvents were removed in vacuo to give the HCl salt of methyl (S)-4-(3-chlorophenyl)-4-hydroxy-4-((R)-piperidin-3-yl)butylcarbamate, which was used without further purification. LC-MS (3 min) t$_R$=0.98 min, m/z 343, 341 (M+H$^+$), 323.

Preparation 4

(R)-1-(3-Chloro-2-fluorophenyl)-5-methoxy-1-((R)-morpholin-2-yl)pentan-1-ol

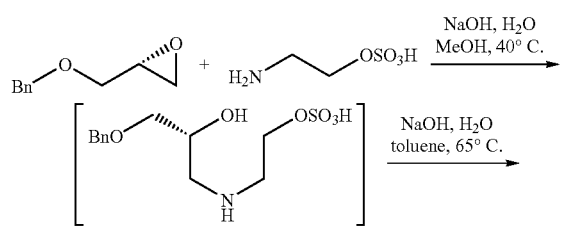

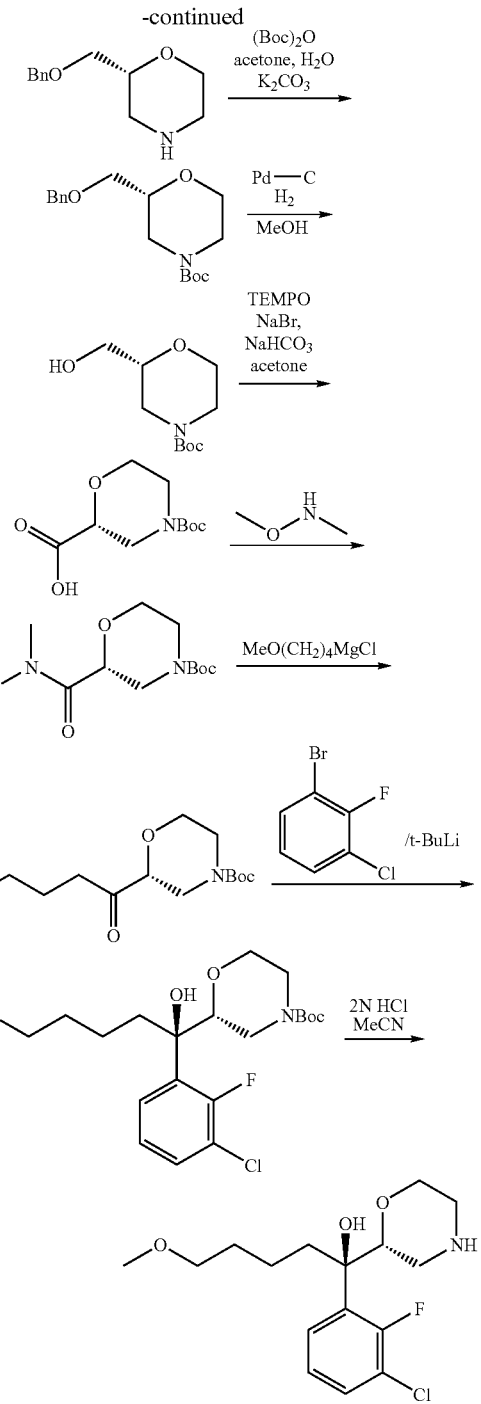

Step 1. (R)-2-(Benzyloxymethyl)morpholine

To a stirred mixture of (R)-2-(benzyloxymethyl)oxirane (10.0 g, 60.9 mmol) and NaOH (19.49 g, 487.2 mmol) in H$_2$O (46 mL) and MeOH (18 mL), there was added 2-aminoethyl hydrogen sulfate (36.8 g, 255.8 mmol) in portions. After addition, the reaction mixture was stirred at 40° C. for 2 h. After cooling, the mixture was treated with NaOH (15.0 g, 375.0 mmol) then toluene (70 mL) and stirred at 65° C. overnight. The mixture was cooled, diluted with toluene (27 mL) and H$_2$O (92 mL). The toluene layer was separated and the aqueous layer was extracted with CH$_2$Cl$_2$ (2×50 mL). The combined organic layers were concentrated to give crude (R)-2-(benzyloxymethyl)morpholine (~14 g), which was used without purification. MS m/z 208 (M+H$^+$).

Step 2. (R)-tert-Butyl 2-(benzyloxymethyl)morpholine-4-carboxylate

To a solution of crude (R)-2-(benzyloxymethyl)morpholine (~14 g) in acetone (100 mL) and H$_2$O (30 mL) at 0° C., was added K$_2$CO$_3$ (25.2 g, 182.7 mmol), followed by (Boc)$_2$O (14.6 g, 67.0 mmol). The resulting solution was warned to rt, and stirred until no starting material remained (~30 min). Acetone was removed under vacuum and the aqueous solution was extracted with CH$_2$Cl$_2$ (4×10 mL). The combined organic layers were washed with H$_2$O (10 mL) and the solvent was removed. The residue was purified by flash column chromatography to give (R)-tert-butyl 2-(benzyloxymethyl)morpholine-4-carboxylate (8.33 g, 44% over 2 steps). $^1$H NMR (400 MHz, CDCl$_3$): 7.34 (m, 5H), 4.56 (s, 2H), 3.88 (d, 2H), 3.82 (br, 1H), 3.40 (m, 1H), 3.48 (m, 3H), 2.94 (m, 1H), 2.76 (m, 1H), 1.44 (s, 9H); MS m/z 330 (M+Na$^+$).

Step 3. (R)-tert-Butyl 2-(hydroxymethyl)morpholine-4-carboxylate

To a solution of (R)-tert-butyl 2-(benzyloxymethyl)morpholine-4-carboxylate (8.33 g, 27.1 mmol) in EtOH was added Pd-C (wet, 3.6 g), and the resulting mixture was stirred at rt under a H$_2$ balloon overnight. After filtration, the solvent was removed under vacuum and the residue was purified by flash column chromatography to give (R)-tert-butyl 2-(hydroxymethyl)morpholine-4-carboxylate (5.84 g, 99%) as a clear oil. $^1$H NMR (400 MHz, CDCl$_3$): 3.88 (d, 2H), 3.82 (br, 1H), 3.64 (d, 1H), 3.56 (m, 3H), 2.94 (m, 1H), 2.76 (m, 1H), 1.90 (br, 1H), 1.44 (s, 9H); MS m/z 218 (M+H$^+$).

Step 4. (R)-4-(tert-Butoxycarbonyl)morpholine-2-carboxylic Acid

Satd aq NaHCO$_3$ (15 mL) was added to a solution of (R)-tert-butyl 2-(hydroxymethyl)-morpholine-4-carboxylate (1.09 g, 5.0 mmol) in acetone (50 mL), stirred and maintained at 0° C. Solid NaBr (0.1 g, 1 mmol) and TEMPO (0.015 g, 0.1 mmol) were added. Trichloroisocyanuric acid (2.32 g, 10.0 mmol) was then added slowly within 20 min at 0° C. After addition the mixture was warmed to rt and stirred overnight. 2-Propanol (3 mL) was added, and the resulting solution was stirred at rt for 30 min, filtered through a pad of Celite, concentrated under vacuum, and treated with satd aq Na$_2$CO$_3$ (15 mL). The aqueous solution was washed with EtOAc (5 mL), acidified with 6 N HCl, and extracted with EtOAc (5×10 mL). These EtOAc extracts were combined, dried over Na$_2$SO$_4$ and concentrated to give (R)-4-(tert-butoxycarbonyl)morpholine-2-carboxylic acid (1.07 g, 92%) as a white solid. $^1$H NMR (400 MHz, CDCl$_3$): 4.20 (br, 1H), 4.12 (d, 1H), 4.02 (d, 1H), 3.84 (m, 1H), 3.62 (m, 1H), 3.04 (m, 2H), 1.44 (s, 9H); MS m/z 232 (M+H$^+$).

Step 5. (R)-tert-Butyl 2-(methoxy(methyl)carbamoyl)morpholine-4-carboxylate

To a solution of (R)-4-(tert-butoxycarbonyl)morpholine-2-carboxylic acid (1.05 g, 4.54 mmol) in DMF (10 mL) at 0° C. were added N,O-dimethylhydroxylamine hydrochloride (1.36 g, 13.62 mmol), DIEA (3.9 mL, 22.7 mmol), HBTU (1.89 g, 4.99 mmol) and HOBt (0.67 g, 4.99 mmol). The resulting solution was warmed to rt and stirred until no starting material remained (~2 h). The mixture was diluted with H$_2$O (10 mL) and extracted with EtOAc (4×10 mL). The combined organic layers were washed with 1 N aq HCl (10 mL), 1 N aq NaOH (3×10 mL), water (2×10 mL) and brine (10 mL), and dried over Na$_2$SO$_4$. The solvent was removed under vacuum to give (R)-t-butyl 2-(methoxy(methyl)carbamoyl)morpholine-4-carboxylate (1.40 g, quant.), which was used for the next step without further purification; $^1$H NMR (400 MHz, CDCl$_3$) δ: 4.36 (br, 1H), 4.08 (m, 1H), 4.00 (d, 1H), 3.84 (m, 1H), 3.76 (s, 3H), 3.58 (m, 1H), 3.20 (s, 3H), 3.04 (m, 2H), 1.44 (s, 9H); MS m/z 297 (M+Na$^+$).

Step 6. (R)-tert-Butyl 2-(5-methoxypentanoyl)morpholine-4-carboxylate

To a solution of (R)-tert-butyl 2-(methoxy(methyl)carbamoyl)morpholine-4-carboxylate (1.37 g, 5.0 mmol) in THF (10 mL) at −20° C., there was added (4-methoxybutyl)magnesium chloride in THF (1.47 M, 10.2 mL, 15.0 mmol) dropwise such that the temperature remained below −20° C. After addition, the resulting solution was warmed to rt, and quenched with 1 N aq HCl (10 mL). The organic layer was separated, and the aqueous layer was extracted with ether (3×5 mL). The combined organic layers were washed with satd aq NaHCO$_3$ (10 mL) and brine (5 mL), and dried over Na$_2$SO$_4$. The solvent was then removed in vacuo to give (R)-tert-butyl 2-(5-methoxypentanoyl)morpholine-4-carboxylate (1.41 g, 93%), which was used for the next step without purification; MS m/s 324 (M+Na$^+$).

Step 7. (R)-tert-Butyl 2-((R)-1-(3-chloro-2-fluorophenyl)-1-hydroxy-5-methoxypentyl)-morpholine-4-carboxylate To a solution of 1-bromo-3-chloro-2-fluorobenzene (1.42 g, 6.77 mmol) in THF (8 mL) at −70° C., was added t-BuLi in pentane (1.7 M, 7.96 mL, 13.5 mmol) dropwise such that the temperature remained below −70° C. The resulting solution (A) was stirred at the same temperature for another 30 min, and used directly in the next step.

To a solution of (R)-tert-butyl 2-(5-methoxypentanoyl) morpholine-4-carboxylate (0.64 g, 2.12 mmol) in toluene (5 mL) at −20° C., solution A prepared above was added dropwise. The resulting solution was allowed to warm to rt slowly, and kept at same temperature for 1 h. The reaction was quenched with satd aq NH$_4$Cl (8 mL) and extracted with diethyl ether (4×10 mL). The combined organic layers were washed with water and brine, and solvent was removed in vacuo to give a crude product, which was purified by flash column chromatography to afford (R)-tert-butyl 2-((R)-1-(3-chloro-2-fluorophenyl)-1-hydroxy-5-methoxypentyl)morpholine-4-carboxylate (0.40 g, 43%). $^1$H NMR (400 MHz, CDCl$_3$) δ: 7.44 (dd, 1H), 7.32 (dd, 1H), 7.04 (dd, 1H), 4.18 (br, 1H), 3.80 (m, 3H), 3.42 (dd, 1H), 3.24 (st, 5H), 3.04-2.80 (m, 3H), 2.04 (m, 1H), 1.68 (m, 1H), 1.44 (s, 9H), 1.30 (m, 3H), 0.86 (m, 1H); MS m/z 454 (M+Na$^+$).

Step 8. (R)-1-(3-Chloro-2-fluorophenyl)-5-methoxy-1-((R)-morpholin-2-yl)pentan-1-ol To a solution of (R)-tert-butyl 2-((R)-1-(3-chloro-2-fluorophenyl)-1-hydroxy-5-methoxypentyl)morpholine-4-carboxylate (0.38 g, 0.88 mmol) in MeCN (50 mL), 2 N aq HCl (50 mL) was added slowly at rt. The resulting solution was stirred at rt overnight, basified to pH=10 with 10 N aq NaOH, and evaporated under reduced pressure to remove MeCN. The aqueous layer was extracted with CH$_2$Cl$_2$ (4×5 mL). The combined organic layers were washed with brine and dried over Na$_2$SO$_4$. The solvent was removed in vacuo to give (R)-1-(3-chloro-2-fluorophenyl)-5-methoxy-1-((R)-morpholin-2-yl)pentan-1-ol (0.27 g, 93%) as a free amine. The crude product was used for next step without purification; MS m/z 332 (M+H$^+$).

Preparation 5

(R)-tert-butyl 3-((R)-(3-methoxypropoxy)(phenyl)methyl)piperidine-1-carboxylate

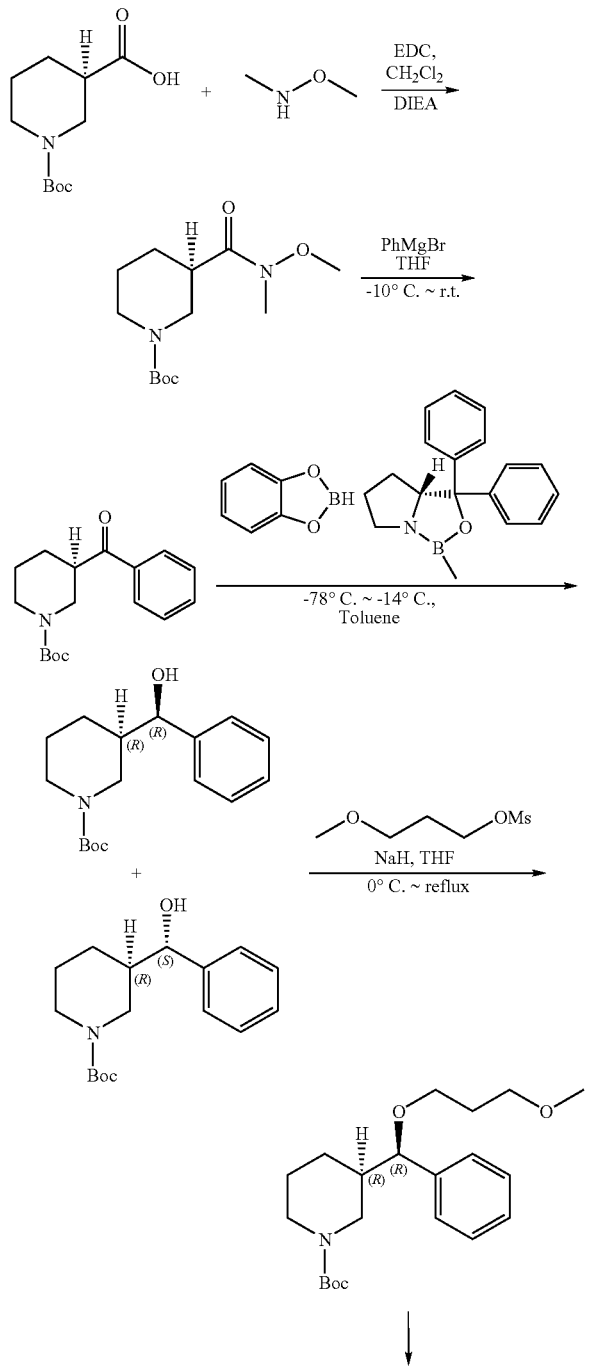

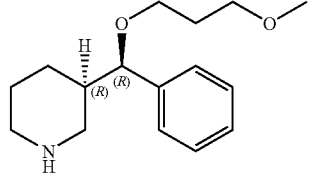

Step 1. (R)-tert-butyl 3-(N-methoxy-N-methylcarbamoyl)piperidine-1-carboxylate (R)-1-(tert-Butoxycarbonyl)piperidine-3-carboxylic acid (25 g, 0.1 mol, 1.0 equiv), N,O-dimethylhydroxylamine hydrochloride, (10.5 g, 0.14 mol, 1.25 equiv), EDC.HCl (26.3 g, 0.14 mol, 1.25 equiv), and diisopropylethylamine (48 mL, 0.28 mol, 2.5 equiv) were dissolved in CH$_2$Cl$_2$ (400 mL) and stirred overnight at rt. The reaction mixture was diluted with EtOAc, washed with 5% aq HCl (2×150 mL), satd aq NaHCO$_3$ (150 mL), and brine (100 mL) and dried over Na$_2$SO$_4$. Concentration afforded (R)-tert-butyl 3-(N-methoxy-N-methylcarbamoyl)-piperidine-1-carboxylate (24.42 g, 82%) as a clear oil. LC-MS (3 min) t$_R$=1.41 min, m/z 295 (M+Na). $^1$H NMR (CDCl$_3$) δ 4.19-4.00 (m, 2H), 3.77 (m, 3H), 3.12 (s, 3H), 2.79 (m, 2H), 2.64 (m, 1H), 1.89 (m, 1H), 1.71-1.52 (m, 2H), 1.51-1.33 (m, 10H). Chiral HPLC indicated 100% purity. The crude product was used for next step without further purification.

Step 2. (R)-tert-butyl 3-benzoylpiperidine-1-carboxylate (R)-tert-Butyl 3-(N-methoxy-N-methylcarbamoyl)piperidine-1-carboxylate (13.6 g, 50 mmol) was dissolved in anhydrous THF (200 mL) and cooled to −10° C. (ice/MeOH bath). Phenylmagnesium bromide solution in THF (200 mL of 1.0 M, 100 mmol, 2 equiv) was added slowly. After 15 min, the reaction mixture was warmed up to rt slowly and stirred for 1 h. LC-MS showed the reaction was complete. 5% aq HCl (100 mL) was added slowly to quench the reaction and the mixture was stirred for 20 min. After separation, the aqueous layer was extracted with ether (2×200 mL). The combined organic layers were washed with satd aq NaHCO$_3$ (150 mL) and brine (100 mL), and dried over Na$_2$SO$_4$. Concentration afforded crude (R)-tert-butyl 3-benzoylpiperidine-1-carboxylate (16.45 g, 110%) as a clear oil which was used for the next step without further purification. LC-MS (3 min) t$_R$=1.91 min, m/z 302 (M+Na). $^1$H NMR (CDCl$_3$) δ 7.94 (d, 2H), 7.54 (t, 1H), 7.47 (t, 2H), 4.28 (br d, 1H), 4.09 (d, 1H), 3.38 (t, 1H), 2.92 (br t, 1H), 2.72 (t, 1H), 2.01 (d, 1H), 1.79-1.45 (m, 3H) 1.42 (s, 9H). Chiral HPLC indicated 100% purity.

Step 3. (R)-tert-butyl 3-((R)-hydroxy(phenyl)methyl)piperidine-1-carboxylate

A solution of (R)-tert-butyl 3-benzoylpiperidine-1-carboxylate (10.3 g, 35.64 mmol) in anhydrous toluene (120 mL) was cooled to −78° C. and (R)-2-methyl-CBS-oxazaborolidine (1.0M in toluene, 17.8 mL, 17.8 mmol, 0.5 equiv) was added slowly. After 5 min, catecholborane (11.4 mL, 107 mmol, 3 equiv) was added slowly. The reaction mixture was then transferred into the freezer (−14° C.) and left overnight. LC-MS (16 min) showed a 9:1 ratio of the R to the S isomer. The mixture was cooled to 0° C. and water was added dropwise to quench the reaction. The reaction mixture was diluted with ether, washed with 5% aq NaOH (2×150 mL), water (150 mL), 5% aq HCl (100 mL), and brine (100 mL), and dried over $Na_2SO_4$. After concentration, the crude product was purified by flash chromatography on a 120-g silica gel column eluted with a 4-35% EtOAc in hexanes gradient. The purified product was recrystallized from an ether/hexanes mixture to afford (R)-tert-butyl 3-((R)-hydroxy(phenyl)methyl)piperidine-1-carboxylate (4.45 g, 43%) as a white solid with the ratio of R/S isomers 23.5:1. LC-MS (3 min) $t_R$=1.70 min; LC-MS (3 min) $t_R$=10.62 min, m/z 314 (M+Na). $^1H$ NMR ($CDCl_3$) δ 7.28 (m, 5H), 4.46 (d, 1H), 3.87 (d, 1H), 3.89-3.51 (br s, free exchange 1H), 3.00 (m, 2H), 2.68 (t, 1H), 2.52 (t, 1H), 1.94 (m, 1H), 1.76 (m, 1H), 1.65 (m, 1H), 1.42-1.20 (m, 10H).

Step 4. (R)-tert-Butyl 3-((R)-(3-methoxypropoxy)(phenyl)methyl)piperidine-1-carboxylate An oven dried flask was charged with (R)-tert-butyl 3-((R)-hydroxy(phenyl)-methyl)piperidine-1-carboxylate (162 mg, 0.557 mmol) and 60% NaH in mineral oil (112 mg, 5 equiv.). The flask was purged with $N_2$ gas, cooled to 0° C. and anhydrous THF (6 mL) was added slowly. After 5 min, the reaction mixture was allowed to warm to rt slowly. A solution of 3-methoxypropyl methanesulfonate (468 mg, 4 equiv.) in anhydrous THF (5 mL) was added. The mixture was heated at reflux for 4 h. LC-MS indicated the reaction was complete. The reaction mixture was cooled to 0° C. and water was added dropwise. After separation, the aqueous layer was extracted with ether (3×). The combined organic layers were washed with 5% aq HCl, satd aq $NaHCO_3$ and brine, and dried over $Na_2SO_4$. After concentration, the crude product was purified by flash chromatography on a 4-g silica gel cartridge eluted with a 0-35% EtOAc in hexanes gradient to afford (R)-tert-butyl 3-((R)-(3-methoxypropoxy)(phenyl)-methyl)piperidine-1-carboxylate (196 mg, 97% yield) as a clear oil. LC-MS (3 min) $t_R$=2.19 min, m/z 386 (M+Na).

Step 5. (R)-3-((R)-(3-Methoxypropoxy)(phenyl)methyl)piperidine (R)-tert-Butyl 3-((R)-(3-methoxypropoxy)(phenyl)methyl)piperidine-1-carboxylate (27 mg, 0.074 mmol) was mixed with 4M HCl in 1,4-dioxane (3 mL) and stirred for 30 min at rt. LC-MS showed complete removal of the Boc protecting group. The mixture was concentrated to afford (R)-3-((R)-(3-methoxypropoxy)(phenyl)methyl)piperidine as its HCl salt. This material was used without purification.

The following compounds were prepared using procedures analogous to those described above with the modifications noted:

(3R)-3-((3-Methoxypropoxy)(phenyl)methyl)piperidine was prepared by using $NaBH_4$ in methanol in place of (R)-2-methyl-CBS-oxazaborolidine and catecholborane in Step 3.

3-((3-Methoxypropoxy)(phenyl)methyl)piperidine was prepared by starting with racemic 1-(tert-butoxycarbonyl)piperidine-3-carboxylic acid in Step 1 and using $NaBH_4$ in methanol in place of (R)-2-methyl-CBS-oxazaborolidine and catecholborane in Step 3.

3-(1-(3-Methoxypropoxy)-2-methylpropyl)piperidine was prepared by starting with racemic 1-(tert-butoxycarbonyl)piperidine-3-carboxylic acid in Step 1, using i-PrMgBr in Step 2, and using $NaBH_4$ in methanol in place of (R)-2-methyl-CBS-oxazaborolidine and catecholborane in Step 3.

3-((2-Methoxyethoxy)(phenyl)methyl)piperidine was prepared starting with racemic 1-(tert-butoxycarbonyl)piperidine-3-carboxylic acid in Step 1, using $NaBH_4$ in methanol in place of (R)-2-methyl-CBS-oxazaborolidine and catecholborane in Step 3, and using 2-methoxyethyl bromide in Step 4.

3-((4-Methoxybutoxy)(phenyl)methyl)piperidine was prepared starting with racemic 1-(tert-butoxycarbonyl)piperidine-3-carboxylic acid in Step 1, using $NaBH_4$ in methanol in place of (R)-2-methyl-CBS-oxazaborolidine and catecholborane in Step 3, and using 4-methoxybutyl bromide in Step 4.

3-(Butoxyphenyl)methyl)piperidine was prepared starting with racemic 1-(tert-butoxycarbonyl)-piperidine-3-carboxylic acid in Step 1, using $NaBH_4$ in methanol in place of (R)-2-methyl-CBS-oxazaborolidine and catecholborane in Step 3, and using butyl iodide in Step 4.

3-(Hexyloxy(phenyl)methyl)piperidine was prepared starting with racemic 1-(tert-butoxycarbonyl)piperidine-3-carboxylic acid in Step 1, using $NaBH_4$ in methanol in place of (R)-2-methyl-CBS-oxazaborolidine and catecholborane in Step 3, and using hexyl iodide in Step 4.

Preparation 6

3-((4-methoxybutoxy)(phenyl)methyl)pyrrolidine

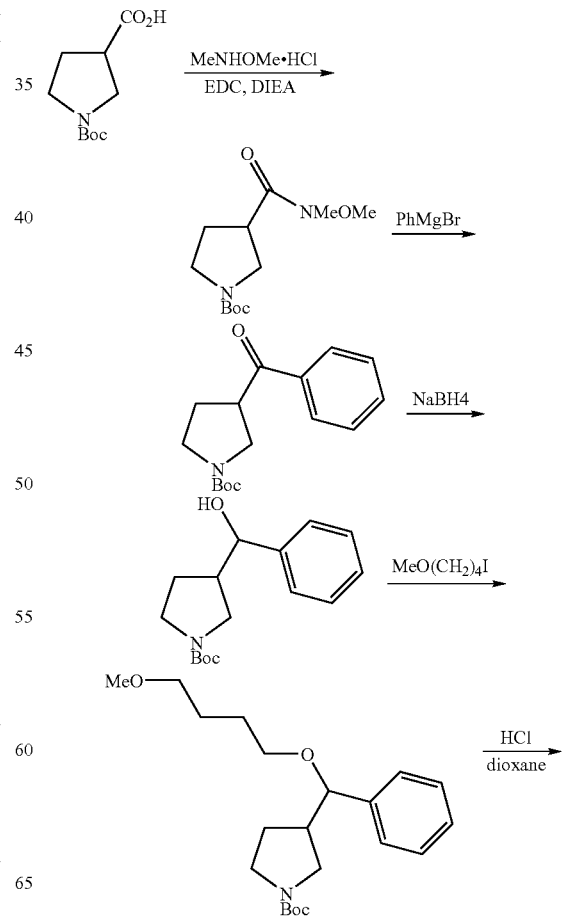

-continued

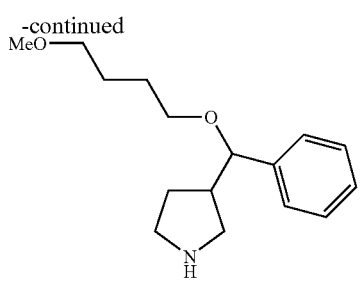

Step 1. tert-Butyl 3-(methoxy(methyl)carbamoyl) pyrrolidine-1-carboxylate

To a stirred solution of 1-(tert-butoxycarbonyl)pyrrolidine-3-carboxylic acid (4.00 g, 18.6 mmol), N,O-dimethylhydroxylamine hydrochloride (1.69 g, 17.4 mmol), and DIEA (7.5 mL, 41.8 mmol) in $CH_2Cl_2$ (80 mL) was added solid EDC.HCl (4.00 g, 20.9 mmol). The mixture was stirred at rt for 18 h and concentrated under reduced pressure. The residue was taken up in ether (175 mL), washed with 5% aq HCl (2×50 mL) and satd aq $NaHCO_3$ (50 mL), and dried over $MgSO_4$. Removal of the solvent left tert-butyl 3-(methoxy (methyl)carbamoyl)pyrrolidine-1-carboxylate (3.16 g, 65%) as an oil.

Step 2. tert-Butyl 3-benzoylpyrrolidine-1-carboxylate

A stirred solution of tert-butyl 3-(methoxy(methyl)carbamoyl)pyrrolidine-1-carboxylate (2.27 g, 8.8 mmol) in dry THF (40 mL) was cooled in an ice bath and 1 M PhMgBr in THF (20 mL, 20.0 mmol) was added dropwise over 2 min. The mixture was stirred and the ice bath was allowed to melt. After 3 h, the mixture was poured into satd aq $NH_4Cl$ and extracted with ether (2×200 mL). The combined ether extracts were dried over $MgSO_4$ and concentrated to leave an oil. Flash chromatography on a 40-g silica cartridge eluted with a 0 to 50% EtOAc in hexanes gradient afforded tert-butyl 3-benzoylpyrrolidine-1-carboxylate (2.04 g, 84%) as a clear colorless oil.

Step 3. tert-Butyl 3-(hydroxy(phenyl)methyl)pyrrolidine-1-carboxylate

To a stirred solution of tert-butyl 3-benzoylpyrrolidine-1-carboxylate (0.77 g, 2.8 mmol) in methanol (40 mL) was added granular $NaBH_4$ (0.21 g, 5.6 mmol). The mixture was stirred at rt for 3 d and solvent was removed under reduced pressure. The residue was taken up in 5% aq HCl (50 mL) and extracted with ether (2×100 mL). The combined ether extracts were washed with satd aq $NaHCO_3$ (25 mL) and dried over $MgSO_4$. Removal of the solvent left tert-butyl 3-(hydroxy(phenyl)methyl)pyrrolidine-1-carboxylate (0.93 g, quant) as an oil.

Step 4. tert-Butyl 3-((4-methoxybutoxy)(phenyl) methyl)pyrrolidine-1-carboxylate To a stirred solution of tert-butyl 3-(hydroxy(phenyl)methyl)pyrrolidine-1-carboxylate (205 mg, 0.74 mmol) and 4-methoxybutyl iodide (750 mg, 3.5 mmol) in dry THF (5 mL) under $N_2$ was added 60& NaH in oil (0.14 g, 3.5 mmol). $H_2$ evolution occurred. The mixture was heated at reflux for 8 h. The mixture was cooled, diluted with ether (90 mL), and washed with water (25 mL) and brine (25 mL), and dried over $MgSO_4$. Removal of the solvent left an oil which was purified by flash chromatography on a 12-g silica cartridge eluted with a 0 to 100% EtOAc in hexanes gradient to afford tert-butyl 3-((4-methoxybutoxy)(phenyl)methyl)pyrrolidine-1-carboxylate (47 mg, 17%) as an oil.

Step 5. 3-((4-Methoxybutoxy)(phenyl)methyl)pyrrolidine tert-Butyl 3-((4-methoxybutoxy)(phenyl)methyl)pyrrolidine-1-carboxylate (47 mg, 0.13 mmol) was dissolved in 4 M HCl in dioxane (4 mL, 16 mmol). The solution was stirred at rt for 2 h and concentrated to afford 3-((4-methoxybutoxy)(phenyl)methyl)pyrrolidine hydrochloride (41.3 mg, quant) as an oil.

The following compounds were prepared using procedures analogous to those described above with the changes indicated:

3-((3-ethoxypropoxy)(phenyl)methyl)pyrrolidine using 3-methoxypropyl bromide in Step 4.

3-((2-methoxyethoxy)(phenyl)methyl)pyrrolidine using 2-methoxyethyl-bromide in Step 4.

Preparation 7

5-methoxy-1-phenyl-1-(pyrrolidin-3-yl)pentan-1-ol

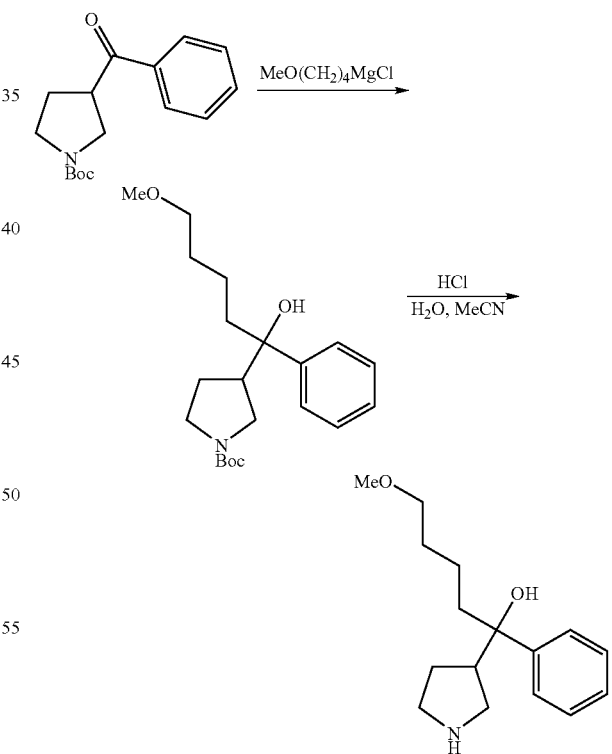

Step 1. tert-Butyl 3-(1-hydroxy-5-methoxy-1-phenylpentyl)pyrrolidine-1-carboxylate A stirred solution of tert-butyl 3-benzoylpyrrolidine-1-carboxylate (489 mg, 1.78 mmol) in dry THF (10 mL) was cooled to −70° C. and 2 M 4-methoxybutylmagnesium chloride in THF (8 mL, 16 mmol) was added. The mixture was stirred at −70° C. for 1 h and poured into satd aq NH₄Cl (100 mL). The mixture was extracted with ether (2×100 mL) and the combined ether extracts were dried over Na₂SO₄. Removal of the solvent left an oil which was purified by flash chromatography on a 40-g silica cartridge eluted with a 0 to 100% ethyl acetate in hexanes gradient to afford tert-butyl 3-(1-hydroxy-5-methoxy-1-phenylpentyl)pyrrolidine-1-carboxylate (290 mg, 44%).

Step 2. 5-Methoxy-1-phenyl-1-(pyrrolidin-3-yl)pentan-1-ol

To a stirred solution of tert-butyl 3-(1-hydroxy-5-methoxy-1-phenylpentyl)pyrrolidine-1-carboxylate (290 mg, 0.80 mmol) in MeCN (20 mL) was added 5% aq HCl (20 mL). The mixture was stirred at rt for 17 h and solid K₂CO₃ was added until CO₂ evolution ceased. MeCN was removed under reduced pressure and the aqueous residue was extracted with CH₂Cl₂ (2×90 mL). The combined organic extracts were dried over Na₂SO₄ and concentrated to afford 5-methoxy-1-phenyl-1-(pyrrolidin-3-yl)pentan-1-ol (140 mg, 66%) as an oil.

Preparation 8

(S)-1-(2-(2-ethylphenoxy)phenyl)-5-methoxy-1-((R)-piperidin-3-yl)pentan-1-ol

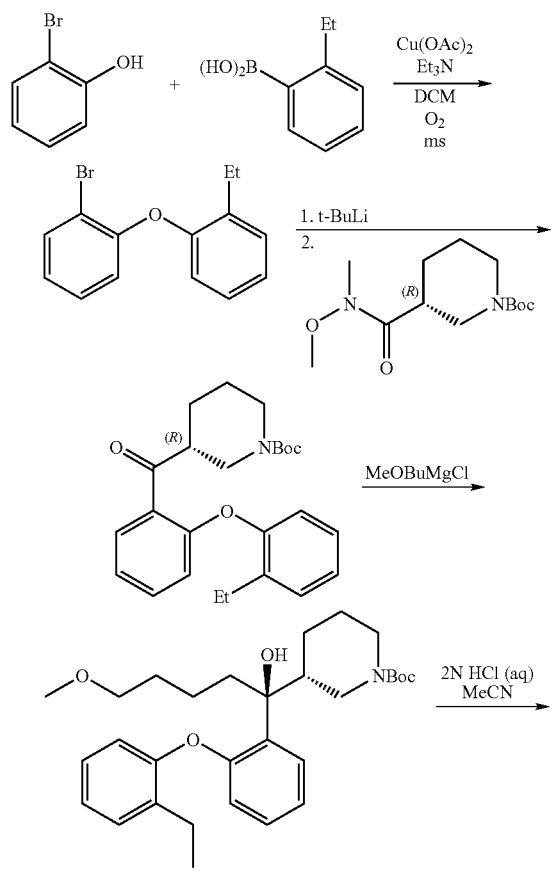

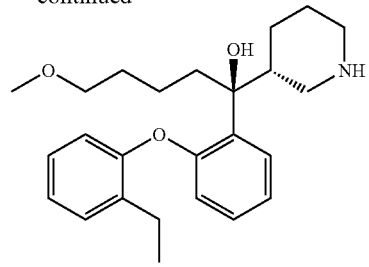

Step 1. 1-Bromo-2-(2-ethylphenoxy)benzene

To a solution of 2-ethylphenylboronic acid (4.50 g, 30 mmol), 2-bromophenol (3.54 g, 20 mmol), and Cu(OAc)₂ (1.86 g, 10 mmol) in anhydrous CH₂Cl₂ (50 mL) were added activated 4 Å molecular sieves (~0.5 g), followed by anhydrous Et₃N (7.0 mL, 50 mmol). The resulting dark green solution was stirred at rt for 48 h. The solvent was removed under vacuum and the residue was triturated several times with ether (~200 mL). The combined organic solutions were washed with satd aq NH₄Cl, and 1 N aq HCl aqueous solution, and solvent was removed under vacuum to give a crude product. Flash column chromatography gave 1-bromo-2-(2-ethylphenoxy)benzene (1.72 g, 31%) as a clear oil; ¹H NMR (CDCl₃, 400 MHz) δ: 7.62 (dd, 1H), 7.28 (m, 1H), 7.22-7.08 (m, 3H), 6.96 (m, 1H), 6.78 (m, 2H), 2.64 (q, 2H), 1.22 (t, 3H); MS no ionization was observed.

Step 2. (R)-tert-Butyl 3-(2-(2-ethylphenoxy)benzoyl)piperidine-1-carboxylate

To a solution of 1-bromo-2-(2-ethylphenoxy)benzene (1.70 g, 6.13 mmol) in THF (15 mL) at −70° C., t-BuLi in pentane (1.7 M, 7.2 mL, 12.2 mmol) was added dropwise such that the temperature remained below −70° C. The mixture was stirred at the same temperature for another 30 min to give solution A.

To a solution of (R)-tert-butyl 3-(N-methoxy-N-methylcarbamoyl)piperidine-1-carboxylate (1.11 g, 4.09 mmol) in THF (7 mL) at −20° C., solution A was added dropwise. After the addition was complete, the resulting solution was allowed to warm to rt slowly, and kept at rt for 1 h. The reaction was quenched with 1N aq HCl (~10 mL), and extracted with ether (4×10 mL). The combined organic layers were washed with satd aq NaHCO₃ and brine, and dried over Na₂SO₄. Solvent was removed under vacuum to give crude (R)-tert-butyl 3-(2-(2-ethylphenoxy)benzoyl)piperidine-1-carboxylate (2.25 g, quant.), which was used in next step without further purification; MS m/z 432 (M+Na⁺).

Step 3. (R)-tert-Butyl 3-((S)-1-(2-(2-ethylphenoxy)phenyl)-1-hydroxy-5-methoxypentyl)-piperidine-1-carboxylate To a solution of (R)-tert-butyl 3-(2-(2-ethylphenoxy)benzoyl)piperidine-1-carboxylate (2.25 g, 4.09 mmol) in THF (7 mL) at −20° C., 4-methoxybutylmagnesium chloride in THF (1.63 M, 5.0 mL, 8.15 mmol) was added dropwise. The resulting solution was warmed to rt slowly, and the completion of reaction was confirmed by LC-MS (~20 min). The reaction was quenched with satd aq NH₄Cl (8 mL) and extracted with ether (4×10 mL). The combined organic layers were washed with water and brine, and solvent was removed under vacuum to give a crude product, which was purified by flash column chromatography to give (R)-tert-butyl 3-((S)-1-(2-(2-ethylphenoxy)phenyl)-1-hydroxy-5-methoxypentyl)piperidine-1-carboxylate (1.52 g, 75%). $^1$H NMR (CDCl$_3$, 400 MHz) δ: 7.52 (d, 1H), 7.26 (dd, 1H), 7.20-7.00 (m, 4H), 6.78 (d, 1H), 6.60 (d, 1H), 4.34 (d, 1H), 4.00 (d, 1H), 3.30 (t, 2H), 3.24 (s, 3H), 2.78 (dd, 1H), 2.64 (q, 2H), 2.62 (m, 1H), 2.40 (m, 1H), 2.26 (m, 1H), 1.92 (m, 1H), 1.56 (m, 4H), 1.40 (s, 9H), 1.30 (m, 3H), 1.22 (t, 3H); MS m/z 520 (M+Na$^+$).

Step 4. (S)-1-(2-(2-Ethylphenoxy)phenyl)-5-methoxy-1-((R)-piperidin-3-yl)pentan-1-ol To a solution of (R)-tert-butyl 3-((S)-1-(2-(2-ethylphenoxy)phenyl)-1-hydroxy-5-methoxypentyl)piperidine-1-carboxylate (1.50 g, 3.01 mmol) in MeCN (50 mL), 2 N aq. HCl (50 mL) was added slowly at rt. The resulting solution was stirred at room temperature overnight, then basified to pH=10 with 10 N aq NaOH aq, and MeCN was removed under vacuum. The aqueous residue was extracted with CH$_2$Cl$_2$ (4×10 mL). The combined organic layers were washed with brine and dried over Na$_2$SO$_4$. The solvent was removed under vacuum to give (S)-1-(2-(2-ethylphenoxy)phenyl)-5-methoxy-1-((R)-piperidin-3-yl)pentan-1-ol (1.16 g, 97%) as a free amine. The crude product was used for next step without purification; MS m/z 398 (M+H$^+$).

Preparation 9 tert-butyl (S)-2-cyclohexyl-1-((S)-oxiran-2-yl)ethylcarbamate

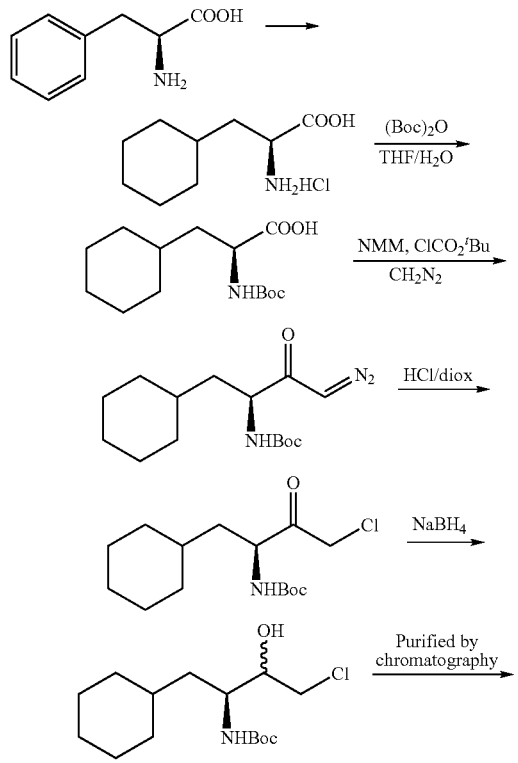

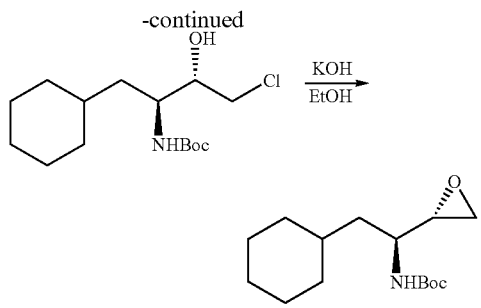

Step 1. (S)-2-Amino-3-cyclohexyl-propionic acid

To a solution of S-2-amino-3-phenyl-propionic acid (100 g, 0.606 mol) in 3 N aq HCl (1200 mL) was added 5% Rh/C (12 g), and the mixture was hydrogenated at 60° C. and 50 psi for 48 h. The mixture was cooled, filtered to remove Rh/C and the filter cake was washed with water. The filtrate was concentrated to give (S)-2-amino-3-cyclohexylpropanoic acid hydrochloride (118 g, 94%) as a white solid.

Step 2. (S)-2-(tert-Butoxycarbonylamino)-3-cyclohexylpropanoic Acid

To a solution of (S)-2-amino-3-cyclohexylpropanoic acid hydrochloride (118 g, 0.57 mol) in 0.5 N aq NaOH (1200 mL) was added a solution of Boc$_2$O (137 g, 0.63 mol) in THF (600 mL) and the mixture was stirred for 2 h. After removing the organic solvent, the aqueous layer was washed with Et$_2$O (2×400 mL). The aqueous layer was acidified to pH 5 by addition of 2 N aq HCl. The mixture was extracted with EtOAc (3×400 mL). The combined EtOAc extracts were washed with brine, dried over Na$_2$SO$_4$ and evaporated to give (S)-2-(tert-butoxycarbonylamino)-3-cyclohexylpropanoic acid (142 g, 92%) as an oil. $^1$H NMR: 0.92 (m, 1H), 1.09-1.30 (m, 3H), 1.52 (m, 1H), 1.48 (s, 9H), 1.51 (m, 1H), 1.66 (m, 5H), 1.78 (m, 1H), 4.32 (m, 1H), 4.88 (m, 1H), 8.55-9.48 (brs, 1H).

Step 3. (S)-tert-Butyl 1-cyclohexyl-4-diazo-3-oxobutan-2-ylcarbamate

To a solution of (S)-2-(tert-butoxycarbonylamino)-3-cyclohexylpropanoic acid (37 g, 0.136 mmol) in anhydrous THF (300 mL) cooled to −20° C. was added dropwise N-methylmorpholine (16.6 mL, 0.15 mmol), followed by isobutyl chloroformate (20 mL, 0.15 mmol) and the reaction mixture was stirred at −20° C. for 30 min. The mixture was warmed to 0° C., and an etheral solution of CH$_2$N$_2$ (0.8 mol) was added. Stirring was continued overnight at rt. Excess diazomethane was decomposed by addition of acetic acid. The mixture was diluted with ether, washed with brine, satd aq NaHCO$_3$ and brine to give a solution of crude (S)-tert-butyl 1-cyclohexyl-4-diazo-3-oxobutan-2-ylcarbamate (48 g, 100%), which was used without isolation.

Step 4. (S)-tert-Butyl 4-chloro-1-cyclohexyl-3-oxobutan-2-ylcarbamate

To a solution of the crude (S)-tert-butyl 1-cyclohexyl-4-diazo-3-oxobutan-2-ylcarbamate (7 g, ~65% pure) in anhydrous ether (150 mL) at 0° C. was added dropwise a solution of 3.65 N HCl in dioxane (4.1 mL, 0.015 mmol). The mixture was stirred until tlc showed the starting material had been consumed. Satd aq NaHCO$_3$ was added and the organic layer was separated, washed with satd aq NaHCO$_3$ and brine, and concentrated to afford a solution of crude (S)-tert-butyl 4-chloro-1-cyclohexyl-3-oxobutan-2-ylcarbamate (5.8 g), which was used in the next step without further purification.

Step 5. (S)-tert-Butyl 4-chloro-1-cyclohexyl-3-hydroxybutan-2-ylcarbamate

To a solution of the crude (S)-tert-butyl 4-chloro-1-cyclohexyl-3-oxobutan-2-ylcarbamate (5.8 g, 0.019 mol) in 9:1 THF/H$_2$O (100 mL) at 0° C. was added NaBH$_4$ (1.8 g, 0.047 mmol). After stirring for 45 min at rt, the solvent was removed in vacuo. The residue was diluted with water (50 mL) and the aqueous layer was extracted with EtOAc (3×50 mL). The combined organic layers were washed with brine, dried over Na$_2$SO$_4$, filtered and concentrated to give the crude product which was purified by flash chromatography to give a mixture of isomeric alcohols, which was recrystallized from n-hexane three times to give pure tert-butyl (2S,3S)-4-chloro-1-cyclohexyl-3-hydroxybutan-2-ylcarbamate (1.15 g, 40%). $^1$H NMR: 0.82 (m, 1H), 0.96 (m, 1H), 1.08-1.40 (m, 5H), 1.43 (s, 9H), 1.65 (m, 4H), 1.82 (m, 1H), 3.08 (m, 1H), 3.52 (m, 1H), 3.58 (r, 1H), 3.79 (m, 2H), 4.51 (m, 1H). MS (E/Z): 306 (M+H$^+$). The mother liquor was concentrated and recrystallized from n-hexane three times to give pure tert-butyl (2S,3R)-4-chloro-1-cyclohexyl-3-hydroxybutan-2-ylcarbamate (0.3 g, 10.3%).

Step 6. tert-Butyl (S)-2-cyclohexyl-1-((S)-oxiran-2-yl)ethylcarbamate tert-Butyl (2S,3S)-4-chloro-1-cyclohexyl-3-hydroxybutan-2-ylcarbamate (1 g, 3.28 mmol) was dissolved in a solution of 0.71 N NaOH in EtOH (5.6 mL, 3.95 mmol, 1.2 eq). After stirring for 1 h, the mixture was concentrated to give a residue, which was dissolved in water and extracted with EtOAc (3×15 mL). The combined organic layers were washed with brine, dried over Na$_2$SO$_4$, filtered and concentrated in vacuo to give tert-butyl (S)-2-cyclohexyl-1-((S)-oxiran-2-yl)ethylcarbamate (0.84 g, 95%). $^1$H NMR: 0.83 (m, 1H), 0.95 (m, 1H), 1.10-1.42 (m, 5H), 1.45 (s, 9H), 1.68 (m, 5H), 1.76 (m, 1H), 2.72 (m, 2H), 2.83 (m, 1H), 3.55 (m, 1H), 4.38 (m, 1H). MS (E/Z): 270 (M+H$^+$).

tert-Butyl (S)-1-((S)-oxiran-2-yl)-2-m-tolylmethylcarbamate was prepared following the procedures described in Steps 2-6 starting with 3-methylphenylalanine.

tert-butyl (S)-3-methyl-1-((S)-oxiran-2-yl)butylcarbamate was prepared following the procedures described in Steps 2-6 starting with (S)-leucine.

Preparation 10 tert-butyl (S)-2-cyclohexyl-1-((R)-oxiran-2-yl)ethylcarbamate

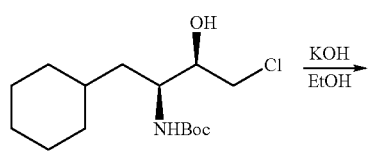

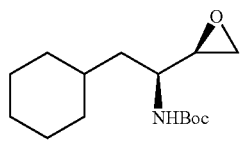

Step 1. tert-Butyl (S)-2-cyclohexyl-1-((R)-oxiran-2-yl)ethylcarbamate tert-Butyl (2S,3R)-4-chloro-1-cyclohexyl-3-hydroxybutan-2-ylcarbamate (1 g, 3.28 mmol) was dissolved in a solution of 0.7 N NaOH in EtOH (5.6 mL, 3.95 mmol, 1.2 eq). After stirring for 1 h, the mixture was concentrated to give the residue, which was dissolved in water, extracted with EtOAc (3×15 mL). The combined organic layers were washed with brine, dried over Na$_2$SO$_4$, filtered, and concentrated in vacuo to give tert-butyl (S)-2-cyclohexyl-1-((R)-oxiran-2-yl)ethylcarbamate (0.83 g, 95%). $^1$H NMR: 0.85 (m, 1H), 0.99 (m, 1H), 1.12-1.32 (m, 3H), 1.41 (m, 3H), 1.45 (s, 9H), 1.58 (m, 4H), 1.88 (m, 1H), 2.59 (m, 1H), 2.73 (m, 1H), 2.98 (m, 1H), 4.04 (m, 1H), 4.32 (m, 1H). MS (E/Z): 270 (M+H$^+$).

Preparation 11

(2R,3S)-3-amino-4-cyclohexyl-1-(N-(3,5-dimethoxybenzyl)-N-((9H-fluoren-9-yl)methoxycarbonyl)amino)butan-2-ol

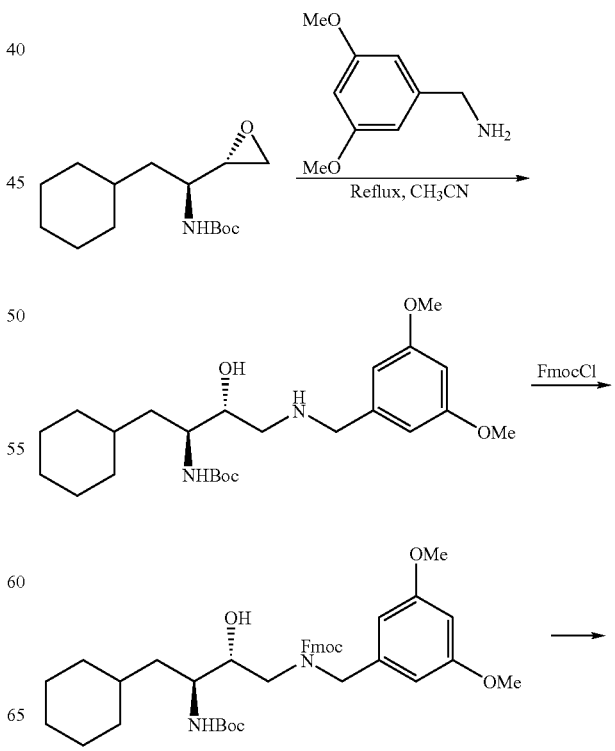

-continued

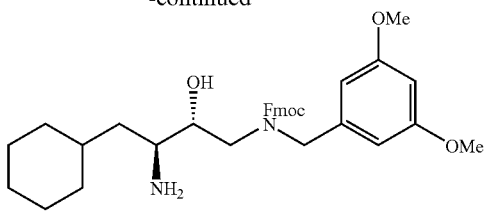

Step 1. tert-Butyl (2S,3R)-1-cyclohexyl-4-(3,5-dimethoxybenzylamino)-3-hydroxybutan-2-ylcarbamate To a solution of tert-butyl (S)-2-cyclohexyl-1-((S)-oxiran-2-yl)ethylcarbamate (67.3 mg, 0.25 mmol) in CH$_3$CN (8 mL) was added 3,5-dimethoxybenzylamine (50 mg, 0.3 mmol) and the mixture was heated under reflux overnight. The solvent was removed in vacuo and the residue was purified by the preparative HPLC to give tert-butyl (2S,3R)-1-cyclohexyl-4-(3,5-dimethoxybenzylamino)-3-hydroxybutan-2-ylcarbamate (66.5 mg, 61%). $^1$H NMR: 0.82 (m, 1H), 0.95 (m, 1H), 1.10-1.48 (m, 6H), 1.42 (s, 9H), 1.65 (m, 4H), 1.80 (m, 1H), 2.67 (m, 2H), 3.46 (m, 1H), 3.64 (m, 1H), 3.72 (d, 2H), 3.79 (s, 6H), 6.35 (m, 1H). MS (E/Z): 437 (M+H$^+$).

Step 2. (2R,3S)-3-(t-Butoxycarbonylamino)-4-cyclohexyl-1-(N-(3,5-dimethoxybenzyl)-N-((9H-fluoren-9-yl)methoxycarbonyl)amino)butan-2-ol To a solution of tert-butyl (2S,3R)-1-cyclohexyl-4-(3,5-dimethoxybenzylamino)-3-hydroxybutan-2-ylcarbamate (66.5 mg, 0.153 mmol) in CH$_2$Cl$_2$ (10 mL) at 0° C. was added DIEA (1.5 mL) followed by 9-fluorenylmethyl chloroformate (39.5 mg, 0.153 mmol) and the resulting mixture was stirred at 0° C. for 2 h and at rt for 2 h. The reaction mixture was concentrated and the residue was diluted with EtOAc and water. The organics were washed with water, dried over Na$_2$SO$_4$, filtered and concentrated in vacuo. The residue was chromatographed on silica gel to provide (2R,3S)-3-(t-butoxycarbonylamino)-4-cyclohexyl-1-(N-(3,5-dimethoxybenzyl)-N-((9H-fluoren-9-yl)methoxycarbonyl)amino)butan-2-ol (78.5 mg, 78%). $^1$H NMR: 0.79 (m, 1H), 0.95 (m, 1H), 1.06-1.38 (m, 6H), 1.42 (s, 9H), 1.56-1.70 (m, 6H), 1.83 (m, 1H), 3.25-3.50 (m, 2H), 3.70 (m, 1H), 3.73 (s, 6H), 3.85 (m, 1H), 4.22 (m, 1H), 4.29-4.70 (m, 5H), 6.35 (m, 3H), 7.20 (m, 1H), 7.32-7.48 (m, 4H), 7.58 (m, 1H), 7.69 (m, 1H), 7.75 (m, 1H). MS (E/Z): 659 (M+H$^+$).

Step 3. (2R,3S)-3-Amino-4-cyclohexyl-1-(N-(3,5-dimethoxybenzyl)-N-((9H-fluoren-9-yl)methoxycarbonyl)amino)butan-2-ol (2R,3S)-3-(t-Butoxycarbonylamino)-4-cyclohexyl-1-(N-(3,5-dimethoxybenzyl)-N-((9H-fluoren-9-yl)methoxycarbonyl)amino)butan-2-ol (255.3 mg, 0.39 mmol) was dissolved in 4 M HCl in dioxane (5 mL) and stirred at rt for 1 h. Removal of the solvent afforded (2R,3S)-3-amino-4-cyclohexyl-1-(N-(3,5-dimethoxybenzyl)-N-((9H-fluoren-9-yl)methoxycarbonyl)-amino)butan-2-ol hydrochloride (253 mg, quant) as a white solid.

The following compound was prepared using procedures analogous to those described above with the modifications indicated:

(2R,3S)-3-amino-1-(N-(3,5-dimethoxybenzyl)-N-((9H-fluoren-9-yl)methoxycarbonyl)amino)-4-m-tolylbutan-2-ol using tert-butyl (S)-1-((S)-oxiran-2-yl)-2-m-tolylethylcarbamate in Step 1.

Preparation 12

(2R,3S)-3-amino-1-(N-(4-cyanobenzyl)-N-(2-(trimethylsilyl)ethoxycarbonyl)amino)-4-cyclohexylbutan-2-ol

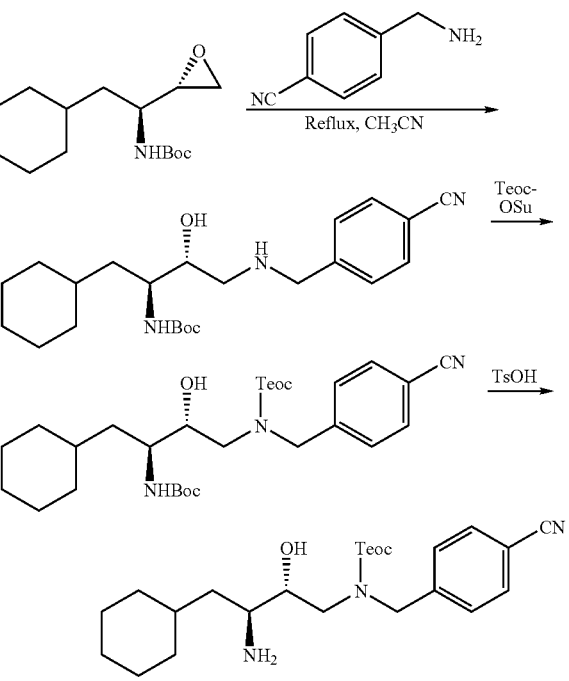

Step 1. tert-Butyl (2S,3R)-4-(4-cyanobenzylamino)-1-cyclohexyl-3-hydroxybutan-2-ylcarbamate To a solution of tert-butyl (S)-2-cyclohexyl-1-((S)-oxiran-2-yl)ethylcarbamate (67.3 mg, 0.25 mmol) in CH$_3$CN (8 mL) was added 4-cyanobenzylamine (39.6 mg, 0.3 mmol) and the mixture was heated under reflux overnight. The solvent was removed in vacuo and the residue was purified by the preparative HPLC to give tert-butyl (2S,3R)-4-(4-cyanobenzylamino)-1-cyclohexyl-3-hydroxybutan-2-ylcarbamate (58 mg, 58%). $^1$H NMR: 0.82 (m, 1H), 0.95 (m, 1H), 1.10-1.48 (m, 5H), 1.45 (s, 9H), 1.55-1.68 (m, 5H), 1.76 (m, 1H), 2.65 (m, 2H), 3.46 (m, 1H), 3.85 (m, 2H), 4.49 (m, 1H), 7.42 (d, 2H), 7.59 (d, 2H). MS (E/Z): 402 (M+H$^+$).

Step 2. tert-Butyl (2S,3R)-4-(N-(4-cyanobenzyl)-N-(2-(trimethylsilyl)ethoxycarbonyl)amino)-1-cyclohexyl-3-hydroxybutan-2-ylcarbamate A solution of tert-butyl (2S,3R)-4-(4-cyanobenzylamino)-1-cyclohexyl-3-hydroxybutan-2-ylcarbamate (600 mg, 1.5 mmol) in CH$_2$Cl$_2$ (30 mL) was treated with Teoc-OSu (762 mg, 3.0 mmol, 2.0 equiv) and Et$_3$N (304 mg, 3.0 mmol, 2.0 equiv). The mixture was allowed to stir overnight at rt. LC-MS analysis showed that all of the free amine had been consumed. The solution was washed with water, 1.0 M aq HCl, and brine, then over dried over Na₂SO₄, filtered and evaporated to leave tert-butyl (2S,3R)-4-(N-(4-cyanobenzyl)-N-(2-(trimethylsilyl)ethoxycarbonyl)amino)-1-cyclohexyl-3-hydroxybutan-2-ylcarbamate. NMR analysis showed that the compound was of sufficient purity to use in the next step.

Step 3. (2R,3S)-3-Amino-1-(N-(4-cyanobenzyl)-N-(2-(trimethylsilyl)ethoxycarbonyl)amino)-4-cyclohexylbutan-2-ol tert-Butyl (2S,3R)-4-(N-(4-cyanobenzyl)-N-(2-(trimethylsilyl)ethoxycarbonyl)amino)-1-cyclohexyl-3-hydroxybutan-2-ylcarbamate (921 mg, 1.68 mmol) was dissolved in EtOH (10 mL) and treated with toluenesulfonic acid monohydrate (337 mg, 1.77 mmol, 1.05 equiv). The mixture was allowed to stir at 65° C. for 40 min. LC-MS analysis showed that the starting material had been consumed and converted to the desired product. The solvent was removed and the residue was dissolved in CH₂Cl₂ (20 mL). The solution was treated with 1.0 M aq NaOH (20 mL) and the biphasic mixture was stirred for 0.5 h. The mixture was transferred to a separatory funnel and the layers were separated. The organic layer was dried over Na₂SO₄, filtered and evaporated to afford (2R,3S)-3-amino-1-(N-(4-cyanobenzyl)-N-(2-(trimethylsilyl)-ethoxycarbonyl)amino)-4-cyclohexylbutan-2-ol.

The following compound was prepared using procedures analogous to those described above with the modifications indicated:
(2S,3S)-3-amino-1-(N-(4-cyanobenzyl)-N-(2-(trimethylsilyl)ethoxycarbonyl)amino)-4-cyclo-hexylbutan-2-ol using tert-butyl (S)-2-cyclohexyl-1-(R)-oxiran-2-yl)ethyl-carbamate in Step 1.
(2R,3S)-3-amino-1-(tert-butylamino)-5-methylhexan-2-ol was prepared using t-BuNH₂ in Step 1 and omitting Step 2.

Preparation 13

2-(Trimethylsilyl)ethyl (2S,3S)-3-amino-4-cyclohexyl-2-hydroxybutylcarbamate

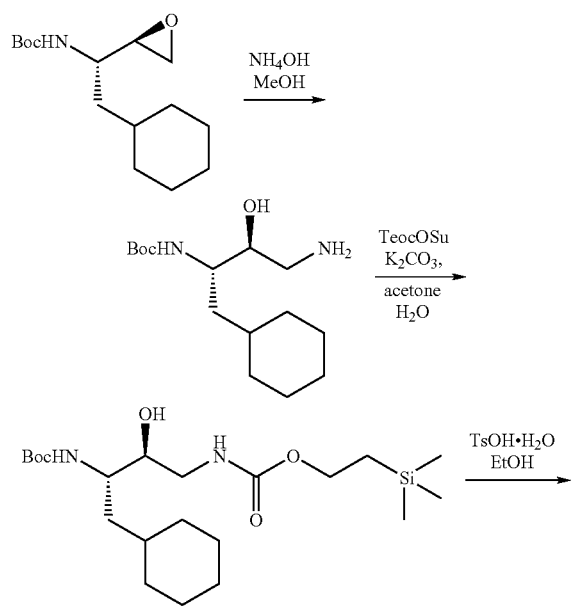

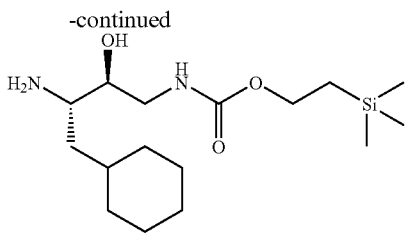

Step 1. tert-Butyl (2S,3S)-4-amino-1-cyclohexyl-3-hydroxybutan-2-ylcarbamate

To a stirred solution of tert-butyl (S)-2-cyclohexyl-1-((R)-oxiran-2-yl)ethylcarbamate (0.20 g, 0.74 mmol) in MeOH (15 mL) at rt, ammonium hydroxide (5 mL) was added. The resulting clear solution was stirred at rt overnight, and completion of reaction was confirmed by LC-MS. Solvent was removed under vacuum to leave tert-butyl (2S,3S)-4-amino-1-cyclohexyl-3-hydroxybutan-2-ylcarbamate (0.21 g, quant.), which was used for the next step without purification; M/S m/z 287 (M+H⁺).

Step 2. 2-(Trimethylsilyl)ethyl (2S,3S)-3-N-t-butoxycarbonyl-amino-4-cyclohexyl-2-hydroxybutyl-carbamate To a stirred solution of tert-butyl (2S,3S)-4-amino-1-cyclohexyl-3-hydroxybutan-2-ylcarbamate (0.21 g, 0.74 mmol) in acetone (10 mL) and water (3 mL), K₂CO₃ (0.31 g, 2.22 mmol) was added, followed by Teoc-OSu (0.19 g, 0.74 mmol). The resulting solution was stirred at rt until no starting materials remained (~2 h). Acetone was removed, and the aqueous solution was extracted with CH₂Cl₂ (4×10 mL). The combined organic layers were washed with water (5 mL) and 10 brine (5 mL). Upon removing solvent, the crude residue was purified by flash column chromatography to afford 2-(trimethylsilyl)ethyl (2S,3S)-3-N-t-butoxycarbonyl-amino-4-cyclohexyl-2-hydroxybutylcarbamate (0.27 g, 87%); ¹H NMR (400 MHz, CDCl₃) δ: 5.42 (br, 1H), 4.60 (d, 1H), 4.12 (m, 2H), 3.62 (m, 2H), 3.36 (m, 1H), 3.04 (m, 1H), 1.78 (m, 1H), 1.64 (m, 5H), 1.42 (s, 9H), 1.38-1.04 (m, 6H), 0.96 (m, 2H), 0.82 (m, 1H), 0.02 (s, 9-H); MS m/z 453 (M+Na⁺).

Step 3. 2-(Trimethylsilyl)ethyl (2S,3S)-3-amino-4-cyclohexyl-2-hydroxybutyl-carbamate To a solution of 2-(trimethylsilyl)ethyl (2S,3S)-3-N-t-butoxycarbonyl-amino-4-cyclohexyl-2-hydroxybutylcarbamate (0.27 g, 0.63 mmol) in ether (3.0 mL) was added a solution of p-toluenesulfonic acid (120 mg, 0.64 mmol) in ethanol (1.0 mL). Transfer of the p-toluenesulfonic acid was completed with the aid of ether (1.0 mL). The solution was placed on a rotary evaporator and the ether was removed at rt. Then, with continuing evacuation, the bath temperature was raised to 60-65° C. for 30 min, during which time gas evolution was evident. After cooling to rt, the solid residue was dissolved in CH₂Cl₂ (10 mL), washed with 1 N aq NaOH (10 mL) and brine (5 mL), and dried over Na₂SO₄. The solvent was removed under vacuum to give 2-(trimethylsilyl)ethyl (2S,3S)-3-amino-4-cyclohexyl-2-hydroxybutylcarbamate (0.18 g, 86%); MS m/z 331 (M+H⁺).

The following compounds were prepared using procedures analogous to those described above with the modifications indicated:

2-(trimethylsilyl)ethyl (2R,3S)-3-amino-4-cyclohexyl-2-hydroxybutylcarbamate using tert-butyl (S)-2-cyclohexyl-1-((S)-oxiran-2-yl)ethylcarbamate in Step 1.

2-(trimethylsilyl)ethyl (2R,3S)-3-amino-4-cyclohexyl-2-hydroxybutyl(methyl)carbamate using tert-butyl (S)-2-cyclohexyl-1-((S)-oxiran-2-yl)ethylcarbamate and methylamine in Step 1.

Preparation 14

Methyl 2-((R)-(3-chlorophenyl)((R)-piperidin-3-yl)methoxy)ethylcarbamate

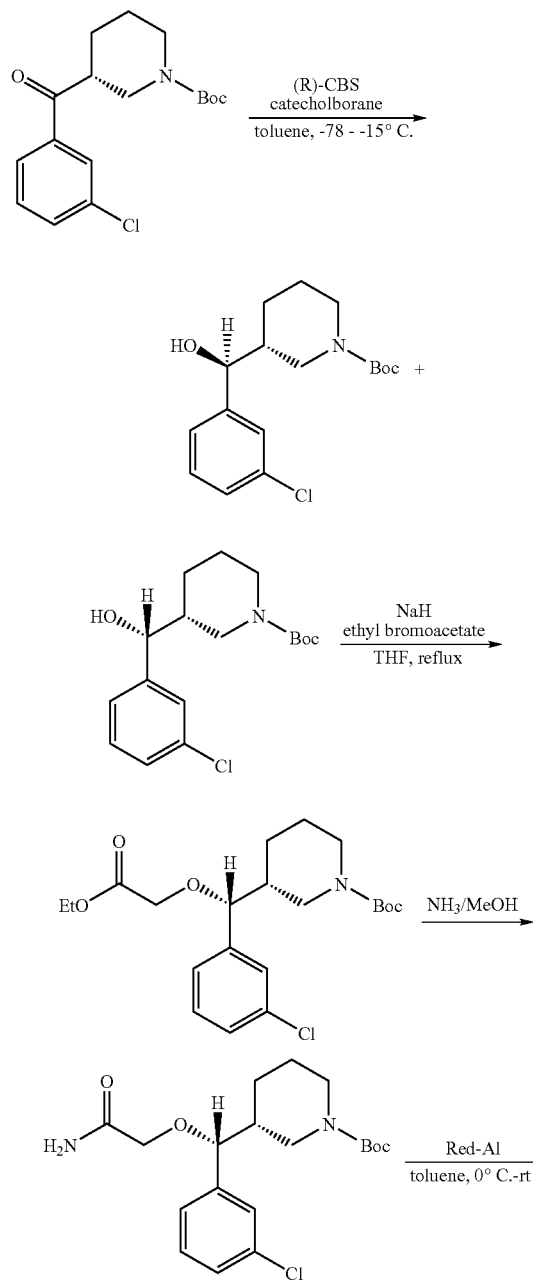

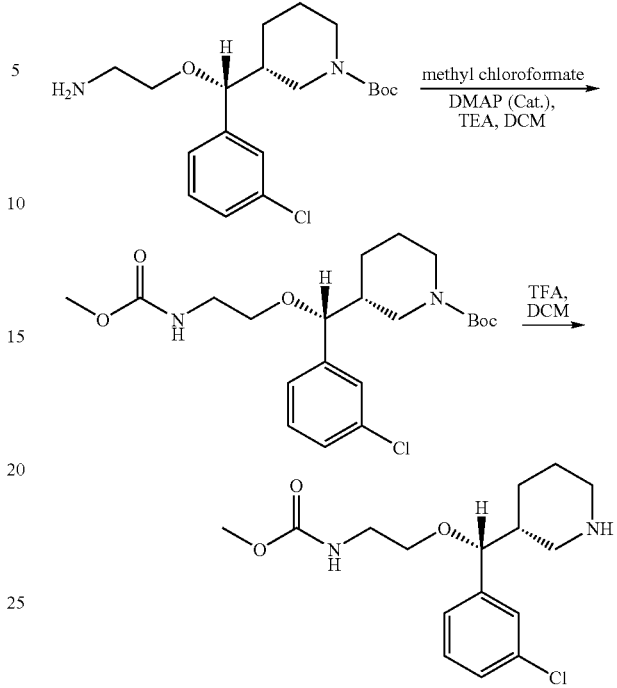

Step 1: (R)-tert-Butyl 3-((R)-(3-chlorophenyl)(hydroxy)methyl)piperidine-1-carboxylate To a solution of (R)-tert-butyl 3-(3-chlorobenzoyl)piperidine-1-carboxylate (5.60 g, 17.29 mmol) and (R)-2-methyl-CBS-oxazaborolidine (1 M in toluene, 9 mL, 9.00 mmol) cooled to −78° C. was added catecholborane (5.6 mL, 54.0 mmol) dropwise. After 20 min, the reaction temperature was allowed to warm to −15° C. and stirred overnight. The reaction was quenched at 0° C. by careful addition of water and diluted with ether. The resulting suspension was filtered through Celite and washed with ether. The filtrate was washed successively with 1 M aq NaOH (3×50 mL), 1 M aq HCl (3×50 mL), satd aq NaHCO$_3$ and brine, and dried over Na$_2$SO$_4$. The solution was filtered, the filtrate was evaporated under vacuum, and the residue was purified by preparative HPLC to afford (R)-tert-butyl 3-((R)-(3-chlorophenyl)(hydroxy)methyl)piperidine-1-carboxylate (2.44 g) and (R)-tert-butyl 3-((S)-(3-chlorophenyl)(hydroxy)methyl)piperidine-1-carboxylate (1.21 g). MS: 348 (M+Na)$^+$.

Step 2: (R)-tert-Butyl 3-((R)-(3-chlorophenyl)(2-ethoxy-2-oxoethoxy)methyl)piperidine-1-carboxylate To a suspension of 60% NaH in oil (960 mg, 24.0 mmol) in anhydrous THF at 0° C. was added a solution of (R)-tert-butyl 3-((R)-(3-chlorophenyl)(2-ethoxy-2-oxoethoxy)methyl)-piperidine-1-carboxylate (1.429 g, 4.40 mmol) in anhydrous THF (10 mL). The reaction mixture was stirred at rt for 30 min and a solution of ethyl bromoacetate (2.204 g, 13.2 mmol) in anhydrous THF (10 mL) was added dropwise. The resulting suspension was heated at reflux for 3 h and cooled to 0° C. again. The same amount of NaH as before was added and stirred for 30 min at rt, followed by addition the same amount of ethyl bromoacetate, and the mixture was heated at reflux overnight. The reaction mixture was cooled to 0° C. and quenched by careful addition of aq NH₄Cl. The mixture was extracted with EtOAc (3×). The combined organic phases were washed with brine, dried over Na₂SO₄, and filtered. The filtrate was evaporated and the residue was purified by flash chromatography on silica gel to afford (R)-tert-butyl 3-((R)-(3-chlorophenyl)(2-ethoxy-2-oxoethoxy)methyl)piperidine-1-carboxylate (1.62 g). MS: 412 (M+H)⁺.

Step 3: (R)-tert-Butyl 3-((R)-(2-amino-2-oxoethoxy)(3-chlorophenyl)methyl)piperidine-1-carboxylate (R)-tert-Butyl 3-((R)-(3-chlorophenyl)(2-ethoxy-2-oxoethoxy)methyl)piperidine-1-carboxylate (1.50 g, 3.65 mmol) was dissolved in 7 M NH₃ in MeOH, and stirred at rt for 6 h. The mixture was evaporated under reduced pressure to afford the (R)-tert-butyl 3-((R)-(2-amino-2-oxoethoxy)(3-chlorophenyl)methyl)piperidine-1-carboxylate in quantitative yield. MS: 383 (M+H)⁺.

Step 4: (R)-tert-Butyl 3-((R)-(2-aminoethoxy)(3-chlorophenyl)methyl)piperidine-1-carboxylate (R)-tert-Butyl 3-((R)-(2-amino-2-oxoethoxy)(3-chlorophenyl)methyl)piperidine-1-carboxylate (1.10 g, 2.60 mmol) was dissolved in anhydrous toluene (30 mL) and cooled to 0° C. Red-Al (65% in toluene, 2.6 mL, 8.64 mmol) was added dropwise. After the addition, the reaction was stirred at rt for 12 h and quenched by adding water slowly. The resulting mixture was filtered through Celite, washing with THF. The filtrate was evaporated under reduced pressure to give crude (R)-tert-butyl 3-((R)-(2-aminoethoxy)(3-chlorophenyl)methyl)piperidine-1-carboxylate (1.05 g), which was used for next step without further purification.

Step 5: (R)-tert-Butyl 3-((R)-(3-chlorophenyl)(2-(methoxycarbonylamino)ethoxy)methyl)piperidine-1-carboxylate To a solution of (R)-tert-butyl 3-((R)-(2-aminoethoxy)(3-chlorophenyl)methyl)piperidine-1-carboxylate (1.05 g, ca. 2.6 mmol), Et₃N (3.96 mL, 2.85 mmol), and DMAP (174 mg, 1.43 mmol) in anhydrous CH₂Cl₂ (20 mL) cooled to 0° C. was added a solution of methyl chloroformate (1.35 g, 14.25 mmol) in dichloromethane (20 mL) within 30 min. The reaction was stirred overnight, and evaporated under vacuum. The residue was purified by flash chromatography on silica gel to afford (R)-tert-butyl 3-((R)-(3-chlorophenyl)(2-(methoxycarbonylamino)ethoxy)methyl)piperidine-1-carboxylate (0.65 g). MS: 427 (M+H)⁺.

Step 6: Methyl 2-((R)-(3-chlorophenyl)((R)-piperidin-3-yl)methoxy)ethylcarbamate To a stirred solution of (R)-tert-butyl 3-((R)-(3-chlorophenyl)(2-(methoxycarbonylamino)-ethoxy)methyl)piperidine-1-carboxylate (91 mg, 0.21 mmol) in CH₂Cl₂ (3 mL) at rt was added TFA (0.5 mL). The mixture was stirred until complete removal of the Boc group had occurred. The solvent was removed under vacuum to give methyl 2-((R)-(3-chlorophenyl)((R)-piperidin-3-yl)methoxy)ethylcarbamate as its TFA salt. MS: 327 (M+H)⁺.

The following compound was prepared using procedures analogous to those described above:

Methyl 2-((R)-(3-fluorophenyl)((R)-piperidin-3-yl)methoxy)ethylcarbamate using (R)-tert-butyl 3-(3-fluorobenzoyl)piperidine-1-carboxylate in Step 1.

Preparation 15

(2R,3S)-3-amino-1-azido-4-cyclohexylbutan-2-ol

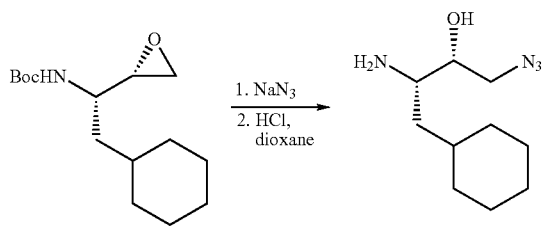

Step 1. (2R,3S)-3-(t-Butoxycarbonylamino)-1-azido-4-cyclohexylbutan-2-ol tert-Butyl (S)-2-cyclohexyl-1-((S)-oxiran-2-yl)ethylcarbamate (492 mg, 1.82 mmol), sodium azide (600 mg, 9.2 mmol), and ammonium chloride (540 mg, 10 mmol) were dissolved in MeOH (26 mL). The reaction was heated to 70° C. for 15 h. The solution was cooled to rt and quenched with water (80 mL). The solution was extracted with EtOAc (3×). The combined organic layers were washed with brine, dried over MgSO₄, and the solvent was removed. The crude (2R,3S)-3-amino-1-azido-4-cyclohexylbutan-2-ol (524 mg) was used without further purification.

Step 2. (2R,3S)-3-Amino-1-azido-4-cyclohexylbutan-2-ol (2R,3S)-3-(t-Butoxycarbonylamino)-1-azido-4-cyclohexylbutan-2-ol (94 mg, (0.30 mmol) was dissolved in dioxane (1 mL) and treated with 4M HCl in dioxane (1 mL). The reaction was allowed to stir for 2 h at rt. The solvent was evaporated and the hydrochloric acid salt of (3R)-3-(1-hydroxy-5-methoxy-1-(2-phenoxyphenyl)pentyl)-N-(piperidin-3-yl)piperidine-1-carboxamide (~74 mg) was used directly.

Preparation 16

(2R,3S)-N¹-methyl-N¹-(2-(trimethylsilyl)ethoxycarbonyl)-4-(tetrahydro-2H-pyran-4-yl)-2-(trimethylsilyloxy)butane-1,3-diamine

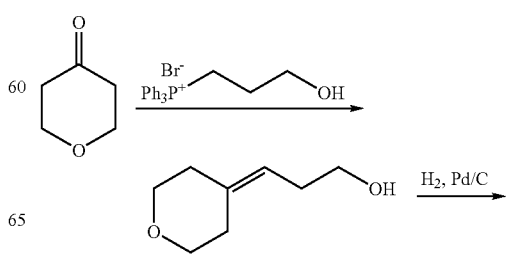

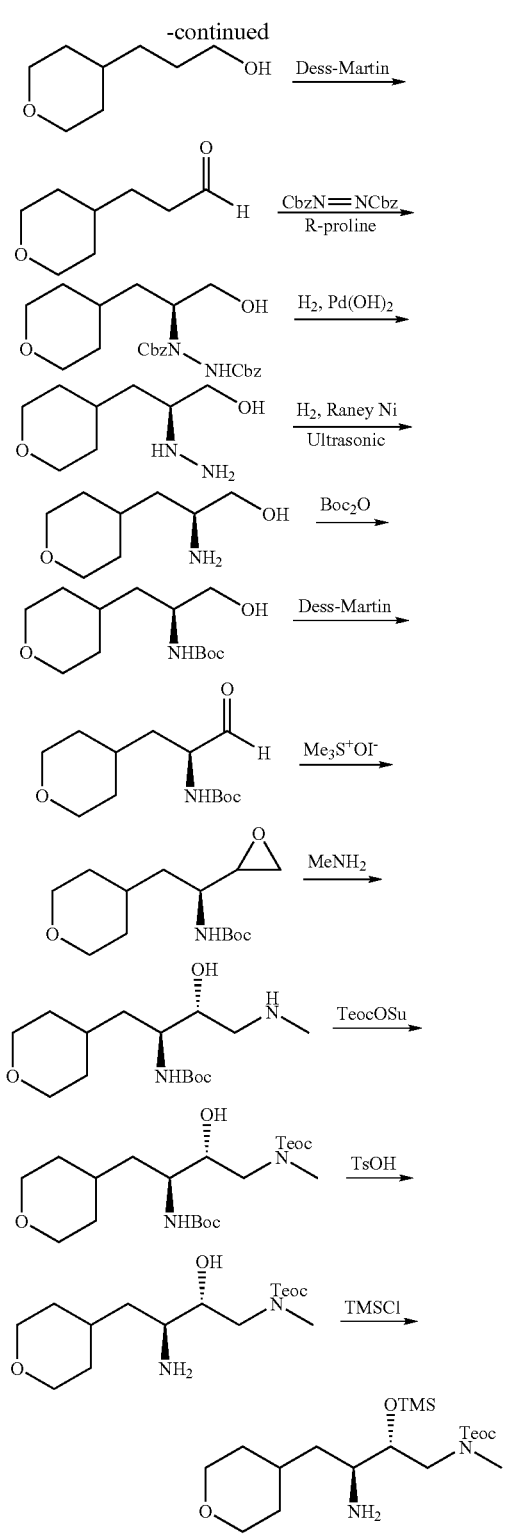

Step 1. 3-(2H-pyran-4(3H,5H,6H)-ylidene)propan-1-ol

To a suspension of the phosphonium salt (90.2 g, 1.5 eq) in dry THF (1100 mL) at 0° C. under nitrogen atmosphere was added n-BuLi (2.5 M, 216 mL, 0.54 mol). The solution was stirred for 1 h, followed by addition of dihydro-2H-pyran-4 (3H)-one (15 g, 0.15 mol). Stirring was continued at rt overnight. The mixture was quenched with satd aq $NH_4Cl$, and then filtered. The filtrate was dried over $Na_2SO_4$, and concentrated under vacuum to give the crude product, which was purified by column chromatography to give the product (13.1 g, 61%). $^1H$ NMR ($CD_3OD$) δ 2.1-2.3 (m, 6H), 2.5 (s, 1H), 3.5-3.7 (m, 6H), 5.1-5.2 (t, 1H).

Step 2. 3-(tetrahydro-pyran-4-yl)-propan-1-ol

To a solution of 3-(2H-pyran-4(3H, 5H, 6H)-ylidene)propan-1-ol (13 g, 0.0916 mol) in methanol (260 mL) was added $Pd(OH)_2/C$ (1.3 g). The reaction flask was evacuated and filled with $H_2$. Stirring was continued until the starting material had disappeared. The mixture was filtered through celite, and the filter cake was washed with MeOH (2×10 mL). The combined organic extracts were dried over $Na_2SO_4$, and concentrated under vacuum to give the product (11.8 g, 90%), which was used for the next step without purification. $^1H$ NMR ($CD_3OD$) δ 1.1-1.3 (m, 4H), 1.4-1.6 (m, 5H), 2.1-2.3 (s, 1H), 3.3-3.4 (t, 2H), 3.5-3.6 (t, 2H), 3.8-3.9 (dd, 2H).

Step 3. 3-(Tetrahydro-pyran-4-yl)-propionaldehyde

To a solution of 3-(tetrahydro-pyran-4-yl)-propan-1-ol (11.8 g, 0.0825 mol) in $CH_2Cl_2$ (200 mL) was added Dess-Martin periodinane (70.27 g, 0.165 mol). The mixture was stirred at rt. When the reaction was complete, the solution was poured into $Et_2O$ (300 mL) and anhydrous $K_2CO_3$ (19.84 g, 0.165 mol) was added. The mixture was filtered. The filtrate was dried over $Na_2SO_4$, and concentrated under vacuum to give the crude product, which was purified by column chromatography to give 3-(tetrahydro-pyran-4-yl)-propionaldehyde (8.59 g, 83%). $^1H$ NMR ($CD_3OD$) δ 1.1-1.3 (m, 4H), 1.4-1.6 (m, 5H), 2.4-2.5 (t, 2H), 3.2-3.3 (m, 2H), 3.8-3.97 (m, 2H), 9.7-9.8 (s, 1H).

Step 4. (S)-dibenzyl 1-(1-hydroxy-3-(tetrahydro-2H-pyran-4-yl)propan-2-yl)hydrazine-1,2-dicarboxylate To a stirred solution of 3-(tetrahydro-pyran-4-yl)-propionaldehyde (8.59 g, 0.06 mol) and dibenzyl azodicarboxylate (12.8 g, 0.042 mol) in MeCN (250 mL) at 0° C. was added (R-proline) (0.48 g, 0.0042 mol). After stirring the mixture at 0° C. for 15 h, ethanol (100 mL) and $NaBH_4$ (1.56 g, 0.042 mol) were added, and the mixture was stirred at 0° C. for 40 min. The reaction was quenched by slow addition of 10% aq citric acid (15 mL), and the whole solution was concentrated in vacuo. This residue was diluted with EtOAc (200 mL), washed with brine (50 mL), dried over $Na_2SO_4$, and concentrated in vacuo to give crude product which was purified by column chromatography to give (S)-dibenzyl 1-(1-hydroxy-3-(tetrahydro-2H-pyran-4-yl)propan-2-yl)hydrazine-1,2-dicarboxylate (16.52 g, 89%). $^1H$ NMR ($CD_3OD$) δ 1.0-1.5 (m, 8H), 2.9-3.3 (m, 2H), 3.4-3.6 (m, 2H), 3.7-3.9 (m, 2H), 4.4-4.7 (m, 2H), 5.1-5.4 (m, 4H), 7.2-7.4 (m, 10H).

Step 5. 2-Hydrazino-3-(tetrahydro-pyran-4-yl)-propan-1-ol

To a solution of (S)-dibenzyl 1-(1-hydroxy-3-(tetrahydro-2H-pyran-4-yl)propan-2-yl)hydrazine-1,2-dicarboxylate (16.52 g, 0.0374 mol) in methanol (320 mL) was added $Pd(OH)_2/C$ (1.65 g). The reaction flask was evacuated and filled with $H_2$. Stirring was continued until the starting material had disappeared. The mixture was filtered through celite, and the filter cake was washed with MeOH (2×30 mL). The combined organic solvent was dried over Na$_2$SO$_4$, and concentrated in vacuum to give 2-hydrazino-3-(tetrahydro-pyran-4-yl)-propan-1-ol (6.15 g, 94%), which was used for the next step without purification. $^1$H NMR (CD$_3$OD) δ 1.2-1.7 (m, 7H), 2.2-2.7 (s, 4H), 2.8-2.9 (m, 1H), 3.3-3.4 (m, 3H), 3.7-3.8 (m, 1H), 3.9-4.0 (m, 2H).

Step 6. 2-Amino-3-(tetrahydro-pyran-4-yl)-propan-1-ol

To a solution of 2-hydrazino-3-(tetrahydro-pyran-4-yl)-propan-1-ol (6.15 g, 0.035 mol) in MeOH (120 mL) was added Raney Ni. The flask was evacuated and equipped with a hydrogen inflated balloon. The flask was dipped into an ultrasound bath filled with water and sonicated for 4 h at rt until the starting material was completely consumed. The mixture was filtered through celite, and the filter cake was washed with MeOH (2×30 mL). Concentration of the filtrate under reduced pressure gave 2-amino-3-(tetrahydro-pyran-4-yl)-propan-1-ol (5.1 g, 91%). $^1$H NMR (CD$_3$OD) δ 1.2-1.5 (m, 4H), 1.5-1.7 (m, 3H), 1.9-2.2 (s, 3H), 2.9-3.0 (m, 1H), 3.2-3.3 (m, 1H), 3.3-3.4 (m, 2H), 3.5-3.6 (m, 1H), 3.9-4.0 (m, 2H).

Step 7. (S)-tert-butyl 1-hydroxy-3-(tetrahydro-2H-pyran-4-yl)propan-2-ylcarbamate To a solution of 2-amino-3-(tetrahydro-pyran-4-yl)-propan-1-ol (5.1 g, 0.032 mol) and Et$_3$N (9.7 g, 0.096 mol) in CH$_2$Cl$_2$ (5 mL) at 0° C. was added Boc$_2$O (8.37 g, 0.038 mol). After stirring at rt for 2 h, the mixture was concentrated to give (S)-tert-butyl 1-hydroxy-3-(tetrahydro-2H-pyran-4-yl)propan-2-ylcarbamate (9.8 g), which was used for the next reaction without purification.

Step 8. (S)-tert-butyl 1-oxo-3-(tetrahydro-2H-pyran-4-yl)propan-2-ylcarbamate

To a solution of (S)-tert-butyl 1-hydroxy-3-(tetrahydro-2H-pyran-4-yl)propan-2-ylcarbamate (1.7 g, 6.6 mmol) in CH$_2$Cl$_2$ (20 mL) was added Dess-Martin periodionane (3.4 g, 7.9 mmol). The reaction was stirred at r.t. for 1 h. Tlc showed the starting material had disappeared. The mixture was poured into Et$_2$O (100 mL) and K$_2$CO$_3$ (5 g) was added. The organic phase was dried over Na$_2$SO$_4$ and concentrated. The residue was purified by chromatography to give (S)-tert-butyl 1-oxo-3-(tetrahydro-2H-pyran-4-yl)propan-2-ylcarbamate (1.2 g, 71%). $^1$H NMR (CD$_3$OD) δ 1.45 (s, 9H), 2.07 (m, 2H), 3.90 (m, 3H), 4.30 (b, 1H), 5.0 (b, 1H), 9.55 (s, 1H).

Step 9. tert-butyl (1S)-1-(oxiran-2-yl)-2-(tetrahydro-2H-pyran-4-yl)ethylcarbamate A 100 mL flask was charged with NaH (116 mg, 2.9 mmol) and Me$_3$S$^+$OI$^-$ (639 mg, 2.9 mmol) under N$_2$. Dry DMSO (6 mL) was added. The mixture was stirred at rt for 1 h. A second 100 mL flask was charged with (S)-tert-butyl 1-oxo-3-(tetrahydro-2H-pyran-4-yl)propan-2-ylcarbamate (500 mg, 1.9 mmol) dissolved in THF (5 mL) under N$_2$. The solution of NaH and Me$_3$S$^+$OI$^-$ was added through a syringe. The resulting mixture was stirred for 1 h. at rt. Brine was added and the mixture was extracted with EtOAc (3×10 mL). The organic phase was dried over Na$_2$SO$_4$, filtered and concentrated in vacuo. The residue was purified by chromatography to give tert-butyl (1S)-1-(oxiran-2-yl)-2-(tetrahydro-2H-pyran-4-yl) ethylcarbamate (150 mg, 29%). $^1$H NMR (CD$_3$OD) δ 1.45 (s, 9H), 2.60 (b, 1 h), 2.75 (m, 1H), 3.0 (b, 1H), 3.35 (m, 2H), 4.0 (m, 3H), 4.30 (b, 1H), 5.30 (s, 2H).

Step 10. tert-butyl (2S,3R)-3-hydroxy-4-(methylamino)-1-(tetrahydro-2H-pyran-4-yl)butan-2-ylcarbamate A 250 mL flask was charged with [1-oxiranyl-2-(tetrahydro-pyran-4-yl)-ethyl]-carbamic acid tert-butyl ester (150 mg, 0.55 mmol) dissolved in MeNH$_2$/EtOH solution and stirred overnight at 30-40° C. Then the mixture was concentrated and used directly in the next step.

Step 11. tert-butyl (2S,3R)-3-hydroxy-4-(N-methyl-N-(2-(trimethylsilyl)ethoxycarbonyl)amino)-1-(tetrahydro-2H-pyran-4-yl)butan-2-ylcarbamate Solid TeocOSu was added to a vigorously stirred 2-phase solution of tert-butyl (2S,3R)-3-hydroxy-4-(methylamino)-1-(tetrahydro-2H-pyran-4-yl)butan-2-ylcarbamate (200 mg, 0.66 mmol), K$_2$CO$_3$ (164 mg, 1.12 mmol), H$_2$O (5 mL) and CH$_2$Cl$_2$ (10 mL). After stirring for 2 h at rt, the mixture was diluted with CH$_2$Cl$_2$ (30 mL), washed with satd aq NaHCO$_3$ and brine, dried over Na$_2$SO$_4$, filtered and concentrated to give an oil. The residue was purified by chromatography to give tert-butyl (2S,3R)-3-hydroxy-4-N-methyl-N-(2-(trimethylsilyl)ethoxycarbonyl)amino)-1-(tetrahydro-2H-pyran-4-yl)butan-2-ylcarbamate (180 mg, 53%).

Step 12. 2-(trimethylsilyl)ethyl (2R,3S)-3-amino-2-hydroxy-4-(tetrahydro-2H-pyran-4-yl)butyl(methyl)carbamate tert-butyl (2S,3R)-3-hydroxy-4-(N-methyl-N-(2-(trimethylsilyl)ethoxycarbonyl)amino)-1-(tetrahydro-2H-pyran-4-yl)butan-2-ylcarbamate (180 mg, 0.4 mmol) was dissolved in a minimal volume of Et$_2$O (5 mL) and added to a solution of TsOH (76 mg, 0.44 mmol) in EtOH (15 mL). The solution was placed on a rotary evaporator and the Et$_2$O was removed at rt. The flask was then lowered into the water bath and the selective deprotection of the Boc group proceeded concurrent with removal of the remainder of solvent. The reaction was completed after 2 h and gave a white solid. The residue was dissolved in EtOH/H$_2$O (1:1, 50 mL) and washed with hexane/EtOAc (5:1, 3×15 mL). 1N aq NaOH was added until the pH>10 and the mixture was extracted with EtOAc (3×15 mL). The organic layers were combined, washed with brine, dried over Na$_2$SO$_4$, filtered and concentrated to give 2-(trimethylsilyl)ethyl (2R,3S)-3-amino-2-hydroxy-4-(tetrahydro-2H-pyran-4-yl)butyl(methyl)carbamate (100 mg, 72%).

Step 13. 2-(trimethylsilyl)ethyl (2R,3S)-3-amino-4-(tetrahydro-2H-pyran-4-yl)-2-(trimethylsilyloxy)butyl(methyl)carbamate A 100 mL flask was charged with 2-(trimethylsilyl)ethyl (2R,3S)-3-amino-2-hydroxy-4-(tetrahydro-2H-pyran-4-yl)butyl(methyl)carbamate (100 mg, 0.29 mmol) dissolved in THF (10 mL), pyridine (68 mg, 0.87 mmol) was added at 0° C. Me$_3$SiCl (94 mg, 0.87 mmol) was added and the mixture was stirred for 2 h at rt. The mixture was quenched with 1% aq HCl and extracted with EtOAc (3×15 mL). The organic layers were combined, dried over Na$_2$SO$_4$, filtered and concentrated. The residue was purified by chromatography to give 2-(trimethylsilyl)ethyl (2R,3S)-3-amino-4-(tetrahydro-2H-pyran-4-yl)-2-(trimethylsilyloxy)butyl(methyl)carbamate (110 mg, 92%)

Preparation 17

Methyl 2-((S)-(3-chlorophenyl)((R)-morpholin-2-yl)methoxy)ethylcarbamate

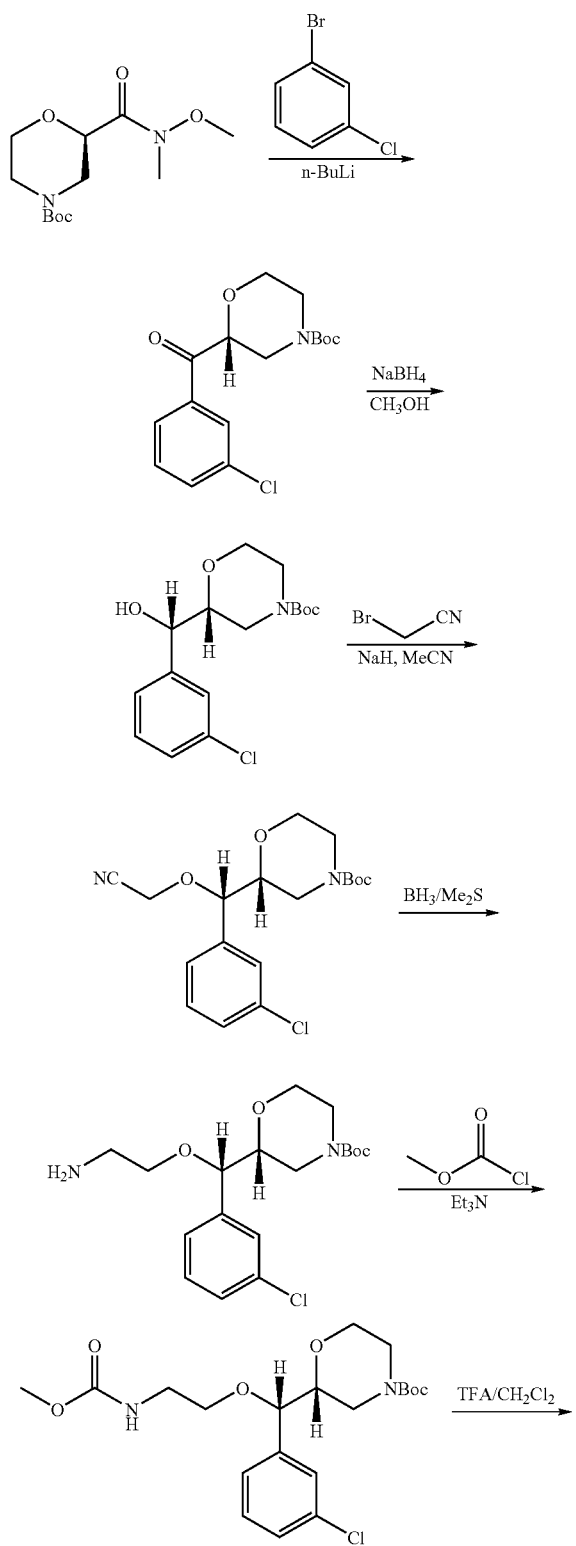

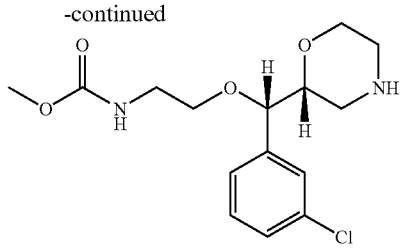

Step 1. (R)-tert-butyl 2-(3-chlorobenzoyl)morpholine-4-carboxylate

To a solution of 1-bromo-3-chlorobenzene (5 g, 18.2 mmol) in anhydrous THF (25 mL) at −78° C. under nitrogen was added dropwise a solution of 2.5 M n-BuLi in hexane (18.2 mmol). After stirring for 1 h at −78° C., a solution of (R)-tert-butyl 2-(methoxy(methyl)carbamoyl)morpholine-4-carboxylate (3.47 g, 18.2 mmol) in anhydrous THF (10 mL) was added dropwise. After addition, the reaction mixture was allowed to warm to rt and stirred for 2 h. Tlc indicated the reaction was complete. The mixture was quenched with satd aq NH$_4$Cl (50 mL) and extracted with EtOAc (3×20 mL). The combined organic layers were washed with brine, dried over Na$_2$SO$_4$ and concentrated in vacuo to give the crude product (5.5 g, 93%), which was used immediately for next step without purification.

Step 2. (R)-tert-butyl 2-((S)-(3-chlorophenyl)(hydroxy)methyl)morpholine-4-carboxylate To a solution of (R)-tert-butyl 2-(3-chlorobenzoyl)morpholine-4-carboxylate (5.5 g, 16.9 mmol) in MeOH (50 mL), NaBH$_4$ (5.14 g, 135 mmol) was added in portions. The mixture was stirred overnight and water (50 mL) was added, The mixture was concentrated in vacuo until MeOH was removed. The aqueous residue was extracted with EtOAc. The organic extracts were washed with brine and dried over Na$_2$SO$_4$. The crude product was purified by chromatography to afford (R)-tert-butyl 2-((S)-(3-chlorophenyl)(hydroxy)methyl)morpholine-4-carboxylate (4.3 g, 78%)

Step 3. (R)-tert-butyl 2-((S)-(3-chlorophenyl)(cyanomethoxy)methyl)morpholine-4-carboxylate To a solution of (R)-tert-butyl 2-((S)-(3-chlorophenyl)(hydroxy)methyl)morpholine-4-carboxylate (1.3 g, 3.98 mmol) in MeCN (20 mL), NaH (230 mg, 9.55 mmol) was added at 0° C. The mixture was stirred for 1 h at rt. The mixture was cooled to −40° C., and bromoacetonitrile (1.14 g, 9.55 mmol) was added in portions. The mixture was stirred for 0.5 h at −20° C. The solution was evaporated and H$_2$O (50 mL) was added. 1N aq HCl was added and the mixture was extracted with CH$_2$Cl$_2$. The organic layer was washed with aq NaHCO$_3$ and brine, dried over Na$_2$SO$_4$ and concentrated. The crude product was used directly in the next step.

Step 4. (R)-tert-butyl 2-((S)-(2-aminoethoxy)(3-chlorophenyl)methyl)morpholine-4-carboxylate (R)-tert-butyl 2-((S)-(3-chlorophenyl)(cyanomethoxy)methyl)morpholine-4-carboxylate (1.3 g, 3.55 mmol) was dissolved in anhydrous THF (25 mL), and the solution was heated to reflux under N$_2$. A solution of BH$_3$.Me$_2$S in THF (5 mL) was added dropwise, and stirring was continued under reflux overnight. The resulting solution was cooled to rt, MeOH was added dropwise to quench the reaction until gas evolution ceased. After evaporation of the solution, the crude product was used for the next step.

Step 5. (R)-tert-butyl 2-((S)-(3-chlorophenyl)(2-(methoxycarbonylamino)ethoxy)methyl)morpholine-4-carboxylate To a solution of (R)-tert-butyl 2-((S)-(2-aminoethoxy)(3-chlorophenyl)methyl)morpholine-4-carboxylate (1.62 g, 4.38 mmol) and DMAP (280 mg) in dry $CH_2Cl_2$ (15 mL), $Et_3N$ (1.33 g, 13.14 mmol) was added. The resulting mixture was cooled to 0-5° C. in an ice-water bath and a solution of methyl chloroformate (2.06 g, 21.9 mmol) in dry $CH_2Cl_2$ (5 mL) was added dropwise. The reaction mixture was stirred for 1-2 h at 0-5° C. Tlc showed the starting material had disappeared. Water (30 mL) was added and the aqueous layer was extracted with $CH_2Cl_2$ (3×10 mL). The combined organic layers were washed with 10% aq citric acid (2×10 mL) and brine, dried over $Na_2SO_4$, filtered and concentrated to the crude product, which was purified by preparative HPLC to afford the desired product (120 mg, 6%). $^1H$ NMR (MeOD) 1.45 (s, 9H), 2.80-2.92 (m, 2H), 3.0 (m, 1H), 3.60 (s, 3H), 4.15 (m, 2H), 4.25 (d, 1H), 7.20-7.35 (m, 4H).

Step 6. Methyl 2-((S)-(3-chlorophenyl)((R)-morpholin-2-yl)methoxy)ethylcarbamate (R)-tert-butyl 2-((S)-(3-chlorophenyl)(2-(methoxycarbonylamino)ethoxy)methyl)morpholine-4-carboxylate (120 mg, 0.28 mmol) was dissolved in a solution of 20% (V/V) $TFA/CH_2Cl_2$ (5 mL). The reaction mixture was stirred at rt for 20 min and a solution of satd aq $NaHCO_3$ was added dropwise to adjust pH=7-8. The resulting mixture was extracted with $CH_2Cl_2$ (3×10 mL). The combined organic extracts were washed with brine, dried over $Na_2SO_4$, and concentrated in vacuo to afford methyl 2-((S)-(3-chlorophenyl)((R)-morpholin-2-yl)methoxy)ethylcarbamate (120 mg, 100%), which was used without purification.

Compounds of Formula I were synthesized as described in the Examples below.

EXAMPLE 1

(3R)-3-((S)-1-(2-(2-Ethylphenoxy)phenyl)-1-hydroxy-5-methoxypentyl)-N-(3-amino-2-hydroxypropyl)piperidine-1-carboxamide (I-1A)

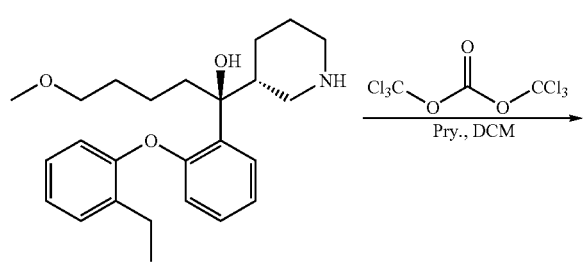

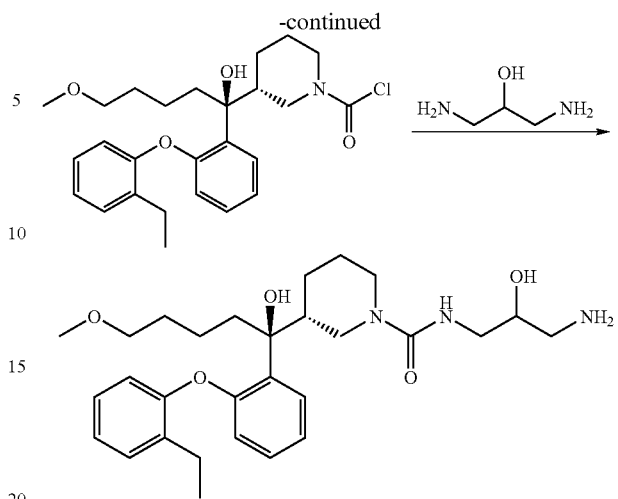

Step 1. (R)-3-((S)-1-(2-(2-Ethylphenoxy)phenyl)-1-hydroxy-5-methoxypentyl)piperidine-1-carbonyl Chloride To a solution of (S)-1-(2-(2-ethylphenoxy)phenyl)-5-methoxy-1-((R)-piperidin-3-yl)pentan-1-ol (19.9 mg, 0.05 mmol) and pyridine (20 μL, 0.15 mmol) in $CH_2Cl_2$ (2 mL) at 0° C. was added triphosgene (22.7 mg, 0.08 mmol) in $CH_2Cl_2$ (0.5 mL). The resulting solution was warmed to rt, and stirred for 1 h. The completion of reaction was confirmed by LC-MS, and the product was used for next step without workup.

Step 2. (3R)-3-((S)-1-(2-(2-Ethylphenoxy)phenyl)-1-hydroxy-5-methoxypentyl)-N-(3-amino-2-hydroxypropyl)piperidine-1-carboxamide To a solution of (R)-3-((S)-1-(2-(2-ethylphenoxy)phenyl)-1-hydroxy-5-methoxy pentyl)piperidine-1-carbonyl chloride (<0.05 mmol) in $CH_2Cl_2$, there was added excess 1,3-diaminopropan-2-ol (~0.1 mL). The resulting solution was stirred at rt for 1 h, the $CH_2Cl_2$ was removed, and the residue was purified by prep HPLC to give (3R)-3-((S)-1-(2-(2-ethylphenoxy)phenyl)-1-hydroxy-5-methoxypentyl)-N-(3-amino-2-hydroxypropyl)piperidine-1-carboxamide (10.0 mg, 39%) as its TFA salt. $^1H$ NMR (400 MHz, $CD_3OD$): 7.64 (d, 1H), 7.32 (d, 1H), 7.04-7.20 (m, 4H), 6.74 (d, 1H), 6.56 (d, 1-H), 4.40 (d, 1H), 3.82 (m, 2H), 3.26 (t, 2H), 3.24 (s, 3H), 2.96 (m, 1H), 2.78 (m, 2H), 2.62 (q, 2H), 2.40 (m, 2H), 1.94 (m, 1H), 1.22-1.64 (m, 7H), 1.08 (t, 3H), 0.98 (m, 1H); MS m/z 514 (M+H$^+$).

The following compounds were prepared using procedures analogous to those described above:

methyl 2-((R)-((R)-1-((2R,3S)-1-(tert-butylamino)-2-hydroxy-5-methylhexan-3-ylcarbamoyl)piperidin-3-yl)(3-chlorophenyl)methoxy)ethylcarbamate (I-29A) was prepared following procedures analogous to those described above using methyl 2-((R)-(3-chlorophenyl)((R)-piperidin-3-yl)methoxy)ethylcarbamate in Step 1 and (2R,3S)-3-amino-1-(tert-butylamino)-5-methylhexan-2-ol in Step 2.

EXAMPLE 2

(R)-N-((2S,3S)-4-Amino-1-cyclohexyl-3-hydroxybutan-2-yl)-3-((S)-1-(3-chloro-2-fluorophenyl)-1-hydroxy-5-methoxypentyl)piperidine-1-carboxamide
(I-5A)

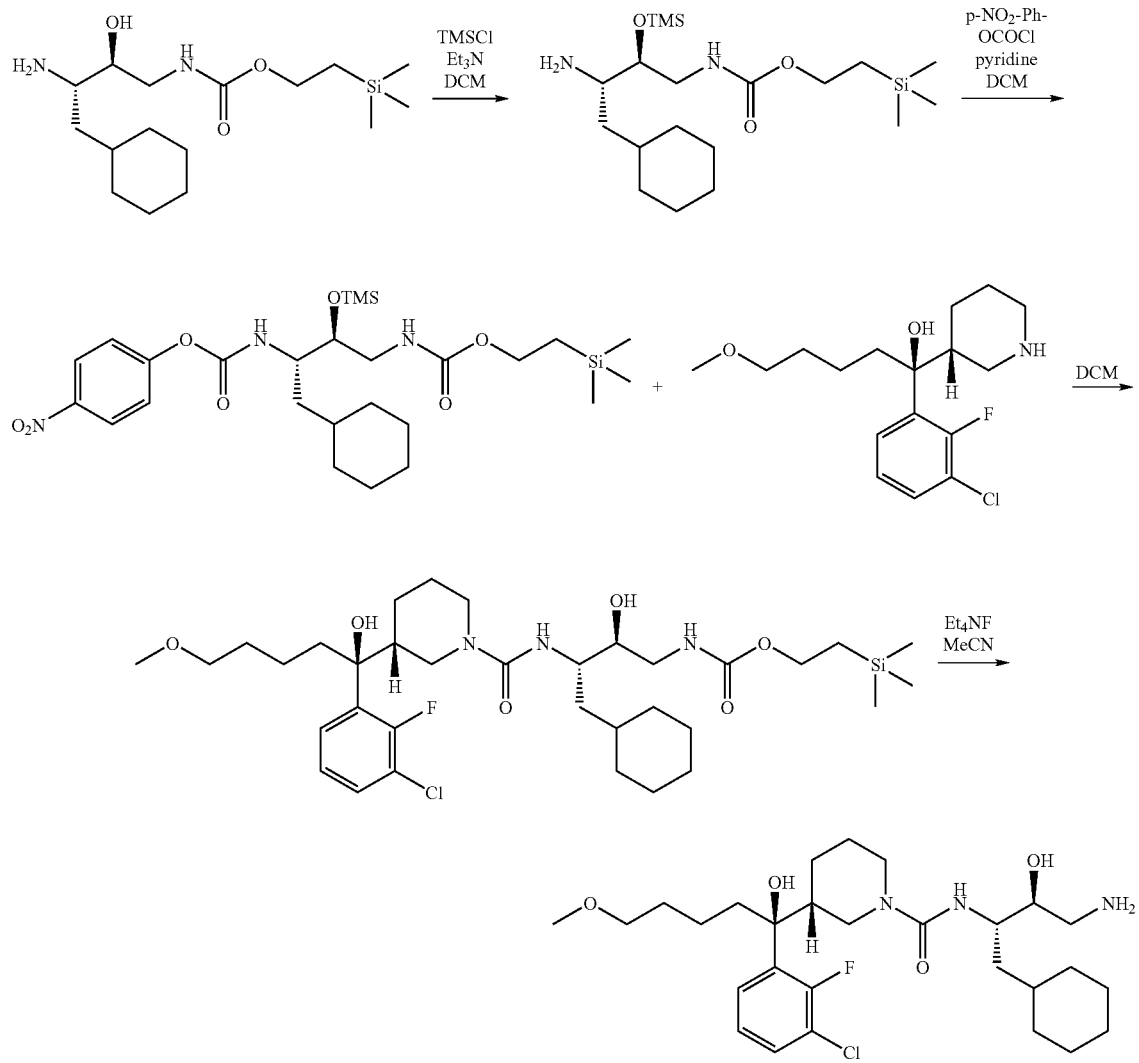

Step 1. 2-(Trimethylsilyl)ethyl (2S,3S)-3-amino-4-cyclohexyl-2-(trimethylsilyloxy)-butylcarbamate To a stirred solution of 2-(trimethylsilyl)ethyl (2S,3S)-3-amino-4-cyclohexyl-2-hydroxybutylcarbamate (0.18 g, 0.54 mmol) in anhydrous $CH_2Cl_2$ (1.5 mL) at 0° C., triethylamine (0.41 mL, 2.70 mmol) was added, followed by chlorotrimethylsilane (176 mg, 1.62 mmol). The resulting white mixture was warmed to rt slowly, and stirred at rt for another 40 min. Solvent was removed under vacuum, and the residue was redissolved in anhydrous $CH_2Cl_2$ (1 mL), and evaporated to dryness under vacuum to give 2-(trimethylsilyl)ethyl (2S,3S)-3-amino-4-cyclohexyl-2-(trimethylsilyloxy)butylcarbamate (quant.) as a white solid; MS m/z 403 (M+H$^+$).

Step 2. 2-(Trimethylsilyl)ethyl (2S,3S)-3-(4-nitrophenoxycarbonylamino)-4-cyclohexyl-2-(trimethylsilyloxy)butylcarbamate To a solution of 2-(trimethylsilyl)ethyl (2S,3S)-3-amino-4-cyclohexyl-2-(trimethylsilyloxy)butylcarbamate in $CH_2Cl_2$ (2 mL) at rt, pyridine (170 mg, 2.2 mmol) was added, followed by 4-nitrophenyl chloroformate (103.4 mg, 0.51 mmol). The resulting solution was stirred at rt for 2 h, and the formation of 2-(trimethylsilyl)ethyl (2S,3S)-3-(4-nitrophenoxycarbonylamino)-4-cyclohexyl-2-(trimethylsilyloxy)butylcarbamate was confirmed by LC-MS. MS m/z 590 (M+Na$^+$). The reaction mixture was used directly in the next step without isolation.

Step 3. 2-(Trimethylsilyl)ethyl (2S,3S)-3-((R)-3-((S)-1-(3-chloro-2-fluorophenyl)-1-hydroxy-5-methoxypentyl)piperidine-1-carboxamido)-4-cyclohexyl-2-hydroxybutyl-carbamate To a solution of (S)-1-(3-chloro-2-fluorophenyl)-5-methoxy-1-((R)-piperidin-3-yl)pentan-1-ol (33.0 mg, 0.10 mmol)

in CH$_2$Cl$_2$ (2 mL), DIEA (39 mg, 0.30 mmol) was added, followed by the solution of 2-(trimethylsilyl)ethyl (2S,3S)-3-(4-nitrophenoxycarbonylamino)-4-cyclohexyl-2-(trimethylsilyloxy)butylcarbamate in CH$_2$Cl$_2$ (0.8 mL, 0.2 mmol) prepared in the previous step. The resulting yellow solution was stirred at rt for 30 min, and completion of reaction was confirmed by LC-MS. Solvent was removed under vacuum, and the residue was purified by preparative HPLC to give 2-(trimethylsilyl)ethyl (2S,3S)-3-((R)-3-((S)-1-(3-chloro-2-fluorophenyl)-1-hydroxy-5-methoxypentyl)piperidine-1-carboxamido)-4-cyclohexyl-2-hydroxybutylcarbamate (25.8 mg, 38%); MS m/z 686 (M+H$^+$).

Step 4. (R)-N-((2S,3S)-4-Amino-1-cyclohexyl-3-hydroxybutan-2-yl)-3-((S)-1-(3-chloro-2-fluorophenyl)-1-hydroxy-5-methoxypentyl)piperidine-1-carboxamide To a solution of 2-(trimethylsilyl)ethyl (2S,3S)-3-((R)-3-((S)-1-(3-chloro-2-fluorophenyl)-1-hydroxy-5-methoxypentyl)piperidine-1-carboxamido)-4-cyclohexyl-2-hydroxybutylcarbamate (25.8 mg, 0.038 mmol) in acetonitrile (2 mL), tetraethylammonium fluoride (excess) was added. The resulting solution was stirred at 50° C. for 2 h, and purified directly with preparative HPLC to give (R)-N-((2S,3S)-4-amino-1-cyclohexyl-3-hydroxybutan-2-yl)-3-((S)-1-(3-chloro-2-fluorophenyl)-1-hydroxy-5-methoxy-pentyl)piperidine-1-carboxamide (24.1 mg, 96%) as its TFA salt; $^1$H NMR (400 MHz, CD$_3$OD) δ 7.54 (dd, 1H), 7.38 (dd, 1H), 7.14 (dd, 1H), 4.36 (d, 1H); 3.94 (m, 2H), 3.78 (m, 1H), 3.28 (m, 2H), 3.24 (s, 3H), 2.94 (dd, 1H), 2.84 (m, 2H), 2.64 (dd, 1H), 2.16 (m, 1H), 1.98 (m, 3H), 0.78-1.86 (m, 20H); MS m/z 542 (M+H$^+$).

EXAMPLE 3

The following compounds were prepared using procedures analogous to those described in Example 2 with the modifications indicated:

(R)-3-((S)-1-(3-chlorophenyl)-1-hydroxy-5-methoxypentyl)-N-((2S,3R)-1-cyclohexyl-3-hydroxy-4-(methylamino)butan-2-yl)piperidine-1-carboxamide (I-3A) using 2-(trimethylsilyl)ethyl (2R,3S)-3-amino-4-cyclohexyl-2-hydroxybutylcarbamate in Step 1 and (S)-1-(3-chlorophenyl)-5-methoxy-1-((R)-piperidin-3-yl)pentan-1-ol in Step 3;

(R)-N-((2S,3R)-1-cyclohexyl-3-hydroxy-4-(methylamino)butan-2-yl)-3-((S)-1-(2,3-difluorophenyl)-1-hydroxy-5-methoxypentyl)piperidine-1-carboxamide (I-4A) using 2-(trimethylsilyl)ethyl (2R,3S)-3-amino-4-cyclohexyl-2-hydroxybutylcarbamate in Step 1 and (S)-1-(2,3-difluorophenyl)-5-methoxy-1-((R)-piperidin-3-yl)pentan-1-ol in Step 3;

(R)-N-((2S,3R)-4-amino-1-cyclohexyl-3-hydroxybutan-2-yl)-3-((S)-1-(3-chloro-2-fluorophenyl)-1-hydroxy-5-methoxypentyl)piperidine-1-carboxamide (I-5B) using 2-(trimethylsilyl)ethyl (2R,3S)-3-amino-4-cyclohexyl-2-hydroxybutylcarbamate in Step 1;

(R)-N-((2S,3R)-4-amino-1-cyclohexyl-3-hydroxybutan-2-yl)-2-((R)-1-(3-chloro-2-fluorophenyl)-1-hydroxy-5-methoxypentyl)morpholine-4-carboxamide (I-6A) using 2-(trimethylsilyl)ethyl (2R,3S)-3-amino-4-cyclohexyl-2-hydroxybutylcarbamate in Step 1 and (R)-1-(3-chloro-2-fluorophenyl)-5-methoxy-1-((R)-morpholin-2-yl)pentan-1-ol in Step 3;

(R)-N-((2S,3S)-4-amino-1-cyclohexyl-3-hydroxybutan-2-yl)-2-((R)-1-(3-chloro-2-fluorophenyl)-1-hydroxy-5-methoxypentyl)morpholine-4-carboxamide (I-6B) using (R)-1-(3-chloro-2-fluorophenyl)-5-methoxy-1-((R)-morpholin-2-yl)pentan-1-ol in Step 3;

methyl (S)-4-((R)-1-((2S,3S)-4-amino-1-cyclohexyl-3-hydroxybutan-2-ylcarbamoyl)piperidin-3-yl)-4-(3-chlorophenyl)-4-hydroxybutylcarbamate (I-7A) using methyl (S)-4-(3-chlorophenyl)-4-hydroxy-4-((R)-piperidin-3-yl)butylcarbamate in Step 3;

methyl (S)-4-((R)-1-((2S,3R)-4-amino-1-cyclohexyl-3-hydroxybutan-2-ylcarbamoyl)piperidin-3-yl)-4-(3-chlorophenyl)-4-hydroxybutylcarbamate (I-7B) using 2-(trimethylsilyl)ethyl (2R,3S)-3-amino-4-cyclohexyl-2-hydroxybutylcarbamate in Step 1 and methyl (S)-4-(3-chlorophenyl)-4-hydroxy-4-((R)-piperidin-3-yl)butylcarbamate in Step 3;

(R)-3-((S)-1-(3-chloro-2-fluorophenyl)-1-hydroxy-5-methoxypentyl)-N-((2S,3R)-1-cyclohexyl-3-hydroxy-4-(methylamino)butan-2-yl)piperidine-1-carboxamide (I-8A) using 2-(trimethylsilyl)ethyl (2R,3S)-3-amino-4-cyclohexyl-2-hydroxybutyl(methyl)carbamate in Step 1 and (R)-1-(3-chloro-2-fluorophenyl)-5-methoxy-1-((R)-morpholin-2-yl)pentan-1-ol in Step 3;

(R)-2-((R)-1-(3-chloro-2-fluorophenyl)-1-hydroxy-5-methoxypentyl)-N-((2S,3R)-1-cyclohexyl-3-hydroxy-4-(methylamino)butan-2-yl)morpholine-4-carboxamide (I-9A) using 2-(trimethylsilyl)ethyl (2R,3S)-3-amino-4-cyclohexyl-2-hydroxybutyl(methyl)carbamate in Step 1 and (R)-1-(3-chloro-2-fluorophenyl)-5-methoxy-1-((R)-morpholin-2-yl)pentan-1-ol in Step 3;

N-((2S,3R)-4-(4-cyanobenzylamino)-1-cyclohexyl-3-hydroxybutan-2-yl)-3-((3-methoxypropoxy)(phenyl)methyl)piperidine-1-carboxamide (I-10A) using (2R,3S)-1-(N-(4-cyanobenzyl)-N-(2-(trimethylsilyl)ethoxycarbonyl)amino)-2-hydroxy-3-amino-4-cyclohexylbutane in Step 1 and 3-((3-methoxypropoxy)(phenyl)methyl)piperidine in Step 3;

methyl 2-((R)-((R)-1-((2S,3R)-4-amino-1-cyclohexyl-3-hydroxybutan-2-ylcarbamoyl)piperidin-3-yl)(3-chlorophenyl)methoxy)ethylcarbamate (I-24A) using 2-(trimethylsilyl)ethyl (2R,3S)-3-amino-4-cyclohexyl-2-hydroxybutylcarbamate in Step 1 and methyl 2-((R)-(3-chlorophenyl)((R)-piperidin-3-yl)methoxy)ethylcarbamate in Step 3; and methyl 2-((R)-(3-chlorophenyl)((R)-1-((2S,3R)-1-cyclohexyl-3-hydroxy-4-(methylamino)butan-2-ylcarbamoyl)piperidin-3-yl)methoxy)ethylcarbamate (I-25A) using 2-(trimethylsilyl)ethyl (2R,3S)-3-amino-4-cyclohexyl-2-hydroxybutyl(methyl)carbamate in Step 1 and methyl 2-((R)-(3-chlorophenyl)((R)-piperidin-3-yl)methoxy)ethylcarbamate in Step 3.

methyl 2-((S)-(3-fluorophenyl)((R)-4-((2S,3R)-1-cyclohexyl-3-hydroxy-4-(methylamino)butan-2-ylcarbamoyl)morpholin-2-yl)methoxy)ethylcarbamate (I-26A) using 2-(trimethylsilyl)ethyl (2R,3S)-3-amino-4-cyclohexyl-2-hydroxybutyl(methyl)carbamate in Step 1 and methyl 2-((S)-(3-fluorophenyl)((R)-morpholin-2-yl)methoxy)ethylcarbamate in Step 3.

EXAMPLE 4

N-((2S,3R)-1-cyclohexyl-4-(3,5-dimethoxybenzylamino)-3-hydroxybutan-2-yl)-2-(3-((4-methoxybutoxy)(phenyl)methyl)pyrrolidin-1-yl)-2-oxoacetamide (I-17A)

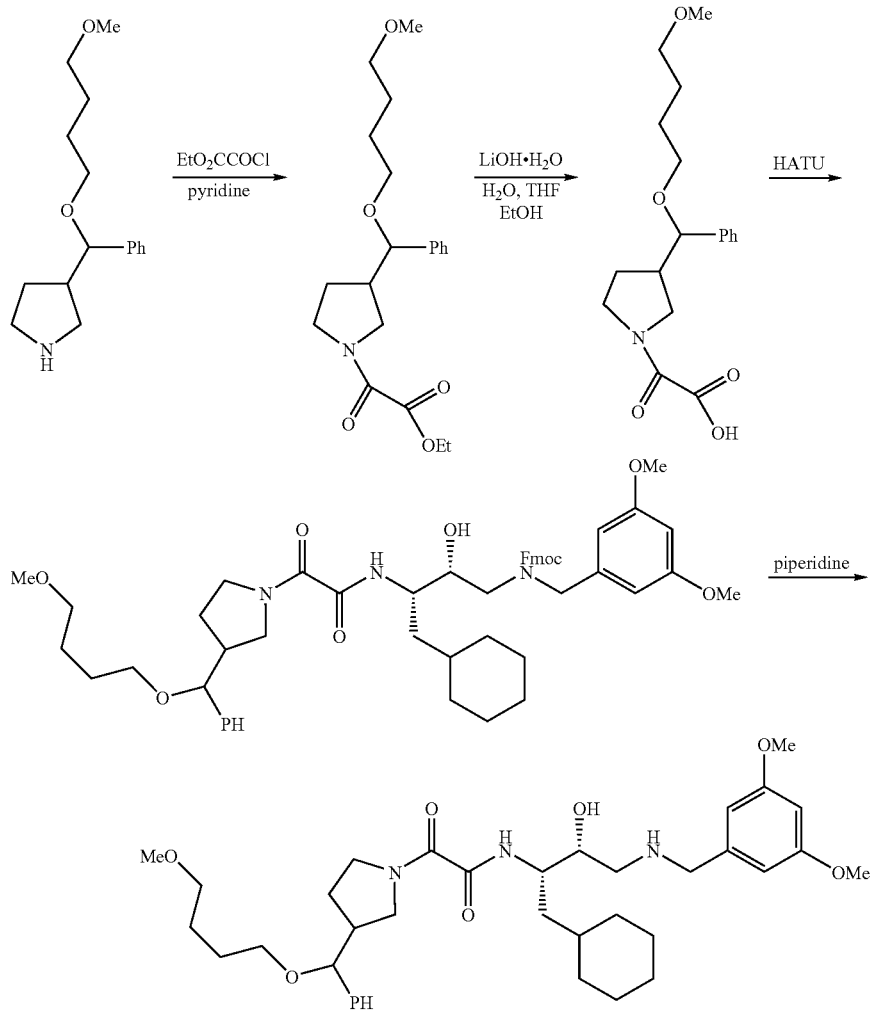

Step 1. Ethyl 2-(3-((4-methoxybutoxy)(phenyl)methyl)pyrrolidin-1-yl)-2-oxoacetate A stirred solution of 3-((4-methoxybutoxy)(phenyl)methyl)pyrrolidine (41 mg, 0.14 mmol) and pyridine (0.05 mL, 0.62 mmol) in $CH_2Cl_2$ (2 mL) was cooled in an ice bath and ethyl oxalyl chloride (17 µL, 0.15 mmol) was added. The ice bath was allowed to melt and the mixture was stirred for 2 h. LC-MS indicated partial conversion to the desired product. Additional ethyl oxalyl chloride (10 µL) was added and stirring was continued overnight at rt. The mixture was diluted with ether (80 mL), washed with 5% aq HCl (30 mL) and satd aq $NaHCO_3$ (30 mL), and dried over $MgSO_4$. Removal of the solvent gave an oil which was applied to a 2 g silica cartridge and eluted sequentially with 0, 10, 25, 50, 75 and 100% ethyl acetate in hexanes (15 mL of each) to give six fractions. Fractions 3 and 4 were pooled and concentrated to afford ethyl 2-(3-((4-methoxybutoxy)(phenyl)methyl)pyrrolidin-1-yl)-2-oxoacetate (42 mg, 84%) as an oil.

Step 2. 2-(3-((4-Methoxybutoxy)(phenyl)methyl)pyrrolidin-1-yl)-2-oxoacetic acid Ethyl 2-(3-((4-methoxybutoxy)(phenyl)methyl)pyrrolidin-1-yl)-2-oxoacetate (42 mg, 0.12 mmol) was dissolved in water (0.5 mL), THF (0.5 mL) and EtOH (1 mL). Solid $LiOH \cdot H_2O$ (5 mg, 0.12 mmol) was added and the resulting solution was stirred for 3 d. The mixture was evaporated to dryness to afford 2-(3-((4-methoxybutoxy)(phenyl)methyl)pyrrolidin-1-yl)-2-oxoacetic acid as its lithium salt (44 mg, quant).

Step 3. N-((2S,3R)-1-Cyclohexyl-4-(N-(3,5-dimethoxybenzyl)-N-((9H-fluoren-9-yl)methoxycarbonyl)amino)-3-hydroxybutan-2-yl)-2-(3-((4-methoxybutoxy)(phenyl)methyl)pyrrolidin-1-yl)-2-oxoacetamide 2-(3-((4-Methoxybutoxy)(phenyl)methyl)pyrrolidin-1-yl)-2-oxoacetic acid (23 mg, 67 µmol), (2R,3S)-3-amino-4-cyclohexyl-1-(N-(3,5-dimethoxybenzyl)-N-((9H-fluoren-9-yl)methoxycarbonyl)amino)butan-2-ol (40 mg, 67 µmol) and DIEA (25 µL, 134 µmol) were dissolved in DMF (0.5 mL) and $CH_2Cl_2$ (0.5 mL) and solid HATU (38 mg, 101 µmol) was added. The mixture was stirred at rt for 3 h, diluted with ether (90 mL), washed with 5% aq HCl (30 mL) and satd aq NaHCO$_3$ (30 mL), and dried over MgSO$_4$. Removal of the solvent gave an oil (49 mg) which was applied to a 2-g silica SPE cartridge and eluted sequentially with 0, 10, 25, 50, 75 and 100% EtOAc in hexanes (15 mL of each) to give six fractions. Fractions 4 and 5 were pooled and concentrated to afford N-((2S,3R)-1-cyclohexyl-4-(N-(3,5-dimethoxybenzyl)-N-((9H-fluoren-9-yl)methoxycarbonyl)amino)-3-hydroxybutan-2-yl)-2-(3-((4-methoxybutoxy)-(phenyl)methyl)pyrrolidin-1-yl)-2-oxoacetamide (38 mg, 64%) as an oil.

Step 4. N-((2S,3R)-1-Cyclohexyl-4-(3,5-dimethoxybenzylamino)-3-hydroxybutan-2-yl)-2-(3-((4-methoxybutoxy)(phenyl)methyl)pyrrolidin-1-yl)-2-oxoacetamide A solution of N-((2S,3R)-1-cyclohexyl-4-N-(3,5-dimethoxybenzyl)-N-((9H-fluoren-9-yl)methoxycarbonyl)amino)-3-hydroxybutan-2-yl)-2-(3-((4-methoxybutoxy)(phenyl)methyl)-pyrrolidin-1-yl)-2-oxoacetamide (38 mg, 44 µmol) in piperidine (0.2 mL) and THF (0.8 mL) was stirred overnight at rt. The mixture was concentrated to leave a yellow solid (45 mg) which was purified by preparative HPLC to afford N-((2S,3R)-1-cyclohexyl-4-(3,5-dimethoxybenzylamino)-3-hydroxybutan-2-yl)-2-(3-((4-methoxybutoxy)(phenyl)methyl)pyrrolidin-1-yl)-2-oxoacetamide as its TFA salt (15.1 mg, 45%).

EXAMPLE 5

The following compounds were prepared using the procedures described in Example 4 with the modifications indicated:

N-((2S,3R)-1-cyclohexyl-4-(3,5-dimethoxybenzylamino)-3-hydroxybutan-2-yl)-2-(3-((2-methoxyethoxy)(phenyl)methyl)pyrrolidin-1-yl)-2-oxoacetamide (I-12A) using 3-((2-methoxyethoxy)(phenyl)methyl)pyrrolidine in Step 1;

N-((2S,3R)-1-cyclohexyl-4-(3,5-dimethoxybenzylamino)-3-hydroxybutan-2-yl)-2-(3-((3-methoxypropoxy)(phenyl)methyl)pyrrolidin-1-yl)-2-oxoacetamide (I-13A) using 3-((3-methoxypropoxy)(phenyl)methyl)pyrrolidine in Step 1; and N-((2S,3R)-1-cyclohexyl-4-(3,5-dimethoxybenzylamino)-3-hydroxybutan-2-yl)-2-(3-(1-hydroxy-5-methoxy-1-phenylpentyl)pyrrolidin-1-yl)-2-oxoacetamide (I-18A) using 5-methoxy-1-phenyl-1-(pyrrolidin-3-yl)pentan-1-ol in Step 1.

EXAMPLE 6

4-(((2R,3S)-4-cyclohexyl-2-hydroxy-3-(2-(3-((3-methoxypropoxy)(phenyl)methyl)piperidin-1-yl)-3,4-dioxocyclobut-1-enylamino)butylamino)methyl)benzonitrile (I-15A)

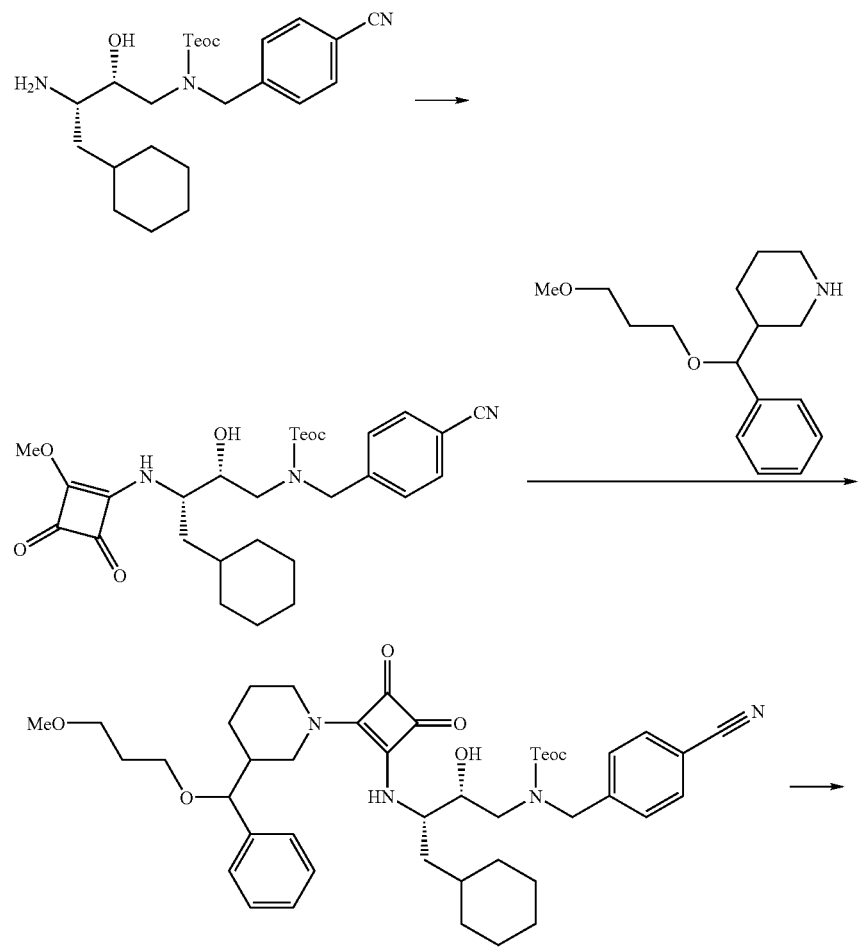

-continued

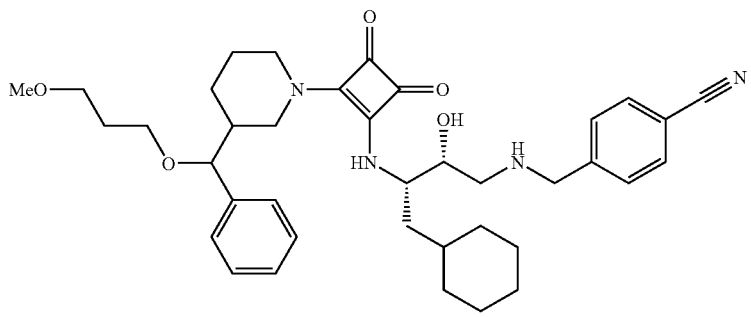

Step 1. 3-((2S,3R)-4-(N-(4-Cyanobenzyl)-N-(2-(trimethylsilyl)ethoxycarbonyl)amino)-1-cyclohexyl-3-hydroxybutan-2-ylamino)-4-methoxycyclobut-3-ene-1,2-dione A solution of (2R,3S)-1-(N-(4-cyanobenzyl)-N-(2-(trimethylsilyl)ethoxycarbonyl)amino)-2-hydroxy-3-amino-4-cyclohexylbutane (764 mg, 1.68 mmol) in EtOH (20 mL) was treated with 3,4-dimethoxycyclobut-3-ene-1,2-dione (300 mg, 2.10 mmol, 1.25 equiv) and Et₃N (212 mg, 1.25 equiv). The resulting solution was allowed to stir at rt for 17 h. The excess 3,4-dimethoxycyclobut-3-ene-1,2-dione was removed by flash chromatography on silica gel, eluting with 0-65% EtOAc in hexanes. Analysis of the compound by LC-MS showed that it was of sufficient purity to employ in the subsequent steps.

Steps 2 and 3. 4-(((2R,3S)-4-cyclohexyl-2-hydroxy-3-(2-(3-((3-methoxypropoxy)(phenyl)-methyl)piperidin-1-yl)-3,4-dioxocyclobut-1-enylamino)butylamino)methyl)benzonitrile A solution of ((3-methoxypropoxy)(phenyl)methyl)piperidine (8.4 mg, 0.03 mmol) in acetonitrile (0.4 mL) was added to 2-(trimethylsilyl)ethyl (4-cyanobenzyl)((2R,3S)-4-cyclohexyl-2-hydroxy-3-(2-methoxy-3,4-dioxocyclobut-1-enylamino)butyl)carbamate (17.8 mg, 0.032 mmol) in acetonitrile (0.5 mL). The reaction was allowed to stir overnight. Tetraethyl-ammonium fluoride (48 mg, 0.32 mmol) was added and the mixture was heated to 60° C. for 90 min. The acetonitrile was evaporated and the crude material was redissolved in CH₂Cl₂. The mixture was washed with water and the organic layer was dried over Na₂SO₄, filtered, and evaporated. The crude material was purified by preparative HPLC to afford 4-(((2R,3S)-4-cyclohexyl-2-hydroxy-3-(2-(3-((3-methoxypropoxy)(phenyl)methyl)piperidin-1-yl)-3,4-dioxocyclobut-1-enylamino)butylamino)methyl)benzonitrile as its TFA salt (13.3 mg). MS m/z 643 (M+H⁺).

EXAMPLE 7

The following compounds were prepared using procedures analogous to those described in Example 6.
4-(((2R,3S)-4-cyclohexyl-3-(2-(3-(hexyloxy(phenyl)methyl)piperidin-1-yl)-3,4-dioxocyclobut-1-enylamino)-2-hydroxybutylamino)methyl)benzonitrile (I-19A) using 3-(hexyloxy(phenyl)methyl)-piperidine in Step 2;
4-(((2R,3S)-4-cyclohexyl-2-hydroxy-3-(2-(3-((4-methoxybutoxy)(phenyl)methyl)piperidin-1-yl)-3,4-dioxocyclobut-1-enylamino)butylamino)methyl)benzonitrile (I-20A) using 3-((4-methoxybutoxy)(phenyl)methyl)piperidine in Step 2;
4-(((2S,3S)-4-cyclohexyl-2-hydroxy-3-(2-(3-((3-methoxypropoxy)(phenyl)methyl)piperidin-1-yl)-3,4-dioxocyclobut-1-enylamino)butylamino)methyl)benzonitrile (I-15B) using (2R,3R)-1-(N-(4-cyanobenzyl)-N-(2-(trimethylsilyl)ethoxycarbonyl)amino)-3-amino-4-cyclohexylbutan-2-ol in Step 1;
3-((2S,3R)-1-cyclohexyl-4-(3,5-dimethoxybenzylamino)-3-hydroxybutan-2-ylamino)-4-(3-(hydroxy(phenyl)methyl)piperidin-1-yl)cyclobut-3-ene-1,2-dione (I-11A) using in (2R,3S)-3-amino-4-cyclohexyl-1-(N-(3,5-dimethoxybenzyl)-N-((9H-fluoren-9-yl)methoxycarbonyl)-amino)butan-2-ol in Step 1 and phenyl(piperidin-3-yl)methanol in Step 2 and Fmoc removal with piperidine in Step 3;
3-((2S,3R)-1-cyclohexyl-4-(3,5-dimethoxybenzylamino)-3-hydroxybutan-2-ylamino)-4-(3-(hydroxy(phenyl)methyl)piperidin-1-yl)cyclobut-3-ene-1,2-dione (I-21A) using (2R,3S)-3-amino-4-cyclohexyl-1-(N-(3,5-dimethoxybenzyl)-N-((9H-fluoren-9-yl)methoxycarbonyl)amino)butan-2-ol in Step 1 and 3-(butoxy(phenyl)methyl)piperidine in Step 2 and Fmoc removal with piperidine in Step 3;
3-((2S,3R)-1-cyclohexyl-4-(3,5-dimethoxybenzylamino)-3-hydroxybutan-2-ylamino)-4-(3-((3-methoxypropoxy)(phenyl)methyl)piperidin-1-yl)cyclobut-3-ene-1,2-dione (I-23A) using (2R,3S)-3-amino-4-cyclohexyl-1-(N-(3,5-dimethoxybenzyl)-N-((9H-fluoren-9-yl)methoxycarbonyl)-amino)butan-2-ol in Step 1 and Fmoc removal with piperidine in Step 3;
3-((2S,3R)-1-cyclohexyl-4-(3,5-dimethoxybenzylamino)-3-hydroxybutan-2-ylamino)-4-(3-((2-methoxyethoxy)(phenyl)methyl)piperidin-1-yl)cyclobut-3-ene-1,2-dione (I-22A) using (2R,3S)-3-amino-4-cyclohexyl-1-(N-(3,5-dimethoxybenzyl)-N-((9H-fluoren-9-yl)methoxycarbonyl)amino)-butan-2-ol in Step and 3-((2-methoxyethoxy)(phenyl)methyl)piperidine in Step 2 and Fmoc removal with piperidine in Step 3; and
3-((2S,3R)-1-cyclohexyl-4-(3,5-dimethoxybenzylamino)-3-hydroxybutan-2-ylamino)-4-(3-(1-(3-methoxypropoxy)-2-methylpropyl)piperidin-1-yl)cyclobut-3-ene-1,2-dione (I-16A) using (2R,3S)-3-amino-4-cyclohexyl-1-(N-(3,5-dimethoxybenzyl)-N-((9H-fluoren-9-yl)methoxycarbonyl)amino)butan-2-ol in Step 1 and 3-(1-(3-methoxypropoxy)-2-methylpropyl)piperidine in Step 2 and Fmoc removal with piperidine in Step 3.

EXAMPLE 8

3-((2S,3R)-4-amino-1-cyclohexyl-3-hydroxybutan-2-ylamino)-4-(3-((3-methoxypropoxy)(phenyl)methyl)piperidin-1-yl)cyclobut-3-ene-1,2-dione

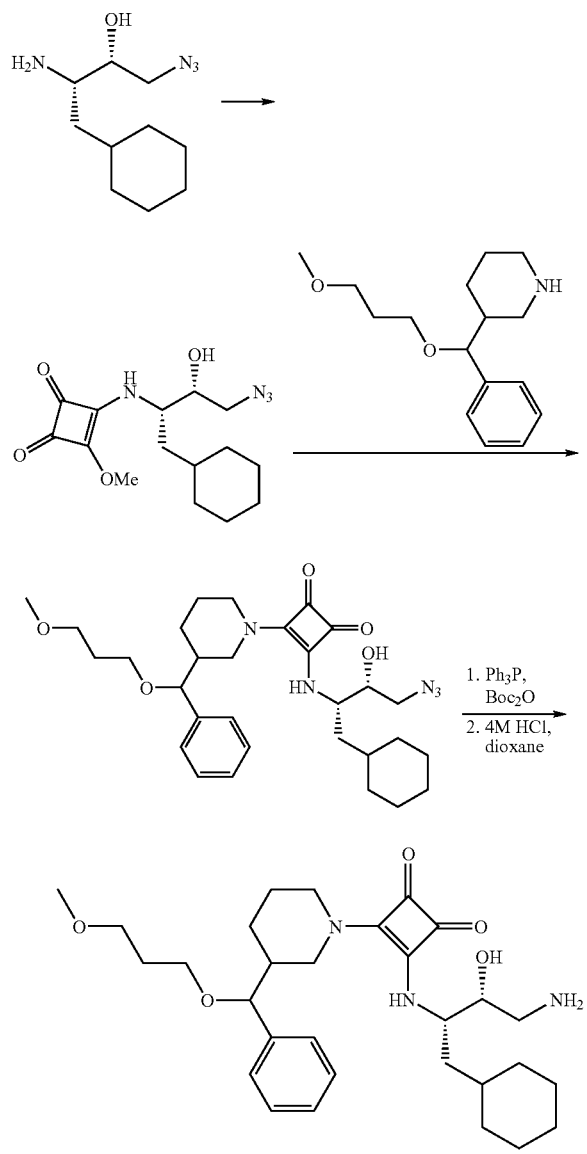

Step 1. 3-((2S,3R)-4-Azido-1-cyclohexyl-3-hydroxybutan-2-ylamino)-4-methoxycyclobut-3-ene-1,2-dione The HCl salt of (2R,3S)-3-amino-1-azido-4-cyclohexylbutan-2-ol (~74 mg, 0.30 mmol) and 3,4-dimethoxycyclobut-3-ene-1,2-dione (70 mg, 0.49 mmol) were dissolved in acetonitrile (3 mL). Triethylamine (84 µL, 0.60 mmol) was added. The reaction was stirred at rt for 4 h. The solvent was evaporated and the crude material was redissolved in CH$_2$Cl$_2$. The solution was washed with 2% aq HCl, followed by brine, and dried over Na$_2$SO$_4$. The solution was filtered and the solvent removed under reduced pressure. The crude material was purified by flash chromatography on silica gel eluting with hexanes/EtOAc. 3-((2S,3R)-4-Azido-1-cyclohexyl-3-hydroxybutan-2-ylamino)-4-methoxycyclobut-3-ene-1,2-dione (63 mg) was isolated as a solid; MS m/z 323.

Step 2. 3-((2S,3R)-4-Azido-1-cyclohexyl-3-hydroxybutan-2-ylamino)-4-(3-((3-methoxypropoxy)-(phenyl)methyl)piperidin-1-yl)cyclobut-3-ene-1,2-dione 3-((2S,3R)-4-Azido-1-cyclohexyl-3-hydroxybutan-2-ylamino)-4-methoxycyclobut-3-ene-1,2-dione (35 mg, 0.11 mmol), the HCl salt of 3-((3-methoxypropoxy)(phenyl)methyl)piperidine (48 mg, 0.16 mmol), and Et$_3$N (100 µL, 0.7 mmol) were dissolved in acetonitrile (1 mL). The reaction was allowed to stir at rt overnight. The solvent was evaporated and the product was isolated by preparative HPLC to give 3-((2S,3R)-4-azido-1-cyclohexyl-3-hydroxybutan-2-ylamino)-4-(3-((3-methoxypropoxy)(phenyl)methyl)piperidin-1-yl)cyclobut-3-ene-1,2-dione (41 mg). MS m/z 554 (M+H$^+$).

Step 3. tert-Butyl (2R,3S)-4-cyclohexyl-2-hydroxy-3-(2-(3-((3-methoxypropoxy)(phenyl)-methyl)piperidin-1-yl)-3,4-dioxocyclobut-1-enylamino)butylcarbamate 3-((2S,3R)-4-azido-1-cyclohexyl-3-hydroxybutan-2-ylamino)-4-methoxycyclobut-3-ene-1,2-dione (41 mg, 0.07 mmol) was dissolved in THF (1 mL) followed by addition of triphenylphosphine (35 mg, 0.13 mmol) and water (200 µL, 11 mmol). The reaction was stirred at rt for 72 h. The solvent was evaporated and the crude material was taken up in THF (2 mL) followed by the addition of Boc$_2$O (19 mg, 0.09 mmol) and triethylamine (21 µL, 0.15 mmol). The reaction was kept at room temperature for several hours. The solution was washed with water, followed by brine. The organic layer was dried over sodium sulfate and filtered. The solvent was removed and the crude product was isolated by preparative HPLC to give tert-butyl (2R,3S)-4-cyclohexyl-2-hydroxy-3-(2-(3-((3-methoxypropoxy)(phenyl)methyl)piperidin-1-yl)-3,4-dioxocyclobut-1-enylamino)butylcarbamate (37 mg); MS m/z 628 (M+H$^+$).

Step 4. 3-((2S,3R)-4-Amino-1-cyclohexyl-3-hydroxybutan-2-ylamino)-4-(3-((3-methoxy-propoxy)(phenyl)methyl)piperidin-1-yl)cyclobut-3-ene-1,2-dione A solution of tert-butyl (2R,3S)-4-cyclohexyl-2-hydroxy-3-(2-(3-((3-methoxypropoxy)-(phenyl)methyl)piperidin-1-yl)-3,4-dioxocyclobut-1-enylamino)butylcarbamate (37 mg, 0.06 mmol) was dissolved in dioxane (1 mL) and treated with 4M HCl in dioxane (1 mL). The reaction was allowed to stir for 3 h. Evaporation of the solvent provided 3-((2S,3R)-4-amino-1-cyclohexyl-3-hydroxybutan-2-ylamino)-4-(3-((3-methoxypropoxy)(phenyl)methyl)piperidin-1-yl)cyclobut-3-ene-1,2-dione as its HCl salt (32 mg); MS m/z 528 (M+H$^+$).

EXAMPLE 9

N-((2S,3R)-1-cyclohexyl-4-(3,5-dimethoxybenzylamino)-3-hydroxybutan-2-yl)-2-(3-((3-methoxypropoxy)(phenyl)methyl)piperidin-1-yl)acetamide (I-14A)

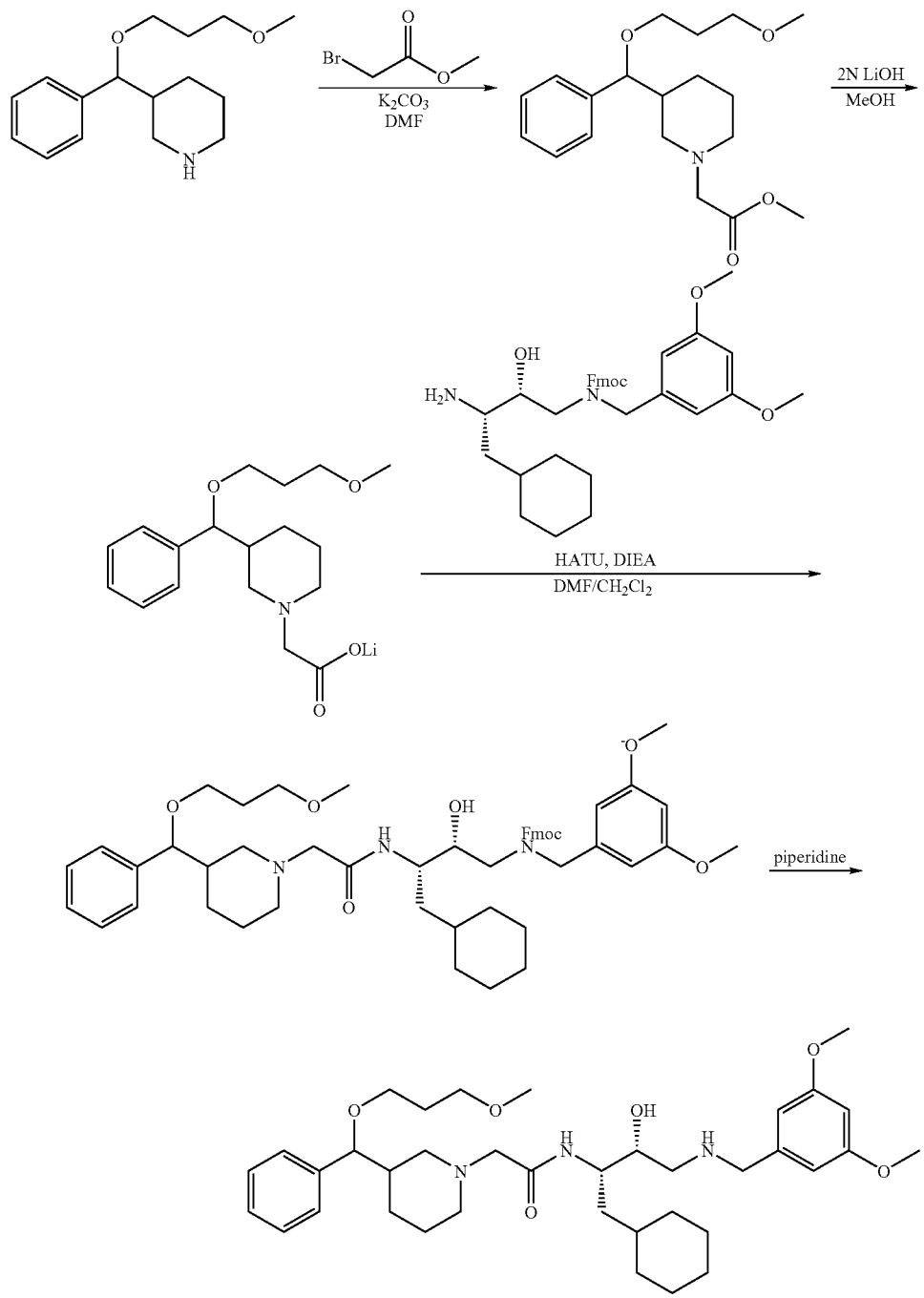

Step 1. Methyl 2-(3-((3-methoxypropoxy)(phenyl)methyl)piperidin-1-yl)acetate 3-((3-Methoxypropoxy)(phenyl)methyl)piperidine HCl salt (63 mg, 0.212 mmol) was mixed with methyl bromoacetate (20 μL), $K_2CO_3$ (75 mg, 2.5 equiv.), and anhydrous DMF (3 mL). The mixture was stirred overnight at rt. LC-MS indicated the reaction was complete. The mixture was diluted with EtOAc and washed with water. The water layer was extracted with EtOAc. The combined organic layers were washed with water and brine, and dried over $Na_2SO_4$. After concentration, the residue was purified by flash chromatography on a 4-g silica gel cartridge eluted with a 0-10% methanol in dichloromethane gradient to afford methyl 2-(3-((3-methoxypropoxy)(phenyl)methyl)piperidin-1-yl)acetate (19 mg, 27% yield). LC-MS (3 min) $t_R$=1.07 min, m/z 336 (M+1).

Step 2. Lithium 2-(3-((3-methoxypropoxy)(phenyl) methyl)piperidin-1-yl)acetate Methyl 2-(3-((3-methoxypropoxy)(phenyl)methyl)piperidin-1-yl)acetate (19 mg, 0.0567 mmol) was mixed with a 1:1 mixture of 2 N aq LiOH (2 mL) and methanol (2 mL). The mixture was stirred overnight at r.t. LC-MS indicated the reaction was complete. The mixture was concentrated and the crude product was used without purification. LC-MS (3 min) $t_R$=1.05 min, m/z 322 (M+1).

Step 3. N-((2S,3R)-1-Cyclohexyl-4-(N-3,5-dimethoxybenzyl-N-(9H-(9-fluorenyl)methoxy-carbonyl)amino)-3-hydroxybutan-2-yl)-2-(3-((3-methoxypropoxy)(phenyl)methyl)piperidin-1-yl) acetamide Lithium 2-(3-((3-methoxypropoxy)(phenyl)methyl)piperidin-1-yl)acetate (0.0567 mmol), (2S,3S)-3-amino-4-cyclohexyl-1-(N-(3,5-dimethoxybenzyl)-N-((9H-fluoren-9-yl)methoxy-carbonyl)amino)butan-2-ol (0.0608 mmol), HATU (30 mg, 0.0789 mmol), DIEA (36 mL, 0.2067 mmol) were mixed and dissolved in DMF (1 mL) and CH$_2$Cl$_2$ (1 mL). The reaction mixture was stirred 4 h at rt. LC-MS indicated the reaction was complete. The mixture was concentrated and the crude product was used without purification. LC-MS (3 min) $t_R$=2.06 min, m/z 862 (M+1).

Step 4. (2R,3S)-4-Cyclohexyl-1-(3,5-dimethoxybenzylamino)-3-(2-(3-((3-methoxypropoxy)-(phenyl) methyl)piperidin-1-yl)ethylamino)butan-2-ol The crude N-((2S,3R)-1-cyclohexyl-4-(N-3,5-dimethoxybenzyl-N-(9H-(9-fluorenyl)-methoxycarbonyl)amino)-3-hydroxybutan-2-yl)-2-(3-((3-methoxypropoxy)(phenyl)-methyl)piperidin-1-yl)acetamide from the previous step was dissolved in CH$_2$Cl$_2$ (5 mL). Piperidine (1.5 mL) was added to the solution. The mixture was stirred overnight at r.t. LC-MS indicated the reaction was complete. The mixture was concentrated and the crude product was purified by preparative HPLC to afford N-((2S,3R)-1-cyclohexyl-4-(3,5-dimethoxybenzylamino)-3-hydroxybutan-2-yl)-2-(3-((3-methoxypropoxy)(phenyl)methyl)piperidin-1-yl)acetamide (13.3 mg, 37% yield for two steps). LC-MS (3 min) $t_R$=1.29 min, m/z 640 (M+1). $^1$H NMR (CDCl$_3$) δ 7.35-7.19 (m, 5H), 6.65-6.57 (m, 2H), 6.45 (s, 1H), 3.74 (s, 6H), 3.26 (s, 3H), 0.88 (m, 1H), 0.74 (m, 1H).

EXAMPLE 10

Methyl 2-((S)-(3-chlorophenyl)((R)-4-((2S,3R)-3-hydroxy-4-(methylamino)-1-(tetrahydro-2H-pyran-4-yl)butan-2-ylcarbamoyl)morpholin-2-yl)methoxy) ethylcarbamate (I-28A)

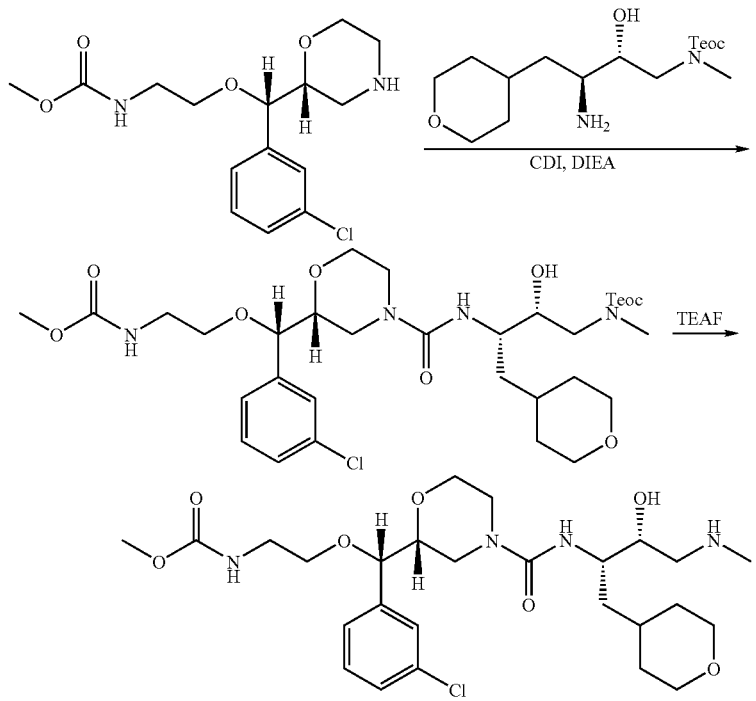

Step 1. Methyl 2-((S)-(3-chlorophenyl)((R)-4-((2S, 3R)-3-hydroxy-4-(N-methyl-N-(2-(trimethylsilyl) ethoxycarbonyl)amino)-1-(tetrahydro-2H-pyran-4-yl)butan-2-ylcarbamoyl)morpholin-2-yl)methoxy) ethylcarbamate To a solution of 2-(trimethylsilyl)ethyl (2R,3S)-3-amino-2-hydroxy-4-(tetrahydro-2H-pyran-4-yl)butyl(methyl)carbamate (50 mg, 0.12 mmol) and CDI (20 mg, 0.12 mmol) in anhydrous CH$_2$Cl$_2$ (10 mL) cooled in an ice bath, DIEA (78 mg, 0.6 mmol) was added. After addition, the mixture was stirred for 1 h at 0° C. and added to a solution of methyl 2-((S)-(3-chlorophenyl)((R)-morpholin-2-yl)methoxy)ethylcarbamate (59 mg, 0.18 mmol) in anhydrous CH$_2$Cl$_2$ (2 mL). The reaction mixture was allowed to warm to rt and stirred overnight. After the reaction was complete, the solvent was removed in vacuo. The product was purified by preparative tlc to afford the desired product (30 mg, 36%).

Step 2. Methyl 2-((S)-(3-chlorophenyl)((R)-4-((2S,3R)-3-hydroxy-4-(methylamino)-1-(tetrahydro-2H-pyran-4-yl)butan-2-ylcarbamoyl)morpholin-2-yl)methoxy)ethylcarbamate A 10 mL flask was charged with methyl 2-((S)-(3-chlorophenyl)((R)-4-((2S,3R)-3-hydroxy-4-(N-methyl-N-(2-(trimethylsilyl)ethoxycarbonyl)amino)-1-(tetrahydro-2H-pyran-4-yl)butan-2-ylcarbamoyl)morpholin-2-yl)methoxy)ethylcarbamate (30 mg, 0.043 mmol) dissolved in MeCN (4 mL) and Et$_4$NF (14 mg, 0.094 mmol) was added. The mixture was stirred for 0.5 h under reflux. After stirring, it was monitored by HPLC until the reaction ended. The solution was concentrated in vacuo and purified by HPLC to give the target compound (2.97 mg, 12%). $^1$H NMR (MeOD) 1.27-1.30 (m, 2H), 1.32-1.40 (m, 2H), 1.51-1.62 (m, 2H), 1.65-1.80 (m, 2H), 2.70 (s, 3H), 1.75-1.90 (m, 2H), 1.90-3.10 (m, 4H), 3.65 (s, 3H), 3.80-3.95 (m, 5H), 4.05-4.20 (m, 1H), 4.30 (m, 1H), 7.25-7.40 (m, 4H).

The following compound was prepared using procedures analogous to those described above:
methyl 2-((S)-(3-chlorophenyl)((R)-4-((2S,3R)-1-cyclohexyl-3-hydroxy-4-(methylamino)butan-2-ylcarbamoyl)morpholin-2-yl)methoxy)ethylcarbamate (I-27A) using 2-(trimethylsilyl)ethyl (2R,3S)-3-amino-4-cyclohexyl-2-hydroxybutyl(methyl)carbamate in Step 1.

The following are compounds of the invention. Compound names were generated with the assistance of ChemDraw® versions 8.0 and 9.0 (CambridgeSoft Corporation, 100 CambridgePark Drive, Cambridge, Mass. 02140 USA). When the stereochemistry at a chiral center is not defined in the compound name this indicates that the sample prepared contained a mixture of isomers at this center.

Table of Compounds

| Cpd. No. | Compound Name | Example No. | LC-MS (3 min) | $t_R$ (min) | Mass observed | 1H NMR solvent | Selected 1H NMR |
|---|---|---|---|---|---|---|---|
| I-1A | (3R)—N-(3-amino-2-hydroxypropyl)-3-((S)-1-(2-(2-ethylphenoxy)phenyl)-1-hydroxy-5-methoxypentyl)piperidine-1-carboxamide | 1 | 1.45 | | 514 | CD$_3$OD | 0.94 (m), 1.18 (t), 1.22-1.64 (m), 1.94 (m), 2.42 (m), 2.64 (q), 2.78 (m), 2.96 (m), 3.24 (sm), 3.30 (m), 3.84 (m), 4.38 (d), 6.56 (d), 6.74 (d), 7.04-7.20 (m), 7.32 (d), 7.64 (d) |
| I-2A | 3-((2S,3R)-4-amino-1-cyclohexyl-3-hydroxybutan-2-ylamino)-4-(3-((3-methoxypropoxy)(phenyl)methyl)piperidin-1-yl)cyclobut-3-ene-1,2-dione | 8 | 1.47 | | 528 | CD$_3$OD | 7.37-7.29 (m), 3.31 (ap s) |
| I-3A | (R)-3-((S)-1-(3-chlorophenyl)-1-hydroxy-5-methoxypentyl)-N-((2S,3R)-1-cyclohexyl-3-hydroxy-4-(methylamino)butan-2-yl)piperidine-1-carboxamide | 3 | 1.55 | | 538 | CD$_3$OD | 0.82-2.04 (m), 2.56 (m), 2.66 (s), 3.02 (m), 3.24 (s), 3.26 (t), 3.62 (m), 3.72 (m), 3.98 (d), 4.28 (d), 7.20-7.34 (m), 7.42 (s) |
| I-4A | (R)—N-((2S,3R)-1-cyclohexyl-3-hydroxy-4-(methylamino)butan-2-yl)-3-((S)-1-(2,3-difluorophenyl)-1-hydroxy-5-methoxypentyl)piperidine-1-carboxamide | 3 | 1.49 | | 540 | CD$_3$OD | 0.82-1.82 (m), 1.98 (m), 2.16 (m), 2.64 (m), 2.66 (s), 2.83 (m), 3.04 (m), 3.24 (s), 3.26 (t), 3.62 (m), 3.74 (m), 4.00 (d); 4.36 (d), 7.16 (m), 7.38 (m) |
| I-5A | (R)—N-((2S,3S)-4-amino-1-cyclohexyl-3-hydroxybutan-2-yl)-3-((S)-1-(3-chloro-2-fluorophenyl)-1-hydroxy-5-methoxypentyl)piperidine-1-carboxamide | 2 | 1.52 | | 542 | CD$_3$OD | 0.78-1.86 (m), 1.98 (m), 2.16 (m), 2.64 (dd), 2.84 (m), 2.94 (dd), 3.24 (s), 3.28 (m), 3.78 (m), 3.94 (m), 4.36 (d), 7.14 (dd), 7.38 (dd), 7.54 (dd) |
| I-5B | (R)—N-((2S,3R)-4-amino-1-cyclohexyl-3-hydroxybutan-2-yl)-3-((S)-1-(3-chloro-2-fluorophenyl)-1-hydroxy-5-methoxypentyl)piperidine-1-carboxamide | 3 | 1.52 | | 542 | CD$_3$OD | 0.82 (m), 1.00-1.84 (m), 1.98 (m), 2.16 (m), 2.62 (dd), 2.82 (dd), 2.94 (dd), 3.02 (dd), 3.24 (s), 3.26 (m), 3.58 (m), 3.72 (m), 3.98 (m), 4.36 (d), 7.14 (dd), 7.38 (dd), 7.54 (dd) |
| I-6A | (R)—N-((2S,3R)-4-amino-1-cyclohexyl-3-hydroxybutan-2-yl)-2-((R)-1-(3-chloro-2-fluorophenyl)-1-hydroxy-5-methoxypentyl)morpholine-4-carboxamide | 3 | 1.45 | | 544 | CD$_3$OD | 0.84 (m), 1.02-1.60 (m), 1.64-1.84 (m), 2.04 (m), 2.94 (m), 3.02 (m), 3.24 (s), 3.26 (t), 3.40 (dd), 3.58 (m), 3.80 (m), 4.12 (d), 7.12 (dd), 7.38 (dd), 7.56 (dd) |
| I-6B | (R)—N-((2S,3S)-4-amino-1-cyclohexyl-3-hydroxybutan-2-yl)-2-((R)-1-(3-chloro-2-fluorophenyl)-1-hydroxy-5-methoxypentyl)morpholine-4-carboxamide | 3 | 1.44 | | 544 | CD$_3$OD | 0.80-1.84 (m), 2.04 (m), 2.80-3.04 (m), 3.24 (s), 3.26 (t), 3.42 (dd), 3.78 (m), 3.94 (d), 4.18 (d), 7.14 (dd), 7.38 (dd), 7.56 (dd) |
| I-7A | methyl (S)-4-((R)-1-((2S,3S)-4-amino-1-cyclohexyl-3-hydroxybutan-2-ylcarbamoyl)piperidin-3-yl)-4-(3-chlorophenyl)-4-hydroxybutylcarbamate | 3 | 1.48 | | 553 | CD$_3$OD | 0.82-2.02 (m), 2.58 (m), 2.96 (m), 3.04 (m), 3.60 (sm), 3.72 (m), 3.98 (d), 4.34 (d), 7.22-7.38 (m), 7.42 (s) |

-continued

Table of Compounds

| Cpd. No. | Compound Name | Example No. | LC-MS $t_R$ (3 min) (min) | Mass observed | 1H NMR solvent | Selected 1H NMR |
|---|---|---|---|---|---|---|
| I-7B | methyl (S)-4-((R)-1-((2S,3R)-4-amino-1-cyclohexyl-3-hydroxybutan-2-ylcarbamoyl)piperidin-3-yl)-4-(3-chlorophenyl)-4-hydroxybutylcarbamate | 3 | 1.40 | 553 | CD$_3$OD | 0.82-1.52 (m), 1.60-2.00 (m), 2.56 (m), 2.82 (dd), 2.92 (dd), 3.02 (m), 3.60 (s), 3.76 (m), 3.94 (m), 4.28 (d), 7.22-7.34 (m), 7.42 (s) |
| I-8A | (R)-3-((S)-1-(3-chloro-2-fluorophenyl)-1-hydroxy-5-methoxypentyl)-N-((2S,3R)-1-cyclohexyl-3-hydroxy-4-(methylamino)butan-2-yl)piperidine-1-carboxamide | 3 | 1.56 | 556 | CD$_3$OD | 0.82 (m), 1.00-1.84 (m), 1.98 (m), 2.16 (m), 2.64 (m), 2.68 (s), 2.82 (dd), 3.04 (m), 3.24 (s), 3.26 (t), 3.62 (m), 3.74 (m), 4.00 (d), 4.36 (d), 7.16 (dd), 7.38 (dd), 7.54 (dd) |
| I-9A | (R)-2-((R)-1-(3-chloro-2-fluorophenyl)-1-hydroxy-5-methoxypentyl)-N-((2S,3R)-1-cyclohexyl-3-hydroxy-4-(methylamino)butan-2-yl)morpholine-4-carboxamide | 3 | 1.48 | 558 | CD$_3$OD | 0.78-1.84 (m), 2.06 (m), 2.68 (s), 2.90 (m), 3.06 (m), 3.24 (s), 3.26 (t), 3.40 (m), 3.62 (m), 3.78 (m), 4.10 (d), 7.14 (dd), 7.38 (dd), 7.56 (dd) |
| I-10A | N-((2S,3R)-4-(4-cyanobenzylamino)-1-cyclohexyl-3-hydroxybutan-2-yl)-3-((3-methoxypropoxy)(phenyl)methyl)piperidine-1-carboxamide | 3 | 1.8 | 591 | CD$_3$OD | 7.72-7.21 (m), 6.41 (br s), 3.30 (ap d), 3.28 (s) |
| I-11A | 3-((2S,3R)-1-cyclohexyl-4-(3,5-dimethoxybenzylamino)-3-hydroxybutan-2-ylamino)-4-(3-(hydroxy(phenyl)methyl)piperidin-1-yl)cyclobut-3-ene-1,2-dione | 7 | 1.45 | 606 | CDCl$_3$ | 7.22 (m), 6.56 (s), 6.33 (s), 3.67 (m) |
| I-12A | N-((2S,3R)-1-cyclohexyl-4-(3,5-dimethoxybenzylamino)-3-hydroxybutan-2-yl)-2-(3-((2-methoxyethoxy)(phenyl)methyl)pyrrolidin-1-yl)-2-oxoacetamide | 5 | 1.6 | 626 | CD$_3$OD | 2.60 (m, 2H), 3.30 (3H), 3.75 (6H), 6.50 (1H), 6.62 (2H), 7.30 (5H) |
| I-13A | N-((2S,3R)-1-cyclohexyl-4-(3,5-dimethoxybenzylamino)-3-hydroxybutan-2-yl)-2-(3-((3-methoxypropoxy)(phenyl)methyl)pyrrolidin-1-yl)-2-oxoacetamide | 5 | 1.65 | 640 | CD$_3$OD | 2.60 (m, 2H), 3.75 (6H), 4.07 (m, 3H), 6.55 (1H), 6.62 (2H), 7.15 (5H) |
| I-14A | N-((2S,3R)-1-cyclohexyl-4-(3,5-dimethoxybenzylamino)-3-hydroxybutan-2-yl)-2-(3-((3-methoxypropoxy)(phenyl)methyl)piperidin-1-yl)acetamide | 9 | 1.29 | 640 | CDCl$_3$ | 7.40-7.22 (m, 5H), 6.63 (m, 2H), 6.43 (s, 1H), 3.74 (s, 6H), 3.25 (s, 3H), 0.87 (m, 1H), 0.73 (br s, 1H). |
| I-15A | 4-(((2R,3S)-4-cyclohexyl-2-hydroxy-3-(2-(3-((3-methoxypropoxy)(phenyl)methyl)piperidin-1-yl)-3,4-dioxocyclobut-1-enylamino)butylamino)methyl)benzonitrile | 6 | | 643 | CDCl$_3$ | 9.21 (br s), 7.64 (s), 7.35-7.20 (m), 5.94 (br m), 3.30 (s), 3.26 (d) |
| I-15B | 4-(((2S,3S)-4-cyclohexyl-2-hydroxy-3-(2-(3-((3-methoxypropoxy)(phenyl)methyl)piperidin-1-yl)-3,4-dioxocyclobut-1-enylamino)butylamino)methyl)benzonitrile | 7 | | 643 | CD$_3$OD | 0.86 (m, 1H), 1.04 (m, 1H), 3.28 (s, 3H), 3.48 (m, 3H), 3.92-4.02 (m, 2H), 4.20-4.32 (m, 3H), 4.46 (m, 1H), 7.28-7.42 (m, 5H), 7.66 (m, 2H), 7.82 (m, 2H) |
| I-16A | 3-((2S,3R)-1-cyclohexyl-4-(3,5-dimethoxybenzylamino)-3-hydroxybutan-2-ylamino)-4-(3-(1-(3-methoxypropoxy)-2-methylpropyl)piperidin-1-yl)cyclobut-3-ene-1,2-dione | 7 | | 644 | CD$_3$OD | 0.88 (m, 1H), 0.94 (m, 6H), 2.85 (m, 1H), 3.08 (m, 4H), 3.29 (s, 3H), 3.55 (m, 5H), 3.79 (s, 6H), 4.14 (m, 2H), 4.38 (m, 1H), 6.56 (m, 1H), 6.64 (m, 2H) |
| I-17A | N-((2S,3R)-1-cyclohexyl-4-(3,5-dimethoxybenzylamino)-3-hydroxybutan-2-yl)-2-(3-((4-methoxybutoxy)(phenyl)methyl)pyrrolidin-1-yl)-2-oxoacetamide | 4 | 1.72 | 654 | CD$_3$OD | 2.55 (m, 2H), 3.30 (3H), 3.75 (6H), 4.10 (m, 3H), 6.55 (1H), 6.62 (2H), 7.35 (5H) |
| I-18A | N-((2S,3R)-1-cyclohexyl-4-(3,5-dimethoxybenzylamino)-3-hydroxybutan-2-yl)-2-(3-(1-hydroxy-5-methoxy-1-phenylpentyl)pyrrolidin-1-yl)-2-oxoacetamide | 5 | 1.6 | 654 | CD$_3$OD | 3.25 (3H), 3.75 (6H), 4.10 (2H), 6.50 (1H), 6.60 (2H), 7.35 (5H) |
| I-19A | 4-(((2R,3S)-4-cyclohexyl-3-(2-(3-(hexyloxy(phenyl)methyl)piperidin-1-yl)-3,4-dioxocyclobut-1-enylamino)-2-hydroxybutylamino)methyl)benzonitrile | 7 | | 655 | CDCl$_3$ | 7.64 (s), 7.34-7.21 (s), 3.95 (d), 0.83 (m) |

-continued

Table of Compounds

| Cpd. No. | Compound Name | Example No. | LC-MS $t_R$ (3 min) (min) | Mass observed | 1H NMR solvent | Selected 1H NMR |
|---|---|---|---|---|---|---|
| I-20A | 4-(((2R,3S)-4-cyclohexyl-2-hydroxy-3-(2-(3-((4-methoxybutoxy)(phenyl)methyl)piperidin-1-yl)-3,4-dioxocyclobut-1-enylamino)butylamino)methyl)benzonitrile | 7 | | 657 | CDCl₃ | 9.32 (br s), 7.66 (s), 7.35-7.21 (m), 3.32 (ap s), 3.29 (ap s) |
| I-21A | 3-(3-(butoxy(phenyl)methyl)piperidin-1-yl)-4-((2S,3R)-1-cyclohexyl-4-(3,5-dimethoxybenzylamino)-3-hydroxybutan-2-ylamino)cyclobut-3-ene-1,2-dione | 7 | 1.88, 1.92 | 662 | CDCl₃ | 7.33-7.20 (m), 6.61 (s), 6.43 (s), 5.45 (br m), 3.74 (m), 0.88 (m) |
| I-22A | 3-((2S,3R)-1-cyclohexyl-4-(3,5-dimethoxybenzylamino)-3-hydroxybutan-2-ylamino)-4-(3-((2-methoxyethoxy)(phenyl)methyl)piperidin-1-yl)cyclobut-3-ene-1,2-dione | 7 | 1.6 | 664 | CDCl₃ | 7.34-7.21 (m), 6.62 (m), 6.43 (s), 3.75 (s), 3.33 (d) |
| I-23A | 3-((2S,3R)-1-cyclohexyl-4-(3,5-dimethoxybenzylamino)-3-hydroxybutan-2-ylamino)-4-(3-((3-methoxypropoxy)(phenyl)methyl)piperidin-1-yl)cyclobut-3-ene-1,2-dione | 7 | 1.64 | 678 | CDCl₃ | 7.33-7.20 (m), 6.62 (s), 6.43 (s), 5.12 (br s), 3.74 (s), 3.29 (s), 3.27 (d) |
| I-24A | methyl 2-((R)-((R)-1-((2S,3R)-4-amino-1-cyclohexyl-3-hydroxybutan-2-ylcarbamoyl)piperidin-3-yl)(3-chlorophenyl)methoxy)ethylcarbamate | 3 | 1.56 | 539 | CD₃OD | 7.35-7.31 (m, 3H), 7.20 (d, J = 7.2 Hz, 1H), 4.07-4.00 (m, 2H), 3.80 (brd, J = 12.8 Hz, 1H), 3.72 (m, 1H), 3.63 (s, 3H), 3.58 (m, 1H), 3.30-3.10 (m, 5H), 2.99-2.94 (m, 3H), 1.78-1.60 (m, 8H), 1.51-1.20 (m, 8H), 1.08 (m, 1H), 0.87 (m, 1H). |
| I-25A | methyl 2-((R)-(3-chlorophenyl)((R)-1-((2S,3R)-1-cyclohexyl-3-hydroxy-4-(methylamino)butan-2-ylcarbamoyl)piperidin-3-yl)methoxy)ethylcarbamate | 3 | 1.59 | 553 | CD₃OD | 7.37-7.32 (m, 3H), 7.21 (d, J = 7.2 Hz, 1H), 4.09 (d, J = 13.6 Hz, 1H), 4.02 (d, J = 8.8 Hz, 1H), 3.84 (brd, J = 14.0 Hz, 1H), 3.74-3.61 (m, 2H), 3.63 (s, 3H), 3.35 (m, 4H), 3.09-3.04 (m, 2H), 2.92 (m 1H), 2.68 (s, 3H), 1.78-1.60 (m, 8H), 1.51-1.19 (m, 8H), 1.06 (m, 1H), 0.87 (m, 1H). |
| I-26A | methyl 2-((R)-((R)-1-((2S,3R)-1-cyclohexyl-3-hydroxy-4-(methylamino)butan-2-ylcarbamoyl)piperidin-3-yl)(3-fluorophenyl)methoxy)ethylcarbamate | 3 | 1.61 | 537 | CD₃OD | 7.37 (m, 1H), 7.09 (d, J = 7.6 Hz, 1H), 7.05-7.03 (m, 2H), 4.88-4.05 (m, 2H), 3.94 (brd, J = 7.4 Hz, 1H), 3.73 (m, 1H), 3.63 (s, 3H), 3.61 (m, 1H), 3.34 (m, 1H), 3.27-3.20 (m, 5H), 3.10-2.96 (m, 3H), 2.93 (m, 1H), 2.68 (s, 3H), 1.78-1.60 (m, 8H), 1.51-1.16 (m, 8H), 1.09 (m, 1H), 0.87 (m, 1H). |
| I-27A | methyl 2-((S)-(3-chlorophenyl)((R)-4-((2S,3R)-1-cyclohexyl-3-hydroxy-4-(methylamino)butan-2-ylcarbamoyl)morpholin-2-yl)methoxy)ethylcarbamate | 10 | | 555 | CD₃OD | 1.28 (m, 8H), 1.52-1.79 (m, 5H), 2.65 (s, 3H), 2.89-3.12 (m, 3H), 3.23 (m, 4H), 3.42 (m, 6H), 3.59 (m, 4H), 3.78 (m, 3H), 4.06 (m, 1H), 4.26 (d, 1H), 7.29 (m, 4H) |
| I-28A | methyl 2-((S)-(3-chlorophenyl)((R)-4-((2S,3R)-3-hydroxy-4-(methylamino)-1-(tetrahydro-2H-pyran-4-yl)butan-2-ylcarbamoyl)morpholin-2-yl)methoxy)ethylcarbamate | 10 | | 557 | CD₃OD | 1.28-1.43 (m, 4H), 1.52-1.79 (m, 4H), 2.71 (m, 3H), 2.73-3.06 (m, 6H), 3.34-3.52 (m, 7H), 3.64 (s, 3H), 3.70-3.94 (m, 5H), 4.12 (m, 1H), 4.31 (m, 1H), 7.42 (m, 4H) |
| I-29A | methyl 2-((R)-((R)-1-((2R,3S)-1-(tert-butylamino)-2-hydroxy-5-methylhexan-3-ylcarbamoyl)piperidin-3-yl)(3-chlorophenyl)methoxy)ethylcarbamate | 1 | | 553 | CD₃OD | 0.88 (d, 3H), 1.00 (d, 3H), 1.31 (m, 1H), 1.33 (s, 9H), 1.36-1.79 (m, 7H), 2.81-3.07 (m, 4H), 3.23 (m, 4H), 3.61 (s, 5H), 3.83 (m, 1H), 4.05 (m, 1H), 4.17 (m, 1H), 7.17-7.41 (m, 4H) |

The following prophetic compounds could be prepared by applying the procedures described above to the appropriate starting materials:

| | |
|---|---|
| PI-1a | methyl 2-((R)-((R)-1-((2S,3R)-4-amino-3-hydroxy-1-((S)-tetrahydro-2H-pyran-3-yl)butan-2-ylcarbamoyl)piperidin-3-yl)(3-chlorophenyl)methoxy)ethylcarbamate |
| PI-2a | methyl 2-((S)-((R)-4-((2S,3R)-4-amino-3-hydroxy-1-((S)-tetrahydro-2H-pyran-3-yl)butan-2-ylcarbamoyl)morpholin-2-yl)(3-chlorophenyl)methoxy)ethylcarbamate |
| PI-3a | methyl 2-((R)-(3-chlorophenyl)((R)-1-((2S,3R)-3-hydroxy-4-(methylamino)-1-((S)-tetrahydro-2H-pyran-3-yl)butan-2-ylcarbamoyl)piperidin-3-yl)methoxy)ethylcarbamate |
| PI-3b | methyl 2-((R)-(3-chlorophenyl)((R)-1-((2S,3S)-3-hydroxy-4-(methylamino)-1-((S)-tetrahydro-2H-pyran-3-yl)butan-2-ylcarbamoyl)piperidin-3-yl)methoxy)ethylcarbamate |
| PI-4a | methyl 2-((S)-(3-chlorophenyl)((R)-4-((2S,3R)-3-hydroxy-4-(methylamino)-1-((S)-tetrahydro-2H-pyran-3-yl)butan-2-ylcarbamoyl)morpholin-2-yl)methoxy)ethylcarbamate |
| PI-4b | methyl 2-((S)-(3-chlorophenyl)((R)-4-((2S,3S)-3-hydroxy-4-(methylamino)-1-((S)-tetrahydro-2H-pyran-3-yl)butan-2-ylcarbamoyl)morpholin-2-yl)methoxy)ethylcarbamate |
| PI-5a | (R)-3-((R)-(2-acetamidoethoxy)(3-chlorophenyl)methyl)-N-((2S,3R)-3-hydroxy-4-(methylamino)-1-((S)-tetrahydro-2H-pyran-3-yl)butan-2-yl)piperidine-1-carboxamide |
| PI-6a | (R)-2-((S)-(2-acetamidoethoxy)(3-chlorophenyl)methyl)-N-((2S,3R)-3-hydroxy-4-(methylamino)-1-((S)-tetrahydro-2H-pyran-3-yl)butan-2-yl)morpholine-4-carboxamide |
| PI-7a | methyl (S)-4-(3-chlorophenyl)-4-hydroxy-4-((R)-1-((2S,3R)-3-hydroxy-4-(methylamino)-1-((S)-tetrahydro-2H-pyran-3-yl)butan-2-ylcarbamoyl)piperidin-3-yl)butylcarbamate |
| PI-8a | methyl (R)-4-(3-chlorophenyl)-4-hydroxy-4-((R)-4-((2S,3R)-3-hydroxy-4-(methylamino)-1-((S)-tetrahydro-2H-pyran-3-yl)butan-2-ylcarbamoyl)morpholin-2-yl)butylcarbamate |
| PI9a | (R)-3-((R)-(3-chlorophenyl)(2-(ethylamino)-2-oxoethoxy)methyl)-N-((2S,3S)-3-hydroxy-4-(methylamino)-1-((S)-tetrahydro-2H-pyran-3-yl)butan-2-yl)piperidine-1-carboxamide |
| PI-10a | (R)-2-((S)-(3-chlorophenyl)(2-(ethylamino)-2-oxoethoxy)methyl)-N-((2S,3S)-3-hydroxy-4-(methylamino)-1-((S)-tetrahydro-2H-pyran-3-yl)butan-2-yl)morpholine-4-carboxamide |

EXAMPLE 11

In Vitro Activity Studies—$IC_{50}$ Values for Renin Inhibition

The action of renin inhibitors was demonstrated experimentally by means of an in vitro test which measures the increase in fluorescence of an internally quenched peptide substrate. The sequence of this peptide corresponds to the sequence of human angiotensinogen. The following test protocol was used:

All reactions were carried out in a flat bottom white opaque microtiter plate. A 4 µL aliquot of 400 µM renin substrate (DABCYL-☐-Abu-Ile-His-Pro-Phe-His-Leu-Val-Ile-His-Thr-EDANS) in 192 µL assay buffer (50 mM BES, 150 mM NaCl, 0.25 mg/mL bovine serum albumin, pH7.0) was added to 4 µL of test compound in DMSO at various concentrations ranging from 10 µM to 1 nM final concentrations. Next, 100 µL of trypsin-activated recombinant human renin (final enzyme concentration of 0.2-2 nM) in assay buffer was added, and the solution was mixed by pipetting. The increase in fluorescence at 495 nm (excitation at 340 nm) was measured for 60-360 minutes at room temperature using a Perkin-Elmer Fusion microplate reader. The slope of a linear portion of the plot of fluorescence increase as a function of time was then determined, and the rate was used for calculating percent inhibition in relation to uninhibited control. The percent inhibition values were plotted as a function of inhibitor concentration, and the $IC_{50}$ was determined from a fit of this data to a four parameter equation. The $IC_{50}$ was defined as the concentration of a particular inhibitor that reduces the formation of product by 50% relative to a control sample containing no inhibitor.

In the in vitro systems the compounds of the invention exhibit inhibiting activities at minimum concentrations of from approximately $5 \times 10^{-5}$ M to approximately $10^{-12}$ M. Preferred compounds of the invention exhibit inhibiting activities at minimum concentrations of from approximately $5 \times 10^{-8}$ M to approximately $10^{-12}$ M. More preferred compounds of the invention exhibit inhibiting activities at minimum concentrations of from approximately $5 \times 10^{-9}$ M to approximately $10^{-12}$ M. (Wang G. T. et al. *Anal. Biochem.* 1993, 210, 351; Nakamura, N. et al. *J. Biochem.* (*Tokyo*) 1991, 109, 741; Murakami, K. et al. *Anal Biochem.* 1981, 110, 232).

EXAMPLE 12

Inhibition in Human Plasma

The action of renin inhibitors in vitro in human plasma can also be demonstrated experimentally by the decrease in plasma renin activity (PRA) levels observed in the presence of the compounds. Incubations mixtures contain in the final volume of 250 µL 95.5 mM N,N-bis(2-hydroxyethyl)-2-aminoethanesulfonic acid, pH 7.0, 8 mM EDTA, 0.1 mM neomycin sulfate, 1 mg/mL sodium azide, 1 mM phenylmethanesulfonyl fluoride, 2% DMSO and 87.3% of pooled mixed-gender human plasma stabilized with EDTA. For plasma batches with low PRA (less than 1 ng/ml/hr) ~2 pM of recombinant human renin is added to achieve PRA of 3-4 ng/ml/hr. The cleavage of endogenous angiotensinogen in plasma is carried out at 37° C. for 90 min and the product angiotensin I is measured by competitive radioimmunoassay using Dia-Sorin PRA kit. Uninhibited incubations containing 2% DMSO and fully inhibited controls with 2 µM of isovaleryl-Phe-Nle-Sta-Ala-Sta-OH are then used for deriving percent of inhibition for each concentration of inhibitors and fitting dose-response data into a four parametric model from which IC$_{50}$ values, defined as concentrations of inhibitors at which 50% inhibition occurs, are determined.

Highly preferred compounds of the invention exhibit inhibiting activities at minimum concentrations of from approximately $10^{-8}$ M to approximately $10^{-12}$ M in this assay and from $5 \times 10^{-9}$ M to approximately $10^{-12}$ M in the assay described in Example 11.

EXAMPLE 13

In Vivo Activity

The cardiac and systemic hemodynamic efficacy of selective renin inhibitors can be evaluated in vivo in sodium-depleted, normotensive cynomolgus monkeys and in sodium-depleted, normotensive beagle dogs following a single oral and intravenous administration of the test compound. Arterial blood pressure is monitored by telemetry in freely moving, conscious animals.

Cynomolgus Monkey: Six male naïve cynomolgus monkeys weighing between 2.5 and 3.5 kg can be used in the studies. At least 4 weeks before the experiment, the monkeys are anesthetized with ketamine hydrochloride (15 mg/kg, i.m.) and xylazine hydrochloride (0.7 mg/kg, i.m.), and are implanted into the abdominal cavity with a transmitter (Model #TL11M2-D70-PCT, Data Sciences, St. Paul, Minn.). The pressure catheter is inserted into the lower abdominal aorta via the femoral artery. The bipotential leads are placed in Lead II configuration. The animals are housed under constant temperature (19-25° C.), humidity (>40%) and lighting conditions (12 h light and dark cycle), are fed once daily, and are allowed free access to water. The animals are sodium depleted by placing them on a low sodium diet (0.026%, Expanded Primate Diet 829552 MP-VENaCl (P), Special Diet Services, Ltd., UK) 7 days before the experiment and furosemide (3 mg/kg, intramuscularly i.m., Aventis Pharmaceuticals) is administered at −40 h and −16 h prior to administration of test compound.

For oral dosing, the renin inhibitors are formulated in 0-5% methylcellulose at dose levels of 10 and 30 mg/kg (5 mL/kg) by infant feeding tubes. For intravenous delivery, a silastic catheter is implanted into posterior vena cava via a femoral vein. The catheter is attached to the delivery pump via a tether system and a swivel joint. Test compound (dose levels of 0.1 to 10 mg/kg, formulated at 5% dextrose) is administered by continuous infusion (1.67 mL/kg/h) or by bolus injection (3.33 mL/kg in 2 min).

Arterial blood pressures (systolic, diastolic and mean) and body temperature are recorded continuously at 500 Hz and 50 Hz, respectively, using the Dataquest™ A.R.T. (Advanced Research Technology) software. Heart rate is derived from the phasic blood pressure tracing. During the recording period, the monkeys are kept in a separate room without human presence to avoid pressure changes secondary to stress. All data are expressed as mean±SEM. Effects of the renin inhibitors on blood pressure are assessed by ANOVA, taking into account the factors dose and time compared with the vehicle group.

Beagle Dogs: Non-naive Beagle dogs (2 per sex) weighing between 9 and 11 kg can be used in the studies. Each animal is implanted subcutaneously with a telemetry transmitter (Data Sciences) and the blood pressure catheter is inserted into the left femoral artery. The electrocardiogram leads are also tunneled subcutaneously to the appropriate anatomical regions. The animals are housed under constant temperature and lighting conditions, are fed once daily, and are allowed free access to water. A sodium depleted state is produced by placing them on a low-sodium diet (<4 meq/day, a combination of canned Prescription Diet canine h/d, from Hill's Pet Products and dry pellets from Bio-Serv Inc., Frenchtown, N.J.) beginning 10 days before the experiment, and furosemide (3 mg/kg i.m.; Aventis Pharmaceuticals) is administered at −40 and −16 h prior to administration of test compound.

A renin inhibitor is orally administered by orogastric gavage to all overnight fasted animals at a dose level of 30 mg/kg (4 mL/kg formulated in 0.5% methylcellulose). Food is given 4 h postdose. In some experiments, the renin inhibitor is administered by bolus i.v. at increasing dose levels of 1, 3 and 6 mg/kg (2, 6 and 20 mg/mL formulated in sterile saline). Cardiovascular parameters are collected continuously at least 80 min predose and 3 h postdose, followed by every 10 min for 5 h and every 30 min for 16 h postdose. The Dataquest™ ART (version 2.2) software package from DSI (Data Sciences International) is used to collect telemetered cardiovascular data.

EXAMPLE 14

The efficacy of the renin inhibitors can also be evaluated in vivo in double transgenic rats engineered to express human renin and human angiotensinogen (Bohlender J, Fukamizu A, Lippoldt A, Nomura T, Dietz R, Menard J, Murakami K, Luft F C, Ganten D. High human renin hypertension in transgenic rats. *Hypertension* 1997, 29, 428-434).

Experiments are conducted in 6-week-old double transgenic rats (dTGRs). The model has been described in detail earlier. Briefly, the human renin construct used to generate transgenic animals made up the entire genomic human renin gene (10 exons and 9 introns), with 3.0 kB of the 5'-promoter region and 1.2 kB of 3' additional sequences. The human angiotensinogen construct made up the entire human angiotensinogen gene (5 exons and 4 introns), with 1.3 kB of 5'-flanking and 2.4 kB of 3'-flanking sequences. The rats can be purchased from RCC Ltd (Füllinsdorf, Switzerland). Radio telemetry transmitters can be surgically implanted at 4 weeks of age. The telemetry system provides 24-h recordings of systolic, mean, diastolic arterial pressure (SAP, MAP, DAP, respectively) and heart rate (HR). Beginning on day 42, animals are transferred to telemetry cages. A 24 h telemetry reading is obtained. Rats are then dosed orally on the following 4 consecutive days (days 43-46). The rats are monitored continuously and allowed free access to standard 0.3%-sodium rat chow and drinking water.

While this invention has been particularly shown and described with references to preferred embodiments thereof, it will be understood by those skilled in the art that various changes in form and details may be made therein without departing from the scope of the invention encompassed by the appended claims.

What is claimed is:

1. A compound represented by the following structural formula:

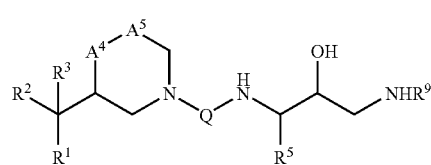

wherein

R¹ is:
a) $(C_1-C_9)$alkyl, $(C_3-C_7)$cycloalkyl, $(C_4-C_9)$cycloalkylalkyl, halo$(C_1-C_9)$alkyl, halo$(C_3-C_7)$cycloalkyl, halo$(C_4-C_9)$cycloalkylalkyl, or saturated heterocyclyl each optionally substituted with 1 to 3 groups independently selected from the groups consisting of fluorine, $(C_1-C_3)$alkyl, halo$(C_1-C_3)$alkyl or oxo; or
b) phenyl, napthyl, heteroaryl, or bicyclic heteroaryl each optionally substituted with 1 to 3 groups independently selected from the groups consisting of:
  1) fluorine, chlorine, bromine, cyano, nitro, $(C_1-C_6)$alkyl, $(C_3-C_6)$cycloalkyl, $(C_4-C_7)$cycloalkylalkyl, $(C_2-C_6)$alkenyl, $(C_5-C_6)$cycloalkenyl, $(C_5-C_8)$cycloalkylalkenyl, $(C_2-C_6)$alkynyl, $(C_3-C_6)$cycloalkylethynyl, halo$(C_1-C_6)$alkyl, halo$(C_3-C_6)$cycloalkyl, halo$(C_4-C_7)$-cycloalkylalkyl, halo$(C_2-C_6)$alkenyl, halo$(C_3-C_6)$alkynyl, halo$(C_3-C_6)$cycloalkylethynyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_3-C_6)$alkenyloxy, and $(C_1-C_6)$alkanesulfonyl; and
  2) phenyl, heteroaryl, phenoxy, heteroaryloxy, phenylthio, heteroarylthio, benzyl, heteroarylmethyl, benzyloxy, and heteroaryloxy, each optionally substituted with 1 to 3 groups independently selected from the group consisting of fluorine, chlorine, cyano, $(C_1-C_3)$alkyl, halo$(C_1-C_3)$alkyl, $(C_1-C_3)$-alkoxy, halo$(C_1-C_3)$alkoxy, and aminocarbonyl;

R² is —H, $(C_1-C_8)$alkyl, $(C_1-C_8)$oxoalkyl $(C_4-C_8)$cycloalkylalkyl, fluoro$(C_1-C_8)$alkyl, fluoro$(C_4-C_8)$-cycloalkylalkyl, $(C_1-C_8)$alkoxy, $(C_4-C_8)$cycloalkylalkoxy, fluoro$(C_1-C_8)$alkoxy, hydroxy$(C_1-C_8)$alkyl, $(C_1-C_5)$alkoxy$(C_1-C_5)$alkyl, halo$(C_1-C_5)$alkylamino$(C_1-C_5)$alkyl, $(C_1-C_5)$alkoxy$(C_1-C_5)$hydroxyalkyl, $(C_3-C_4)$cycloalkoxy$(C_1-C_5)$alkyl, fluoro$(C_1-C_5)$alkoxy$(C_1-C_5)$alkyl, fluoro$(C_3-C_4)$cycloalkoxy$(C_1-C_5)$alkyl, $(C_1-C_5)$alkylthio$(C_1-C_5)$alkyl, $(C_1-C_5)$alkoxy$(C_1-C_5)$alkoxy, hydroxy$(C_1-C_8)$alkoxy, $(C_3-C_4)$cycloalkoxy$(C_1-C_5)$alkoxy, fluoro$(C_1-C_5)$alkoxy$(C_1-C_5)$alkoxy, fluoro$(C_3-C_4)$cycloalkoxy$(C_1-C_5)$alkoxy, $(C_1-C_3)$alkoxy$(C_1-C_3)$alkoxy$(C_1-C_3)$alkyl, fluoro$(C_1-C_3)$-alkoxy$(C_1-C_3)$alkoxy$(C_1-C_3)$alkyl, aminocarbonylamino$(C_1-C_8)$alkyl, aminocarbonylamino$(C_1-C_8)$alkoxy, $(C_1-C_5)$alkanoylamino$(C_1-C_5)$alkyl, $(C_1-C_5)$alkanoylamino$(C_1-C_5)$alkoxy, fluoro$(C_1-C_5)$alkanoylamino$(C_1-C_5)$alkyl, fluoro$(C_1-C_5)$alkanoylamino$(C_1-C_5)$alkoxy, $(C_1-C_3)$alkoxy$(C_1-C_5)$alkanoylamino$(C_1-C_5)$alkyl, $(C_1-C_3)$alkoxy$(C_1-C_5)$alkanoylamino$(C_1-C_5)$alkoxy, $(C_3-C_4)$-cycloalkanecarbonyllamino$(C_1-C_5)$alkyl, $(C_3-C_4)$cycloalkanecarbonyllamino$(C_1-C_5)$alkoxy, aminosulfonylamino$(C_1-C_8)$alkyl, aminosulfonylamino$(C_1-C_8)$alkoxy, $(C_1-C_5)$alkanesulfonylamino$(C_1-C_5)$alkyl, $(C_1-C_5)$alkanesulfonylamino$(C_1-C_5)$alkoxy, formylamino$(C_1-C_5)$alkyl, formylamino$(C_1-C_5)$alkoxy, $(C_1-C_5)$alkoxycarbonylamino$(C_1-C_5)$alkyl, $(C_1-C_5)$alkoxycarbonylamino$(C_1-C_5)$alkoxy, $(C_1-C_5)$alkylaminocarbonylamino$(C_1-C_5)$alkyl, $(C_1-C_5)$alkylaminocarbonylamino$(C_1-C_5)$alkyl, di$(C_1-C_5)$alkylaminocarbonylamino$(C_1-C_5)$alkoxy, aminocarbonyl$(C_1-C_5)$alkyl, aminocarbonyl$(C_1-C_5)$alkoxy, $(C_1-C_5)$alkylaminocarbonyl$(C_1-C_5)$alkyl, $(C_1-C_5)$alkylaminocarbonyl-$(C_1-C_5)$alkoxy, aminocarboxy$(C_1-C_5)$alkyl, aminocarboxy$(C_1-C_5)$alkoxy, $(C_1-C_5)$alkylamino-carboxy$(C_1-C_5)$alkyl, $(C_1-C_5)$alkylaminocarboxy$(C_1-C_5)$alkoxy, $(C_1-C_8)$alkoxycarbonylamino, $(C_1-C_8)$alkylaminocarbonylamino, $(C_1-C_8)$alkanoylamino, fluoro$(C_1-C_8)$ alkoxycarbonylamino, fluoro$(C_1-C_8)$ alkylaminocarbonylamino, or fluoro$(C_1-C_8)$alkanoylamino;

R³ is —H, halogen, OH, $(C_1-C_4)$alkanoylamino, or $(C_1-C_3)$alkoxy;

provided that:
i) R² and R³ are not both —H; and
ii) when R³ is hydroxyl or halogen, R² is not $(C_1-C_8)$alkoxy, $(C_4-C_8)$cycloalkylalkoxy, fluoro$(C_1-C_8)$alkoxy, $(C_1-C_5)$alkoxy$(C_1-C_5)$alkoxy, hydroxy$(C_1-C_8)$alkoxy, $(C_3-C_4)$cycloalkoxy$(C_1-C_5)$alkoxy, fluoro$(C_1-C_5)$alkoxy$(C_1-C_5)$alkoxy, fluoro$(C_3-C_4)$cycloalkoxy$(C_1-C_5)$alkoxy, aminocarbonyl-amino$(C_1-C_8)$alkoxy, $(C_1-C_5)$alkanoylamino$(C_1-C_5)$alkoxy, fluoro$(C_1-C_5)$alkanoyl-amino$(C_1-C_5)$alkoxy, $(C_1-C_3)$alkoxy$(C_1-C_5)$alkanoylamino$(C_1-C_5)$alkoxy, $(C_3-C_4)$-cycloalkanecarbonyllamino$(C_1-C_5)$alkoxy, aminosulfonylamino$(C_1-C_8)$alkoxy, $(C_1-C_5)$alkanesulfonylamino$(C_1-C_5)$alkoxy, formylamino$(C_1-C_5)$alkoxy, $(C_1-C_5)$alkoxy-carbonylamino$(C_1-C_5)$alkoxy, di$(C_1-C_5)$alkylaminocarbonylamino$(C_1-C_5)$alkoxy, aminocarbonyl$(C_1-C_5)$alkoxy, $(C_1-C_5)$alkylaminocarbonyl$(C_1-C_5)$alkoxy, amino-carboxy$(C_1-C_5)$alkoxy, $(C_1-C_5)$alkylaminocarboxy$(C_1-C_5)$alkoxy, $(C_1-C_8)$alkoxy-carbonylamino, $(C_1-C_8)$alkylaminocarbonylamino, $(C_1-C_8)$alkanoylamino, fluoro$(C_1-C_8)$alkoxycarbonylamino, fluoro$(C_1-C_8)$ alkylaminocarbonylamino, or fluoro$(C_1-C_8)$ alkanoylamino;

$A^4$ is $CH_2$ and $A^5$ is $CH_2$;

Q is Q1, Q2, Q4, Q5, Q6, Q7, Q9, or Q10:

-continued

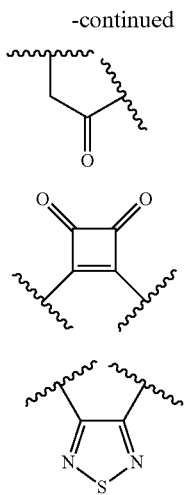

Q7

Q9

Q10

$R^5$ is:
a) —H;
b) $(C_1-C_{10})$alkyl, $(C_3-C_7)$cycloalkyl$(C_1-C_2)$alkyl, $(C_4-C_{10})$bicycloalkyl$(C_1-C_2)$alkyl, $(C_8-C_{12})$tricycloalkyl $(C_1-C_2)$alkyl, $(C_1-C_6)$alkoxy$(C_1-C_6)$alkyl, $(C_3-C_7)$cycloalkoxy$(C_1-C_3)$alkyl, $(C_1-C_5)$alkylthio$(C_1-C_5)$alkyl, or saturated heterocyclyl$(C_1-C_3)$alkyl, each optionally substituted with 1 to 3 groups independently selected from the group consisting of halogen, cyano, hydroxyl, $(C_1-C_2)$alkyl, $(C_1-C_2)$alkoxy, $(C_3-C_6)$cycloalkyl, $(C_3-C_6)$cycloalkoxy, halo$(C_1-C_2)$alkyl, halo$(C_1-C_2)$alkoxy, halo$(C_3-C_6)$cycloalkyl, and halo$(C_3-C_6)$cycloalkoxy; or
c) phenyl$(C_1-C_2)$alkyl or heteroaryl$(C_1-C_2)$alkyl each optionally substituted with 1 to 3 groups independently selected from the group consisting of fluorine, chlorine, cyano, $(C_1-C_3)$alkyl, halo$(C_1-C_3)$alkyl, $(C_1-C_3)$alkoxy, and halo$(C_1-C_3)$alkoxy;

$R^9$ is:
a) —H, $(C_1-C_6)$alkyl, halo$(C_1-C_6)$alkyl, $(C_4-C_{10})$cycloalkylalkyl, $(C_1-C_5)$alkoxy$(C_1-C_5)$alkyl, aminocarbonyl$(C_1-C_5)$alkyl, $(C_1-C_6)$alkylaminocarbonyl$(C_1-C_6)$alkyl, or di$(C_1-C_6)$alkylaminocarbonyl$(C_1-C_6)$alkyl; or
b) phenyl$(C_1-C_2)$alkyl optionally substituted with 1 to 3 groups independently selected from fluorine, chlorine, cyano, $(C_1-C_3)$alkyl, halo$(C_1-C_3)$alkyl, $(C_1-C_3)$alkoxy, and halo$(C_1-C_3)$alkoxy;

or an enantiomer, diastereomer or pharmaceutically acceptable salt thereof.

2. The compound of claim 1, wherein:
$R^1$ is:
a) isopropyl, cyclohexyl, or trifluoromethyl; or
b) phenyl, 2-thienyl, 3-thienyl, 2-pyridyl, 2-imidazolyl, 2-thiazolyl, 2-benzothienyl, 4-benzofuryl, 4-benzothienyl, 7-benzofuryl, 2,3-dihydro-7-benzofuryl, 7-benzothienyl, 1,3-benzodioxol-4-yl, 7-indazolyl, or 8-quinolinyl each optionally substituted with 1 to 3 substituents independently selected from the group consisting of fluorine, chlorine, bromine, cyano, methyl, ethyl, isopropyl, t-butyl, isobutyl, trifluoromethyl, allyl, cyclohexyl, cyclohexen-1-yl, cyclopropylethynyl, methoxy, trifluoromethoxy, neopentyloxy, methylthio, allyloxy, cyclopropylmethoxy, 2-(cyclopropyl)ethoxy, cyclopentyloxy, cyclopentylmethoxy, benzyloxy, hydroxyl, aminocarbonyl, methoxycarbonyl, phenyl, phenoxy, benzyloxy, and heteroaryloxy, wherein the phenyl phenoxy, benzyloxy and heteroaryloxy groups are optionally substituted with 1 to 3 substituents independently selected from the group consisting of fluorine, chlorine, cyano, methyl, trifluoromethyl, and aminocarbonyl;

$R^2$ is —H, methyl, ethyl, propyl, butyl, hexyl, 5-pentenyl, 3,3,3-trifluoropropyl, 4,4-difluoropentyl, 3-(cyclopropyl)propyl, 4-(cyclopropyl)butyl, 3-hydroxypropyl, 4-hydroxybutyl, 4-hydroxypentyl, 4-hydroxyhexyl, 5-hydroxyhexyl, 2-hydroxyethoxy, 5-oxohexyl, 3-ethoxypropyl, 4-methoxybutyl, 4-ethoxybutyl, butoxy, hexyloxy, 2-(ethoxy)-ethoxy, 2-(methoxy)-ethoxy, 3-methoxypropoxy, 4-(methoxy)-butoxy, 3-ethoxypropoxy, 3-propoxypropoxy, 2-cyclopropylethoxy, (2-(methoxy)ethoxy)methyl, 3-(2,2,2-trifluoroethylamino)propyl, 3-(formylamino)propyl, 3-(acetylamino)propyl, 3-(propionyl-amino)propyl, 3-(butanoylamino)propyl, 3-((2-methoxypropionyl)amino)propyl, 3-(cyclopropanecarbonylamino)propyl, 3-(trifluoroacetylamino)propyl, 3-(methoxycarbonylamino)propyl, 3-(ethoxycarbonylamino)propyl, 2-(methoxycarbonylamino)ethoxy, 2-(ethoxycarbonylamino)ethoxy, 3-(methylaminocarbonylamino)propyl, 3-(dimethylaminocarbonyl-amino)propyl, 3-(aminocarbonyl)propyl, 3-(methylaminocarbonyl)propyl, 3-(ethylamino-carbonyl)propyl, 2-(acetylamino)ethoxy, 2-(propionylamino)ethoxy, aminocarbonylmethoxy, methylaminocarbonylmethoxy, ethylaminocarbonylmethoxy, propylaminocarbonylmethoxy, 2-(methylaminocarbonyl)ethoxy, 2-(ethylaminocarbonyl)ethoxy, 2-(propylaminocarbonyl)ethoxy, (2-(methoxy)ethoxy)carbonylamino, methoxymethylcarbonylaminomethyl, or 3-(aminosulfonylamino)propyl, $R^3$ is —H, —F, —OH, methoxy, acetylamino, propionylamino, (2-methylpropionyl)amino, or butanoylamino, provided that when $R^3$ is F or OH, $R^2$ is not butoxy, hexyloxy, 2-(ethoxy)ethoxy, 3-methoxypropoxy, 3-ethoxypropoxy, 3-propoxypropoxy, 2-cyclopropylethoxy, 2-2-(methoxycarbonylamino)ethoxy, 2-(ethoxycarbonylamino)ethoxy, (acetylamino)ethoxy, 2-(propionylamino)ethoxy, aminocarbonylmethoxy, methylaminocarbonylmethoxy, ethylaminocarbonylmethoxy, propylaminocarbonylmethoxy, 2-(methylaminocarbonyl)ethoxy, 2-(ethylaminocarbonyl)ethoxy, 2-(propylaminocarbonyl)ethoxy, or (2-(methoxy)ethoxy)carbonylamino;

$A^4$ is $CH_2$ and $A^5$ is $CH_2$;
Q is Q1, Q2, Q4, Q5, Q6, Q7, Q9, or Q10

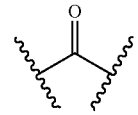

Q1

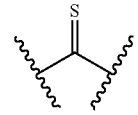

Q2

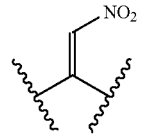

Q4

-continued

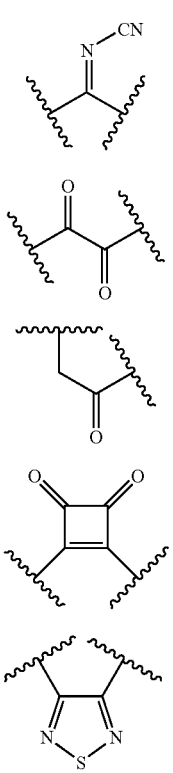

R[5] is —H, methyl, isobutyl, t-butylmethyl, 2,2,2-trifluoroethyl, 2-(trifluoromethyl)propyl, cyclopentylmethyl, cyclohexylmethyl, (3,3-difluorocyclobutyl)methyl, 3,4-difluorocyclopentyl)methyl, 4,4-difluorocyclohexylmethyl, (4-methylcyclohexyl)methyl, tert-butoxymethyl, (4-tetrahydropyranyl)methyl, benzyl, (1-fluorocyclohexyl)methyl, (4-fluorocyclohexyl)methyl, 1-hydroxy-2-methylpropyl, (cyclopentyl)(hydroxy)methyl, (cyclohexyl)(hydroxy)methyl, (cycloheptyl)(hydroxy)methyl, (1-hydroxycyclohexyl)methyl, (4-hydroxycyclohexyl)methyl, (4-hydroxy-4-methylcyclohexyl)methyl, (3-noradamantyl)(hydroxy)methyl, 2-methoxy-2-methylpropyl, 2,2-dimethyl-3-methoxypropyl, (3-tetrahydrofuryl)methyl, (3-tetrahydropyranyl)methyl or (4-tetrahydropyranyl)methyl;

R[9] is —H, methyl, ethyl, propyl, butyl, isobutyl, t-butyl, pentyl, isopentyl, aminocarbonylmethyl;

or an enantiomer, diastereomer or a pharmaceutically acceptable salt thereof.

3. The compound of claim 2 wherein R[5] is —H, methyl, isobutyl, t-butylmethyl, 2,2,2-trifluoroethyl, 2-(trifluoromethyl)propyl, cyclopentylmethyl, cyclohexylmethyl, (3,3-difluorocyclobutyl)methyl, 4,4-difluoro-cyclohexylmethyl, (4-methylcyclohexyl)methyl, tert-butoxymethyl, (4-tetrahydropyranyl)methyl, benzyl, (1-fluorocyclohexyl)methyl, (4-fluorocyclohexyl)methyl, 1-hydroxy-2-methylpropyl, (cyclopentyl)(hydroxy)methyl, (cyclohexyl)(hydroxy)methyl, (cycloheptyl)(hydroxy)methyl, (1-hydroxycyclohexyl)methyl, (4-hydroxycyclohexyl)methyl, (4-hydroxy-4-methylcyclohexyl)methyl, (3-noradamantyl)(hydroxy)methyl, 2-methoxy-2-methylpropyl, or 2,2-dimethyl-3-methoxypropyl; and R[9] is —H, methyl, ethyl, propyl, butyl, isobutyl, pentyl, isopentyl, aminocarbonylmethyl.

4. The compound of claim 1, wherein

R[1] is a) isopropyl; or b) phenyl, optionally substituted with 1 to 3 substituents independently selected from the groups consisting of fluorine, chlorine, cyano, methyl and phenoxy, wherein the phenoxy group is optionally substituted with 1 to 3 substituents independently selected from fluorine, chlorine, methyl, and ethyl;

R[2] is hydrogen, butoxy, hexyloxy, 2-(methoxy)ethoxy, 3-(methoxy)propoxy, 4-(methoxy)butoxy, 4-(methoxy)butyl, 3-(methoxycarbonylamino)propyl, or 2-(methoxycarbonylamino)ethoxy;

R[3] is —H or —OH; provided that when R[3] is —OH, R[2] is not 2-(methoxy)ethoxy, 3-(methoxy)propoxy, 4-(methoxy)butoxy, or 2-(methoxycarbonylamino)ethoxy;

A[4] is CH$_2$ and A[5] is CH$_2$;

Q is Q1, Q6, Q7, or Q9;

R[5] is —H, or cyclohexylmethyl;

R[9] is —H, methyl, 4-cyanobenzyl, or 3,5-dimethoxybenzyl;

or an enantiomer, diastereomer or pharmaceutically acceptable salt thereof.

5. The compound of claim 1 wherein the compound is represented by the following structural formula:

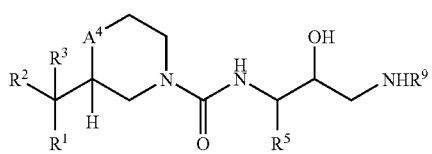

or an enantiomer, diastereomer or pharmaceutically acceptable salt thereof.

6. The compound of claim 1 wherein the compound is represented by the following structural formula:

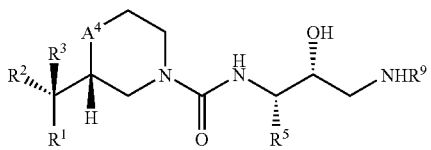

or an enantiomer, diastereomer or pharmaceutically acceptable salt thereof.

7. The compound of claim 1 wherein the compound is selected from the group:

N-(3-amino-2-hydroxypropyl)-3-(1-(2-(2-ethylphenoxy)phenyl)-1-hydroxy-5-methoxypentyl)piperidine-1-carboxamide,
3-(4-amino-1-cyclohexyl-3-hydroxybutan-2-ylamino)-4-(3-((3-methoxypropoxy)(phenyl)methyl)piperidin-1-yl)cyclobut-3-ene-1,2-dione,
3-(1-(3-chlorophenyl)-1-hydroxy-5-methoxypentyl)-N-(1-cyclohexyl-3-hydroxy-4-(methylamino)butan-2-yl)piperidine-1-carboxamide,
N-(1-cyclohexyl-3-hydroxy-4-(methylamino)butan-2-yl)-3-(1-(2,3-difluorophenyl)-1-hydroxy-5-methoxypentyl)piperidine-1-carboxamide,
N-(4-amino-1-cyclohexyl-3-hydroxybutan-2-yl)-3-(1-(3-chloro-2-fluorophenyl)-1-hydroxy-5-methoxypentyl)piperidine-1-carboxamide,
N-(4-amino-1-cyclohexyl-3-hydroxybutan-2-yl)-3-(1-(3-chloro-2-fluorophenyl)-1-hydroxy-5-methoxypentyl)piperidine-1-carboxamide,
N-(4-amino-1-cyclohexyl-3-hydroxybutan-2-yl)-2-(1-(3-chloro-2-fluorophenyl)-1-hydroxy-5-methoxypentyl)morpholine-4-carboxamide,
methyl 4-(1-(4-amino-1-cyclohexyl-3-hydroxybutan-2-ylcarbamoyl)piperidin-3-yl)-4-(3-chlorophenyl)-4-hydroxybutylcarbamate,
3-(1-(3-chloro-2-fluorophenyl)-1-hydroxy-5-methoxypentyl)-N-(1-cyclohexyl-3-hydroxy-4-(methylamino)butan-2-yl)piperidine-1-carboxamide,
2-(1-(3-chloro-2-fluorophenyl)-1-hydroxy-5-methoxypentyl)-N-(1-cyclohexyl-3-hydroxy-4-(methylamino)butan-2-yl)morpholine-4-carboxamide,
N-(4-(4-cyanobenzylamino)-1-cyclohexyl-3-hydroxybutan-2-yl)-3-((3-methoxypropoxy)(phenyl)methyl)piperidine-1-carboxamide,
3-(1-cyclohexyl-4-(3,5-dimethoxybenzylamino)-3-hydroxybutan-2-ylamino)-4-(3-(hydroxy(phenyl)methyl)piperidin-1-yl)cyclobut-3-ene-1,2-dione,
N-(1-cyclohexyl-4-(3,5-dimethoxybenzylamino)-3-hydroxybutan-2-yl)-2-(3-((2-methoxyethoxy)(phenyl)methyl)pyrrolidin-1-yl)-2-oxoacetamide,
N-(1-cyclohexyl-4-(3,5-dimethoxybenzylamino)-3-hydroxybutan-2-yl)-2-(3-((3-methoxypropoxy)(phenyl)methyl)pyrrolidin-1-yl)-2-oxoacetamide,
N-(1-cyclohexyl-4-(3,5-dimethoxybenzylamino)-3-hydroxybutan-2-yl)-2-(3-((3-methoxypropoxy)(phenyl)methyl)piperidin-1-yl)acetamide,
4-((4-cyclohexyl-2-hydroxy-3-(2-(3-((3-methoxypropoxy)(phenyl)methyl)piperidin-1-yl)-3,4-dioxocyclobut-1-enylamino)butylamino)methyl)benzonitrile,
4-((4-cyclohexyl-2-hydroxy-3-(2-(3-((3-methoxypropoxy)(phenyl)methyl)piperidin-1-yl)-3,4-dioxocyclobut-1-enylamino)butylamino)methyl)benzonitrile,
3-(1-cyclohexyl-4-(3,5-dimethoxybenzylamino)-3-hydroxybutan-2-ylamino)-4-(3-(1-(3-methoxypropoxy)-2-methylpropyl)piperidin-1-yl)cyclobut-3-ene-1,2-dione,
N-(1-cyclohexyl-4-(3,5-dimethoxybenzylamino)-3-hydroxybutan-2-yl)-2-(3-((4-methoxybutoxy)(phenyl)methyl)pyrrolidin-1-yl)-2-oxoacetamide,
N-(1-cyclohexyl-4-(3,5-dimethoxybenzylamino)-3-hydroxybutan-2-yl)-2-(3-(1-hydroxy-5-methoxy-1-phenylpentyl)pyrrolidin-1-yl)-2-oxoacetamide,
4-((4-cyclohexyl-3-(2-(3-(hexyloxy(phenyl)methyl)piperidin-1-yl)-3,4-dioxocyclobut-1-enylamino)-2-hydroxybutylamino)methyl)benzonitrile,
4-((4-cyclohexyl-2-hydroxy-3-(2-(3-((4-methoxybutoxy)(phenyl)methyl)piperidin-1-yl)-3,4-dioxocyclobut-1-enylamino)butylamino)methyl)benzonitrile,
3-(3-(butoxy(phenyl)methyl)piperidin-1-yl)-4-(1-cyclohexyl-4-(3,5-dimethoxybenzylamino)-3-hydroxybutan-2-ylamino)cyclobut-3-ene-1,2-dione,
3-(1-cyclohexyl-4-(3,5-dimethoxybenzylamino)-3-hydroxybutan-2-ylamino)-4-(3-((2-methoxyethoxy)(phenyl)methyl)piperidin-1-yl)cyclobut-3-ene-1,2-dione,
3-(1-cyclohexyl-4-(3,5-dimethoxybenzylamino)-3-hydroxybutan-2-ylamino)-4-(3-((3-methoxypropoxy)(phenyl)methyl)piperidin-1-yl)cyclobut-3-ene-1,2-dione,
methyl 2-((1-(4-amino-1-cyclohexyl-3-hydroxybutan-2-ylcarbamoyl)piperidin-3-yl)(3-chlorophenyl)methoxy)ethylcarbamate,
methyl 2-((3-chlorophenyl)(1-(1-cyclohexyl-3-hydroxy-4-(methylamino)butan-2-ylcarbamoyl)piperidin-3-yl)methoxy)ethylcarbamate, or
methyl 2-((1-(1-cyclohexyl-3-hydroxy-4-(methylamino)butan-2-ylcarbamoyl)piperidin-3-yl)(3-fluorophenyl)methoxy)ethylcarbamate
methyl 2-((3-chlorophenyl)(4-(1-cyclohexyl-3-hydroxy-4-(methylamino)butan-2-ylcarbamoyl)morpholin-2-yl)methoxy)ethylcarbamate
methyl 2-((3-chlorophenyl)(4-(3-hydroxy-4-(methylamino)-1-(tetrahydro-2H-pyran-4-yl)butan-2-ylcarbamoyl)morpholin-2-yl)methoxy)ethylcarbamate
methyl 2-((1-(1-(tert-butylamino)-2-hydroxy-5-methylhexan-3-ylcarbamoyl)piperidin-3-yl)(3-chlorophenyl)methoxy)ethylcarbamate or an enantiomer, diastereomer or pharmaceutically acceptable salt thereof.

8. The compound of claim 1 wherein the compound is selected from the group:

or an enantiomer, diastereomer or pharmaceutically acceptable salt thereof.

9. A pharmaceutical composition comprising a therapeutically effective amount of a compound of claim 1 or an enan-

---

(R)—N-((R)-3-amino-2-hydroxypropyl)-3-((S)-1-(2-(2-ethylphenoxy)phenyl)-1-hydroxy-5-methoxypentyl)piperidine-1-carboxamide,
3-((2S,3R)-4-amino-1-cyclohexyl-3-hydroxybutan-2-ylamino)-4-((R)-3-((R)-(3-methoxypropoxy)(phenyl)methyl)piperidin-1-yl)cyclobut-3-ene-1,2-dione,
(R)-3-((S)-1-(3-chlorophenyl)-1-hydroxy-5-methoxypentyl)-N-((2S,3R)-1-cyclohexyl-3-hydroxy-4-(methylamino)butan-2-yl)piperidine-1-carboxamide,
(R)—N-((2S,3R)-1-cyclohexyl-3-hydroxy-4-(methylamino)butan-2-yl)-3-((S)-1-(2,3-difluorophenyl)-1-hydroxy-5-methoxypentyl)piperidine-1-carboxamide,
(R)—N-((2S,3S)-4-amino-1-cyclohexyl-3-hydroxybutan-2-yl)-3-((S)-1-(3-chloro-2-fluorophenyl)-1-hydroxy-5-methoxypentyl)piperidine-1-carboxamide,
(R)—N-((2S,3R)-4-amino-1-cyclohexyl-3-hydroxybutan-2-yl)-3-((S)-1-(3-chloro-2-fluorophenyl)-1-hydroxy-5-methoxypentyl)piperidine-1-carboxamide,
(R)—N-((2S,3R)-4-amino-1-cyclohexyl-3-hydroxybutan-2-yl)-2-((R)-1-(3-chloro-2-fluorophenyl)-1-hydroxy-5-methoxypentyl)morpholine-4-carboxamide,
(R)—N-((2S,3S)-4-amino-1-cyclohexyl-3-hydroxybutan-2-yl)-2-((R)-1-(3-chloro-2-fluorophenyl)-1-hydroxy-5-methoxypentyl)morpholine-4-carboxamide,
methyl (S)-4-((R)-1-((2S,3S)-4-amino-1-cyclohexyl-3-hydroxybutan-2-ylcarbamoyl)piperidin-3-yl)-4-(3-chlorophenyl)-4-hydroxybutylcarbamate,
methyl (S)-4-((R)-1-((2S,3R)-4-amino-1-cyclohexyl-3-hydroxybutan-2-ylcarbamoyl)piperidin-3-yl)-4-(3-chlorophenyl)-4-hydroxybutylcarbamate,
(R)-3-((S)-1-(3-chloro-2-fluorophenyl)-1-hydroxy-5-methoxypentyl)-N-((2S,3R)-1-cyclohexyl-3-hydroxy-4-(methylamino)butan-2-yl)piperidine-1-carboxamide,
(R)-2-((R)-1-(3-chloro-2-fluorophenyl)-1-hydroxy-5-methoxypentyl)-N-((2S,3R)-1-cyclohexyl-3-hydroxy-4-(methylamino)butan-2-yl)morpholine-4-carboxamide,
(R)—N-((2S,3R)-4-(4-cyanobenzylamino)-1-cyclohexyl-3-hydroxybutan-2-yl)-3-((R)-(3-methoxypropoxy)(phenyl)methyl)piperidine-1-carboxamide,
3-((2S,3R)-1-cyclohexyl-4-(3,5-dimethoxybenzylamino)-3-hydroxybutan-2-ylamino)-4-((R)-3-((S)-hydroxy(phenyl)methyl)piperidin-1-yl)cyclobut-3-ene-1,2-dione,
N-((2S,3R)-1-cyclohexyl-4-(3,5-dimethoxybenzylamino)-3-hydroxybutan-2-yl)-2-((R)-3-((R)-(2-methoxyethoxy)(phenyl)methyl)pyrrolidin-1-yl)-2-oxoacetamide,
N-((2S,3R)-1-cyclohexyl-4-(3,5-dimethoxybenzylamino)-3-hydroxybutan-2-yl)-2-((R)-3-((R)-(3-methoxypropoxy)(phenyl)methyl)pyrrolidin-1-yl)-2-oxoacetamide,
N-((2S,3R)-1-cyclohexyl-4-(3,5-dimethoxybenzylamino)-3-hydroxybutan-2-yl)-2-((R)-3-((R)-(3-methoxypropoxy)(phenyl)methyl)piperidin-1-yl)acetamide,
4-(((2R,3S)-4-cyclohexyl-2-hydroxy-3-(2-((R)-3-((R)-(3-methoxypropoxy)(phenyl)methyl)piperidin-1-yl)-3,4-dioxocyclobut-1-enylamino)butylamino)methyl)benzonitrile,
4-(((2S,3S)-4-cyclohexyl-2-hydroxy-3-(2-((R)-3-((R)-(3-methoxypropoxy)(phenyl)methyl)piperidin-1-yl)-3,4-dioxocyclobut-1-enylamino)butylamino)methyl)benzonitrile,
3-((2S,3R)-1-cyclohexyl-4-(3,5-dimethoxybenzylamino)-3-hydroxybutan-2-ylamino)-4-((R)-3-((S)-1-(3-methoxypropoxy)-2-methylpropyl)piperidin-1-yl)cyclobut-3-ene-1,2-dione,
N-((2S,3R)-1-cyclohexyl-4-(3,5-dimethoxybenzylamino)-3-hydroxybutan-2-yl)-2-((R)-3-((R)-(4-methoxybutoxy)(phenyl)methyl)pyrrolidin-1-yl)-2-oxoacetamide,
N-((2S,3R)-1-cyclohexyl-4-(3,5-dimethoxybenzylamino)-3-hydroxybutan-2-yl)-2-((R)-3-((S)-1-hydroxy-5-methoxy-1-phenylpentyl)pyrrolidin-1-yl)-2-oxoacetamide,
4-(((2R,3S)-4-cyclohexyl-3-(2-((R)-3-((R)-hexyloxy(phenyl)methyl)piperidin-1-yl)-3,4-dioxocyclobut-1-enylamino)-2-hydroxybutylamino)methyl)benzonitrile,
4-(((2R,3S)-4-cyclohexyl-2-hydroxy-3-(2-((R)-3-((R)-(4-methoxybutoxy)(phenyl)methyl)piperidin-1-yl)-3,4-dioxocyclobut-1-enylamino)butylamino)methyl)benzonitrile,
3-((R)-3-((R)-butoxy(phenyl)methyl)piperidin-1-yl)-4-((2S,3R)-1-cyclohexyl-4-(3,5-dimethoxybenzylamino)-3-hydroxybutan-2-ylamino)cyclobut-3-ene-1,2-dione,
3-((2S,3R)-1-cyclohexyl-4-(3,5-dimethoxybenzylamino)-3-hydroxybutan-2-ylamino)-4-((R)-3-((R)-(2-methoxyethoxy)(phenyl)methyl)piperidin-1-yl)cyclobut-3-ene-1,2-dione,
3-((2S,3R)-1-cyclohexyl-4-(3,5-dimethoxybenzylamino)-3-hydroxybutan-2-ylamino)-4-((R)-3-((R)-(3-methoxypropoxy)(phenyl)methyl)piperidin-1-yl)cyclobut-3-ene-1,2-dione,
methyl 2-((R)-((R)-1-((2S,3R)-4-amino-1-cyclohexyl-3-hydroxybutan-2-ylcarbamoyl)piperidin-3-yl)(3-chlorophenyl)methoxy)ethylcarbamate,
methyl 2-((R)-(3-chlorophenyl)((R)-1-((2S,3R)-1-cyclohexyl-3-hydroxy-4-(methylamino)butan-2-ylcarbamoyl)piperidin-3-yl)methoxy)ethylcarbamate, or
methyl 2-((R)-((R)-1-((2S,3R)-1-cyclohexyl-3-hydroxy-4-(methylamino)butan-2-ylcarbamoyl)piperidin-3-yl)(3-fluorophenyl)methoxy)ethylcarbamate
methyl 2-((S)-(3-chlorophenyl)((R)-4-((2S,3R)-1-cyclohexyl-3-hydroxy-4-(methylamino)butan-2-ylcarbamoyl)morpholin-2-yl)methoxy)ethylcarbamate
methyl 2-((R)-((R)-1-((2R,3S)-1-(tert-butylamino)-2-hydroxy-5-methylhexan-3-ylcarbamoyl)piperidin-3-yl)(3-chlorophenyl)methoxy)ethylcarbamate tiomer, diastereomer, or pharmaceutically acceptable salt thereof and a pharmaceutically acceptable carrier or excipient.

10. The pharmaceutical composition of claim 9, further comprising an agent selected from the group consisting of α-blockers, β-blockers, calcium channel blockers, diuretics, angiotensin converting enzyme (ACE) inhibitors, dual ACE and neutral endopeptidase (NEP) inhibitors, angiotensin-receptor blockers (ARBs), aldosterone synthase inhibitors, aldosterone-receptor antagonists, and endothelin receptor antagonists.

* * * * *

UNITED STATES PATENT AND TRADEMARK OFFICE
CERTIFICATE OF CORRECTION

| | |
|---|---|
| PATENT NO. | : 7,872,028 B2 |
| APPLICATION NO. | : 12/225985 |
| DATED | : January 18, 2011 |
| INVENTOR(S) | : John J. Baldwin et al. |

It is certified that error appears in the above-identified patent and that said Letters Patent is hereby corrected as shown below:

In Column 140, Claim 7, Lines 11-12 in the table, please delete
"N-(4-amino-1-cyclohexyl-3-hydroxybutan-2-yl)-3-(1-(3-chloro-2-fluorophenyl)-1-hydroxy-5-methoxypentyl)piperidine-1-carboxamide,"

In Column 140, Claim 7, Lines 13-14 in the table, please delete
"N-(4-amino-1-cyclohexyl-3-hydroxybutan-2-yl)-2-(1-(3-chloro-2-fluorophenyl)-1-hydroxy-5-methoxypentyl)morpholine-4-carboxamide,"

In Column 140, Claim 7, Lines 19-20 in the table, please delete
"2-(1-(3-chloro-2-fluorophenyl)-1-hydroxy-5-methoxypentyl)-N-(1-cyclohexyl-3-hydroxy-4-(methylamino)butan-2-yl)morpholine-4-carboxamide,"

In Column 140, Claim 7, Lines 25-28 in the table, please delete
"N-(1-cyclohexyl-4-(3,5-dimethoxybenzylamino)-3-hydroxybutan-2-yl)-2-(3-((2-methoxyethoxy)(phenyl)methyl)pyrrolidin-1-yl)-2-oxoacetamide,
N-(1-cyclohexyl-4-(3,5-dimethoxybenzylamino)-3-hydroxybutan-2-yl)-2-(3-((3-methoxypropoxy)(phenyl)methyl)pyrrolidin-1-yl)-2-oxoacetamide,"

In Column 140, Claim 7, Lines 34-36 in the table, please delete
"4-((4-cyclohexyl-2-hydroxy-3-(2-(3-((3-methoxypropoxy)(phenyl)methyl)piperidin-1-yl)-3,4-dioxocyclobut-1-enylamino)butylamino)methyl)benzonitrile,"

In Column 140, Claim 7, Lines 39-42 in the table, please delete
"N-(1-cyclohexyl-4-(3,5-dimethoxybenzylamino)-3-hydroxybutan-2-yl)-2-(3-((4-methoxybutoxy)(phenyl)methyl)pyrrolidin-1-yl)-2-oxoacetamide,
N-(1-cyclohexyl-4-(3,5-dimethoxybenzylamino)-3-hydroxybutan-2-yl)-2-(3-(1-hydroxy-5-methoxy-1-phenylpentyl)pyrrolidin-1-yl)-2-oxoacetamide,"

Signed and Sealed this
First Day of November, 2011

David J. Kappos
*Director of the United States Patent and Trademark Office*

CERTIFICATE OF CORRECTION (continued)
U.S. Pat. No. 7,872,028 B2

In Column 140, Claim 7, Lines 59-64 in the table, please delete
"methyl 2-((3-chlorophenyl)(4-(1-cyclohexyl-3-hydroxy-4-(methylamino)butan-2-ylcarbamoyl)morpholin-2-yl)methoxy)ethylcarbamate
methyl 2-((3-chlorophenyl)(4-(3-hydroxy-4-(methylamino)-1-(tetrahydro-2H-pyran-4-yl)butan-2-ylcarbamoyl)morpholin-2-yl)methoxy)ethylcarbamate"

In Column 140, Claim 7, at the end of Line 66 in the table, please add ","

In Column 141, Claim 8, Lines 13-16 in the table, please delete
"(R)-N-((2S,3R)-4-amino-1-cyclohexyl-3-hydroxybutan-2-yl)-2-((R)-1-(3-chloro-2-fluorophenyl)-1-hydroxy-5-methoxypentyl)morpholine-4-carboxamide,
(R)-N-((2S,3S)-4-amino-1-cyclohexyl-3-hydroxybutan-2-yl)-2-((R)-1-(3-chloro-2-fluorophenyl)-1-hydroxy-5-methoxypentyl)morpholine-4-carboxamide,"

In Column 141, Claim 8, Lines 23-24 in the table, please delete
"(R)-2-((R)-1-(3-chloro-2-fluorophenyl)-1-hydroxy-5-methoxypentyl)-N-((2S,3R)-1-cyclohexyl-3-hydroxy-4-(methylamino)butan-2-yl)morpholine-4-carboxamide,"

In Column 141, Claim 8, Lines 29-32 in the table, please delete
"N-((2S,3R)-1-cyclohexyl-4-(3,5-dimethoxybenzylamino)-3-hydroxybutan-2-yl)-2-((R)-3-((R)-(2-methoxyethoxy)(phenyl)methyl)pyrrolidin-1-yl)-2-oxoacetamide,
N-((2S,3R)-1-cyclohexyl-4-(3,5-dimethoxybenzylamino)-3-hydroxybutan-2-yl)-2-((R)-3-((R)-(3-methoxypropoxy)(phenyl)methyl)pyrrolidin-1-yl)-2-oxoacetamide,"

In Column 141, Claim 8, Lines 44-48 in the table, please delete
"N-((2S,3R)-1-cyclohexyl-4-(3,5-dimethoxybenzylamino)-3-hydroxybutan-2-yl)-2-((R)-3-((R)-(4-methoxybutoxy)(phenyl)methyl)pyrrolidin-1-yl)-2-oxoacetamide,
N-((2S,3R)-1-cyclohexyl-4-(3,5-dimethoxybenzylamino)-3-hydroxybutan-2-yl)-2-((R)-3-((S)-1-hydroxy-5-methoxy-1-phenylpentyl)pyrrolidin-1-yl)-2-oxoacetamide,"

In Column 141, Claim 8, at the end of Line 67 in the table, please add ", and"

In Column 141, Claim 8, Lines 68-69 in the table, please delete
"methyl 2-((S)-(3-chlorophenyl)((R)-4-((2S,3R)-1-cyclohexyl-3-hydroxy-4-(methylamino)butan-2-ylcarbamoyl)morpholin-2-yl)methoxy)ethylcarbamate"

In Column 141, Claim 8, at the end of Line 71 in the table, please add ","